United States Patent
Teschner et al.

(10) Patent No.: US 9,084,743 B2
(45) Date of Patent: Jul. 21, 2015

(54) STABLE CO-FORMULATION OF HYALURONIDASE AND IMMUNOGLOBULIN, AND METHODS OF USE THEREOF

(75) Inventors: Wolfgang Teschner, Vienna (AT); Sonja Svatos, Berg (AT); Leopold Bruckschwaiger, Vienna (AT); Alfred Weber, Vienna (AT); Hans-Peter Schwarz, Vienna (AT); Laura Lei, Los Angeles, CA (US)

(73) Assignees: Baxter International Inc., Deerfield, IL (US); Baxter Healthcare S.A., Zurich-Opfikon (CH)

(*) Notice: Subject to any disclaimer, the term of this patent is extended or adjusted under 35 U.S.C. 154(b) by 713 days.

(21) Appl. No.: 12/807,991

(22) Filed: Sep. 16, 2010

(65) Prior Publication Data

US 2011/0066111 A1 Mar. 17, 2011

Related U.S. Application Data

(60) Provisional application No. 61/277,045, filed on Sep. 17, 2009.

(51) Int. Cl.

| | | |
|---|---|---|
| A61K 39/395 | (2006.01) | |
| A61K 39/00 | (2006.01) | |
| A61K 9/00 | (2006.01) | |
| A61K 47/42 | (2006.01) | |
| C07K 16/00 | (2006.01) | |
| C07K 16/06 | (2006.01) | |
| C12N 9/26 | (2006.01) | |

(52) U.S. Cl.
CPC .............. *A61K 39/00* (2013.01); *A61K 9/0021* (2013.01); *A61K 39/39591* (2013.01); *A61K 47/42* (2013.01); *C07K 16/00* (2013.01); *C07K 16/06* (2013.01); *C12N 9/2474* (2013.01); *C12Y 302/01035* (2013.01); *A61K 2039/505* (2013.01); *C07K 2317/21* (2013.01)

(58) Field of Classification Search
None
See application file for complete search history.

(56) References Cited

U.S. PATENT DOCUMENTS

| | | | |
|---|---|---|---|
| 3,869,436 A | 3/1975 | Falksveden et al. | 260/112 |
| 3,966,906 A | 6/1976 | Schultze et al. | 424/177.1 |
| 4,002,531 A | 1/1977 | Royer | 435/188 |
| 4,093,606 A | 6/1978 | Coval | 530/390.5 |
| 4,124,576 A | 11/1978 | Coval | 530/390.5 |
| 4,126,605 A | 11/1978 | Schneider et al. | 530/390.5 |
| 4,165,370 A | 8/1979 | Coval | 424/177.1 |
| 4,179,337 A | 12/1979 | Davis et al. | 435/181 |
| 4,186,192 A | 1/1980 | Lundblad et al. | 424/177.1 |
| 4,362,661 A | 12/1982 | Ono et al. | 424/177.1 |
| 4,374,763 A | 2/1983 | Takagi | 530/390.5 |
| 4,396,608 A | 8/1983 | Tenold | 424/177.1 |
| 4,439,421 A | 3/1984 | Hooper et al. | 424/177.1 |
| 4,499,073 A | 2/1985 | Tenold | 424/159.1 |
| 4,597,966 A | 7/1986 | Zolton et al. | 424/141.1 |
| 4,876,088 A | 10/1989 | Hirao et al. | 424/101 |
| 4,952,496 A | 8/1990 | Studier et al. | 435/91.41 |
| 5,033,252 A | 7/1991 | Carter | 53/425 |
| 5,052,558 A | 10/1991 | Carter | 206/439 |
| 5,122,373 A | 6/1992 | Eibl et al. | 424/171.1 |
| 5,122,614 A | 6/1992 | Zalipsky | 548/520 |
| 5,177,194 A | 1/1993 | Sarno et al. | 530/390.1 |
| 5,180,810 A | 1/1993 | Gomi et al. | 530/350 |
| 5,323,907 A | 6/1994 | Kalvelage | 206/531 |
| 5,324,844 A | 6/1994 | Zalipsky | 548/520 |
| 5,409,990 A | 4/1995 | Linnau et al. | 525/54.1 |
| 5,446,090 A | 8/1995 | Harris | 525/54.1 |
| 5,608,038 A | 3/1997 | Eibl et al. | 530/387.1 |
| 5,612,460 A | 3/1997 | Zalipsky | 530/391.9 |
| 5,643,575 A | 7/1997 | Martinez et al. | 424/194.1 |
| 5,665,069 A | 9/1997 | Cumer et al. | 604/116 |
| 5,672,662 A | 9/1997 | Harris et al. | 525/408 |
| 5,721,348 A | 2/1998 | Primakoff et al. | 536/22.1 |
| 5,747,027 A | 5/1998 | Stern et al. | 424/94.62 |
| 5,766,581 A | 6/1998 | Bartley et al. | 424/85.1 |
| 5,795,569 A | 8/1998 | Bartley et al. | 424/85.1 |
| 5,808,096 A | 9/1998 | Zalipsky | 548/520 |
| 5,827,721 A | 10/1998 | Stern et al. | 435/201 |
| 5,854,046 A | 12/1998 | Au-Young et al. | 435/201 |
| 5,871,736 A | 2/1999 | Bruegger et al. | 424/177.1 |
| 5,900,461 A | 5/1999 | Harris | 525/54.11 |
| 5,919,455 A | 7/1999 | Greenwald et al. | 424/178.1 |
| 5,932,462 A | 8/1999 | Harris et al. | 435/188 |

(Continued)

FOREIGN PATENT DOCUMENTS

| | | |
|---|---|---|
| CH | 684 164 | 7/1994 |
| EP | 0177836 | 4/1986 |

(Continued)

OTHER PUBLICATIONS

Bee et al., "Recombinant human PH2O is well tolerated at higher intravenous and subcutaneous doses in cynomolgus monkeys," EUFEPS 2008, Munich, Germany, 3 pages.

Berger et al., "Immunoglobulin replacement therapy by slow subcutaneous infusion," Ann Intern Med 93:55-56 (1980).

Berger et al., "Subcutaneous immunoglobulin therapy in primary immunodeficiencies," Clin Immuno 112:1-7 (2004).

Gardulf et al., "Safety of rapic subcutaneous gammaglobulin by rapid infusion in patients with primary antibody deficiency," Immunodeficiency 4:81-84 (1993).

(Continued)

*Primary Examiner* — Yunsoo Kim
(74) *Attorney, Agent, or Firm* — McKenna Long & Aldridge LLP; Stephanie Seidman

(57) ABSTRACT

Provided herein are stable co-formulations of immunoglobulin and hyaluronidase that are stable to storage in liquid form at room temperature for at least 6 months and at standard refrigerator temperatures for 1-2 years. Such co-formulations can be used in methods of treating IG-treatable diseases or conditions by subcutaneous administration.

29 Claims, No Drawings

(56) References Cited

U.S. PATENT DOCUMENTS

| | | | |
|---|---|---|---|
| 5,945,098 A | 8/1999 | Sarno et al. | 424/85.5 |
| 5,958,750 A | 9/1999 | Au-Young et al. | 435/201 |
| 5,985,263 A | 11/1999 | Lee et al. | 424/85.2 |
| 5,990,237 A | 11/1999 | Bentley et al. | 525/54.2 |
| 6,057,110 A | 5/2000 | Au-Young et al. | 435/6 |
| 6,069,236 A | 5/2000 | Burnouf-Radosevich et al. | 530/416 |
| 6,113,906 A | 9/2000 | Greenwald et al. | 424/194.1 |
| 6,123,938 A | 9/2000 | Stern et al. | 424/94.62 |
| 6,193,963 B1 | 2/2001 | Stern et al. | 424/94.6 |
| 6,214,966 B1 | 4/2001 | Harris | 528/322 |
| 6,258,351 B1 | 7/2001 | Harris | 424/78.3 |
| 6,340,742 B1 | 1/2002 | Burg et al. | 530/351 |
| 6,395,880 B1 | 5/2002 | Linnau et al. | 530/393 |
| 6,413,507 B1 | 7/2002 | Bentley et al. | 424/78.02 |
| 6,420,339 B1 | 7/2002 | Gegg et al. | 514/12 |
| 6,437,025 B1 | 8/2002 | Harris et al. | 523/406 |
| 6,448,369 B1 | 9/2002 | Bentley et al. | 528/425 |
| 6,461,802 B1 | 10/2002 | Van Thillo et al. | 430/336 |
| 6,495,659 B2 | 12/2002 | Bentley et al. | 528/425 |
| 6,552,170 B1 | 4/2003 | Thompson et al. | 530/351 |
| 6,737,505 B2 | 5/2004 | Bentley et al. | 528/425 |
| 6,828,401 B2 | 12/2004 | Nho et al. | 526/333 |
| 6,828,431 B1 | 12/2004 | Frudakis et al. | 536/23.1 |
| 6,858,736 B2 | 2/2005 | Chang-min ET AL | 546/290 |
| 6,875,848 B2 | 4/2005 | Ristol Debart et al. | 530/390.1 |
| 7,105,330 B2 | 9/2006 | Stern et al. | 435/200 |
| 7,148,201 B2 | 12/2006 | Stern et al. | 514/44 |
| 7,309,810 B2 | 12/2007 | Takai et al. | 800/3 |
| 7,368,108 B2 | 5/2008 | DeFrees et al. | 424/94.5 |
| 7,544,499 B2 | 6/2009 | Frost et al. | 435/200 |
| 7,767,429 B2 | 8/2010 | Bookbinder et al. | 435/201 |
| 7,781,397 B2 | 8/2010 | Stern et al. | 514/2 |
| 8,105,586 B2 | 1/2012 | Bookbinder et al. | 424/94.3 |
| 8,187,855 B2 | 5/2012 | Baker et al. | 435/201 |
| 8,202,517 B2 | 6/2012 | Bookbinder et al. | 424/94.62 |
| 8,431,124 B2 | 4/2013 | Bookbinder et al. | 424/94.62 |
| 8,431,380 B2 | 4/2013 | Bookbinder et al. | 435/201 |
| 8,450,470 B2 | 5/2013 | Bookbinder et al. | 536/23.2 |
| 8,580,252 B2 | 11/2013 | Bookbinder et al. | 424/85.2 |
| 8,765,685 B2 | 7/2014 | Bookbinder et al. | 514/20.9 |
| 8,772,246 B2 | 7/2014 | Bookbinder et al. | 435/200 |
| 2001/0021763 A1 | 9/2001 | Harris | 528/75 |
| 2001/0044526 A1 | 11/2001 | Shen | 530/409 |
| 2001/0046481 A1 | 11/2001 | Bentley et al. | 424/78.18 |
| 2002/0052430 A1 | 5/2002 | Harris et al. | 523/406 |
| 2002/0072573 A1 | 6/2002 | Bentley et al. | 525/409 |
| 2002/0156047 A1 | 10/2002 | Zhao | 514/58 |
| 2003/0114647 A1 | 6/2003 | Harris et al. | 530/402 |
| 2003/0143596 A1 | 7/2003 | Bentley et al. | 435/6 |
| 2003/0158333 A1 | 8/2003 | Roberts et al. | 525/54.11 |
| 2003/0170243 A1 | 9/2003 | Stern et al. | 424/146.1 |
| 2003/0220447 A1 | 11/2003 | Harris | 525/54.1 |
| 2004/0013637 A1 | 1/2004 | Bentley et al. | 424/78.17 |
| 2004/0096921 A1 | 5/2004 | Stern et al. | 435/7.92 |
| 2004/0142867 A1 | 7/2004 | Oi et al. | 514/12 |
| 2004/0235734 A1 | 11/2004 | Bossard et al. | 514/12 |
| 2004/0268425 A1 | 12/2004 | Bookbinder et al. | 800/18 |
| 2005/0053598 A1* | 3/2005 | Burke et al. | 424/130.1 |
| 2005/0114037 A1 | 5/2005 | Desjarlais et al. | 702/19 |
| 2005/0171328 A1 | 8/2005 | Harris | 528/322 |
| 2005/0209416 A1 | 9/2005 | Harris | 525/523 |
| 2005/0260186 A1 | 11/2005 | Bookbinder et al. | 424/94.61 |
| 2005/0287134 A1 | 12/2005 | Klein | 424/94.61 |
| 2006/0104968 A1 | 5/2006 | Bookbinder et al. | 424/94.61 |
| 2007/0134228 A1 | 6/2007 | Stern et al. | 424/94.61 |
| 2007/0148156 A1 | 6/2007 | Frost et al. | 424/94.61 |
| 2008/0171014 A1 | 7/2008 | Wu et al. | 530/387.9 |
| 2009/0123367 A1 | 5/2009 | Bookbinder et al. | 424/1.49 |
| 2009/0181013 A1 | 7/2009 | Bookbinder et al. | 424/130.1 |
| 2009/0181032 A1 | 7/2009 | Bookbinder et al. | 424/141.1 |
| 2009/0214505 A1 | 8/2009 | Bookbinder et al. | 424/94.1 |
| 2009/0253175 A1 | 10/2009 | Bookbinder et al. | 435/69.1 |
| 2009/0304665 A1 | 12/2009 | Frost et al. | 424/94.5 |
| 2009/0311237 A1 | 12/2009 | Frost | 424/94.62 |
| 2010/0003238 A1 | 1/2010 | Frost et al. | 424/94.62 |
| 2010/0074885 A1 | 3/2010 | Schiff et al. | |
| 2010/0143457 A1 | 6/2010 | Wei et al. | 424/450 |
| 2010/0172892 A1 | 7/2010 | Uvarkina et al. | 424/94.62 |
| 2010/0196423 A1 | 8/2010 | Bookbinder et al. | 424/247.1 |
| 2010/0211015 A1 | 8/2010 | Bookbinder et al. | 604/187 |
| 2010/0330071 A1 | 12/2010 | Teschner et al. | 530/412 |
| 2011/0152359 A1 | 6/2011 | Bookbinder et al. | 435/200 |
| 2011/0212074 A1 | 9/2011 | Frost et al. | 424/85.1 |
| 2011/0293598 A1 | 12/2011 | Bruckschwaiger et al. | 424/530 |
| 2011/0293638 A1 | 12/2011 | Bruckschwaiger et al. | 424/140.1 |
| 2012/0020951 A1 | 1/2012 | Shepard et al. | 424/130.1 |
| 2012/0076772 A1 | 3/2012 | Butterweck et al. | 424/133.1 |
| 2012/0076779 A1 | 3/2012 | Butterweck et al. | 424/130.1 |
| 2012/0093770 A1 | 4/2012 | Bookbinder et al. | 424/94.62 |
| 2012/0148555 A1 | 6/2012 | Bookbinder et al. | 424/94.3 |
| 2012/0171153 A1 | 7/2012 | Frost et al. | 424/78.17 |
| 2013/0022588 A1 | 1/2013 | Yang et al. | 424/94.3 |
| 2013/0251786 A1 | 9/2013 | Li et al. | 424/94.62 |
| 2013/0302275 A1 | 11/2013 | Wei et al. | 424/94.62 |
| 2013/0302400 A1 | 11/2013 | Maneval et al. | 435/195 |
| 2014/0199282 A1 | 7/2014 | Bookbinder et al. | 435/200 |

FOREIGN PATENT DOCUMENTS

| | | |
|---|---|---|
| EP | 0246579 | 5/1987 |
| EP | 0278422 | 8/1988 |
| EP | 0440483 | 8/1991 |
| EP | 0822199 | 2/1998 |
| EP | 1064951 | 6/2000 |
| JP | 54020124 | 2/1979 |
| JP | 57031623 | 2/1982 |
| JP | 57128635 | 8/1982 |
| JP | S63-192724 | 8/1988 |
| JP | H10-265407 A | 10/1998 |
| JP | 4346934 | 12/2002 |
| JP | 2004-238392 A | 8/2004 |
| JP | 2006-524507 A | 11/2006 |
| JP | 2007-511566 A | 5/2007 |
| WO | WO 94/28024 | 12/1994 |
| WO | WO 94/29334 | 12/1994 |
| WO | WO 96/07429 | 3/1996 |
| WO | WO 98/042376 | 10/1998 |
| WO | WO 00/02017 | 1/2000 |
| WO | WO 00/176640 | 10/2001 |
| WO | WO 01/87925 | 11/2001 |
| WO | WO 02/49673 | 6/2002 |
| WO | WO 2004/056312 | 7/2004 |
| WO | WO 2004/078140 | 9/2004 |
| WO | WO 2005/000360 | 1/2005 |
| WO | WO 2005/049078 | 6/2005 |
| WO | WO 2006/091871 | 8/2006 |
| WO | WO 2008/127271 | 10/2008 |
| WO | WO 2009/111066 | 9/2009 |
| WO | WO 2009/117085 | 9/2009 |
| WO | WO 2009/128917 | 10/2009 |
| WO | WO 2010/138736 | 12/2010 |
| WO | WO 2011/034604 | 3/2011 |

OTHER PUBLICATIONS

Halozyme Therapeutics, Analyst and Investor Meeting presentations "Matrix Therapeutics for Life" presentations including Lim, J., "Introduction and strategy overview, Roche program update," Gustafson, K., "Strategic deployment of cash," Wasserman, R., "HyQ treatment of primary immunodeficiency patients," Muchmore, D., "Ultrafast insulin-clinical results and ongoing trials," Cefalu, W., "Unmet needs in diabetes management," Little, R., Market overview-ultrafast insulin and SC immunoglobin and Frost, G., "PEGPH20 and HTI-501 status report," Presented 10.14.10 in New York, NY. (124 pages).

Hofer, "Human Recombinant Hyaluronidase Increases the Convection of Molecules up to 0.2 μm in Athymic Nude Mice," American Association for Laboratory Animal Science, 2006, Salt Lake City, UT. Abstract published in J. Am. Assoc. Lab. Animal Sci., 45:120, 2006, abstract P97. [2 pages].

(56) References Cited

OTHER PUBLICATIONS

Horowitz et al. "Viral safety of solvent/detergent-treated blood products," Blood Coagul. Fibrin. 5(3):S21-S28 (1994).
Kempf et al., "Virus inactivation during production of intravenous immunoglobulin," Transfusion 31(5):423-427 (1991).
Mayer, M., "Quantitative C' Fixation Analysis, Complement and Complement Fixation," in *Experimental Immunochemistry* Eds., Kabat, E. And M. Meyer, Thomas, Springfield, Il., pp. 214-216 and pp. 227-228 (1961).
McCoy et al., "Pharmacokinetics of 10% Immunoglobulin Administered Intravenously or Subcutaneously Alone of Following Recombinant Human Hyaluronidase in Subjects with PID," Retrieved from the Internet: <URL baxter.com/downloads/press_roorn/press_releases/2010/BAXTER_HyQ_PK_ESID_10_2010.PDF, (accessed Dec. 9, 2010; 1 page).
Olsson, O. and O. Lofgren, "Hyaluronidase as a factor hastening the spread and absorption of water-soluble radiopaque substances deposited intracutaneously, subcutaneously, or intramuscularly," Acta radiol. 31:250-256 (1949).
Palmer, D. And S. Whaley, "Complement Fixation Test," in *Manual of Clinical Laboratory Immunology*, Eds., Rose et al., American Society for Microbiology, Washington, D.C., pp. 57-66 (1986).
Pearlman, R. And T. Nguyen, "Analysis of protein drugs," in Peptide and Protein Drug Delivery Ed., Lee, V., Peptide and Protein Drug Delivery, 247-301, Marcel Dekker:New York, N.Y., pp. 247-301 (1991).
Roord et al., "Home treatment in patients with antibody deficiency by slow subcutaneous infusion of gammaglobulin," Lancet 1(8273):689-690 (1982).
Wang, Y. And M. Hanson, "Parenteral formulations of proteins and peptides: Stability and stabalizers," J. of Parenteral Science & Technology 42(supp):S4-S26 (1988).
International Search Report and Written Opinion, issued Aug. 31, 2009, in connection with related International Patent Application No. PCT/US2009/001670 19 pages.
International Preliminary Report on Patentability issued Jun. 8, 2010, in connection with related International Patent Application No. PCT/US2009/001670 10 pages.
Letter/Written Disclosure of the Supplemental Information Disclosure Statement for the above-references application, mailed on Jul. 29, 2012, 2 pages.
Derwent English language patent abstract for Ch 684 164 (Item AO). Inventor: Friedli et al., Publication Date: Jul, 29, 1994, Dialog File No. 351, Accession No. 6846186, 1 page.
Leesch et al., "30-day pharmacokinetic evaluation of IV versus subcutaneous administration of immunoglobulin with and without recombinant human hyaluronidase in dogs," J Allergy and Clin Immunol 123(2, Suppl. S):S10 (2009), Abstract, 1 page.
Lu, H. And E. Wimmer, "An autoimmune animal model of the Lambert-Eaton syndrome," Proc. Natl. Acad. Sci (USA) 93:1412-1417 (1996).
Melamed et al., "Recombinant human hyaluronidase facilitates dispersion of subcutaneously administered gammagard liquid and enables administration of a full monthly dose in a single site to patients with immunodeficiency diseases," J Allergy and Clin Immunol 121(2, suppl.):S83 (2008), Abstract, 1 page.
Misbah et al., "Subcutaneous immunoglobin: opportunities and outlook," J Transl Immunol 158 (Suppl. 1):51-59 (2009). Available on-line Oct. 30, 2009.
Planitzer et al., "Neutralization of different echovirus serotypes by individual lots of intravenous immunoglobulin," J Med Virol 83(2):305-310 (2011).
Skoda-Smith et al., "Subcutaneous immunoglobulin replacement therapy in the treatment of patients with primary immunodeficiency disease," Ther Clin Risk Manag 6:1-10 (2010).
Williams, R., "The effects of continuous local injection of hyaluronidase on skin and subcutaneous tissue in rats," Anat. Rec. 122:349-361 (1955).
World Health Organization (WHO) guideline: cf. D21, WHO Technical Report Series, No. 814 "Guidelines for assuring the quality of pharmaceutical and biological products prepared by recombinant DNA technology," (1991).
McCoy et al., "Pharmacokinetics of 10% immunoglobulin administered intravenously or subcutaneously alone or following recombinant human hyaluronidase in subjects with PID," XIVth Meeting of the European Society for Immunodeficienies (ESID) Istanbul, Turkey Oct. 6-10, 2010. Poster, 1 page.
Schiff et al., "Tolerability of immunoglobulin subcutaneous 10% administered SC following administration of recombinant human hyaluronidase in subjects with PID," XIVth Meeting of the European Society for Immunodeficienies (ESID) Istanbul, Turkey Oct. 6-10, 2010, Poster, 1 page.
Stein et al., "Tolerability and efficacy of recombinant human hyaluronidase (rHuPH2O)-facilitated subcutaneous infusion of immune globulin (Human), 10% (IGHy) in patients with Primary Immunodeficiency Disease (PI)," American College of Allergy, Asthma, & Immunology Meeting, Boston, MA, Nov. 5, 2011, Poster, 1 page.
Wasserman et al., "Pharmacokinetics of recombinant human hyaluronidase (rHuPH2O)-facilitated subcutaneous infusion of immune globulin (Human), 10% (IGHy) in patients with Primary Immunodeficiency Disease (PI)," American College of Allergy, Asthma, & Immunology Meeting, Boston, MA, Nov. 5, 2011, Poster, 1 page.
Halozyme Website, "Products & pipeline-PEGPH2O," [online][retrieved on Nov. 17, 2011] Retrieved from:<URL:halozyme.com/Products-And-Pipeline/Pipeline/PEGPH20/default.aspx [2 pages].
News Release, "Baxter and Halozyme announce top-line results of phase III study of HyQ in patients with primary immunodeficiency," Published on Jul. 8, 2011 [online][retrieved on Nov. 30, 2011] Retrieved from:<URL:baxter.com/downloads/press_room/press_releases/2011/07_08_11_hyq.pdf[4 pages].
News Release, "Baxter presents data from interim analyses of phase III clinical trial of HyQ at European Society for Immunodeficiencies meeting," Published on Oct. 6, 2010 [online][retrieved on Oct. 6, 2010] Retrieved from:<URL:baxter.com/press room/press releases/2010/10_06_10_hyq.html [3 pages].
News Release, "Baxter presents phase III HyQ efficacy and tolerability data at American College of Allergy, Asthma & Immunology meeting," Published on Nov. 7, 2011 [online][retrieved on 11-30-2011] Retrieved from:<URL:baxter.com/press_room/press_releases/2011/11_07_11_hyq_acaai.html [3 pages].
News Release, Halozyme Therapeutics, Inc., "First Quarter 2011 Financial Results Conference Call Transcript," Published on May 6, 2011[online][retrieved on Jul. 25, 2011] Retrieved from:<URL:phx.corporate ir.net/External.File?item=UGFyZW5OSUQ9NDI5MD-MwfENoaWxkSUQ9NDQ2Mjl4fFR5cGU9MQ==&t=1 [12 pages].
News Release, Halozyme Therapeutics, Inc., "Fourth quarter and full year 2010 conference call transcript," Published on Mar. 11, 2011[online][retrieved on Apr. 7, 2011] Retrieved from:<URL:phx.corporate-ir.net/External.File?item=UGFyZW5OSUQ9NDE5MjUyfENoaWxk-SUQ9NDMyNDcwfFR5cGU9 MQ==&t=1 [18 pages].
News Release, Halozyme Therapeutics, Inc., "Baxter presents latest clinical trial results of Gammagard Liquid administered subcutaneously," Published on Mar. 16, 2008[online][retrieved on Jun. 7, 2011] Retrieved from:<URL: rxtimes.corn/baxter-presents-latest-clinical-trial-results-ofgammagard-liquid-administered-subcutaneously/ [5 pages].
News Release, "Data Presented at AAAAI reinforce Baxter's commitment to making gammagard liquid Therapy more convenient," Published on Mar. 16, 2009 [online][retrieved on Nov. 30, 2011] Retrieved from:<URL:baxter.com/press_room/press_releases/2009/03_16_09_aaaai.html [5 pages].
News Release, Halozyme Therapeutics, Inc., "Phase III Trial begins for Gammagard Liquid plus rHuPH2O in primary immunodeficiency patients," Published on Jan. 5, 2009[online][retrieved on Jan. 6,

(56) References Cited

OTHER PUBLICATIONS

2009] Retrieved from:<URL:phx.corporate-innet/phoenix.zhtml?c=175436&p=irol-newsArticle_Print&Id=1170737&highlight= [3 pages].

Response to Written Opinion, issued Aug. 31, 2009, in connection with related International Application No. PCT/US2009/001670, 32 pages.

International Search Report and Written Opinion, issued Oct. 13, 2011, in connection with corresponding International Patent Application No. PCT/US2010/002545, 17 pages.

International Preliminary Report on Patentability, issued Mar. 2, 2012, in connection with corresponding International Application No. PCT/US2010/002545, 25 pages.

Weber et al., "Intravenous immunoglobulin gammagard liquid contains anti-RAGE IgG and sLRP," Presented at the 19th Meeting of the European Neurological Society, Jun. 23, 2009, Abstract, 1 page.

News Release: Baxter International Inc., "Baxter and Halozyme Provide Update on HyQ Biologics License Application," Published on Apr. 16, 2012 [online][retrieved on Jul. 27, 2012] Retrieved from: <URL:finance.yahoo.com/news/baxter-halozyme-hyq-biologics-license-120000974.html [2 pages].

News Release: Baxter International Inc., "Baxter Announces FDA Approval for Gammagard liquid as a Treatment for Multifocal Motor Neuropathy," Published on Jun. 25, 2012 [online] [retrieved on Jul. 27, 2012] Retrieved from: <URL: finance.yahoo.com/news/baxter-announces-fda-approvalgammagard-130000672.html [3 pages].

News Release: Baxter International Inc., "Baxter Gets FDA Nod for Gammagard," Published on Jun. 27, 2012 [online][retrieved on Jul. 27, 2012] Retrieved from:<URL: finance.yahoo.com/news/baxter-getsfda-nod-gammagard-181520622.html [3 pages].

News Release: Baxter International Inc., "Baxter Presents Phase III HyQ Efficacy and Tolerability Data at American College of Allergy, Asthma & Immunology Meeting," Published 2012 [online] [retrieved on Jul. 27, 2012] Retrieved from: <URL:fiercebiotech.com/press-releases/baxter-presentsphase-iii-hyq-efficacy-and-tolerability-data-american-colle [3 pages].

News Release, Baxter International Inc., "Baxter shares fall on news of FDA delay: Regulator requests more long-term data before approving HyQ immune system treatment," Chicago Tribune. Published Apr. 16, 2012 [online][retrieved on Jul. 27, 2012] Retrieved from: <URL: articles.chicagotribune.com/2012-04-16/business/ct-biz-0417-baxter-20120416_1_baxter-sharesgammagard-baxter-stock [2 pages].

Melamed et al., "Long-term safety and pharmacokinetics of facilitated subcutaneous infusion of immuneglobulin (HUMAN) 10% and recombinant human hyaluronidase (IGHy) in a phase III extension study in patients with primary immunodeficiency (PI) " Presented May 18, 2012 at the Clinical Immunolgy Society Annual Meeting: Primary Immune Deficiency Disease North American Conference, Chicago, IL. Abstract, 1 page.

Stein et al., "Pharmacokinetic (PK) of human immuneglobulin 10% (IgG) administered intravenously (IGIV), subcutaneously (IGSC) or facilitated subcutaneously with recombinant human hyaluronidase hyaluronidase (IGHy) in a subset of patients with primary immunodeficiency (PI) ," Presented May 18, 2012 at the Clinical Immunolgy Society Annual Meeting: Primary Immune Deficiency Disease North American Conference, Chicago, IL. Abstract, 2 pages.

Stein et al., "Tolerability and efficacy of facilitated —subcutaneous infusion of immuneglobulin (HUMAN) 10% and recombinant human hyaluronidase (IGHy) in patients with primary immunodeficiency (PI)," Presented May 18, 2012 at the Clinical Immunolgy Society Annual Meeting: Primary Immune Deficiency Disease North American Conference, Chicago, IL. Abstract, 1 page.

Teschner et al., "Preclinical Characterization of a New Liquid "Immune Globulin Intravenous (Human), 10% Triple Virally Reduced Solution"(IGIV, 10%TVR)," The Journal of Allergy and Clinical Immunology. 113(2):S45 (2004). Abstract 79, 1 page.

Wasserman et al., Pharmacokinetic (PK) of human immuneglobulin 10% (IgG) administered intravenously (IGIV), subcutaneously (IGSC) or facilitated subcutaneously with recombinant human hyaluronidase hyaluronidase (IGHy) in a subset of patients with primary immunodeficiency (PI) Presented May 18, 2012 at the Clinical Immunology Society Annual Meeting: Primary Immune Deficiency Disease North American Conference May 17-20, 2012, Chicago, IL. Abstract, 1 page.

Wasserman et al., "Tolerability and efficacy of facilitated —subcutaneous infusion of immuneglobulin (Human) 10% and recombinant human hyaluronidase (IGHy) in patients with primary immunodeficiency (PI)," Presented May 18, 2012 at the Clinical Immunolgy Society Annual Meeting: Primary Immune Deficiency Disease North American Conference, Chicago, IL. Abstract, 2 pages.

Adams et al., "The c-myc oncogene driven by immunoglobulin enhancers induces lymphoid malignancy in transgenic mice," Nature 318:533-538 (1985).

Afify et al., "Purification and characterization of human serum hyaluronidases," Arch. Biochem. Biophys. 305:434-441 (1993).

Alexander et al., "Expression of the c-myc oncogene under control of an immunoglobulin enhancer in E mu-myc transgenic mice," Mol. Cell Biol. 7:1436-1444 (1987).

Allen et al., "Recombinant Human Hyaluronidase-Enabled Subcutaneous Pediatric Rehydration," Pediatrics 124(5):e858-e867, Retrieved from the Internet: <URL: pediatrics.aappublications.org/cgi/content/abstract/124/5/e858 (2009). Altschul, S., "Basic local alignment search tool," J Molec Biol 215(3):403-410 (1990).

Altschul, S., "Basic local alignment search tool," J Molec Biol 215(3):403-410 (1990).

Ansel, H., Introduction to Pharmaceutical Dosage Forms, Fourth Edition, Philadelphia: Lea & Febiger, p. 126 (1985).

Arming et al., "In vitro mutagenesis of PH-20 hyaluronidase from human sperm," Eur J Biochem 247(3):810-814 (1997).

Barandun et al., "Intravenous administration of human gammaglobulin," Vox Sang., 7:157-174 (1962).

Baxter Health Care Corporation (R. Schiff, MD), "Gammagard Liquid and rHuPH2O in PID," Retrieved from the Internet: <URL:clinicaltrials.govict2/show/NCT00814320, last updated Oct. 27, 2009, 5 pages.

Baxter Health Care Corporation, Gammagard Liquid (Immune Globulin Intravenous (Human) 10%] product literature, Retrieved from the Internet: <URL: baxter.com/products/biopharmaceuticals/downloads/gamliquid_PI.pdf, published Apr. 2005, 4 pages.

Baxter Healthcare Corporation, "Study to determine the dose of recombinant human hyaluronidase needed to infuse a dose of IGIV subcutaneously," Retrieved from the Internet: <URL: clinicaltrials.govict2/show/NCT00782106 [accessed on May 13, 2009] [3 pages].

Bee et al., "Effects of Recombinant Human Hyaluronidase (rHuPH2O) on Subcutaneous Administration of 10% and 20% IgG in Yucatan Mini Pigs," AAAAI Feb. 26-Mar. 2, 2010, New Orleans, 1 page.

Bee et al., "Effects of rHuPH2O on SC Administration of 10% and 20% IgG in Yucatan Mini Pigs," AAAAI Feb. 26-Mar. 2, 2010, New Orleans, 1 page.

Bee et al., "Recombinant human PH2O is well tolerated at higher intravenous and subcutaneous doses in cynomolgus monkeys," EUFEPS 2008, Munich, Germany, 1 page.

Benhar et al., "Pseudomonas exotoxin a mutants. Replacement of surface-exposed residues in domain III with cysteine residues that can be modified with polyethylene glycol in a site-specific manner," J. Biol. Chem. 269:13398-14404 (1994).

Berger, M., "Principles of and advances in immunoglobulin replacement therapy for primary immunodeficiency," Immunol. Allergy Clin. North Am. 28(2):413-437 (2008).

Bemoist, C. And P. Chambon, "In vivo sequence requirements of the SV40 early promotor region," Nature 290:304-310 (1981).

Bianchi et al., "Synthetic depsipeptide substrates for the assay of human hepatitis C virus protease," Anal. Biochem. 237:239-244 (1996).

BioWorld Today, "Clinic roundup," BioWorld Today 20(2):5 (2009).

Björkander et al.,"Prospective open-label study of pharmacokinetics, efficacy and safety of a new 10% liquid intravenous immunoglobulin in patients with hypo- or agammaglobulinemia," Vox Sanguinis 90(4):286-293 (2006).

(56) References Cited

OTHER PUBLICATIONS

Bookbinder et al., "A recombinant human enzyme for enhanced interstitial transport of therapeutics," J Control Release. 114(2):230-241 (2006) Epub 2006 Jun 7.
Bookbinder et al., "Biochemical Characterization of Recombinant Human PH2O (SPAM1) Hyaluronidase," Hyaluronan (ISHAS) 2007, Charleston, SC, 2 pages.
Bookbinder et al., "Enhancing Drug Transport Through Temporary Matrix Depolymerization," Keystone Symposia 2005, 13 pages.
Bookbinder et al., "EnhanzeTM Technology for Antibody Dispersion," Strategic Research Institute Antibody World Summit, 2005, Jersey City, NJ, 41 pages.
Bookbinder et al., "Evaluation of the compatibility and pharmacokinetics of co-formulated biologics with recombinant human hyaluronidase: Dose Response," American Association of Pharmaceutical Scientists Conference, Nov. 2006, 3 pp.
Bordier, C., "Phase separation of integral membrane proteins in Triton X-114 solution," J. Biol. Chem. 256:1604-1607 (1981).
Bouffard et al., "An in vitro assay for hepatitis C virus NS3 serine proteinase," Virology 209:52-59 (1995).
Brinster et al., "Regulation of metallothionein--thymidine kinase fusion plasmids injected into mouse eggs," Nature 296:39-42 (1982).
Brumeanu et al., "Derivatization with monomethoxypolyethylene glycol of Igs expressing viral epitopes obviates adjuvant requirements," J Immunol. 154:3088-3095 (1995).
Buckley, R. And R. Schiff, "The use of intravenous immune globulin in immunodeficiency diseases," n. Engl J Med. 325(2):110-117 (1991).
Byerley et al., "'Cutting out the bull'. Recombinant human hyaluronidase: Moving to an animal-free system," Association of Clinical Embryologists, 2006, Dublin, Ireland. Abstract published in Human Fertility 9(2):110 (2006).
Caliceti, P. And F. Veronese, "Pharmacokinetic and biodistribution properties of poly(ethylene glycol)-protein conjugates,"Adv. Drug Deliv. Rev. 55(10):1261-1277 (2003).
Carrillo, H. And D. Lipman, "The multiple-sequence alignment problem in biology," Siam J Applied Math 48(5):1073-1082 (1988).
Chapel et al., "Randomised trial of intravenous immunoglobulin as prophylaxis against infection in plateau-phase multiple myeloma. The UK Group for Immunoglobulin Replacement Therapy in Multiple Myeloma," Lancet 343:1059-1063 (1994).
Chapman et al., "Therapeutic antibody fragments with prolonged in vivo half-lives," Nature Biotech. 17:780-783 (1999).
Cheng et al., "PEGylated adenoviruses for gene delivery to the intestinal epithelium by the oral route," Pharm. Res. 20(9):1444-1451 (2003).
Cherr et al., "The dual functions of Gpi-anchored Ph-20: hyaluronidase and intracellular signaling," Matrix Biol., 20:515-525, 2001.
Cherr et al., "The PH-20 protein in cynomolgus macaque spermatozoa: identification of two different forms exhibiting hyaluronidase activity," Dev. Biol. 175:142-153 (1996).
Cho et al., "Construction of hepatitis C-SIN virus recombinants with replicative dependency on hepatitis C virus serine protease activity," J. Virol. Meth. 65:201-207 (1997).
Christadoss et al., "Animal models of myasthenia gravis," Clin Immunol. 94:75-87 (2000).
Church et al., "Efficacy, safety and tolerability of a new 10% liquid intravenous immune globulin [IGIV 10%] in patients with primary immunodeficiency," US-PID-IGIV 10% -Study Group 10. J Clin Immunol. 26(4):388-395 (2006).
Cohn et al., "Preparation and properties of serum and plasma proteins; a system for the separation into fractions of the protein and lipoprotein components of biological tissues and fluids," J. Am. Chem. Soc. 68:459-467 (1946).
Csoka et al., "Hyaluronidases in tissue invasion," Invasion Metastasis 17:297-311 (1997).
Csoka et al., "Purification and microsequencing of hyaluronidase isozymes from human urine," FEBS Lett., 417(3):307-310 (1997).

Csoka et al., "The six hyaluronidase-like genes in the human and mouse genomes," Matrix Biol. 20:499-508 (2001).
Czitrom et al., "The function of antigen-presenting cells in mice with severe combined immunodeficiency," J Immunol 134:2276-2280 (1985).
Dalakas, M., "The use of intravenous immunoglobulin in the treatment of autoimmune neuromuscular diseases: evidence-based indications and safety profile," Pharmacol Ther 102(3):177-193 (2004).
Dalakas et al., "A controlled trial of high-dose intravenous immune globulin infusions as treatment for dermatomyositis," N Engl J Med 329(27):1993-2000 (1993).
Dalakas et al., "High-dose intravenous immune globulin for stiff-person syndrome," N Engl J Med 345(26):1870-1876 (2001).
Dalakas et al., "A controlled study of intravenous immunoglobulin combined with prednisone in the treatment of IBM," Neurology 56(3):323-327 (2001).
Danilkovitch-Miagkova, et al., "Hyaluronidase 2 negatively regulates RON receptor tyrosine kinase and mediates transformation of epithelial cells by jaagsiekte sheep retrovirus," Proc Natl Acad Sci USA. 100(8):4580-4585 (2003).
Deboer et al., "The tac promoter: a functional hybrid derived from the trp and lac promoters," Proc. Natl. Acad. Sci. USA 80:21-25 (1983).
Delpech et al., "Enzyme-linked hyaluronectin: a unique reagent for hyaluronan assay and tissue location and for hyaluronidase activity detection," Anal. Biochem. 229:35-41 (1995).
Derwent patent abstract citing JP 4346934 published Dec. 2, 2002, for: "Liq. Compsn. For intravenous injection for infectious disease treatment-comprises chemically unmodified mol. Type gamma globulin with low conductivity and contains no sorbitol," Inventor: Kamimura et al. Dialog File No. 351. Accession No. 6231217 [2 pages].
Derwent patent abstract citing JP 54020124 published Feb. 15, 1979, for: "Intraveneously injectable gamma-globulin compsn. Prodn.-by addn. Of amino acids, sugars and neutral salts as dissociation agents," Inventor: Funakoshi et al. Dialog File No. 351. Accession No. 1699807 [2 pages].
Derwent patent abstract citing Jp 57128635 published Aug. 10, 1982, for: "Gamma-globulin prepn. For intravenous injection-contains sodium chloride and L-arginine or L-lysine," Inventor: Matsuo et al. Dialog File No. 351. Accession No. 2496703 [2 pages].
Devereux, J., et al, "A comprehensive set of sequence analysis programs for the VAX," Nucleic Acids Research 12:387-395 (1984).
Dodel et al., "Intravenous immunoglobulins containing antibodies against beta-amyloid for the treatment of Alzheimer's disease," J Neurol Neurosurg. Psychiatry 75:1472-1474 (2004).
D'Souza et al., "In vitro cleavage of hepatitis C virus polyprotein substrates by purified recombinant NS3 protease," J. Gen. Virol. 76:1729-1736 (1995).
Ellmeier et al., "Severe B cell deficiency in mice lacking the tec kinase family members Tec and Btk," J Exp Med. 192:1611-1624 (2000).
Federal Register Sep. 23, 1970 (35 FR 14800); Wydase NDA 6-343, (40 pages).
Felix et al., "Pegylated peptides. IV. Enhanced biological activity of site-directed pegylated GRF analogs," Int. J. Peptide Res. 46:253-264 (1995).
Fernandes, P. And J. Lundblad, "preparation of a stable intavenous gamma-globulin: process design and scale-up," Vox Sang 39:101-112 (1980).
Filocamo et al., "Chimeric Sindbis viruses dependent on the NS3 protease of hepatitis C virus," J.Virology 71(2):1417-1427 (1997).
Form 10-Q for Halozyme Therapeutics dated May 8, 2009, retrieved from the Internet:<URL: biz.yahoo.com/e/090508/halo10-q.html>. [retrieved on Nov. 25, 2009] [6 pages].
Frost et al., "Puntuated Equilibrium: The Evolution of Recombinant Human Hyaluronidase,"Ophthalmic Anesthesia Society, 2006, Chicago, IL, 36 pages.
Frost et al., "Purification, cloning, and expression of human plasma hyaluronidase," Biochem. Biophys. Res. Commun. 236:10-15 (1997).
Frost et al., "Subcutaneous Strategies for Monoclonal Antibody Delivery," Drug Delivery 2007: Where Science and Business Meet, 2007, San Diego, CA, 1 page.

(56) References Cited

OTHER PUBLICATIONS

Frost G., "Subcutaneous Strategies for Monoclonal Antibody Delivery." IBC Life Sciences Antibodies and Beyond Antibodies: Optimizing Antibody Leads and Exploring Next Generation Scaffolds for Protein Therapeutics, Coronado CA, 2006 [20 pages].
Frost, G. And R. Stem, "A microtiter-based assay for hyaluronidase activity not requiring specialized reagents," Anal. Biochem. 251:263-269 (1997).
Frost, G., "Recombinant human hyaluronidase (rHuPH2O): an enabling platform for subcutaneous drug and fluid administration," Expert Opin. Drug. Deliv. 4:427-440 (2007).
Gardner et al., "The complete nucleotide sequence of an infectious clone of cauliflower mosaic virus by M13mp7 shotgun sequencing," Nucleic Acids Res. 9:2871-2888 (1981).
Gardulf et al., "Subcutaneous immunoglobulin replacement in patients with primary antibody deficiencies:safety and costs" Lancet 345:365-369 (1995).
Gardulf et al., "Home treatment of hypogammaglobulinaemia with subcutaneous gammaglobulin by rapid infusion," Lancet 338:162-166 (1991).
Gardulf et al., "Lifelong treatment with gammaglobulin for primary antibody deficiencies: the patients' experiences of subcutaneous self-infusions and home therapy," J Adv. Nurs. 21:917-927 (1995).
Gardulf et al., "Rapid subcutaneous IgG replacement therapy is effective and safe in children and adults with primary immunodeficiencies--a prospective, multi-national study," J Clin. Immunol. 26(2):177-185 (2006).
Gardulf et al., "The life situations of patients with primary antibody deficiency untreated or treated with subcutaneous gammaglobulin infusions," Clin. Exp. Immunol. 92:200-204 (1993).
Gardulf, a. And U. Nicolay, "Replacement IgG therapy and self-therapy at home improve the health-related quality of life in patients with primary antibody deficiencies," Curr. Opin. Allergy Clin. Immunol. 6:434-442 (2006).
Gellene, D., "San Diego's Halozyme Injects New Life into Old Drugs" Feb. 28, 2010, Retrieved from the Internet: <URL:signonsandiego.com/news/2010/feb/28/ww-wxconomycom60025/, on 4/26/10 [3 pages].
Gilbert, W. And L. Villa-Komaroff, "Useful Proteins from Recombinant Bacteria," Scientific American 242(4):74-94 (1980).
Godeau et al., "Intravenous immunoglobulin for adults with autoimmune thrombocytopenic purpura: results of a randomized trial comparing 0.5 and 1 g/kg b.w.," Br J Haematol 107(4):716719 (1999).
Godeau et al., "Treatment of adult chronic autoimmune thrombocytopenic purpura with repeated high-dose intravenous immunoglobulin," Blood 82(5):1415-1421 (1993).
Gribskov et al., "Sigma factors from *E. coli, B. subtilis,* phage SP01, and phage T4 are homologous proteins," Nucl. Acids Res. 14:6745-6763 (1986).
Griffiths et al., "Crossover study of immunoglobulin replacement therapy in patients with low-grade B-cell tumors," Blood 73:366-368 (1989).
Grosschedl et al., "Introduction of a mu immunoglobulin gene into the mouse germ line: specific expression in lymphoid cells and synthesis of functional antibody," Cell 38:647-658 (1984).
Grunebaum et al., "Novel aspects of hypogammaglobulinemic states: subcutaneous immunoglobulin treatment." Isr. Med. Assoc J 4:288-289 (2002).
Guiotto et al., "An improved procedure for the synthesis of branched polyethylene glycols (PEGs) with the reporter dipeptide Met-betaAla for protein conjugation," Bioorg. Med. Chem. Lett. 12:177-180 (2002).
Guo et al., "Protein tolerance to random amino acid change," Proc. Nat'l. Acad. Sci. USA 101:9205-9210 (2004).
Gustafson et al., "Rapid subcutaneous immunoglobulin administration every second week results in high and stable serum immunoglobulin G levels in patients with primary antibody deficiencies," Immunol. 152(2):274-279 (2008).

Hakim et al., "Generation of a novel poliovirus with a requirement of hepatitis C virus protease NS3 activity," Virology 226:318-326 (1996).
Haller et al., "Escaping the Interstitial Matrix With Enzyme-Mediated Drug Delivery," Drug Delivery Technology 5(5):1-6 (2005).
Haller et al., "Recombinant Human Hyaluronidase for the Interstitial Transport of Therapeutics," American Association of Pharmaceutical Scientists Conference, Jun. 2006, San Antonio, TX, 2 pages.
Haller et al., "Recombinant Human Hyaluronidase for the Interstitial Transport of Therapeutics," Controlled Release Society Conference, Vienna, Austria, 2006, 2 pages.
Haller et al., "Revolutionizing Drug Dispersion with Enhanze Technology," Biotechnology Industry Organization (Bio) Annual Meeting, 2005, Philadelphia, PA,. Jun. 19-22, 4 pages.
Haller et al., "Revolutionizing Drug Dispersion with Enhanze Technology," American Association of Pharmaceutical Scientists Annual Meeting, Nov 6-10, 2005, Nashville, TN, 1 page.
Haller et al., "The Effects of Recombinant Human Hyaluronidase on Drug Dispersion," American Association of Pharmaceutical Scientists Annual Meeting, Nashville, TN, abstract in AAPS Journal 7(S2) May 5, 2005; 3 pages.
Haller, "Enhanze Technology —An Enzymatic Drug Delivery System (DDS)," Japanese Export Trade Organization, Nov. 2005, Santa Clara, CA, 2 pages.
Haller, "Halozyme's Enhanze Technology for the Enhanced Dispersion of Co-Injected Pharmaceuticals," Japanese Export Trade Organization, Sep. 2004, Chicago, IL, 2 pages.
Haller, M., "Converting intravenous dosing to subcutaneous dosing with recombinant human hyaluronidase," Pharmaceut Tech. Newsletter, Oct. 2007, 14 pgs.
Haller, "Enzyme-facilitated Parenteral Drug Transport." Strategic Research Institute's 10th Anniversary Drug Delivery Technology and Deal-making Summit, 2005 New Brunswick, NJ [24 pages].
Haller, M., "Focus on Enhanced and Innovative Recombinant Human Enzymes," Japanese Export Trade Organization, Sep. 2004, Chicago, IL, 16 pages.
Halozyme Therapeutics, "Halozyme Therapeutic, Inc. Prospectus Supplement," Jun. 23, 2009 [84 pages].
Halozyme Therapeutics, "Securities and Exchange Comission Form 10Q," Nov. 6, 2009 [44 pages].
Halozyme Therapeutics, "Securities and Exchange Comission Form 10Q," Aug. 7, 2009 [44 pages].
Halozyme Therapeutics, "Securities and Exchange Comission Form 10K," Mar. 13, 2009 [121 pages].
Halozyme Therapeutics, "Securities and Exchange Comission Form 10K," Mar. 12, 2010 [121 pages].
Halozyme Therapeutics, Analyst and Investor Meeting presentations including by Lim, J., "Introduction and strategic review," Little, R., "Leveraging the technology across multiple partners," Frost, G., "Discovery and early development pipeline update," and D. Muchmore, "Ultrafast insulin-PH2O program-where we are going," Presented Oct. 15, 2009 in New York. (88 pages).
Hamamoto et al., "A novel method for removal of human immunodeficiency virus: filtration with polymeric membranes," Vox Sang. 56:230-236 (1989).
Hamatake et al., "Establishment of an in vitro assay to characterize hepatitis C virus NS3-4A protease trans-processing activity ," Intervirology 39:249-258 (1996).
Hammer et al., "Diversity of alpha-fetoprotein gene expression in mice is generated by a combination of separate enhancer elements," Science 235:53-58 (1987).
Hanahan, D., "Heritable formation of pancreatic beta-cell tumours in transgenic mice expressing recombinant insulin/simian virus 40 oncogenes," Nature (3)15:115-122 (1985).
Hansen, R. And J. Balthasar, "Effects of intravenous immunoglobulin on platelet count and antiplatelet antibody disposition in a rat model of immune thrombocytopenia," Blood 100:20872093 (2002).
Harris, J. And R. Chess, "Effect of peglaytion on pharmaceuticals," Nature Reviews 2:214-221 (2003).
Herrera-Estrella et al., "Expression of chimaeric genes transferred into plant cells using a ti-plasmid-derived vector,"Nature 303:209-213 (1984).

(56) References Cited

OTHER PUBLICATIONS

Herrera-Estrella et al., "Light-inducible and chloroplast-associated expression of a chimaeric gene introduced into *Nicotiana tabacum* using a Ti plasmid vetor," Nature 310(5973):115-120 (1984).

Hiemstra et al., "Comparison of antibody activity against various microorganisms in intravenous immunoglobulin preparations determined by Elisa and opsonic assay," J Lab Clin Med 123:241246 (1994).

Hofer, "Human Recombinant Hyaluronidase Increases the Convection of Molecules up to 0.2 μm in Athymic Nude Mice," American Association for Laboratory Animal Science, 2006, Salt Lake City, UT. Abstract published in J. Am. Assoc. Lab. Animal Sci., 45:120, 2006, abstract P97.

Ito et al., "Cultivation of hepatitis C virus in primary hepatocyte culture from patients with chronic hepatitis C results in release of high titre infectious virus," J. Gen. Virol. 77:1043-1054 (1996).

Iupac-Iub Commission on Biochemical Nomenclature, "Abbreviated nomenclature of synthetic poypeptides-polymerized amino acids-revised recommendations," Biochemistry 11:1726-1731 (1972).

Iupac-Iub Commission on Biochemical Nomenclature, "A One-Letter Notation for Amino Acid Sequences: Tentative Rules," J. Biol. Chem. 243:3557-3559 (1968).

Jay et al., "Construction of a general vector for efficient expression of mammalian proteins in bacteria: use of a synthetic ribosome binding site," Proc. Natl. Acad. Sci. USA 78(9):5543-5548 (1981).

Jefferies 2010 Global life science conference Jun. 8-11, 2010 http://www.wsw.com/webcast/jeff46/hzym/ (audio; transcript available) (insulin, gammaguard, hydration, pegph20) 7 pages.

Jefferies Investor Presentation, "Matrix Therapies for Life," New York, NY, Jun. 17, 2009 [30 pages].

Jones, a., "Analysis of polypeptides and proteins," Adv. Drug Delivery Rev. 10: 29-90 (1993).

Keller et al., "Pharmacokinetic, Pharmacodynamic and Toxicologic Effects of a Recombinant Human Hyaluronidase (rHuPH2O) in Rodent and Non-Human Primate models," Hyaluronan (ISHAS) 2007, Charleston, SC, 2 pages.

Kelsey et al., "Species- and tissue-specific expression of human alpha 1-antitrypsin in transgenic mice," Genes and Devel. 1:161-171 (1987).

Kim et al., "An autoimmune animal model of the Lambert-Eaton syndrome," Annals NY Acad Sci 841:670-676 (1998).

Koblet et al., "Turnover of standard-gammaglobulin, pH-4-Gammaglobulin and pepsin desaggregated Gammaglobulin and clinical implications," Vox Sang., 13(1):93-102 (1967).

Kolarich et al., "Biochemical, molecular characterization, and glycoproteomic analyses of alpha(1)proteinase inhibitor products used for replacement therapy," Transfusion, 46(11):1959-1977 (2006).

Kollias et al., "Regulated expression of human a gamma-, beta-, and hybrid gamma beta-globin genes in transgenic mice: manipulation of the developmental expression patterns," Cell 46:89-94 (1986).

Kreil et al., "West Nile virus and the safety of plasma derivatives: verification of high safety margins, and the validity of predictions based on model virus data,"Transfusion 43(8):1023-1038 (2003).

Krumlauf et al., Developmental regulation of alpha-fetoprotein genes in transgenic mice, Mol. Cell. Biol. 5:1639-1648 (1985).

Kumar et al., "The role of proline'In the prevention of aggregation during protein folding in vitro," Biochem. Mol. Biol. Int. 46(3):509-517 (1998).

Lalancette et al, "Characterization of an 80-kilodalton bull sperm protein identified as Ph-20," Biol Reprod. 65(2):628-636 (2001).

Lathrop et al., "cDNA cloning reveals the molecular structure of a sperm surface protein, Ph-20, involved in sperm-egg adhesion and the wide distribution of its gene among mammals," J Cell Biol. 111(6 Pt 2):2939-2949 (1990).

Leder et al., "Consequences of widespread deregulation of the c-myc gene in transgenic mice: multiple neoplasms and normal development," Cell 45:485-495 (1986).

Lee et al "Subcutaneous immunoglobulin administration using recombinant human hyaluronidase: A novel approach for the treatment of peripheral neuropathies in children" abstract for the xIth world congress of ICNC Cairo May 2-7, 2010. Retrieved from the Internet: <URL icnc2010.org/index.php?option=com_content&view=article&id=163&Itemid=9.

Leesch et al., "30-Day Pharmacokientic Evaluation of IV versus Subcutaneous Administration of Immunoglobulin with and without Recombinant Human Hyaluronidase in Dogs" Journal of Allergy and Clinical Immunology col. 123, No. 2, Suppl. S, Feb. 2009, p. s10 and 65th annual meeting of the american academy of allergy asthma and immunology; washington DC, Mar. 13-17, 2009.

Leibl et al. "Efficacy and Safety of a New Intravenous Immunoglobulin in Adult Subjects with Chronic Idiopathic Thrombocytopenic Purpura," Blood (Ash Annual Meeting Abstracts) 106:Abstract 3984, 2 pp. (2005).

Leibl et al., "Multiple infusions of human intravenous immunoglobulin in chimpanzees do not lead to immune elimination," Clin. Exp. Immunol. 81:454-458 (1990).

Lim et al "Matrix Therapies for life" 28th Annual JP Morgan Healthcare Conference San Francisco Jan. 13, 2010, 42 pages.

Lin et al., "A hyaluronidase activity of the sperm plasma membrane protein Ph-20 enables sperm to penetrate the cumulus cell layer surrounding the egg," J Cell Biol. 125(5):1157-1163 (1994).

Lin et al., "Molecular cloning of the human and monkey sperm surface protein PH-20," Proc. Natl. Acad. Sci. USA 90:10071-10075 (1993).

Louie et al., "Inactivation of Hepatitis C Virus in Low pH Intravenous Immunoglobulin," Biologicals 22:13-19 (1994).

Lu, H. And E. Wirnmer., "Poliovirus chimeras replicating under the translational control of genetic elements of hepatitis C virus reveal unusual properties of the internal ribosomal entry site of hepatitis C virus," Proc. Natl. Acad. Sci. Usa 93:1412-1417 (1996).

Lu, Y. And a. Felix, "Pegylated peptides I: Solid-phase synthesis of n. alpha-pegylated peptides using Fmoc strategy," Peptide Res 6:140-146 (1993).

Lu, Y. and A. Felix, "Pegylated peptides. II. Solid-phase synthesis of amino-, carboxy- and side-chain pegylated peptides," Int. J. Peptide Protein Res. 43:127-138 (1994).

Macdonald, R., "Expression of the pancreatic elastase I gene in transgenic mice," Hepatology 7:42S-51S (1987).•.

Magram et al., "Developmental regulation of a cloned adult beta-globin gene in transgenic mice," Nature 315:338-340 (1985).

Marcus, D., "A study of the mechanism of the anticomplementary activity of gamma-globulin," J. Immunol. 84:273-284 (1960).

Mason et al., "The hypogonadal mouse: reproductive functions restored by gene therapy," Science 234:1372-1378 (1986). •.

Mehvar, R., "Modulation of the pharmacokinetics and pharmacodynamics of proteins by polyethylene glycol conjugation," J. Pharm. Pharmaceut. Sci. 3(1):125-136 (2000).

Melamed et al., "Recombinant Human Hyaluronidase Facilitates Dispersion of Subcutaneously Administered Gammagard Liquid and Enables Administration of a Full Monthly Dose in a Single Site to Patients with Immunodeficiency Diseases," J Allergy Clin Immunol, vol. 121 No. 2, Supp1.1, Feb. 2008 (2008-02), p. S83 [1 page].

Melamed et al., "Recombinant human hyaluronidase facilitates dispersion of subcutaneously administered gammagard liquid and enables administration of a full monthly dose in a single site to patients with immunodeficiency diseases," Am Acad Allergy Asthma Immunol Poster 2008 Philadelphia, PA, and Abstract #3204, 6 pages (2008).

Mizutani et al., Characterization of hepatitis C virus replication in cloned cells obtained from a human T-cell leukemia virus type 1-infected cell line, Mt-2, J.Virol. 70:7219-7223 (1996).

Mizutani et al., "Inhibition of hepatitis C virus replication by antisense oligonucleotide in culture cells," Biochem. Biophys. Res. Commun. 212:906-911 (1995).

Mizutani et al., "Long-term human T-cell culture system supporting hepatitis C virus replication," Biochem. Biophys. Res. Commun. 227:822-826 (1996).

Modena et al., "Hyaluronidase-injectable microparticles intended for the treatment of extravasation," J. Microencapsulation 15(1):85-92 (1998).

(56) References Cited

OTHER PUBLICATIONS

Molineux, G., "Pegylation: engineering improved biopharmaceuticals for oncology," Pharmacotherapy 23 (8 Pt 2):3S-8S (2003).
Monfardini et al, "A branched monomethoxypoly(ethylene glycol) for protein modification," Bioconjugate Chem. 6:62-69 (1995).
Needleman, S. And C. Wunsch "A general method applicable to the search for similarities in the amino acid sequence of two proteins," J Mol Biol. 48:443-453 (1970).
News Release, "Baxter Presents Data from Interim Analyses of Phase III Clinical Trial of HyQ at European Society for Immunodeficiencies Meeting" Oct. 6, 2010, Retrieved from the Internet: <URL:finance.yahoo.com/news/Baxter-Presents-Data-from-bw-3233016796.html?x=0 [retrieved on Oct. 6, 2010]. 5 pages.
News Release, "Halozyme Therapeutics Inc., Second Quarter 2010 Financial Results Conference Call Transcript" Aug. 6, 2010, [retrieved on Sep. 3, 2010] 16 pages.
News Release, "Halozyme Therapeutics Reports Fourth Quarter and Year End 2008 Financial Results," Mar. 13, 2009, Retrieved from the Internet: <URL:sec.gov/Archives/edgar/data/1159036/000129993309001189/exhibitl.htm [retrieved on Mar. 30, 2010] [5 pages].
News Release, "KIOVIG, Baxter's New IVIG Product Received Unanimous Positive Opinion in Europe as Replacement Therapy for Immunodeficiencies and for Immunomodulation in Immune-Mediated Diseases" Nov. 22, 2005, Retrieved from the Internet: <URL:baxter.com/press room/press releases/2005/11-23-05-Iciovig.html [retrieved Oct. 20, 2010] 4 pages.
News Release, Halozyme Therapeutics Inc. Q3 2008 Earnings Call Transcript retrieved from the Internet: <URL:seelcingalpha.com/article/106797-halozyme-therapeutics-inc-q3-2008-earningscall-transcript?page=-1>, [accessed on Nov. 6, 2009] [9 pages].
News Release, Halozyme Therapeutics Inc. Q3 2009 Earnings Call Transcript retrieved from the Internet:<URL: seeldngalpha.com/article/171883-halozyme-therapeutics-inc-q3-2009-earningscall-transcript?page=-1>, [accessed on Nov. 6, 2009] [11 pages].
News Release, Halozyme Therapeutics Inc. Q4 2007 Earnings Call Transcript retrieved from the Internet:<URL: seelcingalpha.com/article/68609-halozyme-therapeutics-q4-2007-earnings-calltranscript>, [accessed on Jun. 24, 2009] [12 pages].
News Release, Halozyme Therapeutics Inc., "First Quarter 2010 Financial Results Conference Call" May 7, 2010. 4 pages.
News Release, Halozyme Therapeutics Inc., "Halozyme Therapeutics and Baxter Healthcare Corporation Sign Exclusive Sales and Marketing Agreement for Halozyme's Investigational Therapeutic, Enhanze SC," Aug. 16, 2004, retrieved from the Internet:<URL:sec.gov/Archives/edgar/data/1159036/000095013704006885/a01296exv99wl.txt, [retrieved on Mar. 29, 2009] [2 pages].
News Release, Halozyme Therapeutics Inc., "Halozyme Therapeutics Reports Second Quarter 2009 Financial Results" Aug. 7, 2009, retrieved from the Internet<Url: sec.gov/Archives/edgar/data/1159036/000129993309003275/exhibitl.htm, [retrieved on 03.30.10] [5 pp.].
News Release, Halozyme Therapeutics Inc., "Baxter Presents Latest Clinical Trial Results of Gammagard Liquid Administered Subcutaneously," Philadelphia, PA, Mar. 16, 2008, Retrieved from the Internet: <URL:phx.corporate-irnet/phoenix.zhtml?c=175436&p=irolnewsArtiele_Print&Id=1120341&highlight= (accessed Jan. 6, 2009), 4 pages.
News Release, Halozyme Therapeutics Inc., "Data Presented at Aaaai Reinforce Baxter's Commitment to Making Gammagard Liquid Therapy More Convenient" Deerfield IL, Mar. 16, 2009, Retrieved from the Internet: <URL:businesswire.com/portal/site/google/?ndmViewId=news_view&newsId=20090316005731&newsL ang=en. [5 pages].
News Release, Halozyme Therapeutics Inc., "Halozyme and Baxter Announce Availability of Hylenex for Subcutaneous Delivery of Medications and Fluids," San Diego, CA, Jun. 27, 2006, Retrieved from the Internet: <URL:phx.corporate-ir.net/phoenix.zhtml?c=175436&p=irolnewsArticle Print&Id=876530&highlight= (accessed 01/06/09), 3 pp.
News Release, Halozyme Therapeutics Inc., "Halozyme Therapeutics Announces Roche Begins Phase 1 Clinical Trial and Selects Fourth Exclusive Biologic Target," San Diego, CA, Dec. 8, 2008, Retrieved from the Internet: <URL:phx.corporate-ir.net/phoenix.zhtml?c=175436&p=irolnewsArticle_Print&Id=1233454&highlight= (accessed Jan. 6, 2009), 2 pages.
News Release, Halozyme Therapeutics Inc., "Halozyme Therapeutics Releases Results of Enhanze Technology Clinical Trial to Improve the Subcutaneous Absorption of a Large Protein Molecule Therapeutic," San Diego, CA, Jan. 22, 2007, Retrieved from the Internet: URL:phx.corporate-ir.net/phoenix.zhtml c175436&pirol-newsArticle Print&Id952285&highlight(accessed Jan. 6, 2009), 3 pages.
News Release, Halozyme Therapeutics Inc., "Halozyme Therapeutics Completes Enrollment of Enhanze Technology Clinical Trial to Improve the Subcutaneous Absorption of a Large Protein Molecule Therapeutic," San Diego, CA, Nov. 27, 2006, Retrieved from the Internet: <URL:phx.corporate-ir.net/phoenix.zhtml?c=175436&p=irol-newsArticle_Print&Id=935824&highlight= (accessed Jan. 6, 2009), 2 pages.
News Release, Halozyme Therapeutics Inc., "Halozyme Therapeutics Initiates First Enhanze Technology Clinical Trial to Improve the Subcutaneous Absorption of a Large Molecule Protein Therapeutic," San Diego, CA, Aug. 8, 2006, Retrieved from the Internet: <URL:phx.corporateinnet/phoenix.zhtml?c=175436&p=irol-newsArticle_Print&Id=893361&highlight= (accessed Jan. 6, 2009), 2 pages.
News Release, Halozyme Therapeutics Inc., "Halozyme Therapeutics Files Nda for Enhanze Sc," San Diego, Ca, Mar. 28, 2005, Retrieved from the Internet: <URL: phx.corporateir.net/phoenix.zhtml?c=175436&p=irol-newsArticle_Print&Ld=689194&highlight= (accessed Jan. 6, 2009), 2 pages.
News Release, Halozyme Therapeutics Inc., "Phase III Trial Begins for GAMMAGARD Liquid Plus rHuPH2O in Primary Immunodeficiency Patients," San Diego, CA, Jan. 5, 2009, Retrieved from the Internet: <URL: phx.corporate-ir.net/phoenix.zhtml?c=175436&p=irolnewsArticle_Print&Id=1240232&highlight= (accessed Jan. 6, 2009), 3 pages.
News Release, Halozyme Therapeutics Inc., Q1 2008 Earnings Call Transcript found at: Retrieved from the Internet: <URL:seelcingalpha.com/article/76655-halozyme-therapeutics-inc-q1-2008-earnings-call-transcript [accessed on Jun. 25, 2009] [14 pages].
News Release, Halozyme Therapeutics Inc., Q4 2008 Earnings Call Transcript found at: Retrieved from the Internet: <URL:seelcingalpha.com/article/125929-halozyme-therapeutics-inc-q4-2008-earnings-call-transcript [accessed on May 13, 2009] [12 pages].
Ochs et al., "Safety and efficacy of self-administered subcutaneous immunoglobulin in patients with primary immunodeficiency diseases," J Clin. Immunol. 26:265-273 (2006).
Ohno, N., "Models of Kawasaki disease," Drug Discovery Today: Disease Models 3:83-89 (2006).
Oncley, M. And M. Melin, "The separation of the antibodies, isoagglutinins, prothrombin, plasminogen and betal-lipoprotein into subfractions of human plasma," J Am. Chem. Soc. 71:541550 (1949).
Ornitz et al., "Elastase I promoter directs expression of human growth hormone and SV40 T antigen genes to pancreatic acinar cells in transgenic mice," Cold Spring Harbor Symp. Quant. Biol. 50:399-409 (1986).
Ostresh et al., "Peptide libraries: determination of relative reduction rates of protected amino acids in competitive couplings," Biopolymers 34:1681-1689 (1994).
Oyaizu et al., "(NZW x BXSB)F1 mouse. A new animal model of idiopathic thrombocytopenic purpura," J Exp Med 2017-2022 (1988).
Pearson, W. And D. Lipman "Improved tools for biological sequence comparison," Proc. Natl. Acad. Sci. USA 85:2444 (1988).

(56) References Cited

OTHER PUBLICATIONS

Pham et al., "Large-scale transient transfection of serum-free suspension-growing HEK293 EBNA1 cells: peptone additives improve cell growth and transfection efficiency," Biotechnology and Bioengineering 84:332-342 (2003).
Pinkert et al., "An albumin enhancer located 10 kb upstream functions along with its promoter to direct efficient, liver-specific expression in transgenic mice,"Genes and Devel. 1(3):268-276 (1987).
Pinkstaff et al., "Evaluation of the Compatibility and Pharmacokinetics of Co-formulated Biologics with Recombinant Human Hyaluronidase: Dose Response," American Association of Pharmaceutical Scientists Conference, Jun. 2006, San Antonio, TX [3 pages].
Pinkstaff et al., "Recombinant Human Hyaluronidase for Drug and Fluid Dispersion," American Association of Pharmaceutical Scientists Annual Meeting, Nov. 2006, Boston, MA [3 pages].
Pinlcstaff et al., "Recombinant Human Hyaluronidase for Use with Therapeutic Antibodies," Controlled Release Society Conference, Vienna, Austria, 2006 [2 pages].
Poelsler et al., "A new liquid intravenous inmmunoglobulin with three dedicated virus reduction steps: virus and prion reduction capacity" Vox Sang 94(3):184-192 (2007).
Polson et al., "The Fractionation of protein mixtures by linear polymers of high molecular weight," Biochim. Biophys. Acta. 82:463-475 (1964).
Readhead et al., "Expression of a myelin basic protein gene in transgenic shiverer mice: correction of the dysmyelinating phenotype," Cell 48:703-712 (1987).
Reipert et al., "Fc function of a new intravenous immunoglobulin product:IGIV 10% triple virally inactivated solution." Vox Sang 91(3)256-263 (2006).
Relkin et al., "18-Month study of intravenous immunoglobulin for treatment of mild Alzheimer disease," Neurobiol Aging (2008). [9 pages].
Roberts et al., "Chemistry for peptide and protein PEGylation," Adv. Drug Deliv. Rev. 54:459-476 (2002).
Sato, H., "Enzymatic procedure for site-specific pegylation of proteins," Adv. Drug Deliv. Rev. 54:487-504 (2002).
Schiff et al., "Alterations in the half-life and clearance of IgG during therapy with intravenous gamma-globulin in 16 patients with severe primary humoral immunodeficiency," J. Clin. Immunol. 6:256-264 (1986).
Schiff et al, "Use of a new chemically modified intravenous IgG preparation in severe primary humoral immunodeficiency: clinical efficacy and attempts to individualize dosage," Clin Immunol Immunopathol. 31(1):13-23 (1984).
Schiff et al., "Multicenter Crossover Comparison of the Safety and Efficacy of Intraglobin-F with Gamimune-N, Sandoglobulin and Gammagard in Patients with Primary Immunodeficiency Diseases" Journal of Clinical Immunology 17(1):21-28 (1997).
Schiff, R., "Individualizing the dose of intravenous immune serum globulin for therapy of patients with primary humoral immunodeficiency," Vox Sang. 49 Suppl 1:15-24 (1985).
Schiff, R., "Half-life and clearance of pH 6.8 and pH 4.25 immunoglobulin G intravenous preparations in patients with primary disorders of humoral immunity" Rev Infect Dis (4):S449-S456 (1986).
Schwartz and Dayhoff, eds., Atlas of Protein Science and Structure, National Biomedical Research Foundation, pp. 353-358 (1979).
Shani, M., "Tissue-specific expression of rat myosin light-chain," Nature 314:283-286 (1985).
Shapiro et al., "Intravenous gamma globulin inhibits the production of matrix metalloproteinase-9 in macrophages," Cancer 95:2032-2037 (2002).
Shimizu, Y. And H. Yoshikura, "Multicycle infection of hepatitis C virus in cell culture and inhibition by alpha and beta interferons," J. Virol. 68:8406-8408 (1994).
Smith, T. And M. Waterman, "Comparison of biosequences," Advances in Applied Mathematics 2:482-489 (1981).
Solomon, B., "Intravenous immunoglobulin and Alzheimer's disease immunotherapy," (2007) Curr. Opin. Mol. Ther. 9:79-85 (2007).
Sommer et al., "Paraneoplastic stiff-person syndrome: passive transfer to rats by means of IgG antibodies to amphiphysin," Lancet 365:1406-1411 (2005).
Steinkuhler et al., "Product inhibition of the hepatitis C virus NS3 protease," Biochem. 37:8899- 8905 (1998).
Stiehm et al. "Slow subcutaneous human intravenous immunoglobulin in the treatment of antibody immunodeficiency: Use of an old method with a new product" J Allergy Clin Immunol 101:848-849 (1998).
Strongwater et al., "A murine model of polymyositis induced by coxsackievirus B1 (Tucson strain)," Arthritis Rheum. 27:433-442 (1984).
Sudo et al., "Establishment of an in vitro assay system for screening hepatitis C virus protease inhibitors using high performance liquid chromatography," Antiviral Res. 32:9-18 (1996).
Supersaxo et al., "Effect of molecular weight on the lymphatic absorption of water-soluble compounds following subcutaneous administration," Pharm. Res. 7(2):167-169 (1990).
Swift et al., "Tissue-specific expression of the rat pancreatic elastase I gene in transgenic mice," Cell 38:639-646 (1984).
Takahashi et al., "A fluorimetric Morgan-Elson assay method for hyaluronidase activity," Anal. Biochem. 322:257-263 (2003).
Takeshita et al., "An enzyme-linked immunosorbent assay for detecting proteolytic activity of hepatitis C virus proteinase," Anal. Biochem. 247:242-246 (1997).
Taliani et al., "A continuous assay of hepatitis C virus protease based on resonance energy transfer depsipeptide substrates," Anal. Biochem. 240:60-67 (1996).
Teschner et al., "A new liquid, intravenous immunoglobulin product (IGIV 10%) highly purified by state-of-the-art process" Vox Sanguinis 92(1):42-55 (2007).
Trebst et al., "Expression of chemokine receptors on peripheral blood mononuclear cells of patients with immune-mediated neuropathies treated with intravenous immunoglobins," Eur J Neurology 13:1359-1363 (2006).
Tsubery et al., "Prolonging the action of protein and peptide drugs by a novel approach of reversible polyethylene glycol modification," J Biol. Chem 279(37):38118-38124 (2004).
van Schaik et al., "Intravenous immunoglobulin for chronic inflammatory demyelinating polyradicloneuropathy: a systematic review," Lancet Neurol. 1:497-498 (2002).
Varga et al., "Efficacy and safety of IGIV, 10% TVR solution, a new intravenous immunoglobulin, in adult subjects with chronic idiopathic thrombocytopenic purpura" Transf Med Hemother 33:509514 (2006).
Veronese et al., "Branched and Linear Poly(Ethylene Glycol): Influence of the Polymer Structure on Enzymological, Pharmacokinetic, and Immunological Properties of Protein Conjugates," J. Bioactive Compatible Polymers 12:197-207 (1997).
Wagner et al., "Nucleotide sequence of the thymidine kinase gene of herpes simplex virus type 1," Proc. Natl. Acad. Sci. USA 78:1441-1445 (1981).
Walter et al., "High-dose immunoglobulin therapy in sporadic inclusion body myositis: a double-blind, placebo-controlled study," J Neurol 247(1):22-28 (2000).
Watson et al. Molecular Biology of the Gene, 4th Edition, 1987, the Benjamin/Cummings Pub. co., p. 224).
Wei et al., "Functions of N-linked glycans on human hyaluronidase PH2O," poster 83, 1 page (2009).
Wei et al., "Structure function analysis of the human hyaluronidase enzymes," American Society for Matrix Biology Biennial Meeting, San Diego, CA, Dec. 5, 2008, B4 (2 pages).
Weksler et al., "Drug-Ranging Study of Intravenous Immunoglobulin in Patients with Alzheimer's Disease," Abstracts: Pharmacological Treatments 1(Suppl 1):S94-S95 (2005).
Welch, M. And E. Stiehm, "Slow subcutaneous immunoglobulin therapy in a patient with reactions to intramuscular immunoglobulin," J Clin Imrnunol 3(3):285-286 (1983).
Wilson, M., "Enhanze Technology —An Enzymatic Drug Delivery System (DDS)," Japanese Export Trade Organization, 2005, Santa Clara, CA, 22 pages.

(56) References Cited

OTHER PUBLICATIONS

Yamamoto et al., "Identification of a functional promoter in the long terminal repeat of Rous sarcoma virus," Cell 22:787-797 (1980).
Yocum et al., "Phase IV study of the PK, safety and tolerability of Humira administered with escalating doses of recombinant human hyaluronidase (rHuPH2O); an Enhanze Technology Study with a Large Protein Molecule Therapeutic." Controlled Release Society Conference. Long Beach, CA, Jul. 9, 2007 [20 pages].
Yocum et al., "Assessment and Implication of the Allergic Sensitivity to a Single Dose of Recombinant Human Hyaluronidase Injection: a Double-Blind Placebo-Controlled Clinical Trial," J Infus Nursing. 30:293-299 (2007).
Yuasa et al., "The particle size of hepatitis C virus estimated by filtration through microporous regenerated cellulose fibre," J. Gen. Virol. 72(Pt 8):2021-2024 (1991).
Zalipsky, S and C Lee, "Poly(ethyl ene glycol) Chemistry: Biotechnical and Biomedical Applications," J. Hams, ed., Plenum: NY, Chapter 21, pp. 341-370 (1992).
Letter/Written Disclosure of the Supplemental Information Disclosure Statement for the above-referenced application, mailed on Dec. 21, 2012, 2 pages.
Lloyd, J., "Gammagard therapy offers hope for Alzheimer's patients," USA Today. Published on Jul. 17, 2012 [Retrieved on Dec. 17, 2012] Retrieved from the Internet: URL:usatoday30.usatoday.com/news/health/story/2012-07-16/alzheitners-treatmentgammagard/56270084/1 [6 pages].
Pollack, A., "Small Trial Hints Drug Can Slow Alzheimer's," New York Times. Published Jul. 17, 2012 [online][Accessed Dec. 17, 2012] Retrieved from the Internet: URL: www.nytimes.com/2012/07/18/business/study-shows-drug-may-help-alzheimers-patients.html?_r=0 [3 pages].
Stein et al., "Pharmacokinetics (PK) of Human Immunoglobulin 10% (IgG) Administered Intravenously (IGIV), Subcutaneously (IGSC) or Facilitated Subcutaneously with Recombinant Human Hyaluronidase (IGHy) in a Subset of Patients with Primary Immunodeficiency Disease (PIDD)," J Allergy Clinl Immunol. 129(2):AB14. Presented Mar. 3, 2012 at AAAAI Annual Meeting, Orlando, FL. Abstract #55.
Stein et al., "Pharmacokinetics (PK) of Human Immunoglobulin 10% (IgG) Administered Intravenously (IGIV), Subcutaneously (IGSC) or Facilitated Subcutaneously with Recombinant Human Hyaluronidase (IGHy) in a Subset of Patients with Primary Immunodeficiency Disease (PIDD)," Presented Mar. 3, 2012 at AAAAI Annual Meeting, Orlando, FL. Poster #55, 1 page.
Wasserman et al., "Tolerability and Efficacy of Facilitated-Subcutaneous Infusion of Immune Globulin (Human), 10% and Recombinant Human Hyaluronidase (IGHy) in a Subset of Study Patients With Primary Immunodeficiency Disease (PIDD)," J Allergy Clinl Immunol. 129(2):AB15. Presented Mar. 3, 2012 at the American College of Allergy, Asthma, & Immunology Meeting, Orlando, FL. Abstract #56.
Wasserman et al., "Tolerability and Efficacy of Facilitated-Subcutaneous Infusion of Immune Globulin (Human), 10% and Recombinant Human Hyaluronidase (IGHy) in a Subset of Study Patients With Primary Immunodeficiency Disease (PIDD)" Presented Mar. 3, 2012 at the American College of Allergy, Asthma, & Immunology Meeting, Orlando, FL. Poster #56, 1 page.
Halozyme Therapeutics Investor Presentation, Halozyme Therapeutics, Inc.: Thinking outside the cell,Presented on Oct. 2, 2012 [online][retrieved on Oct. 11, 2012] Retrieved from:<URL:sec.gov/Archives/edgar/data/1159036/000119312512412748/d419091dex991.htm [82 pages].
News Release, Halozyme Therapeutics, Inc., "Halozyme Confirms Baxter Has Received a Complete Response Letter for HyQ BLA," Published Aug. 1, 2012 [online][retrieved on Dec. 17, 2012]Retrieved from: <URL:www.halozyme.com/Investors/News-Releases/News-Release-Details/2012/Halozyme-Confirms-Baxter-Has-Received-A-Complete-Response-Letter-For-HyQ-BLA1130436/default.aspx [3 pages].

News Release, "Baxter presents long-term data on HyQ during Aaaai annual meeting," Published.On Mar. 2, 2012 [online][retrieved on Nov. 6, 2012] Retrieved from:<URL:http://www.baxter.com/press room/press releases/2012/03_02_12_hyq.html [2 pages].
Transcript, "Halozyme Therapeutics's Ceo Hosts Analyst/Investor Day Conference Call. (Transcript)," Published on Oct. 2, 2012 [online] [Retrieved on Oct. 25, 2012] Retrieved from the Internet: URL:http://seekingalpha.com/article/901141-halozyme-therapeutics-s-ceo-hosts-analyst-investor-day-conference-call-transcript?part=single [49 pages].
Response to Written Opinion, issued Oct. 13, 2011, in connection with International Patent Application No. PCT/US2010/002545 (3088PC), 24 pages.
Examination Report, issued Nov. 22, 2012, in connection with Australian Patent Application No. 2010296017 (3088AU), 2 pages.
Office Action and Search Report, issued Jan. 31, 2013 (received. Mar. 15, 2013), in connection with Chinese Patent Application No. 201080051813.3 (3088CN) [English translation], 6 pages.
Letter/Written Disclosure of the Supplemental Information Disclosure Statement for the above-referenced application, mailed the same date herewith, 2 pages. 2013.
Search and Examination Report, mailed May 7, 2013 (received May 28, 2013), in connection with Singapore Patent Application No. 201202729-8, 11 pages.
Notice of Acceptance, issued May 24, 2013 (received May 27, 2013), in connection with Australian Patent Application No. 2010296017, 3 pages.
Letter/Written Disclosure of the Supplemental Information Disclosure Statement for the above-referenced application, mailed Mar. 13, 2014, 2 pages.
Certified English language translation of JP H10-265407 a (Item AF), published Oct. 6, 2008, 6 pages.
Official Action, mailed Feb. 4, 2014 (received Mar. 3, 2013), in connection with Japanese Patent Application No. 2012-529751 [English translation], 2 pages.
Letter/Written Disclosure of hte Supplemental Information Disclosure Statement for the above-referenced application, mailed Sep. 4, 2014, 2 pages.
Ko et al., "Clinical Review Memorandum: BLA STN 125105/708, Baxter's Immune Globulin Infusion (Human) 10%, 10, 25, 50, 100, 200 and 300 mL Solutions for Subcutaneous Administration," Prepared Feb. 21, 2010. Retrieved from:<URL:google.com/url?sa=t&ret=j&q=&esrc=s&frm=1&source=web&cd=3&ved=0CDMQFjAc&url=http%3A%2F%2Fwww.fda.gov°/02Fdownloads%-2FBiologicsBloodVaccines%2FBloodB1 oodProducts%2-FApprovedProducts%2FLicensedProductsBLAs%2FFractionated-PlasmaProducts%2 FUCM275415.pdf&ei=jD-vUov9D8LX2AXNmICYCQ&usg=AFQjCNG5hbn36PZ5ifK__SxhiBdqQmSFw1Q [Retrieved on Dec. 16, 2013], 39 pages.
Frost, G. I., "Halozyme Therapeutics, Inc. Thinking outside the cell," presented at J. P. Morgan Healthcare Conference on Jan. 10, 2013. Presentation. 23 pages.
Halozyme Therapeutics, "United States Securities and Exchange Commission, form 10-K, Part I" for fiscal year ending Dec. 31, 2013, filed Feb. 28, 2014. 32 pages.
Halozyme Therapeutics, "United States Securities and Exchange Commission, form 10-K, Part I," for fiscal year ending Dec. 31, 2012, filed Mar. 1, 2013. 30 pages.
Halozyme Therapeutics, "United States Securities and Exchange Commission Form 10Q" for quarterly period ending Mar. 31, 2013, filed May 8, 2013, 50 pages.
News Release, "Baxter and Halozyme Announce Positive Opinion for HyQvia for Treatment of Primary and Secondary Immunodeficiencies in the European Union," published Mar. 22, 2013 [online][Retrieved on Dec. 16, 2013], Retrieved from:<URL:halozyme.com/Investors/News-Releases/News-Release-Details/2013/Baxter-And-Halozyme-Announce-Positive-Opinion-For-HyQvia-For-Treatment-Of-Primary-And-Secondary-Immunodeficiencies-In-The-European-Union/default.aspx [3 pages].
News Release, "Baxter Receives Marketing Authorization for HyQvia in European Union," May 21, 2013 [online][retrieved on Dec. 16, 2013], Retrieved from:<URL:halozyme.com/Investors/

(56) References Cited

OTHER PUBLICATIONS

NewsReleases/News-Release-Details/2013/Baxter-Receives-Marketing-Authorization-for-HyQvia-inEuropean-Union/default.aspx [4 pages].
News Release,"Baxter Submits Amended Bla to U.S. FDA for HyQvia for Primary Immunodeficiency," Dec. 2, 2013 [online][retrieved on Dec. 16, 2013], Retrieved from: <RL:halozyme.coin/Investors/News-Releases/News-Release-Details/2013/Baxter-SubmitsAmended-Bla-to-US-FDA-for-HyQvia-for-Primary-Immunodeficiency/defaultaspx [3 pages].
News Release, "FDA advisory committee panel provides favorable recommendation on Baxter's HyQvia for primary immunodeficiency," published Jul. 31, 2014 [retrieved on Sep. 2, 2014] Retrieved from:<URL:online.wsj.com/article/Pr-00-20140731-915905.html#printMode, 2 pages.
Final Office Action, mailed Mar. 27, 2014, in connection with related U.S. Application No. 12/381,844, 12 pages.
Amendment After Final, filed Aug. 28, 2014, in response to Final Office Action, mailed Mar. 27, 2014, in connection with related U.S. Application No. 12/381,844, 22 pages.
Response to Examination Report, issued Nov. 22, 2012, in connection with corresponding Australian Patent Application No. 2010296017, 26 pages.
Examination Report, issued Jan. 21, 2014, in connection with corresponding Canadian Patent Application No. 2,774,053, 2 pages.
Response, dated May 28, 2014, to Examination Report, issued Jan. 21, 2014, in connection with corresponding Canadian Patent Application No. 2,774,053, 24 pages.
Notice of Allowance, issued Aug. 4, 2014, in connection with corresponding Canadian Patent Application No. 2,774,053, 1 page.
Instructions, dated Jul. 31, 2013, for response to Office Action, issued Jan. 31, 2013, in connection with corresponding Chinese Patent Application No. 201080051813.3, 13 pages.
Office Action, issued Oct. 12, 2013, in connection with corresponding Chinese Patent Application No. 201080051813.3 [English translation and original document in Chinese], 10 pages.
Instructions, dated Feb. 24, 2014, for Response to Office Action, issued Oct. 12, 2013, in connection with corresponding Chinese Patent Application No. 201080051813.3, 17 pages.
Office Action, issued May 22, 2014 in connection with corresponding Chinese Patent Application No. 201080051813.3 [English translation and original document in Chinese], 4 pages.
Office Action, issued Aug. 13, 2013, in connection with corresponding Colombian Patent Application No. 12-060153, [English translation and original document in Spanish], 8 pages.
Instructions, dated Nov. 12, 2013, for response to Office Action issued, Aug. 13, 2013, in connection with corresponding Colombian Patent Application No. 12-060153, 18 pages.
Office Action, received Dec. 19, 2013, in connection with corresponding Eurasian Patent Application No. 201200490 [English translation], 3 pages.
Instructions, dated Apr. 15, 2014, for response to Office Action, received Dec. 19, 2013, in connection with corresponding Eurasian Patent Application No. 201200490, 19 pages.
Official Action, mailed Feb. 4, 2014, in connection with corresponding Japanese Patent Application No. 2012-529751 [Summary, English translation, and original document in Japanese], 6 pages.
Instructions, dated Jul. 23, 2014 for response to Official Action, mailed Feb. 4, 2014, in connection with corresponding Japanese Patent Application No. 2012-529751, 20 pages.
Office Action, issued Nov. 29, 2013, in connection with corresponding Korean Patent Application No. 10-2012-7009795 [English translation and original document in Korean], 5 pages.
Instructions, dated Jan. 22, 2014, for response to Office Action, issued Nov. 29, 2013, in connection with corresponding Korean Patent Application No. 10-2012-7009795, 10 pages.
Decision of Grant, issued Jun. 27, 2014, in connection with corresponding Korean Patent Application No. 10-2012-7009795 [English translation and original document in Korean], 3 pages.
Letter/Written Disclosure of the Supplemental Information Disclosure Statement for the above-reference pplication, filed herewith Jan. 16, 2015, 2 pages.
News Release, "Baxter Launches HYQVIA in the United States for Adult Patients with Primary Immunodeficiency," Published Oct. 20, 2014 [online][retrieved on Nov. 11, 2014] Retrieved from:<URL:http://www.halozyme.com/Investors/News-Releases/News-ReleaseDetails/2014/Baxter-Launches-HYQV1A-in-the-United-States-for-Adult-Patients-with-PrimaryImmunodeficiency/defaultaspx, 4 pages.
Advisory Action, mailed Sep. 11, 2014, in connection with U.S. Application No. 12/381,844, 2 pages.
Letter, dated Oct. 6, 2014, providing English language translation of Office Action, issued Aug. 21, 2014, in connection with Colombian Patent Application No. 12-060153, [Letter, original document in Spanish, and accompanying documents], 345 pages.
Letter, dated Oct. 30, 2014, providing rejections issued in an Office Action in connection with Eurasian Patent Application No. 201200490, 2 pages.
English language instructions, dated Nov. 7, 2014, and Appeal Brief, filed Nov. 13, 2014, in connection with Japanese Patent Application No. 2011-500795, 22 pages.
Office Action, issued Nov. 14, 2014, and English Language translation issued in connection with corresponding Chinese Patent Application No. 2010080051813.3, 4 pages.
English language instructions, dated Dec. 18, 2014, and Response, filed Dec. 26, 2014, to Office Action, issued Aug. 21, 2014, in connection with Colombian Patent Application No. 12060153, 39 pages.

* cited by examiner

SEQUENCE LISTING

```
<160> NUMBER OF SEQ ID NOS: 56

<210> SEQ ID NO 1
<211> LENGTH: 509
<212> TYPE: PRT
<213> ORGANISM: Homo sapiens
<220> FEATURE:
<223> OTHER INFORMATION: precursor human PH20

<400> SEQUENCE: 1

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
```

```
                130                 135                 140
Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
                180                 185                 190

Glu Lys Ala Gly Lys Asp Phe Leu Val Glu Thr Ile Lys Leu Gly Lys
                195                 200                 205

Leu Leu Arg Pro Asn His Leu Trp Gly Tyr Tyr Leu Phe Pro Asp Cys
210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
                260                 265                 270

Ala Ala Thr Leu Tyr Val Arg Asn Arg Val Arg Glu Ala Ile Arg Val
                275                 280                 285

Ser Lys Ile Pro Asp Ala Lys Ser Pro Leu Pro Val Phe Ala Tyr Thr
                290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
                340                 345                 350

Leu Leu Asp Asn Tyr Met Glu Thr Ile Leu Asn Pro Tyr Ile Ile Asn
                355                 360                 365

Val Thr Leu Ala Ala Lys Met Cys Ser Gln Val Leu Cys Gln Glu Gln
                370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
                420                 425                 430

Phe Tyr Cys Ser Cys Tyr Ser Thr Leu Ser Cys Lys Glu Lys Ala Asp
                435                 440                 445

Val Lys Asp Thr Asp Ala Val Asp Val Cys Ile Ala Asp Gly Val Cys
450                 455                 460

Ile Asp Ala Phe Leu Lys Pro Pro Met Glu Thr Glu Glu Pro Gln Ile
465                 470                 475                 480

Phe Tyr Asn Ala Ser Pro Ser Thr Leu Ser Ala Thr Met Phe Ile Val
                485                 490                 495

Ser Ile Leu Phe Leu Ile Ile Ser Ser Val Ala Ser Leu
                500                 505

<210> SEQ ID NO 2
<211> LENGTH: 474
<212> TYPE: PRT
<213> ORGANISM: Homo sapiens
<220> FEATURE:
<223> OTHER INFORMATION: Mature PH20
```

<400> SEQUENCE: 2

```
Leu Asn Phe Arg Ala Pro Pro Val Ile Pro Asn Val Pro Phe Leu Trp
  1               5                  10                  15

Ala Trp Asn Ala Pro Ser Glu Phe Cys Leu Gly Lys Phe Asp Glu Pro
             20                  25                  30

Leu Asp Met Ser Leu Phe Ser Phe Ile Gly Ser Pro Arg Ile Asn Ala
         35                  40                  45

Thr Gly Gln Gly Val Thr Ile Phe Tyr Val Asp Arg Leu Gly Tyr Tyr
     50                  55                  60

Pro Tyr Ile Asp Ser Ile Thr Gly Val Thr Val Asn Gly Gly Ile Pro
 65                  70                  75                  80

Gln Lys Ile Ser Leu Gln Asp His Leu Asp Lys Ala Lys Lys Asp Ile
                 85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415
```

```
Thr Asp Ala Val Asp Val Cys Ile Ala Asp Gly Val Cys Ile Asp Ala
            420                 425                 430

Phe Leu Lys Pro Pro Met Glu Thr Glu Pro Gln Ile Phe Tyr Asn
            435                 440                 445

Ala Ser Pro Ser Thr Leu Ser Ala Thr Met Phe Ile Val Ser Ile Leu
450                 455                 460

Phe Leu Ile Ile Ser Ser Val Ala Ser Leu
465                 470

<210> SEQ ID NO 3
<211> LENGTH: 482
<212> TYPE: PRT
<213> ORGANISM: Homo sapiens
<220> FEATURE:
<223> OTHER INFORMATION: precursor soluble rHuPH20

<400> SEQUENCE: 3

Met Gly Val Leu Lys Phe Lys His Ile Phe Phe Arg Ser Phe Val Lys
  1               5                  10                  15

Ser Ser Gly Val Ser Gln Ile Val Phe Thr Phe Leu Leu Ile Pro Cys
                20                  25                  30

Cys Leu Thr Leu Asn Phe Arg Ala Pro Pro Val Ile Pro Asn Val Pro
            35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
290                 295                 300
```

```
Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
                355                 360                 365

Val Thr Leu Ala Ala Lys Met Cys Ser Gln Val Leu Cys Gln Glu Gln
        370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
                435                 440                 445

Val Lys Asp Thr Asp Ala Val Asp Val Cys Ile Ala Asp Gly Val Cys
        450                 455                 460

Ile Asp Ala Phe Leu Lys Pro Pro Met Glu Thr Glu Glu Pro Gln Ile
465                 470                 475                 480

Phe Tyr

<210> SEQ ID NO 4
<211> LENGTH: 447
<212> TYPE: PRT
<213> ORGANISM: Homo sapiens
<220> FEATURE:
<223> OTHER INFORMATION: soluble rHuPH20 1-447

<400> SEQUENCE: 4

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
                20                  25                  30

Leu Asp Met Ser Leu Phe Ser Phe Ile Gly Ser Pro Arg Ile Asn Ala
            35                  40                  45

Thr Gly Gln Gly Val Thr Ile Phe Tyr Val Asp Arg Leu Gly Tyr Tyr
        50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175
```

```
Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr
        435                 440                 445

<210> SEQ ID NO 5
<211> LENGTH: 446
<212> TYPE: PRT
<213> ORGANISM: Homo sapiens
<220> FEATURE:
<223> OTHER INFORMATION: soluble rHuPH20 1-446

<400> SEQUENCE: 5

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95
```

```
Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe
        435                 440                 445

<210> SEQ ID NO 6
<211> LENGTH: 445
<212> TYPE: PRT
<213> ORGANISM: Homo sapiens
<220> FEATURE:
<223> OTHER INFORMATION: soluble rHuPH20 1-445

<400> SEQUENCE: 6

Leu Asn Phe Arg Ala Pro Pro Val Ile Pro Asn Val Pro Phe Leu Trp
1               5                   10                  15
```

```
Ala Trp Asn Ala Pro Ser Glu Phe Cys Leu Gly Lys Phe Asp Glu Pro
             20                  25                  30

Leu Asp Met Ser Leu Phe Ser Phe Ile Gly Ser Pro Arg Ile Asn Ala
         35                  40                  45

Thr Gly Gln Gly Val Thr Ile Phe Tyr Val Asp Arg Leu Gly Tyr Tyr
     50                  55                  60

Pro Tyr Ile Asp Ser Ile Thr Gly Val Thr Val Asn Gly Gly Ile Pro
65                   70                  75                  80

Gln Lys Ile Ser Leu Gln Asp His Leu Asp Lys Ala Lys Lys Asp Ile
                 85                  90                  95

Thr Phe Tyr Met Pro Val Asp Asn Leu Gly Met Ala Val Ile Asp Trp
             100                 105                 110

Glu Glu Trp Arg Pro Thr Trp Ala Arg Asn Trp Lys Pro Lys Asp Val
         115                 120                 125

Tyr Lys Asn Arg Ser Ile Glu Leu Val Gln Gln Asn Val Gln Leu
     130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                 165                 170                 175

Pro Asn His Leu Trp Gly Tyr Tyr Leu Phe Pro Asp Cys Tyr Asn His
             180                 185                 190

His Tyr Lys Lys Pro Gly Tyr Asn Gly Ser Cys Phe Asn Val Glu Ile
         195                 200                 205

Lys Arg Asn Asp Asp Leu Ser Trp Leu Trp Asn Glu Ser Thr Ala Leu
     210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                 245                 250                 255

Pro Asp Ala Lys Ser Pro Leu Pro Val Phe Ala Tyr Thr Arg Ile Val
             260                 265                 270

Phe Thr Asp Gln Val Leu Lys Phe Leu Ser Gln Asp Glu Leu Val Tyr
         275                 280                 285

Thr Phe Gly Glu Thr Val Ala Leu Gly Ala Ser Gly Ile Val Ile Trp
     290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                 325                 330                 335

Ala Ala Lys Met Cys Ser Gln Val Leu Cys Gln Glu Gln Gly Val Cys
             340                 345                 350

Ile Arg Lys Asn Trp Asn Ser Ser Asp Tyr Leu His Leu Asn Pro Asp
         355                 360                 365

Asn Phe Ala Ile Gln Leu Glu Lys Gly Gly Lys Phe Thr Val Arg Gly
     370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                 405                 410                 415

Thr Asp Ala Val Asp Val Cys Ile Ala Asp Gly Val Cys Ile Asp Ala
             420                 425                 430

Phe Leu Lys Pro Pro Met Glu Thr Glu Glu Pro Gln Ile
```

<210> SEQ ID NO 7
<211> LENGTH: 444
<212> TYPE: PRT
<213> ORGANISM: Homo sapiens
<220> FEATURE:
<223> OTHER INFORMATION: soluble rHuPH20 1-444

<400> SEQUENCE: 7

```
Leu Asn Phe Arg Ala Pro Pro Val Ile Pro Asn Val Pro Phe Leu Trp
  1               5                  10                  15

Ala Trp Asn Ala Pro Ser Glu Phe Cys Leu Gly Lys Phe Asp Glu Pro
             20                  25                  30

Leu Asp Met Ser Leu Phe Ser Phe Ile Gly Ser Pro Arg Ile Asn Ala
         35                  40                  45

Thr Gly Gln Gly Val Thr Ile Phe Tyr Val Asp Arg Leu Gly Tyr Tyr
     50                  55                  60

Pro Tyr Ile Asp Ser Ile Thr Gly Val Thr Val Asn Gly Gly Ile Pro
 65                  70                  75                  80

Gln Lys Ile Ser Leu Gln Asp His Leu Asp Lys Ala Lys Lys Asp Ile
                 85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
```

```
                   355                 360                 365
Asn Phe Ala Ile Gln Leu Glu Lys Gly Gly Lys Phe Thr Val Arg Gly
                370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                    405                 410                 415

Thr Asp Ala Val Asp Val Cys Ile Ala Asp Gly Val Cys Ile Asp Ala
                420                 425                 430

Phe Leu Lys Pro Pro Met Glu Thr Glu Glu Pro Gln
                435                 440

<210> SEQ ID NO 8
<211> LENGTH: 443
<212> TYPE: PRT
<213> ORGANISM: Homo sapiens
<220> FEATURE:
<223> OTHER INFORMATION: soluble rHuPH20 1-443

<400> SEQUENCE: 8

Leu Asn Phe Arg Ala Pro Pro Val Ile Pro Asn Val Pro Phe Leu Trp
  1               5                  10                  15

Ala Trp Asn Ala Pro Ser Glu Phe Cys Leu Gly Lys Phe Asp Glu Pro
                 20                  25                  30

Leu Asp Met Ser Leu Phe Ser Phe Ile Gly Ser Pro Arg Ile Asn Ala
             35                  40                  45

Thr Gly Gln Gly Val Thr Ile Phe Tyr Val Asp Arg Leu Gly Tyr Tyr
         50                  55                  60

Pro Tyr Ile Asp Ser Ile Thr Gly Val Thr Val Asn Gly Gly Ile Pro
 65                  70                  75                  80

Gln Lys Ile Ser Leu Gln Asp His Leu Asp Lys Ala Lys Lys Asp Ile
                 85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
```

```
                      275                 280                 285
Thr Phe Gly Glu Thr Val Ala Leu Gly Ala Ser Gly Ile Val Ile Trp
290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
                340                 345                 350

Ile Arg Lys Asn Trp Asn Ser Ser Asp Tyr Leu His Leu Asn Pro Asp
                355                 360                 365

Asn Phe Ala Ile Gln Leu Glu Lys Gly Gly Lys Phe Thr Val Arg Gly
                370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
                420                 425                 430

Phe Leu Lys Pro Pro Met Glu Thr Glu Glu Pro
                435                 440

<210> SEQ ID NO 9
<211> LENGTH: 442
<212> TYPE: PRT
<213> ORGANISM: Homo sapiens
<220> FEATURE:
<223> OTHER INFORMATION: soluble rHuPH20 1-442

<400> SEQUENCE: 9

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
                20                  25                  30

Leu Asp Met Ser Leu Phe Ser Phe Ile Gly Ser Pro Arg Ile Asn Ala
                35                  40                  45

Thr Gly Gln Gly Val Thr Ile Phe Tyr Val Asp Arg Leu Gly Tyr Tyr
            50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
                100                 105                 110

Glu Glu Trp Arg Pro Thr Trp Ala Arg Asn Trp Lys Pro Lys Asp Val
            115                 120                 125

Tyr Lys Asn Arg Ser Ile Glu Leu Val Gln Gln Asn Val Gln Leu
                130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
                180                 185                 190

His Tyr Lys Lys Pro Gly Tyr Asn Gly Ser Cys Phe Asn Val Glu Ile
```

```
            195                 200                 205
Lys Arg Asn Asp Asp Leu Ser Trp Leu Trp Asn Glu Ser Thr Ala Leu
            210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
            275                 280                 285

Thr Phe Gly Glu Thr Val Ala Leu Gly Ala Ser Gly Ile Val Ile Trp
            290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
            355                 360                 365

Asn Phe Ala Ile Gln Leu Glu Lys Gly Gly Lys Phe Thr Val Arg Gly
            370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu
            435                 440

<210> SEQ ID NO 10
<211> LENGTH: 450
<212> TYPE: PRT
<213> ORGANISM: Bos taurus
<220> FEATURE:
<223> OTHER INFORMATION: hyaluronidase

<400> SEQUENCE: 10

Met Arg Pro Phe Ser Leu Glu Val Ser Leu His Leu Pro Trp Ala Met
1               5                   10                  15

Ala Ala His Leu Leu Pro Val Cys Thr Leu Phe Leu Asn Leu Leu Ser
            20                  25                  30

Met Thr Gln Gly Ser Arg Asp Pro Val Val Pro Asn Gln Pro Phe Thr
        35                  40                  45

Thr Ile Trp Asn Ala Asn Thr Glu Trp Cys Met Lys Lys His Gly Val
    50                  55                  60

Asp Val Asp Ile Ser Ile Phe Asp Val Val Thr Asn Pro Gly Gln Thr
65                  70                  75                  80

Phe Arg Gly Pro Asn Met Thr Ile Phe Tyr Ser Ser Gln Leu Gly Thr
                85                  90                  95

Tyr Pro Tyr Tyr Thr Ser Ala Gly Glu Pro Val Phe Gly Gly Leu Pro
            100                 105                 110

Gln Asn Ala Ser Leu Asn Ala His Leu Ala Arg Thr Phe Gln Asp Ile
```

```
                    115                 120                 125
Leu Ala Ala Met Pro Glu Pro Arg Phe Ser Gly Leu Ala Val Ile Asp
        130                 135                 140

Trp Glu Ala Trp Arg Pro Arg Trp Ala Phe Asn Trp Asp Thr Lys Asp
145                 150                 155                 160

Ile Tyr Arg Gln Arg Ser Arg Ala Leu Val Gln Lys Gln His Pro Asp
                165                 170                 175

Trp Leu Ala Pro Arg Val Glu Ala Ala Gln Asp Gln Phe Glu Gly
                180                 185                 190

Ala Ala Glu Glu Trp Met Ala Gly Thr Leu Lys Leu Gly Gln Ala Leu
        195                 200                 205

Arg Pro Gln Gly Leu Trp Gly Phe Tyr Asn Phe Pro Glu Cys Tyr Asn
        210                 215                 220

Tyr Asp Phe Lys Ser Pro Asn Tyr Thr Gly Arg Cys Pro Leu Asn Ile
225                 230                 235                 240

Cys Ala Gln Asn Asp Gln Leu Gly Trp Leu Trp Gly Gln Ser Arg Ala
                245                 250                 255

Leu Tyr Pro Ser Ile Tyr Leu Pro Ala Ala Leu Glu Gly Thr Lys Lys
                260                 265                 270

Thr Gln Met Phe Val Gln His Arg Val Ala Glu Ala Phe Arg Val Ala
        275                 280                 285

Ala Gly Ala Gly Asp Pro Lys Leu Pro Val Leu Pro Tyr Met Gln Leu
        290                 295                 300

Phe Tyr Asp Met Thr Asn His Phe Leu Pro Ala Glu Glu Leu Glu His
305                 310                 315                 320

Ser Leu Gly Glu Ser Ala Ala Gln Gly Ala Ala Gly Val Val Leu Trp
                325                 330                 335

Val Ser Trp Leu Ser Thr Ser Thr Lys Glu Ser Cys Gln Ala Ile Lys
                340                 345                 350

Glu Tyr Val Asp Thr Thr Leu Gly Pro Ser Ile Leu Asn Val Thr Ser
                355                 360                 365

Gly Ala Arg Leu Cys Ser Gln Val Leu Cys Ser Gly His Gly Arg Cys
        370                 375                 380

Ala Arg Arg Pro Ser Tyr Pro Lys Ala Arg Leu Ile Leu Asn Ser Thr
385                 390                 395                 400

Ser Phe Ser Ile Lys Pro Thr Pro Gly Gly Gly Pro Leu Thr Leu Gln
                405                 410                 415

Gly Ala Leu Ser Leu Glu Asp Arg Leu Arg Met Ala Val Glu Phe Glu
                420                 425                 430

Cys Arg Cys Tyr Arg Gly Trp Arg Gly Thr Arg Cys Glu Gln Trp Gly
        435                 440                 445

Met Trp
    450

<210> SEQ ID NO 11
<211> LENGTH: 553
<212> TYPE: PRT
<213> ORGANISM: Bos taurus
<220> FEATURE:
<223> OTHER INFORMATION: PH20

<400> SEQUENCE: 11

Met Arg Met Leu Arg Arg His His Ile Ser Phe Arg Ser Phe Ala Gly
  1               5                  10                  15

Ser Ser Gly Thr Pro Gln Ala Val Phe Thr Phe Leu Leu Leu Pro Cys
```

-continued

```
             20                  25                  30
Cys Leu Ala Leu Asp Phe Arg Ala Pro Pro Leu Ile Ser Asn Thr Ser
         35                  40                  45
Phe Leu Trp Ala Trp Asn Ala Pro Val Glu Arg Cys Val Asn Arg Arg
     50                  55                  60
Phe Gln Leu Pro Pro Asp Leu Arg Leu Phe Ser Val Lys Gly Ser Pro
 65                  70                  75                  80
Gln Lys Ser Ala Thr Gly Gln Phe Ile Thr Leu Phe Tyr Ala Asp Arg
                 85                  90                  95
Leu Gly Tyr Tyr Pro His Ile Asp Glu Lys Thr Gly Lys Thr Val Phe
                100                 105                 110
Gly Gly Ile Pro Gln Leu Gly Asn Leu Lys Ser His Met Glu Lys Ala
                115                 120                 125
Lys Asn Asp Ile Ala Tyr Tyr Ile Pro Asn Asp Ser Val Gly Leu Ala
            130                 135                 140
Val Ile Asp Trp Glu Asn Trp Arg Pro Thr Trp Ala Arg Asn Trp Lys
145                 150                 155                 160
Pro Lys Asp Val Tyr Arg Asp Glu Ser Val Glu Leu Val Leu Gln Lys
                165                 170                 175
Asn Pro Gln Leu Ser Phe Pro Glu Ala Ser Lys Ile Ala Lys Val Asp
            180                 185                 190
Phe Glu Thr Ala Gly Lys Ser Phe Met Gln Glu Thr Leu Lys Leu Gly
        195                 200                 205
Lys Leu Leu Arg Pro Asn His Leu Trp Gly Tyr Tyr Leu Phe Pro Asp
210                 215                 220
Cys Tyr Asn His Asn His Asn Gln Pro Thr Tyr Asn Gly Asn Cys Pro
225                 230                 235                 240
Asp Val Glu Lys Arg Arg Asn Asp Leu Glu Trp Leu Trp Lys Glu
                245                 250                 255
Ser Thr Ala Leu Phe Pro Ser Val Tyr Leu Asn Ile Arg Leu Lys Ser
            260                 265                 270
Thr Gln Asn Ala Ala Leu Tyr Val Arg Asn Arg Val Gln Glu Ala Ile
        275                 280                 285
Arg Leu Ser Lys Ile Ala Ser Val Glu Ser Pro Leu Pro Val Phe Val
    290                 295                 300
Tyr Ala Arg Pro Val Phe Thr Asp Gly Ser Ser Thr Tyr Leu Ser Gln
305                 310                 315                 320
Gly Asp Leu Val Asn Ser Val Gly Glu Ile Val Ser Leu Gly Ala Ser
                325                 330                 335
Gly Ile Ile Met Trp Gly Ser Leu Asn Leu Ser Leu Ser Met Gln Ser
            340                 345                 350
Cys Met Asn Leu Gly Thr Tyr Leu Asn Thr Thr Leu Asn Pro Tyr Ile
        355                 360                 365
Ile Asn Val Thr Leu Ala Ala Lys Met Cys Ser Gln Val Leu Cys His
    370                 375                 380
Asn Glu Gly Val Cys Thr Arg Lys His Trp Asn Ser Ser Asp Tyr Leu
385                 390                 395                 400
His Leu Asn Pro Met Asn Phe Ala Ile Gln Thr Gly Glu Gly Gly Lys
                405                 410                 415
Tyr Thr Val Pro Gly Thr Val Thr Leu Glu Asp Leu Gln Lys Phe Ser
            420                 425                 430
Asp Thr Phe Tyr Cys Ser Cys Tyr Ala Asn Ile His Cys Lys Lys Arg
        435                 440                 445
```

```
Val Asp Ile Lys Asn Val His Ser Val Asn Val Cys Met Ala Glu Asp
    450                 455                 460

Ile Cys Ile Asp Ser Pro Val Lys Leu Gln Pro Ser Asp His Ser Ser
465                 470                 475                 480

Ser Gln Glu Ala Ser Thr Thr Thr Phe Ser Ser Ile Ser Pro Ser Thr
                485                 490                 495

Thr Thr Ala Thr Val Ser Pro Cys Thr Pro Glu Lys His Ser Pro Glu
            500                 505                 510

Cys Leu Lys Val Arg Cys Ser Glu Val Ile Pro Asn Val Thr Gln Lys
        515                 520                 525

Ala Cys Gln Ser Val Lys Leu Lys Asn Ile Ser Tyr Gln Ser Pro Ile
    530                 535                 540

Gln Asn Ile Lys Asn Gln Thr Thr Tyr
545                 550

<210> SEQ ID NO 12
<211> LENGTH: 331
<212> TYPE: PRT
<213> ORGANISM: Vespula vulgaris
<220> FEATURE:
<223> OTHER INFORMATION: hyaluronidase A

<400> SEQUENCE: 12

Ser Glu Arg Pro Lys Arg Val Phe Asn Ile Tyr Trp Asn Val Pro Thr
1               5                   10                  15

Phe Met Cys His Gln Tyr Asp Leu Tyr Phe Asp Glu Val Thr Asn Phe
                20                  25                  30

Asn Ile Lys Arg Asn Ser Lys Asp Asp Phe Gln Gly Asp Lys Ile Ala
            35                  40                  45

Ile Phe Tyr Asp Pro Gly Glu Phe Pro Ala Leu Leu Ser Leu Lys Asp
        50                  55                  60

Gly Lys Tyr Lys Lys Arg Asn Gly Val Pro Gln Glu Gly Asn Ile
65                  70                  75                  80

Thr Ile His Leu Gln Lys Phe Ile Glu Asn Leu Asp Lys Ile Tyr Pro
                85                  90                  95

Asn Arg Asn Phe Ser Gly Ile Gly Val Ile Asp Phe Glu Arg Trp Arg
            100                 105                 110

Pro Ile Phe Arg Gln Asn Trp Gly Asn Met Lys Ile His Lys Asn Phe
        115                 120                 125

Ser Ile Asp Leu Val Arg Asn Glu His Pro Thr Trp Asn Lys Lys Met
130                 135                 140

Ile Glu Leu Glu Ala Ser Lys Arg Phe Glu Lys Tyr Ala Arg Phe Phe
145                 150                 155                 160

Met Glu Glu Thr Leu Lys Leu Ala Lys Lys Thr Arg Lys Gln Ala Asp
                165                 170                 175

Trp Gly Tyr Tyr Gly Tyr Pro Tyr Cys Phe Asn Met Ser Pro Asn Asn
            180                 185                 190

Leu Val Pro Glu Cys Asp Val Thr Ala Met His Glu Asn Asp Lys Met
        195                 200                 205

Ser Trp Leu Phe Asn Asn Gln Asn Val Leu Pro Ser Val Tyr Val
210                 215                 220

Arg Gln Glu Leu Thr Pro Asp Gln Arg Ile Gly Leu Val Gln Gly Arg
225                 230                 235                 240

Val Lys Glu Ala Val Arg Ile Ser Asn Asn Leu Lys His Ser Pro Lys
                245                 250                 255
```

```
Val Leu Ser Tyr Trp Trp Tyr Val Tyr Gln Asp Glu Thr Asn Thr Phe
            260                 265                 270

Leu Thr Glu Thr Asp Val Lys Lys Thr Phe Gln Glu Ile Val Ile Asn
            275                 280                 285

Gly Gly Asp Gly Ile Ile Ile Trp Gly Ser Ser Asp Val Asn Ser
            290                 295                 300

Leu Ser Lys Cys Lys Arg Leu Gln Asp Tyr Leu Leu Thr Val Leu Gly
305                 310                 315                 320

Pro Ile Ala Ile Asn Val Thr Glu Ala Val Asn
                325                 330

<210> SEQ ID NO 13
<211> LENGTH: 340
<212> TYPE: PRT
<213> ORGANISM: Vespula vulgaris
<220> FEATURE:
<223> OTHER INFORMATION: hyaluronidase B

<400> SEQUENCE: 13

Asp Arg Thr Ile Trp Pro Lys Lys Gly Phe Ser Ile Tyr Trp Asn Ile
1               5                   10                  15

Pro Thr His Phe Cys His Asn Phe Gly Val Tyr Phe Lys Glu Leu Lys
            20                  25                  30

Gln Phe Asn Ile Lys Tyr Asn Ser Met Asn Asn Phe Arg Gly Glu Thr
        35                  40                  45

Ile Ser Leu Phe Tyr Asp Pro Gly Asn Phe Pro Ser Met Val Leu Leu
    50                  55                  60

Lys Asn Gly Thr Tyr Glu Ile Arg Asn Glu Gly Val Pro Gln Lys Gly
65                  70                  75                  80

Asn Leu Thr Ile His Leu Glu Gln Phe Thr Lys Glu Leu Asp Glu Ile
                85                  90                  95

Tyr Pro Lys Lys Ile Ala Gly Gly Ile Gly Val Ile His Phe His Asn
            100                 105                 110

Trp Arg Pro Ile Phe Arg Arg Asn Val Asp Asn Leu Lys Ile Asn Lys
        115                 120                 125

Asp Ile Ser Ile Asp Leu Val Arg Lys Glu His Pro Lys Trp Asp Lys
    130                 135                 140

Ser Met Ile Glu Lys Glu Ala Ser Asn Arg Phe Glu Thr Ser Ala Lys
145                 150                 155                 160

Ile Phe Met Glu Lys Thr Leu Lys Leu Ala Lys Glu Ile Arg Lys Lys
                165                 170                 175

Thr Glu Trp Gly Tyr His Gly Tyr Pro His Cys Leu Ser Gly Ser Thr
            180                 185                 190

Asp Lys Pro Ser Phe Asp Cys Asp Ala Leu Ser Met Ser Glu Asn Asp
        195                 200                 205

Lys Met Ser Trp Leu Phe Asn Asn Gln Asn Val Leu Leu Pro Ser Ile
    210                 215                 220

Tyr Leu Lys Asn Val Leu Lys Pro Asp Glu Lys Ile His Leu Val Gln
225                 230                 235                 240

Glu Arg Leu Lys Glu Ala Ile Arg Ile Ser Lys Asn Phe Lys His Leu
                245                 250                 255

Pro Lys Val Leu Pro Tyr Trp Trp Tyr Thr Tyr Gln Asp Lys Glu Ser
            260                 265                 270

Ile Phe Leu Thr Glu Ala Asp Val Lys Asn Thr Phe Lys Glu Ile Leu
        275                 280                 285
```

```
Thr Asn Gly Ala Asp Gly Ile Ile Ile Trp Gly Val Ser Tyr Glu Leu
    290                 295                 300

Thr Asp Arg Lys Arg Cys Glu Lys Leu Lys Glu Tyr Leu Met Lys Ile
305                 310                 315                 320

Leu Gly Pro Ile Ala Phe Lys Val Thr Lys Ala Val Lys Glu Asn Thr
                325                 330                 335

Pro Leu Asn Phe
            340

<210> SEQ ID NO 14
<211> LENGTH: 382
<212> TYPE: PRT
<213> ORGANISM: Apis mellifera
<220> FEATURE:
<223> OTHER INFORMATION: hyaluronidase

<400> SEQUENCE: 14

Met Ser Arg Pro Leu Val Ile Thr Glu Gly Met Met Ile Gly Val Leu
1               5                   10                  15

Leu Met Leu Ala Pro Ile Asn Ala Leu Leu Leu Gly Phe Val Gln Ser
                20                  25                  30

Thr Pro Asp Asn Asn Lys Thr Val Arg Glu Phe Asn Val Tyr Trp Asn
            35                  40                  45

Val Pro Thr Phe Met Cys His Lys Tyr Gly Leu Arg Phe Glu Glu Val
        50                  55                  60

Ser Glu Lys Tyr Gly Ile Leu Gln Asn Trp Met Asp Lys Phe Arg Gly
65                  70                  75                  80

Glu Glu Ile Ala Ile Leu Tyr Asp Pro Gly Met Phe Pro Ala Leu Leu
                85                  90                  95

Lys Asp Pro Asn Gly Asn Val Val Ala Arg Asn Gly Gly Val Pro Gln
            100                 105                 110

Leu Gly Asn Leu Thr Lys His Leu Gln Val Phe Arg Asp His Leu Ile
        115                 120                 125

Asn Gln Ile Pro Asp Lys Ser Phe Pro Gly Val Gly Val Ile Asp Phe
130                 135                 140

Glu Ser Trp Arg Pro Ile Phe Arg Gln Asn Trp Ala Ser Leu Gln Pro
145                 150                 155                 160

Tyr Lys Lys Leu Ser Val Glu Val Arg Arg Glu His Pro Phe Trp
                165                 170                 175

Asp Asp Gln Arg Val Glu Gln Glu Ala Lys Arg Arg Phe Glu Lys Tyr
            180                 185                 190

Gly Gln Leu Phe Met Glu Glu Thr Leu Lys Ala Ala Lys Arg Met Arg
        195                 200                 205

Pro Ala Ala Asn Trp Gly Tyr Tyr Ala Tyr Pro Tyr Cys Tyr Asn Leu
    210                 215                 220

Thr Pro Asn Gln Pro Ser Ala Gln Cys Glu Ala Thr Thr Met Gln Glu
225                 230                 235                 240

Asn Asp Lys Met Ser Trp Leu Phe Glu Ser Glu Asp Val Leu Leu Pro
                245                 250                 255

Ser Val Tyr Leu Arg Trp Asn Leu Thr Ser Gly Glu Arg Val Gly Leu
            260                 265                 270

Val Gly Gly Arg Val Lys Glu Ala Leu Arg Ile Ala Arg Gln Met Thr
        275                 280                 285

Thr Ser Arg Lys Lys Val Leu Pro Tyr Tyr Trp Tyr Lys Tyr Gln Asp
    290                 295                 300
```

Arg Arg Asp Thr Asp Leu Ser Arg Ala Asp Leu Glu Ala Thr Leu Arg
305                 310                 315                 320

Lys Ile Thr Asp Leu Gly Ala Asp Gly Phe Ile Trp Gly Ser Ser
            325                 330                 335

Asp Asp Ile Asn Thr Lys Ala Lys Cys Leu Gln Phe Arg Glu Tyr Leu
                340                 345                 350

Asn Asn Glu Leu Gly Pro Ala Val Lys Arg Ile Ala Leu Asn Asn Asn
            355                 360                 365

Ala Asn Asp Arg Leu Thr Val Asp Val Ser Val Asp Gln Val
            370                 375                 380

<210> SEQ ID NO 15
<211> LENGTH: 331
<212> TYPE: PRT
<213> ORGANISM: Dolichovespula maculata
<220> FEATURE:
<223> OTHER INFORMATION: hyaluronidase

<400> SEQUENCE: 15

Ser Glu Arg Pro Lys Arg Val Phe Asn Ile Tyr Trp Asn Val Pro Thr
1               5                   10                  15

Phe Met Cys His Gln Tyr Gly Leu Tyr Phe Asp Glu Val Thr Asn Phe
                20                  25                  30

Asn Ile Lys His Asn Ser Lys Asp Asp Phe Gln Gly Asp Lys Ile Ser
            35                  40                  45

Ile Phe Tyr Asp Pro Gly Glu Phe Pro Ala Leu Leu Pro Leu Lys Glu
50                  55                  60

Gly Asn Tyr Lys Ile Arg Asn Gly Gly Val Pro Gln Glu Gly Asn Ile
65                  70                  75                  80

Thr Ile His Leu Gln Arg Phe Ile Glu Asn Leu Asp Lys Thr Tyr Pro
                85                  90                  95

Asn Arg Asn Phe Asn Gly Ile Gly Val Ile Asp Phe Glu Arg Trp Arg
            100                 105                 110

Pro Ile Phe Arg Gln Asn Trp Gly Asn Met Met Ile His Lys Lys Phe
        115                 120                 125

Ser Ile Asp Leu Val Arg Asn Glu His Pro Phe Trp Asp Lys Lys Met
130                 135                 140

Ile Glu Leu Glu Ala Ser Lys Arg Phe Glu Lys Tyr Ala Arg Leu Phe
145                 150                 155                 160

Met Glu Glu Thr Leu Lys Leu Ala Lys Lys Thr Arg Lys Gln Ala Asp
                165                 170                 175

Trp Gly Tyr Tyr Gly Tyr Pro Tyr Cys Phe Asn Met Ser Pro Asn Asn
            180                 185                 190

Leu Val Pro Asp Cys Asp Ala Thr Ala Met Leu Glu Asn Asp Lys Met
        195                 200                 205

Ser Trp Leu Phe Asn Asn Gln Asn Val Leu Leu Pro Ser Val Tyr Ile
210                 215                 220

Arg His Glu Leu Thr Pro Asp Gln Arg Val Gly Leu Val Gln Gly Arg
225                 230                 235                 240

Val Lys Glu Ala Val Arg Ile Ser Asn Asn Leu Lys His Ser Pro Lys
                245                 250                 255

Val Leu Ser Tyr Trp Trp Tyr Val Tyr Gln Asp Asp Thr Asn Thr Phe
            260                 265                 270

Leu Thr Glu Thr Asp Val Lys Lys Thr Phe Gln Glu Ile Ala Ile Asn
        275                 280                 285

```
Gly Gly Asp Gly Ile Ile Ile Trp Gly Ser Ser Ser Asp Val Asn Ser
            290                 295                 300

Leu Ser Lys Cys Lys Arg Leu Arg Glu Tyr Leu Leu Thr Val Leu Gly
305                 310                 315                 320

Pro Ile Thr Val Asn Val Thr Glu Thr Val Asn
                325                 330

<210> SEQ ID NO 16
<211> LENGTH: 367
<212> TYPE: PRT
<213> ORGANISM: Polistes annularis
<220> FEATURE:
<223> OTHER INFORMATION: hyaluronidase

<400> SEQUENCE: 16

Tyr Val Ser Leu Ser Pro Asp Ser Val Phe Asn Ile Ile Thr Asp Asp
  1               5                  10                  15

Ile Ser His Gln Ile Leu Ser Arg Ser Asn Cys Glu Arg Ser Lys Arg
                 20                  25                  30

Pro Lys Arg Val Phe Ser Ile Tyr Trp Asn Val Pro Thr Phe Met Cys
             35                  40                  45

His Gln Tyr Gly Met Asn Phe Asp Glu Val Thr Asp Phe Asn Ile Lys
 50                  55                  60

His Asn Ser Lys Asp Asn Phe Arg Gly Glu Thr Ile Ser Ile Tyr Tyr
 65                  70                  75                  80

Asp Pro Gly Lys Phe Pro Ala Leu Met Pro Leu Lys Asn Gly Asn Tyr
                 85                  90                  95

Glu Glu Arg Asn Gly Gly Val Pro Gln Arg Gly Asn Ile Thr Ile His
            100                 105                 110

Leu Gln Gln Phe Asn Glu Asp Leu Asp Lys Met Thr Pro Asp Lys Asn
            115                 120                 125

Phe Gly Gly Ile Gly Val Ile Asp Phe Glu Arg Trp Lys Pro Ile Phe
130                 135                 140

Arg Gln Asn Trp Gly Asn Thr Glu Ile His Lys Lys Tyr Ser Ile Glu
145                 150                 155                 160

Leu Val Arg Lys Glu His Pro Lys Trp Ser Glu Ser Met Ile Glu Ala
                165                 170                 175

Glu Ala Thr Lys Lys Phe Glu Lys Tyr Ala Arg Tyr Phe Met Glu Glu
            180                 185                 190

Thr Leu Lys Leu Ala Lys Lys Thr Arg Lys Arg Ala Lys Trp Gly Tyr
            195                 200                 205

Tyr Gly Phe Pro Tyr Cys Tyr Asn Val Thr Pro Asn Asn Pro Gly Pro
210                 215                 220

Asp Cys Asp Ala Lys Ala Thr Ile Glu Asn Asp Arg Leu Ser Trp Met
225                 230                 235                 240

Tyr Asn Asn Gln Glu Ile Leu Phe Pro Ser Val Tyr Val Arg His Glu
                245                 250                 255

Gln Lys Pro Glu Glu Arg Val Tyr Leu Val Gln Gly Arg Ile Lys Glu
            260                 265                 270

Ala Val Arg Ile Ser Asn Asn Leu Glu His Ser Pro Ser Val Leu Ala
            275                 280                 285

Tyr Trp Trp Tyr Val Tyr Gln Asp Lys Met Asp Ile Tyr Leu Ser Glu
        290                 295                 300

Thr Asp Val Glu Lys Thr Phe Gln Glu Ile Val Thr Asn Gly Gly Asp
305                 310                 315                 320
```

```
Gly Ile Ile Ile Trp Gly Ser Ser Asp Val Asn Ser Leu Ser Lys
                325                 330                 335

Cys Lys Arg Leu Arg Glu Tyr Leu Leu Asn Thr Leu Gly Pro Phe Ala
                340                 345                 350

Val Asn Val Thr Glu Thr Val Asn Gly Arg Ser Ser Leu Asn Phe
                355                 360                 365

<210> SEQ ID NO 17
<211> LENGTH: 462
<212> TYPE: PRT
<213> ORGANISM: Mus musculus
<220> FEATURE:
<223> OTHER INFORMATION: hyaluronidase

<400> SEQUENCE: 17

Met Leu Gly Leu Thr Gln His Ala Gln Lys Val Trp Arg Met Lys Pro
  1               5                  10                  15

Phe Ser Pro Glu Val Ser Pro Gly Ser Ser Pro Ala Thr Ala Gly His
                 20                  25                  30

Leu Leu Arg Ile Ser Thr Leu Phe Leu Thr Leu Leu Glu Leu Ala Gln
             35                  40                  45

Val Cys Arg Gly Ser Val Val Ser Asn Arg Pro Phe Ile Thr Val Trp
 50                  55                  60

Asn Gly Asp Thr His Trp Cys Leu Thr Glu Tyr Gly Val Asp Val Asp
 65                  70                  75                  80

Val Ser Val Phe Asp Val Val Ala Asn Lys Glu Gln Ser Phe Gln Gly
                 85                  90                  95

Ser Asn Met Thr Ile Phe Tyr Arg Glu Glu Leu Gly Thr Tyr Pro Tyr
                100                 105                 110

Tyr Thr Pro Thr Gly Glu Pro Val Phe Gly Gly Leu Pro Gln Asn Ala
            115                 120                 125

Ser Leu Val Thr His Leu Ala His Thr Phe Gln Asp Ile Lys Ala Ala
        130                 135                 140

Met Pro Glu Pro Asp Phe Ser Gly Leu Ala Val Ile Asp Trp Glu Ala
145                 150                 155                 160

Trp Arg Pro Arg Trp Ala Phe Asn Trp Asp Ser Lys Asp Ile Tyr Arg
                165                 170                 175

Gln Arg Ser Met Glu Leu Val Gln Ala Glu His Pro Asp Trp Pro Glu
            180                 185                 190

Thr Leu Val Glu Ala Ala Ala Lys Asn Gln Phe Gln Glu Ala Ala Glu
        195                 200                 205

Ala Trp Met Ala Gly Thr Leu Gln Leu Gly Gln Val Leu Arg Pro Arg
    210                 215                 220

Gly Leu Trp Gly Tyr Tyr Gly Phe Pro Asp Cys Tyr Asn Asn Asp Phe
225                 230                 235                 240

Leu Ser Leu Asn Tyr Thr Gly Gln Cys Pro Val Phe Val Arg Asp Gln
                245                 250                 255

Asn Asp Gln Leu Gly Trp Leu Trp Asn Gln Ser Tyr Ala Leu Tyr Pro
            260                 265                 270

Ser Ile Tyr Leu Pro Ala Ala Leu Met Gly Thr Gly Lys Ser Gln Met
        275                 280                 285

Tyr Val Arg His Arg Val Gln Glu Ala Leu Arg Val Ala Ile Val Ser
    290                 295                 300

Arg Asp Pro His Val Pro Val Met Pro Tyr Val Gln Ile Phe Tyr Glu
305                 310                 315                 320
```

```
Met Thr Asp Tyr Leu Leu Pro Leu Glu Glu Leu His Ser Leu Gly
            325                 330                 335

Glu Ser Ala Ala Gln Gly Val Ala Gly Ala Val Leu Trp Leu Ser Ser
            340                 345                 350

Asp Lys Thr Ser Thr Lys Glu Ser Cys Gln Ala Ile Lys Ala Tyr Met
            355                 360                 365

Asp Ser Thr Leu Gly Pro Phe Ile Val Asn Val Thr Ser Ala Ala Leu
            370                 375                 380

Leu Cys Ser Glu Ala Leu Cys Ser Gly His Gly Arg Cys Val Arg His
385                 390                 395                 400

Pro Ser Tyr Pro Glu Ala Leu Leu Thr Leu Asn Pro Ala Ser Phe Ser
                405                 410                 415

Ile Glu Leu Thr His Asp Gly Arg Pro Pro Ser Leu Lys Gly Thr Leu
                420                 425                 430

Ser Leu Lys Asp Arg Ala Gln Met Ala Met Lys Phe Arg Cys Arg Cys
            435                 440                 445

Tyr Arg Gly Trp Arg Gly Lys Trp Cys Asp Lys Arg Gly Met
            450                 455                 460

<210> SEQ ID NO 18
<211> LENGTH: 473
<212> TYPE: PRT
<213> ORGANISM: Mus musculus
<220> FEATURE:
<223> OTHER INFORMATION: Hyaluronidase 2

<400> SEQUENCE: 18

Met Arg Ala Gly Leu Gly Pro Ile Ile Thr Leu Ala Leu Val Leu Glu
1               5                   10                  15

Val Ala Trp Ala Gly Glu Leu Lys Pro Thr Ala Pro Pro Ile Phe Thr
                20                  25                  30

Gly Arg Pro Phe Val Val Ala Trp Asn Val Pro Thr Gln Glu Cys Ala
            35                  40                  45

Pro Arg His Lys Val Pro Leu Asp Leu Arg Ala Phe Asp Val Lys Ala
        50                  55                  60

Thr Pro Asn Glu Gly Phe Phe Asn Gln Asn Ile Thr Thr Phe Tyr Tyr
65                  70                  75                  80

Asp Arg Leu Gly Leu Tyr Pro Arg Phe Asp Ala Ala Gly Thr Ser Val
                85                  90                  95

His Gly Gly Val Pro Gln Asn Gly Ser Leu Cys Ala His Leu Pro Met
            100                 105                 110

Leu Lys Glu Ser Val Glu Arg Tyr Ile Gln Thr Gln Glu Pro Gly Gly
        115                 120                 125

Leu Ala Val Ile Asp Trp Glu Glu Trp Arg Pro Val Trp Val Arg Asn
    130                 135                 140

Trp Gln Glu Lys Asp Val Tyr Arg Gln Ser Ser Arg Gln Leu Val Ala
145                 150                 155                 160

Ser Arg His Pro Asp Trp Pro Ser Asp Arg Val Met Lys Gln Ala Gln
                165                 170                 175

Tyr Glu Phe Glu Phe Ala Ala Arg Gln Phe Met Leu Asn Thr Leu Arg
            180                 185                 190

Tyr Val Lys Ala Val Arg Pro Gln His Leu Trp Gly Phe Tyr Leu Phe
        195                 200                 205

Pro Asp Cys Tyr Asn His Asp Tyr Val Gln Asn Trp Glu Ser Tyr Thr
    210                 215                 220
```

-continued

Gly Arg Cys Pro Asp Val Glu Val Ala Arg Asn Asp Gln Leu Ala Trp
225                 230                 235                 240

Leu Trp Ala Glu Ser Thr Ala Leu Phe Pro Ser Val Tyr Leu Asp Glu
        245                 250                 255

Thr Leu Ala Ser Ser Val His Ser Arg Asn Phe Val Ser Phe Arg Val
            260                 265                 270

Arg Glu Ala Leu Arg Val Ala His Thr His His Ala Asn His Ala Leu
        275                 280                 285

Pro Val Tyr Val Phe Thr Arg Pro Thr Tyr Thr Arg Gly Leu Thr Gly
    290                 295                 300

Leu Ser Gln Val Asp Leu Ile Ser Thr Ile Gly Glu Ser Ala Ala Leu
305                 310                 315                 320

Gly Ser Ala Gly Val Ile Phe Trp Gly Asp Ser Glu Asp Ala Ser Ser
                325                 330                 335

Met Glu Thr Cys Gln Tyr Leu Lys Asn Tyr Leu Thr Gln Leu Leu Val
                340                 345                 350

Pro Tyr Ile Val Asn Val Ser Trp Ala Thr Gln Tyr Cys Ser Trp Thr
            355                 360                 365

Gln Cys His Gly His Gly Arg Cys Val Arg Arg Asn Pro Ser Ala Asn
        370                 375                 380

Thr Phe Leu His Leu Asn Ala Ser Ser Phe Arg Leu Val Pro Gly His
385                 390                 395                 400

Thr Pro Ser Glu Pro Gln Leu Arg Pro Glu Gly Gln Leu Ser Glu Ala
                405                 410                 415

Asp Leu Asn Tyr Leu Gln Lys His Phe Arg Cys Gln Cys Tyr Leu Gly
            420                 425                 430

Trp Gly Gly Glu Gln Cys Gln Arg Asn Tyr Lys Gly Ala Ala Gly Asn
        435                 440                 445

Ala Ser Arg Ala Trp Ala Gly Ser His Leu Thr Ser Leu Leu Gly Leu
    450                 455                 460

Val Ala Val Ala Leu Thr Trp Thr Leu
465                 470

<210> SEQ ID NO 19
<211> LENGTH: 412
<212> TYPE: PRT
<213> ORGANISM: Mus musculus
<220> FEATURE:
<223> OTHER INFORMATION: hyalurinidase 3

<400> SEQUENCE: 19

Met Ile Met His Leu Gly Leu Met Met Val Val Gly Leu Thr Leu Cys
1               5                   10                  15

Leu Met His Gly Gln Ala Leu Leu Gln Val Pro Glu His Pro Phe Ser
                20                  25                  30

Val Val Trp Asn Val Pro Ser Ala Arg Cys Lys Ala His Phe Gly Val
            35                  40                  45

His Leu Pro Leu Asp Ala Leu Gly Ile Val Ala Asn His Gly Gln His
        50                  55                  60

Phe His Gly Gln Asn Ile Ser Ile Phe Tyr Lys Asn Gln Phe Gly Leu
65                  70                  75                  80

Tyr Pro Tyr Phe Gly Pro Arg Gly Thr Ala His Asn Gly Gly Ile Pro
                85                  90                  95

Gln Ala Val Ser Leu Asp His His Leu Ala Arg Ala Ala His Gln Ile
            100                 105                 110

-continued

```
Leu His Ser Leu Gly Ser Ser Phe Ala Gly Leu Ala Val Leu Asp Trp
        115                 120                 125

Glu Glu Trp Tyr Pro Leu Trp Ala Gly Asn Trp Gly Pro His Arg Gln
    130                 135                 140

Val Tyr Leu Ala Ala Ser Trp Val Trp Thr Gln Gln Met Phe Pro Gly
145                 150                 155                 160

Leu Asp Pro Gln Glu Gln Leu His Lys Ala His Thr Ser Phe Glu Gln
                165                 170                 175

Ala Ala Arg Ala Leu Met Glu Tyr Thr Leu Gln Leu Gly Arg Thr Leu
            180                 185                 190

Arg Pro Ser Gly Leu Trp Gly Phe Tyr Arg Tyr Pro Ala Cys Gly Asn
        195                 200                 205

Gly Trp His Lys Met Ala Ser Asn Tyr Thr Gly His Cys His Ala Ala
    210                 215                 220

Ile Thr Thr Gln Asn Thr Gln Leu Arg Trp Leu Trp Ala Ala Ser Ser
225                 230                 235                 240

Ala Leu Phe Pro Ser Ile Tyr Leu Pro Pro Arg Leu Pro Leu Ala Tyr
                245                 250                 255

Arg Gln Ala Phe Val Arg His Arg Leu Glu Glu Ala Phe Arg Val Ala
            260                 265                 270

Leu Leu Glu His Ser His Pro Leu Pro Val Leu Ala Tyr Ser Arg Leu
        275                 280                 285

Thr His Arg Ser Ser Gly Arg Phe Leu Ser Leu Asp Asp Leu Met Gln
    290                 295                 300

Thr Ile Gly Val Ser Ala Ala Leu Gly Thr Ala Gly Val Val Leu Trp
305                 310                 315                 320

Gly Asp Leu Ser Phe Ser Ser Ser Glu Glu Lys Cys Trp Arg Leu His
                325                 330                 335

Asp Tyr Leu Val Gly Thr Leu Gly Pro Tyr Val Ile Asn Val Thr Lys
            340                 345                 350

Ala Asp Met Ala Cys Ser His Gln Arg Cys His Gly His Gly Arg Cys
        355                 360                 365

Ala Arg Lys Asp Pro Gly Gln Met Glu Ala Phe Leu His Leu Gln Pro
    370                 375                 380

Asp Asp Ser Leu Gly Ala Trp Asn Ser Phe Arg Cys His Cys Tyr Ser
385                 390                 395                 400

Gly Trp Ala Gly Pro Thr Cys Leu Glu Pro Lys Pro
                405                 410

<210> SEQ ID NO 20
<211> LENGTH: 435
<212> TYPE: PRT
<213> ORGANISM: Sus scrofa
<220> FEATURE:
<223> OTHER INFORMATION: hyalauronidase

<400> SEQUENCE: 20

Met Ala Ala His Leu Leu Pro Ile Cys Thr Leu Phe Leu Asn Leu Leu
  1               5                  10                  15

Ser Val Ala Gln Gly Ser Arg Asp Pro Val Val Leu Asn Arg Pro Phe
                20                  25                  30

Thr Thr Ile Trp Asn Ala Asn Thr Gln Trp Cys Leu Lys Arg His Gly
            35                  40                  45

Val Asp Val Asp Val Ser Val Phe Glu Val Val Val Asn Pro Gly Gln
        50                  55                  60
```

```
Thr Phe Arg Gly Pro Asn Met Thr Ile Phe Tyr Ser Ser Gln Leu Gly
 65                  70                  75                  80

Thr Tyr Pro Tyr Tyr Thr Ser Ala Gly Glu Pro Val Phe Gly Gly Leu
                 85                  90                  95

Pro Gln Asn Ala Ser Leu Asp Val His Leu Asn Arg Thr Phe Lys Asp
            100                 105                 110

Ile Leu Ala Ala Met Pro Glu Ser Asn Phe Ser Gly Leu Ala Val Ile
        115                 120                 125

Asp Trp Glu Ala Trp Arg Pro Arg Trp Ala Phe Asn Trp Asp Ala Lys
    130                 135                 140

Asp Ile Tyr Arg Gln Arg Ser Arg Ala Leu Val Gln Lys Gln His Pro
145                 150                 155                 160

Asp Trp Pro Ala Pro Trp Val Glu Ala Ala Gln Asp Gln Phe Gln
                165                 170                 175

Glu Ala Ala Gln Thr Trp Met Ala Gly Thr Leu Lys Leu Gly Gln Thr
            180                 185                 190

Leu Arg Pro His Gly Leu Trp Gly Phe Tyr Gly Phe Pro Asp Cys Tyr
        195                 200                 205

Asn Tyr Asp Phe Gln Ser Ser Asn Tyr Thr Gly Gln Cys Pro Pro Gly
    210                 215                 220

Val Ser Ala Gln Asn Asp Gln Leu Gly Trp Leu Trp Gly Gln Ser Arg
225                 230                 235                 240

Ala Leu Tyr Pro Ser Ile Tyr Leu Pro Ser Ala Leu Glu Gly Thr Asn
                245                 250                 255

Lys Thr Gln Leu Tyr Val Gln His Arg Val Asn Glu Ala Phe Arg Val
            260                 265                 270

Ala Ala Ala Ala Gly Asp Pro Asn Leu Pro Val Leu Pro Tyr Ala Gln
        275                 280                 285

Ile Phe His Asp Met Thr Asn Arg Leu Leu Ser Arg Glu Glu Leu Glu
    290                 295                 300

His Ser Leu Gly Glu Ser Ala Ala Gln Gly Ala Ala Gly Val Val Leu
305                 310                 315                 320

Trp Val Ser Trp Glu Asn Thr Arg Thr Lys Glu Ser Cys Gln Ser Ile
                325                 330                 335

Lys Glu Tyr Val Asp Thr Thr Leu Gly Pro Phe Ile Leu Asn Val Thr
            340                 345                 350

Ser Gly Ala Leu Leu Cys Ser Gln Ala Val Cys Ser Gly His Gly Arg
        355                 360                 365

Cys Val Arg Arg Pro Ser His Thr Glu Ala Leu Pro Ile Leu Asn Pro
    370                 375                 380

Ser Ser Phe Ser Ile Lys Pro Thr Pro Gly Gly Pro Leu Thr Leu
385                 390                 395                 400

Gln Gly Ala Leu Ser Leu Lys Asp Arg Val Gln Met Ala Glu Glu Phe
                405                 410                 415

Gln Cys Arg Cys Tyr Pro Gly Trp Arg Gly Thr Trp Cys Glu Gln Gln
            420                 425                 430

Gly Thr Arg
        435

<210> SEQ ID NO 21
<211> LENGTH: 419
<212> TYPE: PRT
<213> ORGANISM: Sus scrofa
<220> FEATURE:
```

<223> OTHER INFORMATION: hyaluronidase 3

<400> SEQUENCE: 21

```
Met Thr Met Gln Leu Gly Leu Ala Leu Val Leu Gly Val Ala Met Cys
 1               5                  10                  15

Leu Gly Cys Gly Gln Pro Leu Leu Arg Ala Pro Glu Arg Pro Phe Cys
             20                  25                  30

Val Leu Trp Asn Val Pro Ser Ala Arg Cys Lys Ala Arg Phe Gly Val
         35                  40                  45

His Leu Pro Leu Glu Ala Leu Gly Ile Thr Ala Asn His Gly Gln Arg
     50                  55                  60

Phe His Gly Gln Asn Ile Thr Ile Phe Tyr Lys Ser Gln Leu Gly Leu
 65                  70                  75                  80

Tyr Pro Tyr Phe Gly Pro Arg Gly Thr Ala His Asn Gly Gly Ile Pro
                 85                  90                  95

Gln Ala Val Ser Leu Asp His His Leu Ala Arg Ala Ala Tyr Gln Ile
            100                 105                 110

His Arg Ser Leu Arg Pro Gly Phe Thr Gly Leu Ala Val Leu Asp Trp
        115                 120                 125

Glu Glu Trp Cys Pro Leu Trp Ala Gly Asn Trp Gly Arg Arg Gln Ala
130                 135                 140

Tyr Gln Ala Ala Ser Cys Ala Trp Ala Gln Arg Val Tyr Pro Asn Leu
145                 150                 155                 160

Asp Pro Gln Glu Gln Leu Cys Lys Ala Arg Ala Gly Phe Glu Glu Ala
                165                 170                 175

Ala Arg Ala Leu Met Glu Asp Thr Leu Arg Leu Gly Arg Met Leu Arg
            180                 185                 190

Pro His Gly Leu Trp Gly Phe Tyr His Tyr Pro Ala Cys Gly Asn Gly
        195                 200                 205

Trp His Gly Thr Ala Ser Asn Tyr Thr Gly His Cys His Ala Ala Ala
    210                 215                 220

Leu Ala Arg Asn Thr Gln Leu Tyr Trp Leu Trp Ala Ala Ser Ser Ala
225                 230                 235                 240

Leu Phe Pro Ser Ile Tyr Leu Pro Pro Gly Leu Pro Pro Ala Tyr His
                245                 250                 255

Gln Ala Phe Val Arg Tyr Arg Leu Glu Glu Ala Phe Arg Val Ala Leu
            260                 265                 270

Val Gly His Pro His Pro Leu Pro Val Leu Ala Tyr Ala Arg Leu Thr
        275                 280                 285

His Arg Asn Ser Gly Arg Phe Leu Ser Gln Asp Glu Leu Val Gln Thr
    290                 295                 300

Ile Gly Val Ser Ala Ala Leu Gly Ala Ser Gly Val Val Leu Trp Gly
305                 310                 315                 320

Asp Leu Ser Phe Ser Ser Ser Glu Glu Glu Cys Trp His Leu Arg Gly
                325                 330                 335

Tyr Leu Val Gly Thr Leu Gly Pro Tyr Val Ile Asn Val Thr Arg Ala
            340                 345                 350

Ala Met Ala Cys Ser His Gln Arg Cys His Gly His Gly Arg Cys Ala
        355                 360                 365

Trp Gln Asp Pro Gly Gln Leu Lys Val Phe Leu His Leu His Pro Gly
    370                 375                 380

Gly Ser Pro Gly Ala Trp Glu Ser Phe Ser Cys Arg Cys Tyr Trp Gly
385                 390                 395                 400
```

Trp Ala Gly Pro Thr Cys Gln Glu Pro Arg Pro Glu Leu Gly Pro Glu
                405                 410                 415

Glu Ala Thr

<210> SEQ ID NO 22
<211> LENGTH: 449
<212> TYPE: PRT
<213> ORGANISM: Rattus norvegicus
<220> FEATURE:
<223> OTHER INFORMATION: hyaluronidase 1

<400> SEQUENCE: 22

Met Lys Pro Phe Ser Pro Glu Val Ser Pro Asp Pro Cys Pro Ala Thr
 1               5                  10                  15

Ala Ala His Leu Leu Arg Thr Tyr Thr Leu Phe Leu Thr Leu Leu Glu
                20                  25                  30

Leu Ala Gln Gly Cys Arg Gly Ser Met Val Ser Asn Arg Pro Phe Ile
            35                  40                  45

Thr Val Trp Asn Ala Asp Thr His Trp Cys Leu Lys Asp His Gly Val
 50                  55                  60

Asp Val Asp Val Ser Val Phe Asp Val Val Ala Asn Lys Glu Gln Asn
65                  70                  75                  80

Phe Gln Gly Pro Asn Met Thr Ile Phe Tyr Arg Glu Leu Gly Thr
                85                  90                  95

Tyr Pro Tyr Tyr Thr Pro Thr Gly Glu Pro Val Phe Gly Gly Leu Pro
                100                 105                 110

Gln Asn Ala Ser Leu Val Thr His Leu Ala His Ala Phe Gln Asp Ile
            115                 120                 125

Lys Ala Ala Met Pro Glu Pro Asp Phe Ser Gly Leu Ala Val Ile Asp
130                 135                 140

Trp Glu Ala Trp Arg Pro Arg Trp Ala Phe Asn Trp Asp Ser Lys Asp
145                 150                 155                 160

Ile Tyr Gln Gln Arg Ser Met Glu Leu Val Arg Ala Glu His Pro Asp
                165                 170                 175

Trp Pro Glu Thr Leu Val Glu Ala Glu Ala Gln Gly Gln Phe Gln Glu
            180                 185                 190

Ala Ala Glu Ala Trp Met Ala Gly Thr Leu Gln Leu Gly Gln Val Leu
        195                 200                 205

Arg Pro Arg Gly Leu Trp Gly Tyr Tyr Gly Phe Pro Asp Cys Tyr Asn
    210                 215                 220

Tyr Asp Phe Leu Ser Pro Asn Tyr Thr Gly Gln Cys Ser Leu Ser Ile
225                 230                 235                 240

His Asp Gln Asn Asp Gln Leu Gly Trp Leu Trp Asn Gln Ser Tyr Ala
                245                 250                 255

Leu Tyr Pro Ser Ile Tyr Leu Pro Ala Ala Leu Met Gly Thr Gly Lys
            260                 265                 270

Ser Gln Met Tyr Val Arg Tyr Arg Val Gln Glu Ala Phe Arg Leu Ala
        275                 280                 285

Leu Val Ser Arg Asp Pro His Val Pro Ile Met Pro Tyr Val Gln Ile
    290                 295                 300

Phe Tyr Glu Lys Thr Asp Tyr Leu Leu Pro Leu Glu Glu Leu Glu His
305                 310                 315                 320

Ser Leu Gly Glu Ser Ala Ala Gln Gly Ala Ala Gly Ala Val Leu Trp
                325                 330                 335

Ile Ser Ser Glu Lys Thr Ser Thr Lys Glu Ser Cys Gln Ala Ile Lys

```
            340                 345                 350
Ala Tyr Met Asp Ser Thr Leu Gly Pro Phe Ile Leu Asn Val Thr Ser
            355                 360                 365

Ala Ala Leu Leu Cys Ser Glu Ala Leu Cys Ser Gly Arg Gly Arg Cys
370                 375                 380

Val Arg His Pro Ser Tyr Pro Glu Ala Leu Leu Thr Leu Ser Pro Ala
385                 390                 395                 400

Ser Phe Ser Ile Glu Pro Thr His Asp Gly Arg Pro Leu Ser Leu Lys
                405                 410                 415

Gly Thr Leu Ser Leu Lys Asp Arg Ala Gln Met Ala Met Lys Phe Lys
                420                 425                 430

Cys Arg Cys Tyr Arg Gly Trp Ser Gly Glu Trp Cys Lys Lys Gln Asp
                435                 440                 445

Met
```

<210> SEQ ID NO 23
<211> LENGTH: 473
<212> TYPE: PRT
<213> ORGANISM: Rattus norvegicus
<220> FEATURE:
<223> OTHER INFORMATION: hyaluronidase 2

<400> SEQUENCE: 23

```
Met Arg Ala Gly Leu Gly Pro Ile Ile Thr Leu Ala Leu Val Leu Glu
1               5                   10                  15

Val Ala Trp Ala Ser Glu Leu Lys Pro Thr Ala Pro Pro Ile Phe Thr
                20                  25                  30

Gly Arg Pro Phe Val Val Ala Trp Asn Val Pro Thr Gln Glu Cys Ala
            35                  40                  45

Pro Arg His Lys Val Pro Leu Asp Leu Arg Ala Phe Asp Val Glu Ala
        50                  55                  60

Thr Pro Asn Glu Gly Phe Phe Asn Gln Asn Ile Thr Thr Phe Tyr Tyr
65                  70                  75                  80

Asp Arg Leu Gly Leu Tyr Pro Arg Phe Asp Ala Ala Gly Met Ser Val
                85                  90                  95

His Gly Gly Val Pro Gln Asn Gly Ser Leu Cys Ala His Leu Pro Met
                100                 105                 110

Leu Lys Glu Ala Val Glu Arg Tyr Ile Gln Thr Gln Glu Pro Ala Gly
            115                 120                 125

Leu Ala Val Ile Asp Trp Glu Glu Trp Arg Pro Val Trp Val Arg Asn
130                 135                 140

Trp Gln Glu Lys Asp Val Tyr Arg Gln Ser Ser Arg Gln Leu Val Ala
145                 150                 155                 160

Ser Arg His Pro Asp Trp Pro Ser Asp Arg Ile Val Lys Gln Ala Gln
                165                 170                 175

Tyr Glu Phe Glu Phe Ala Ala Arg Gln Phe Met Leu Asn Thr Leu Arg
            180                 185                 190

Tyr Val Lys Ala Val Arg Pro Gln His Leu Trp Gly Phe Tyr Leu Phe
        195                 200                 205

Pro Asp Cys Tyr Asn His Asp Tyr Val Gln Asn Trp Asp Ser Tyr Thr
    210                 215                 220

Gly Arg Cys Pro Asp Val Glu Val Ala Gln Asn Asp Gln Leu Ala Trp
225                 230                 235                 240

Leu Trp Ala Glu Asn Thr Ala Leu Phe Pro Ser Val Tyr Leu Asp Lys
                245                 250                 255
```

```
Thr Leu Ala Ser Ser Lys His Ser Arg Asn Phe Val Ser Phe Arg Val
            260                 265                 270

Gln Glu Ala Leu Arg Val Ala His Thr His His Ala Asn His Ala Leu
        275                 280                 285

Pro Val Tyr Val Phe Thr Arg Pro Thr Tyr Thr Arg Arg Leu Thr Glu
    290                 295                 300

Leu Asn Gln Met Asp Leu Ile Ser Thr Ile Gly Glu Ser Ala Ala Leu
305                 310                 315                 320

Gly Ser Ala Gly Val Ile Phe Trp Gly Asp Ser Val Tyr Ala Ser Ser
                325                 330                 335

Met Glu Asn Cys Gln Asn Leu Lys Lys Tyr Leu Thr Gln Thr Leu Val
            340                 345                 350

Pro Tyr Ile Val Asn Val Ser Trp Ala Thr Gln Tyr Cys Ser Trp Thr
        355                 360                 365

Gln Cys His Gly His Gly Arg Cys Val Arg Arg Asn Pro Ser Ala Ser
    370                 375                 380

Thr Phe Leu His Leu Ser Pro Ser Ser Phe Arg Leu Val Pro Gly Arg
385                 390                 395                 400

Thr Pro Ser Glu Pro Gln Leu Arg Pro Glu Gly Glu Leu Ser Glu Asp
                405                 410                 415

Asp Leu Ser Tyr Leu Gln Met His Phe Arg Cys His Cys Tyr Leu Gly
            420                 425                 430

Trp Gly Gly Glu Gln Cys Gln Trp Asn His Lys Arg Ala Ala Gly Asp
        435                 440                 445

Ala Ser Arg Ala Trp Ala Gly Ala His Leu Ala Ser Leu Leu Gly Leu
    450                 455                 460

Val Ala Met Thr Leu Thr Trp Thr Leu
465                 470

<210> SEQ ID NO 24
<211> LENGTH: 412
<212> TYPE: PRT
<213> ORGANISM: Rattus norvegicus
<220> FEATURE:
<223> OTHER INFORMATION: hyaluronidase 3

<400> SEQUENCE: 24

Met Ile Thr Gln Leu Gly Leu Thr Leu Val Gly Leu Thr Leu Cys
  1               5                  10                  15

Leu Val His Val Gln Ala Leu Leu Gln Val Pro Glu Phe Pro Phe Ser
                20                  25                  30

Val Leu Trp Asn Val Pro Ser Ala Arg Cys Lys Thr Arg Phe Gly Val
            35                  40                  45

His Leu Pro Leu Asp Ala Leu Gly Ile Ile Ala Asn His Gly Gln Arg
        50                  55                  60

Phe His Gly Gln Asn Ile Thr Ile Phe Tyr Lys Asn Gln Phe Gly Leu
 65                 70                  75                  80

Tyr Pro Tyr Phe Gly Pro Arg Gly Thr Ala His Asn Gly Ile Pro
                85                  90                  95

Gln Ala Val Ser Leu Asp His Leu Ala Gln Ala His Gln Ile
            100                 105                 110

Leu His Asn Leu Gly Ser Ser Phe Ala Gly Leu Ala Val Leu Asp Trp
        115                 120                 125

Glu Glu Trp Tyr Pro Leu Trp Ala Gly Asn Trp Gly Thr His Arg Gln
    130                 135                 140
```

Val Tyr Gln Ala Ala Ser Trp Ala Trp Ala Gln Gln Met Phe Pro Asp
145                 150                 155                 160

Leu Asn Pro Gln Glu Gln Leu His Lys Ala Gln Thr Gly Phe Glu Gln
            165                 170                 175

Ala Ala Arg Ala Leu Met Glu His Thr Leu Arg Leu Gly Gln Met Leu
        180                 185                 190

Arg Pro His Gly Leu Trp Gly Phe Tyr Arg Tyr Pro Val Cys Gly Asn
    195                 200                 205

Gly Trp His Asn Met Ala Ser Asn Tyr Thr Gly His Cys His Pro Ala
210                 215                 220

Ile Ile Thr Arg Asn Thr Gln Leu Arg Trp Leu Trp Ala Ala Ser Ser
225                 230                 235                 240

Ala Leu Phe Pro Ser Ile Tyr Leu Pro Pro Arg Leu Pro Pro Ala Tyr
            245                 250                 255

His Gln Thr Phe Val Arg His Arg Leu Glu Glu Ala Phe Arg Val Ala
        260                 265                 270

Leu Thr Gly His Ala His Pro Leu Pro Val Leu Ala Tyr Val Arg Leu
    275                 280                 285

Thr His Arg Ser Ser Gly Arg Phe Leu Ser Leu Asp Asp Leu Met Gln
290                 295                 300

Thr Ile Gly Val Ser Ala Ala Leu Gly Ala Ala Gly Val Val Leu Trp
305                 310                 315                 320

Gly Asp Leu Ser Val Ser Ser Glu Glu Glu Cys Trp Arg Leu His
            325                 330                 335

Asp Tyr Leu Val Gly Thr Leu Gly Pro Tyr Val Ile Asn Val Thr Lys
        340                 345                 350

Ala Ala Thr Ala Cys Ser His Gln Arg Cys His Gly His Gly Arg Cys
    355                 360                 365

Ser Trp Lys Asp Pro Gly Gln Met Glu Ala Phe Leu His Leu Gln Pro
370                 375                 380

Asp Asp Asn Leu Gly Ala Trp Lys Ser Phe Arg Cys Arg Cys Tyr Leu
385                 390                 395                 400

Gly Trp Ser Gly Pro Thr Cys Leu Glu Pro Lys Pro
            405                 410

<210> SEQ ID NO 25
<211> LENGTH: 545
<212> TYPE: PRT
<213> ORGANISM: Oryctolagus cuniculus
<220> FEATURE:
<223> OTHER INFORMATION: PH20

<400> SEQUENCE: 25

Met Gly Val Leu Lys Phe Lys His Ile Phe Phe Gly Ser Ala Val Glu
1               5                   10                  15

Leu Ser Gly Val Phe Gln Ile Val Phe Ile Phe Leu Leu Ile Pro Cys
            20                  25                  30

Cys Leu Thr Ala Asn Phe Arg Ala Pro Pro Val Ile Pro Asn Val Pro
        35                  40                  45

Phe Leu Trp Ala Trp Asn Ala Pro Thr Glu Phe Cys Leu Gly Lys Ser
    50                  55                  60

Gly Glu Pro Leu Asp Met Ser Leu Phe Ser Leu Phe Gly Ser Pro Arg
65                  70                  75                  80

Lys Asn Lys Thr Gly Gln Gly Ile Thr Ile Phe Tyr Val Asp Arg Leu
            85                  90                  95

-continued

```
Gly Tyr Tyr Pro Tyr Ile Asp Pro His Thr Gly Ala Ile Val His Gly
            100                 105                 110

Arg Ile Pro Gln Leu Gly Pro Leu Gln Gln His Leu Thr Lys Leu Arg
            115                 120                 125

Gln Glu Ile Leu Tyr Tyr Met Pro Lys Asp Asn Val Gly Leu Ala Val
            130                 135                 140

Ile Asp Trp Glu Glu Trp Leu Pro Thr Trp Leu Arg Asn Trp Lys Pro
145                 150                 155                 160

Lys Asp Ile Tyr Arg Ile Lys Ser Ile Glu Leu Val Lys Ser Gln His
                165                 170                 175

Pro Gln Tyr Asn His Ser Tyr Ala Thr Glu Lys Ala Lys Arg Asp Phe
            180                 185                 190

Glu Lys Ala Gly Lys Asp Phe Met Glu Glu Thr Leu Lys Leu Gly Arg
            195                 200                 205

Leu Leu Arg Pro Asn His Leu Trp Gly Tyr Tyr Leu Phe Pro Asp Cys
            210                 215                 220

Tyr Asn His His Tyr Asp Lys Pro Asn Leu Tyr Lys Gly Ser Cys Phe
225                 230                 235                 240

Asp Ile Glu Lys Lys Arg Asn Asp Asp Leu Ser Trp Leu Trp Lys Glu
                245                 250                 255

Ser Thr Ala Leu Phe Pro Ser Val Tyr Leu Thr Ser Arg Ala Arg Ser
            260                 265                 270

Ala Thr Ala Leu Ser Lys Leu Tyr Val Val Arg Asn Arg Val His Glu
            275                 280                 285

Ala Ile Arg Val Ser Lys Ile Pro Asp Asp Lys Ser Pro Leu Pro Asn
            290                 295                 300

Phe Val Tyr Thr Arg Leu Val Phe Thr Asp Gln Ile Phe Gln Phe Leu
305                 310                 315                 320

Ser His His Asp Leu Val Tyr Thr Ile Gly Glu Ile Val Ala Leu Gly
                325                 330                 335

Ala Ser Gly Ile Val Val Trp Gly Ser Gln Ser Leu Ala Arg Ser Met
            340                 345                 350

Lys Ser Cys Leu His Leu Asp Asn Tyr Met Lys Thr Ile Leu Asn Pro
            355                 360                 365

Tyr Leu Ile Asn Val Thr Leu Ala Ala Lys Met Cys Asn Gln Val Leu
            370                 375                 380

Cys Gln Glu Gln Gly Val Cys Thr Arg Lys Asn Trp Asn Pro Asn Asp
385                 390                 395                 400

Tyr Leu His Leu Asn Pro Gly Asn Phe Ala Ile Gln Leu Gly Ser Asn
                405                 410                 415

Gly Thr Tyr Lys Val Asp Gly Lys Pro Thr Leu Thr Asp Leu Glu Gln
            420                 425                 430

Phe Ser Lys Asn Phe Gln Cys Ser Cys Tyr Thr Asn Leu Asn Cys Lys
            435                 440                 445

Glu Arg Thr Asp Met Asn Asn Val Arg Thr Val Asn Val Cys Ala Val
            450                 455                 460

Glu Asn Val Cys Ile Asp Thr Asn Val Gly Pro Gln Ala Val Thr Tyr
465                 470                 475                 480

Ala Pro Lys Glu Lys Lys Asp Val Ala His Ile Leu Ser Asn Thr Thr
                485                 490                 495

Ser Ile Asn Ser Ser Thr Thr Met Ser Leu Pro Phe Pro Arg Lys His
            500                 505                 510
```

-continued

```
Val Ser Gly Cys Leu Leu Val Leu Cys Met Tyr Ser Gln Tyr Leu Asn
            515                 520                 525

Ile Cys Tyr Arg Leu Val Ala Ile Gly Ile Gln His Gly Tyr Tyr Leu
530                 535                 540

Lys
545

<210> SEQ ID NO 26
<211> LENGTH: 476
<212> TYPE: PRT
<213> ORGANISM: Ovis aries
<220> FEATURE:
<223> OTHER INFORMATION: hyaluronidase 2

<400> SEQUENCE: 26

Met Trp Thr Gly Leu Gly Pro Ala Val Thr Leu Ala Leu Val Leu Val
  1               5                  10                  15

Val Ala Trp Ala Thr Glu Leu Lys Pro Thr Ala Pro Pro Ile Phe Thr
             20                  25                  30

Gly Arg Pro Phe Val Val Ala Trp Asp Val Pro Thr Gln Asp Cys Gly
         35                  40                  45

Pro Arg His Lys Met Pro Leu Asp Pro Lys Asp Met Lys Ala Phe Asp
     50                  55                  60

Val Gln Ala Ser Pro Asn Glu Gly Phe Val Asn Gln Asn Ile Thr Ile
 65                  70                  75                  80

Phe Tyr Arg Asp Arg Leu Gly Met Tyr Pro His Phe Asn Ser Val Gly
                 85                  90                  95

Arg Ser Val His Gly Gly Val Pro Gln Asn Gly Ser Leu Trp Val His
            100                 105                 110

Leu Glu Met Leu Lys Gly His Val Glu His Tyr Ile Arg Thr Gln Glu
        115                 120                 125

Pro Ala Gly Leu Ala Val Ile Asp Trp Glu Asp Trp Arg Pro Val Trp
    130                 135                 140

Val Arg Asn Trp Gln Asp Lys Asp Val Tyr Arg Arg Leu Ser Arg Gln
145                 150                 155                 160

Leu Val Ala Ser His His Pro Asp Trp Pro Pro Glu Arg Ile Val Lys
                165                 170                 175

Glu Ala Gln Tyr Glu Phe Glu Phe Ala Ala Arg Gln Phe Met Leu Glu
            180                 185                 190

Thr Leu Arg Phe Val Lys Ala Phe Arg Pro Arg His Leu Trp Gly Phe
        195                 200                 205

Tyr Leu Phe Pro Asp Cys Tyr Asn His Asp Tyr Val Gln Asn Trp Glu
    210                 215                 220

Thr Tyr Thr Gly Arg Cys Pro Asp Val Glu Val Ser Arg Asn Asp Gln
225                 230                 235                 240

Leu Ser Trp Leu Trp Ala Glu Ser Thr Ala Leu Phe Pro Ser Val Tyr
                245                 250                 255

Leu Glu Glu Thr Leu Ala Ser Ser Thr His Gly Arg Asn Phe Val Ser
            260                 265                 270

Phe Arg Val Gln Glu Ala Leu Arg Val Ala Asp Val His His Ala Asn
        275                 280                 285

His Ala Leu Pro Val Tyr Val Phe Thr Arg Pro Thr Tyr Ser Arg Gly
    290                 295                 300

Leu Thr Gly Leu Ser Glu Met Asp Leu Ile Ser Thr Ile Gly Glu Ser
305                 310                 315                 320
```

-continued

```
Ala Ala Leu Gly Ala Ala Gly Val Ile Leu Trp Gly Asp Ala Gly Phe
                325                 330                 335

Thr Thr Ser Asn Glu Thr Cys Arg Arg Leu Lys Asp Tyr Leu Thr Arg
            340                 345                 350

Ser Leu Val Pro Tyr Val Val Asn Val Ser Trp Ala Ala Gln Tyr Cys
        355                 360                 365

Ser Trp Ala Gln Cys His Gly His Gly Arg Cys Val Arg Arg Asp Pro
    370                 375                 380

Asn Ala His Thr Phe Leu His Leu Ser Ala Ser Ser Phe Arg Leu Val
385                 390                 395                 400

Pro Ser His Ala Pro Asp Glu Pro Arg Leu Arg Pro Glu Gly Glu Leu
                405                 410                 415

Ser Trp Ala Asp Arg Asn His Leu Gln Thr His Phe Arg Cys Gln Cys
            420                 425                 430

Tyr Leu Gly Trp Gly Gly Glu Gln Cys Gln Trp Asp Arg Arg Arg Ala
        435                 440                 445

Ala Gly Gly Ala Ser Gly Ala Trp Ala Gly Ser His Leu Thr Gly Leu
    450                 455                 460

Leu Ala Val Ala Val Leu Ala Phe Thr Trp Thr Ser
465                 470                 475

<210> SEQ ID NO 27
<211> LENGTH: 114
<212> TYPE: PRT
<213> ORGANISM: Ovis aries
<220> FEATURE:
<223> OTHER INFORMATION: PH20 partial sequence

<400> SEQUENCE: 27

Leu Tyr Val Arg Asn Arg Val Arg Glu Ala Ile Arg Leu Ser Lys Ile
 1               5                  10                  15

Ala Ser Val Glu Ser Pro Leu Pro Val Phe Val Tyr His Arg Pro Val
            20                  25                  30

Phe Thr Asp Gly Ser Ser Thr Tyr Leu Ser Gln Gly Asp Leu Val Asn
        35                  40                  45

Ser Val Gly Glu Ile Val Ala Leu Gly Ala Ser Gly Ile Ile Met Trp
    50                  55                  60

Gly Ser Leu Asn Leu Ser Leu Thr Met Gln Ser Cys Met Asn Leu Gly
65                  70                  75                  80

Asn Tyr Leu Asn Thr Thr Leu Asn Pro Tyr Ile Ile Asn Val Thr Leu
                85                  90                  95

Ala Ala Lys Met Cys Ser Gln Val Leu Cys Gln Glu Gly Val Cys
            100                 105                 110

Ile Arg

<210> SEQ ID NO 28
<211> LENGTH: 414
<212> TYPE: PRT
<213> ORGANISM: Pongo pygmaeus
<220> FEATURE:
<223> OTHER INFORMATION: hyaluronidase 3

<400> SEQUENCE: 28

Met Thr Thr Arg Leu Gly Pro Ala Leu Val Leu Gly Val Ala Leu Cys
 1               5                  10                  15

Leu Gly Cys Gly Gln Pro Leu Pro Gln Val Pro Glu Arg Pro Phe Ser
            20                  25                  30
```

Val Leu Trp Asn Val Pro Ser Ala His Cys Lys Ser Arg Phe Gly Val
 35                  40                  45

His Leu Pro Leu Asn Ala Leu Gly Ile Ile Ala Asn Arg Gly Gln His
 50                  55                  60

Phe His Gly Gln Asn Met Thr Ile Phe Tyr Lys Asn Gln Leu Gly Leu
65                   70                  75                  80

Tyr Pro Tyr Phe Gly Pro Lys Gly Thr Ala His Asn Gly Gly Ile Pro
                 85                  90                  95

Gln Ala Leu Pro Leu Asp Arg His Leu Ala Leu Ala Ala Tyr Gln Ile
            100                 105                 110

His His Ser Leu Arg Pro Gly Phe Ala Gly Pro Ala Val Leu Asp Trp
        115                 120                 125

Glu Glu Trp Cys Pro Leu Trp Ala Gly Asn Trp Gly Arg Arg Arg Ala
130                 135                 140

Tyr Gln Ala Ala Ser Trp Ala Trp Ala Gln Gln Val Phe Pro Asp Leu
145                 150                 155                 160

Asp Pro Gln Glu Gln Leu Tyr Lys Ala Tyr Thr Gly Phe Glu Gln Ala
                165                 170                 175

Ala Arg Ala Leu Met Glu Asp Thr Leu Arg Val Ala Gln Ala Leu Arg
            180                 185                 190

Pro His Gly Leu Trp Gly Phe Tyr His Tyr Pro Ala Cys Gly Asn Gly
        195                 200                 205

Trp His Ser Met Ala Ser Asn Tyr Thr Gly Arg Cys His Ala Ala Thr
    210                 215                 220

Leu Ala Arg Asn Thr Gln Leu His Trp Leu Trp Ala Ala Ser Ser Ala
225                 230                 235                 240

Leu Phe Pro Ser Ile Tyr Leu Pro Pro Arg Leu Pro Pro Ala His His
                245                 250                 255

Gln Ala Phe Val Arg His Arg Leu Glu Glu Ala Phe Arg Val Ala Leu
            260                 265                 270

Val Gly His Leu Pro Val Leu Ala Tyr Val Arg Leu Thr His Arg Arg
        275                 280                 285

Ser Gly Arg Phe Leu Ser Gln Asp Asp Leu Val Gln Thr Ile Gly Val
    290                 295                 300

Ser Ala Ala Leu Gly Ala Ala Gly Val Val Leu Trp Gly Asp Leu Ser
305                 310                 315                 320

Leu Ser Ser Ser Glu Glu Cys Trp His Leu His Asp Tyr Leu Val
                325                 330                 335

Asp Thr Leu Gly Pro Tyr Gly Ile Asn Val Thr Arg Ala Ala Met Ala
            340                 345                 350

Cys Ser His Gln Arg Cys His Gly His Gly Arg Cys Ala Arg Arg Asp
        355                 360                 365

Pro Gly Gln Met Glu Ala Phe Leu His Leu Trp Pro Asp Gly Ser Leu
    370                 375                 380

Gly Asp Trp Lys Ser Phe Ser Cys His Cys Tyr Trp Gly Trp Ala Gly
385                 390                 395                 400

Pro Thr Cys Gln Glu Pro Arg Leu Gly Pro Lys Glu Ala Val
                405                 410

<210> SEQ ID NO 29
<211> LENGTH: 510
<212> TYPE: PRT
<213> ORGANISM: Macaca fascicularis
<220> FEATURE:
<223> OTHER INFORMATION: PH20

<400> SEQUENCE: 29

```
Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Ile Ile Pro Asn Val Pro
        35                  40                  45

Phe Leu Trp Ala Trp Asn Ala Pro Ser Glu Phe Cys Leu Gly Lys Phe
    50                  55                  60

Asn Glu Pro Leu Asp Met Ser Leu Phe Thr Leu Met Gly Ser Pro Arg
65              70                  75                  80

Ile Asn Val Thr Gly Gln Gly Val Thr Ile Phe Tyr Val Asp Arg Leu
                85                  90                  95

Gly Tyr Tyr Pro Tyr Ile Asp Leu Thr Thr Gly Val Thr Val His Gly
            100                 105                 110

Gly Ile Pro Gln Lys Val Ser Leu Gln Asp His Leu Asp Lys Ser Lys
        115                 120                 125

Gln Asp Ile Leu Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Asn
                165                 170                 175

Val Gln Leu Ser Leu Pro Gln Ala Thr Asp Lys Ala Lys Gln Glu Phe
            180                 185                 190

Glu Lys Ala Gly Lys Asp Phe Met Leu Glu Thr Ile Lys Leu Gly Arg
        195                 200                 205

Ser Leu Arg Pro Asn His Leu Trp Gly Tyr Tyr Leu Phe Pro Asp Cys
    210                 215                 220

Tyr Asn His His Tyr Arg Lys Pro Gly Tyr Asn Gly Ser Cys Phe Asp
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Val Val
            260                 265                 270

Val Ala Thr Leu Tyr Val Arg Asn Arg Val Arg Glu Ala Ile Arg Val
        275                 280                 285

Ser Lys Ile Pro Asp Ala Lys Asn Pro Leu Pro Val Phe Val Tyr Ala
    290                 295                 300

Arg Leu Val Phe Thr Asp Gln Val Leu Lys Phe Leu Ser Arg Glu Glu
305                 310                 315                 320

Leu Val Ser Thr Leu Gly Glu Thr Val Ala Leu Gly Ala Ser Gly Ile
                325                 330                 335

Val Ile Trp Gly Ser Leu Ser Ile Thr Arg Ser Met Lys Ser Cys Leu
            340                 345                 350

Leu Leu Asp Thr Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asp Trp Asn Ser Ser Asp Tyr Leu His Leu
385                 390                 395                 400

Asn Pro Asp Asn Phe Asp Ile Arg Leu Glu Lys Gly Gly Lys Phe Thr
```

```
                    405                 410                 415
Val His Gly Lys Pro Thr Val Glu Asp Leu Glu Glu Phe Ser Glu Lys
            420                 425                 430

Phe Tyr Cys Ser Cys Tyr Thr Asn Leu Ser Cys Lys Glu Lys Ala Asp
            435                 440                 445

Val Lys Asp Thr Asp Ala Val Asp Val Cys Ile Ala Asp Gly Val Cys
            450                 455                 460

Ile Asp Ala Ser Leu Lys Pro Val Glu Thr Glu Gly Ser Pro
465                 470                 475                 480

Ile Phe Tyr Asn Thr Ser Ser Thr Val Ser Thr Thr Met Phe Ile
            485                 490                 495

Val Asn Ile Leu Phe Leu Ile Ile Ser Ser Val Ala Ser Leu
            500                 505                 510

<210> SEQ ID NO 30
<211> LENGTH: 529
<212> TYPE: PRT
<213> ORGANISM: Cavia porcellus
<220> FEATURE:
<223> OTHER INFORMATION: PH20

<400> SEQUENCE: 30

Met Gly Ala Phe Thr Phe Lys His Ser Phe Gly Ser Phe Val Glu
1               5                   10                  15

Cys Ser Gly Val Leu Gln Thr Val Phe Ile Phe Leu Leu Ile Pro Cys
                20                  25                  30

Cys Leu Ala Asp Lys Arg Ala Pro Leu Ile Pro Asn Val Pro Leu
            35                  40                  45

Leu Trp Val Trp Asn Ala Pro Thr Glu Phe Cys Ile Gly Gly Thr Asn
    50                  55                  60

Gln Pro Leu Asp Met Ser Phe Phe Ser Ile Val Gly Thr Pro Arg Lys
65                  70                  75                  80

Asn Ile Thr Gly Gln Ser Ile Thr Leu Tyr Tyr Val Asp Arg Leu Gly
                85                  90                  95

Tyr Tyr Pro Tyr Ile Asp Pro His Thr Gly Ala Ile Val His Gly Gly
                100                 105                 110

Leu Pro Gln Leu Met Asn Leu Gln Gln His Leu Arg Lys Ser Arg Gln
            115                 120                 125

Asp Ile Leu Phe Tyr Met Pro Thr Asp Ser Val Gly Leu Ala Val Ile
            130                 135                 140

Asp Trp Glu Glu Trp Arg Pro Thr Trp Thr Arg Asn Trp Arg Pro Lys
145                 150                 155                 160

Asp Ile Tyr Arg Asn Lys Ser Ile Glu Leu Val Lys Ser Gln His Pro
                165                 170                 175

Gln Tyr Asn His Ser Tyr Ala Val Ala Val Ala Lys Arg Asp Phe Glu
            180                 185                 190

Arg Thr Gly Lys Ala Phe Met Leu Glu Thr Leu Lys Leu Gly Lys Ser
            195                 200                 205

Leu Arg Pro Ser Ser Leu Trp Gly Tyr Tyr Leu Phe Pro Asp Cys Tyr
    210                 215                 220

Asn Thr His Phe Thr Lys Pro Asn Tyr Asp Gly His Cys Pro Pro Ile
225                 230                 235                 240

Glu Leu Gln Arg Asn Asn Asp Leu Gln Trp Leu Trp Asn Asp Ser Thr
                245                 250                 255

Ala Leu Tyr Pro Ser Val Tyr Leu Thr Ser Arg Val Arg Ser Ser Gln
```

-continued

```
                260                 265                 270

Asn Gly Ala Leu Tyr Val Arg Asn Arg Val His Glu Ser Ile Arg Val
            275                 280                 285

Ser Lys Leu Met Asp Asp Lys Asn Pro Leu Pro Ile Tyr Val Tyr Ile
        290                 295                 300

Arg Leu Val Phe Thr Asp Gln Thr Thr Thr Phe Leu Glu Leu Asp Asp
305                 310                 315                 320

Leu Val His Ser Val Gly Glu Ile Val Pro Leu Gly Val Ser Gly Ile
                325                 330                 335

Ile Ile Trp Gly Ser Leu Ser Leu Thr Arg Ser Leu Val Ser Cys Ile
            340                 345                 350

Gly Leu Glu Asn Tyr Met Lys Gly Thr Leu Leu Pro Tyr Leu Ile Asn
        355                 360                 365

Val Thr Leu Ala Ala Lys Met Cys Gly Gln Val Leu Cys Lys Asn Gln
370                 375                 380

Gly Ile Cys Thr Arg Lys Asp Trp Asn Thr Asn Thr Tyr Leu His Leu
385                 390                 395                 400

Asn Ala Thr Asn Phe Asp Ile Glu Leu Gln Gln Asn Gly Lys Phe Val
                405                 410                 415

Val His Gly Lys Pro Ser Leu Glu Asp Leu Gln Glu Phe Ser Lys Asn
            420                 425                 430

Phe His Cys Ser Cys Tyr Thr Asn Val Ala Cys Lys Asp Arg Leu Asp
        435                 440                 445

Val His Asn Val Arg Ser Val Asn Val Cys Thr Ala Asn Asn Ile Cys
450                 455                 460

Ile Asp Ala Val Leu Asn Phe Pro Ser Leu Asp Asp Asp Glu Pro
465                 470                 475                 480

Pro Ile Thr Asp Asp Thr Ser Gln Asn Gln Asp Ser Ile Ser Asp Ile
                485                 490                 495

Thr Ser Ser Ala Pro Pro Ser Ser His Ile Leu Pro Lys Asp Leu Ser
            500                 505                 510

Trp Cys Leu Phe Leu Leu Ser Ile Phe Ser Gln His Trp Lys Tyr Leu
        515                 520                 525

Leu
```

<210> SEQ ID NO 31
<211> LENGTH: 512
<212> TYPE: PRT
<213> ORGANISM: Rattus norvegicus
<220> FEATURE:
<223> OTHER INFORMATION: PH20

<400> SEQUENCE: 31

```
Met Gly Glu Leu Gln Phe Lys Trp Leu Phe Trp Arg Ser Phe Ala Glu
 1               5                  10                  15

Ser Gly Gly Thr Phe Gln Thr Val Leu Ile Phe Leu Phe Ile Pro Tyr
            20                  25                  30

Ser Leu Thr Val Asp Tyr Arg Ala Thr Pro Val Leu Ser Asp Thr Thr
        35                  40                  45

Phe Val Trp Val Trp Asn Val Pro Thr Glu Ala Cys Val Glu Asn Val
    50                  55                  60

Thr Glu Pro Ile Asp Leu Ser Phe Ser Leu Ile Gly Ser Pro Arg
65                  70                  75                  80

Lys Thr Ala Ile Gly Gln Pro Val Thr Leu Phe Tyr Val Asp Arg Leu
                85                  90                  95
```

```
Gly Asn Tyr Pro His Ile Asp Ala Gln Gln Thr Glu His His Gly Gly
                100                 105                 110

Ile Pro Gln Lys Gly Asp Leu Thr Thr His Leu Val Lys Ala Lys Glu
            115                 120                 125

Asp Val Glu Arg Tyr Ile Pro Thr Asp Lys Leu Gly Leu Ala Ile Ile
130                 135                 140

Asp Trp Glu Glu Trp Arg Pro Thr Trp Met Arg Asn Trp Thr Pro Lys
145                 150                 155                 160

Asp Ile Tyr Arg Asn Lys Ser Ile Glu Leu Val Gln Ala Ala Asp Pro
                165                 170                 175

Ala Ile Asn Ile Thr Glu Ala Thr Val Arg Ala Lys Ala Gln Phe Glu
            180                 185                 190

Gly Ala Ala Lys Glu Phe Met Glu Gly Thr Leu Lys Leu Gly Lys His
            195                 200                 205

Ile Arg Pro Lys His Leu Trp Gly Phe Tyr Leu Phe Pro Asp Cys Tyr
            210                 215                 220

Asn Asn Lys Phe Gln Val Asp Asn Tyr Asp Gly Gln Cys Pro Asp Val
225                 230                 235                 240

Glu Lys Lys Arg Asn Asp Asp Leu Asp Trp Leu Trp Lys Glu Ser Thr
                245                 250                 255

Gly Leu Tyr Pro Ser Val Tyr Leu Lys Lys Asp Leu Lys Ser Ser Arg
            260                 265                 270

Lys Ala Thr Leu Tyr Val Arg Tyr Arg Val Leu Glu Ser Ile Arg Val
            275                 280                 285

Ser Lys Val Ser Asp Glu Ser Asn Pro Val Pro Ile Phe Val Tyr Ile
            290                 295                 300

Arg Leu Val Phe Thr Asp His Val Ser Glu Tyr Leu Leu Glu Asp Asp
305                 310                 315                 320

Leu Val Asn Thr Ile Gly Glu Ile Val Ala Gln Gly Thr Ser Gly Ile
                325                 330                 335

Ile Ile Trp Asp Ala Met Ser Leu Ala Gln Arg Ser Ala Gly Cys Pro
            340                 345                 350

Ile Leu Arg Gln Tyr Met Lys Thr Thr Leu Asn Pro Tyr Ile Val Asn
            355                 360                 365

Val Thr Leu Ala Ala Lys Met Cys Ser Gln Thr Leu Cys Lys Glu Lys
370                 375                 380

Gly Met Cys Ser Arg Lys Thr Glu Ser Ser Asp Ala Tyr Leu His Leu
385                 390                 395                 400

Asp Pro Ser Ser Phe Ser Ile Asn Val Thr Glu Ala Gly Lys Tyr Glu
                405                 410                 415

Val Leu Gly Lys Pro Glu Val Lys Asp Leu Glu Tyr Phe Ser Glu His
            420                 425                 430

Phe Lys Cys Ser Cys Phe Ser Lys Met Thr Cys Glu Glu Thr Ser Asp
            435                 440                 445

Met Arg Ser Ile Gln Asp Val Asn Val Cys Met Gly Asp Asn Val Cys
450                 455                 460

Ile Lys Ala Thr Leu Gly Pro Asn Ser Ala Phe His Leu Leu Pro Gly
465                 470                 475                 480

Lys Gly Leu Leu Leu Met Thr Thr Leu Ala His Ile Leu His His Leu
                485                 490                 495

Pro His Asp Ile Phe Val Phe Pro Trp Lys Met Leu Val Ser Thr Pro
            500                 505                 510
```

<210> SEQ ID NO 32
<211> LENGTH: 512
<212> TYPE: PRT
<213> ORGANISM: Mus musculus
<220> FEATURE:
<223> OTHER INFORMATION: PH20

<400> SEQUENCE: 32

```
Met Gly Glu Leu Arg Phe Lys His Leu Phe Trp Gly Ser Phe Val Glu
 1               5                  10                  15

Ser Gly Gly Thr Phe Gln Thr Val Leu Ile Phe Leu Leu Ile Pro Cys
             20                  25                  30

Ser Leu Thr Val Asp Tyr Arg Ala Ala Pro Ile Leu Ser Asn Thr Thr
         35                  40                  45

Phe Leu Trp Ile Trp Asn Val Pro Thr Glu Arg Cys Val Gly Asn Val
 50                  55                  60

Asn Asp Pro Ile Asp Leu Ser Phe Phe Ser Leu Ile Gly Ser Pro Arg
 65                  70                  75                  80

Lys Thr Ala Thr Gly Gln Pro Val Thr Leu Phe Tyr Val Asp Arg Leu
                 85                  90                  95

Gly Leu Tyr Pro His Ile Asp Ala Asn Gln Ala Glu His Tyr Gly Gly
            100                 105                 110

Ile Pro Gln Arg Gly Asp Tyr Gln Ala His Leu Arg Lys Ala Lys Thr
            115                 120                 125

Asp Ile Glu His Tyr Ile Pro Asp Asp Lys Leu Gly Leu Ala Ile Ile
130                 135                 140

Asp Trp Glu Glu Trp Arg Pro Thr Trp Leu Arg Asn Trp Lys Pro Lys
145                 150                 155                 160

Asp Asn Tyr Arg Asn Lys Ser Ile Glu Leu Val Gln Ser Thr Asn Pro
                165                 170                 175

Gly Leu Ser Ile Thr Glu Ala Thr Gln Lys Ala Ile Gln Gln Phe Glu
            180                 185                 190

Glu Ala Gly Arg Lys Phe Met Glu Gly Thr Leu His Leu Gly Lys Phe
            195                 200                 205

Leu Arg Pro Asn Gln Leu Trp Gly Tyr Tyr Leu Phe Pro Asp Cys Tyr
        210                 215                 220

Asn Asn Lys Phe Gln Asp Pro Lys Tyr Asp Gly Gln Cys Pro Ala Val
225                 230                 235                 240

Glu Lys Lys Arg Asn Asp Asn Leu Lys Trp Leu Trp Lys Ala Ser Thr
                245                 250                 255

Gly Leu Tyr Pro Ser Val Tyr Leu Lys Lys Asp Leu Lys Ser Asn Arg
            260                 265                 270

Gln Ala Thr Leu Tyr Val Arg Tyr Arg Val Glu Ala Ile Arg Val
            275                 280                 285

Ser Lys Val Gly Asn Ala Ser Asp Pro Val Pro Ile Phe Val Tyr Ile
290                 295                 300

Arg Leu Val Phe Thr Asp Arg Thr Ser Glu Tyr Leu Leu Glu Asp Asp
305                 310                 315                 320

Leu Val Asn Thr Ile Gly Glu Ile Val Ala Leu Gly Thr Ser Gly Ile
                325                 330                 335

Ile Ile Trp Asp Ala Met Ser Leu Ala Gln Arg Ala Ala Gly Cys Pro
            340                 345                 350

Ile Leu His Lys Tyr Met Gln Thr Thr Leu Asn Pro Tyr Ile Val Asn
            355                 360                 365
```

```
Val Thr Leu Ala Ala Lys Met Cys Ser Gln Thr Leu Cys Asn Glu Lys
    370                 375                 380

Gly Met Cys Ser Arg Arg Lys Glu Ser Ser Asp Val Tyr Leu His Leu
385                 390                 395                 400

Asn Pro Ser His Phe Asp Ile Met Leu Thr Glu Thr Gly Lys Tyr Glu
                405                 410                 415

Val Leu Gly Asn Pro Arg Val Gly Asp Leu Glu Tyr Phe Ser Glu His
            420                 425                 430

Phe Lys Cys Ser Cys Phe Ser Arg Met Thr Cys Lys Glu Thr Ser Asp
        435                 440                 445

Val Lys Asn Val Gln Asp Val Asn Val Cys Val Gly Asp Asn Val Cys
    450                 455                 460

Ile Lys Ala Lys Val Glu Pro Asn Pro Ala Phe Tyr Leu Leu Pro Gly
465                 470                 475                 480

Lys Ser Leu Leu Phe Met Thr Thr Leu Gly His Val Leu Tyr His Leu
                485                 490                 495

Pro Gln Asp Ile Phe Val Phe Pro Arg Lys Thr Leu Val Ser Thr Pro
            500                 505                 510

<210> SEQ ID NO 33
<211> LENGTH: 807
<212> TYPE: PRT
<213> ORGANISM: Staphylococcus aureus
<220> FEATURE:
<223> OTHER INFORMATION: hyaluronidase

<400> SEQUENCE: 33

Met Thr Tyr Arg Ile Lys Lys Trp Gln Lys Leu Ser Thr Ile Thr Leu
1               5                   10                  15

Leu Met Ala Gly Val Ile Thr Leu Asn Gly Gly Glu Phe Arg Ser Val
            20                  25                  30

Asp Lys His Gln Ile Ala Val Ala Asp Thr Asn Val Gln Thr Pro Asp
        35                  40                  45

Tyr Glu Lys Leu Arg Asn Thr Trp Leu Asp Val Asn Tyr Gly Tyr Asp
    50                  55                  60

Lys Tyr Asp Glu Asn Asn Pro Asp Met Lys Lys Phe Asp Ala Thr
65                  70                  75                  80

Glu Lys Glu Ala Thr Asn Leu Leu Lys Glu Met Lys Thr Glu Ser Gly
                85                  90                  95

Arg Lys Tyr Leu Trp Ser Gly Ala Glu Thr Leu Glu Thr Asn Ser Ser
            100                 105                 110

His Met Thr Arg Thr Tyr Arg Asn Ile Glu Lys Ile Ala Glu Ala Met
        115                 120                 125

Arg Asn Pro Lys Thr Thr Leu Asn Thr Asp Glu Asn Lys Lys Val
130                 135                 140

Lys Asp Ala Leu Glu Trp Leu His Lys Asn Ala Tyr Gly Lys Glu Pro
145                 150                 155                 160

Asp Lys Lys Val Lys Glu Leu Ser Glu Asn Phe Thr Lys Thr Thr Gly
                165                 170                 175

Lys Asn Thr Asn Leu Asn Trp Trp Asp Tyr Glu Ile Gly Thr Pro Lys
            180                 185                 190

Ser Leu Thr Asn Thr Leu Ile Leu Leu Asn Asp Gln Phe Ser Asn Glu
        195                 200                 205

Glu Lys Lys Lys Phe Thr Ala Pro Ile Lys Thr Phe Ala Pro Asp Ser
    210                 215                 220
```

```
-continued

Asp Lys Ile Leu Ser Ser Val Gly Lys Ala Glu Leu Ala Lys Gly Gly
225                 230                 235                 240

Asn Leu Val Asp Ile Ser Lys Val Lys Leu Leu Glu Cys Ile Ile Glu
            245                 250                 255

Glu Asp Lys Asp Met Met Lys Lys Ser Ile Asp Ser Phe Asn Lys Val
            260                 265                 270

Phe Thr Tyr Val Gln Asp Ser Ala Thr Gly Lys Glu Arg Asn Gly Phe
        275                 280                 285

Tyr Lys Asp Gly Ser Tyr Ile Asp His Gln Asp Val Pro Tyr Thr Gly
        290                 295                 300

Ala Tyr Gly Val Val Leu Leu Glu Gly Ile Ser Gln Met Met Pro Met
305                 310                 315                 320

Ile Lys Glu Thr Pro Phe Asn Asp Lys Thr Gln Asn Asp Thr Thr Leu
                325                 330                 335

Lys Ser Trp Ile Asp Asp Gly Phe Met Pro Leu Ile Tyr Lys Gly Glu
            340                 345                 350

Met Met Asp Leu Ser Arg Gly Arg Ala Ile Ser Arg Glu Asn Glu Thr
        355                 360                 365

Ser His Ser Ala Ser Ala Thr Val Met Lys Ser Leu Leu Arg Leu Ser
370                 375                 380

Asp Ala Met Asp Asp Ser Thr Lys Ala Lys Tyr Lys Lys Ile Val Lys
385                 390                 395                 400

Ser Ser Val Glu Ser Asp Ser Ser Tyr Lys Gln Asn Asp Tyr Leu Asn
                405                 410                 415

Ser Tyr Ser Asp Ile Asp Lys Met Lys Ser Leu Met Thr Asp Asn Ser
            420                 425                 430

Ile Ser Lys Asn Gly Leu Thr Gln Gln Leu Lys Ile Tyr Asn Asp Met
        435                 440                 445

Asp Arg Val Thr Tyr His Asn Lys Asp Leu Asp Phe Ala Phe Gly Leu
        450                 455                 460

Ser Met Thr Ser Lys Asn Val Ala Arg Tyr Glu Ser Ile Asn Gly Glu
465                 470                 475                 480

Asn Leu Lys Gly Trp His Thr Gly Ala Gly Met Ser Tyr Leu Tyr Asn
                485                 490                 495

Ser Asp Val Lys His Tyr His Asp Asn Phe Trp Val Thr Ala Asp Met
            500                 505                 510

Lys Arg Leu Ser Gly Thr Thr Leu Asp Asn Glu Ile Leu Lys Asp
        515                 520                 525

Thr Asp Asp Lys Lys Ser Ser Lys Thr Phe Val Gly Gly Thr Lys Val
530                 535                 540

Asp Asp Gln His Ala Ser Ile Gly Met Asp Phe Glu Asn Gln Asp Lys
545                 550                 555                 560

Thr Leu Thr Ala Lys Lys Ser Tyr Phe Ile Leu Asn Asp Lys Ile Val
                565                 570                 575

Phe Leu Gly Thr Gly Ile Lys Ser Thr Asp Ser Ser Lys Asn Pro Val
            580                 585                 590

Thr Thr Ile Glu Asn Arg Lys Ala Asn Gly Tyr Thr Leu Tyr Thr Asp
        595                 600                 605

Asp Lys Gln Thr Thr Asn Ser Asp Asn Gln Glu Asn Asn Ser Val Phe
        610                 615                 620

Leu Glu Ser Thr Asp Thr Lys Lys Asn Ile Gly Tyr His Phe Leu Asn
625                 630                 635                 640

Lys Pro Lys Ile Thr Val Lys Lys Glu Ser His Thr Gly Lys Trp Lys
```

|   | 645 |   |   |   | 650 |   |   |   | 655 |   |   |
|---|-----|---|---|---|-----|---|---|---|-----|---|---|

Glu Ile Asn Lys Ser Gln Lys Asp Thr Gln Lys Thr Asp Glu Tyr Tyr
            660                 665                 670

Glu Val Thr Gln Lys His Ser Asn Ser Asp Asn Lys Tyr Gly Tyr Val
            675                 680                 685

Leu Tyr Pro Gly Leu Ser Lys Asp Val Phe Lys Thr Lys Lys Asp Glu
            690                 695                 700

Val Thr Val Lys Gln Glu Asp Asp Phe His Val Lys Asp Asn
705                 710                 715                 720

Glu Ser Val Trp Ala Gly Val Asn Tyr Ser Asn Ser Thr Gln Thr Phe
            725                 730                 735

Asp Ile Asn Asn Thr Lys Val Glu Val Lys Ala Lys Gly Met Phe Ile
            740                 745                 750

Leu Lys Lys Lys Asp Asp Asn Thr Tyr Glu Cys Ser Phe Tyr Asn Pro
            755                 760                 765

Glu Ser Thr Asn Ser Ala Ser Asp Ile Glu Ser Lys Ile Ser Met Thr
            770                 775                 780

Gly Tyr Ser Ile Thr Asn Lys Asn Thr Ser Thr Ser Asn Glu Ser Gly
785                 790                 795                 800

Val His Phe Glu Leu Thr Lys
            805

```
<210> SEQ ID NO 34
<211> LENGTH: 371
<212> TYPE: PRT
<213> ORGANISM: Streptococcus pyogenes bacteriophage H4489A
<220> FEATURE:
<223> OTHER INFORMATION: hyaluronidase

<400> SEQUENCE: 34
```

Met Thr Glu Asn Ile Pro Leu Arg Val Gln Phe Lys Arg Met Ser Ala
 1               5                  10                  15

Asp Glu Trp Ala Arg Ser Asp Val Ile Leu Leu Glu Gly Glu Ile Gly
            20                  25                  30

Phe Glu Thr Asp Thr Gly Phe Ala Lys Phe Gly Asp Gly Gln Asn Thr
            35                  40                  45

Phe Ser Lys Leu Lys Tyr Leu Thr Gly Pro Lys Gly Pro Lys Gly Asp
 50                  55                  60

Thr Gly Leu Gln Gly Lys Thr Gly Gly Thr Gly Pro Arg Gly Pro Ala
 65                  70                  75                  80

Gly Lys Pro Gly Thr Thr Asp Tyr Asp Gln Leu Gln Asn Lys Pro Asp
            85                  90                  95

Leu Gly Ala Phe Ala Gln Lys Glu Glu Thr Asn Ser Lys Ile Thr Lys
            100                 105                 110

Leu Glu Ser Ser Lys Ala Asp Lys Ser Ala Val Tyr Ser Lys Ala Glu
            115                 120                 125

Ser Lys Ile Glu Leu Asp Lys Lys Leu Ser Leu Thr Gly Gly Ile Val
            130                 135                 140

Thr Gly Gln Leu Gln Phe Lys Pro Asn Lys Ser Gly Ile Lys Pro Ser
145                 150                 155                 160

Ser Ser Val Gly Gly Ala Ile Asn Ile Asp Met Ser Lys Ser Glu Gly
            165                 170                 175

Ala Ala Met Val Met Tyr Thr Asn Lys Asp Thr Thr Asp Gly Pro Leu
            180                 185                 190

Met Ile Leu Arg Ser Asp Lys Asp Thr Phe Asp Gln Ser Ala Gln Phe

```
                195                 200                 205
Val Asp Tyr Ser Gly Lys Thr Asn Ala Val Asn Ile Val Met Arg Gln
210                 215                 220

Pro Ser Ala Pro Asn Phe Ser Ser Ala Leu Asn Ile Thr Ser Ala Asn
225                 230                 235                 240

Glu Gly Gly Ser Ala Met Gln Ile Arg Gly Val Glu Lys Ala Leu Gly
                245                 250                 255

Thr Leu Lys Ile Thr His Glu Asn Pro Asn Val Glu Ala Lys Tyr Asp
            260                 265                 270

Glu Asn Ala Ala Ala Leu Ser Ile Asp Ile Val Lys Lys Gln Lys Gly
                275                 280                 285

Gly Lys Gly Thr Ala Ala Gln Gly Ile Tyr Ile Asn Ser Thr Ser Gly
        290                 295                 300

Thr Ala Gly Lys Met Leu Arg Ile Arg Asn Lys Asn Glu Asp Lys Phe
305                 310                 315                 320

Tyr Val Gly Pro Asp Gly Gly Phe His Ser Gly Ala Asn Ser Thr Val
                325                 330                 335

Ala Gly Asn Leu Thr Val Lys Asp Pro Thr Ser Gly Lys His Ala Ala
            340                 345                 350

Thr Lys Asp Tyr Val Asp Glu Lys Ile Ala Glu Leu Lys Lys Leu Ile
        355                 360                 365

Leu Lys Lys
    370

<210> SEQ ID NO 35
<211> LENGTH: 1628
<212> TYPE: PRT
<213> ORGANISM: Clostridium perfringens
<220> FEATURE:
<223> OTHER INFORMATION: hyaluronidase

<400> SEQUENCE: 35

Met Asn Lys Asn Ile Arg Lys Ile Ile Thr Ser Thr Val Leu Ala Ala
1                   5                   10                  15

Met Thr Ile Ser Val Leu Pro Ser Asn Leu Val Val Phe Ala Thr Asp
                20                  25                  30

Gly Ile Thr Glu Asn Phe Tyr Glu Ile Tyr Pro Lys Pro Gln Glu Ile
            35                  40                  45

Ser Tyr Ser Gly Gly Glu Phe Gln Ile Ser Asp Glu Ile Asn Ile Val
        50                  55                  60

Tyr Asp Asp Gly Ile Asp Thr Tyr Thr Lys Lys Arg Val Asp Glu Val
65                  70                  75                  80

Leu Glu Ala Ser Asn Leu Glu Ala Thr Val Ser Asn Glu Ile Val Pro
                85                  90                  95

Gly Lys Thr Asn Phe Leu Val Gly Ile Asn Glu Ser Gly Gly Val Val
            100                 105                 110

Asp Asn Tyr Phe Asn Lys Asn Ile Pro His Asp Glu Ser Phe Phe Asp
        115                 120                 125

Glu Lys Met Asp Ala Asn Ile Val Ser Val Lys Asp Gly Val Ile Gly
130                 135                 140

Val Ile Gly Glu Asp Thr Asp Ser Ala Phe Tyr Gly Val Thr Thr Leu
145                 150                 155                 160

Lys His Val Phe Asn Gln Leu Glu Glu Gly Asn Lys Ile Gln Ser Phe
                165                 170                 175

Arg Ala Asp Asp Tyr Ala Glu Val Ala His Arg Gly Phe Ile Glu Gly
```

-continued

```
            180                 185                 190
Tyr Tyr Gly Asn Pro Trp Ser Asn Glu Asp Arg Ala Glu Leu Met Lys
            195                 200                 205
Phe Gly Gly Asp Tyr Lys Leu Asn Gln Tyr Val Phe Ala Pro Lys Asp
            210                 215                 220
Asp Pro Tyr His Asn Ser Lys Trp Arg Asp Leu Tyr Pro Glu Glu Lys
225                 230                 235                 240
Leu Ser Glu Ile Lys Lys Leu Ala Gln Val Gly Asn Glu Thr Lys Asn
                245                 250                 255
Arg Tyr Val Tyr Ala Leu His Pro Phe Met Asn Asn Pro Val Arg Phe
                260                 265                 270
Asp Thr Glu Glu Asn Tyr Gln Asn Asp Leu Gly Val Ile Lys Ala Lys
            275                 280                 285
Phe Thr Gln Leu Leu Glu Asn Asp Val Arg Gln Phe Ala Ile Leu Ala
            290                 295                 300
Asp Asp Ala Ser Ala Pro Ala Gln Gly Ala Ser Met Tyr Val Lys Leu
305                 310                 315                 320
Leu Thr Asp Leu Thr Arg Trp Leu Glu Glu Gln Gln Ser Thr Tyr Pro
                325                 330                 335
Asp Leu Lys Thr Asp Leu Met Phe Cys Pro Ser Asp Tyr Tyr Gly Asn
                340                 345                 350
Gly Ser Ser Ala Gln Leu Lys Glu Leu Asn Lys Ala Glu Asp Asn Val
            355                 360                 365
Ser Ile Val Met Thr Gly Gly Arg Ile Trp Gly Glu Val Asp Glu Asn
            370                 375                 380
Phe Ala Asn Asn Phe Met Asn Asn Ile Ser Thr Gly His Pro Gly
385                 390                 395                 400
Arg Ala Pro Phe Phe Trp Ile Asn Trp Pro Cys Ser Asp Asn Ser Lys
                405                 410                 415
Gln His Leu Ile Met Gly Gly Asn Asp Thr Phe Leu His Pro Gly Val
            420                 425                 430
Asp Pro Ser Lys Ile Asp Gly Ile Val Leu Asn Pro Met Gln Gln Ala
            435                 440                 445
Glu Ala Asn Lys Ser Ala Leu Phe Ala Ile Ala Asp Tyr Ala Trp Asn
            450                 455                 460
Ile Trp Asp Asn Lys Glu Glu Ala Asp Glu Asn Trp Asn Asp Ser Phe
465                 470                 475                 480
Lys Tyr Met Asp His Gly Thr Ala Glu Glu Thr Asn Ser Ser Leu Ala
                485                 490                 495
Leu Arg Glu Ile Ser Lys His Met Ile Asn Gln Asn Met Asp Gly Arg
            500                 505                 510
Val Arg Pro Leu Gln Glu Ser Val Glu Leu Ala Pro Lys Leu Glu Ala
            515                 520                 525
Phe Lys Gln Lys Tyr Asp Ser Gly Ala Ser Ile Lys Glu Asp Ala Leu
            530                 535                 540
Glu Leu Ile Ala Glu Phe Thr Asn Leu Gln Lys Ala Ala Asp Tyr Tyr
545                 550                 555                 560
Lys Asn Asn Pro Gly Asn Glu Arg Thr Arg Asp Gln Ile Ile Tyr Trp
                565                 570                 575
Leu Asn Cys Trp Glu Asp Thr Met Asp Ala Ala Ile Gly Tyr Leu Lys
                580                 585                 590
Ser Ala Ile Ala Ile Glu Glu Gly Asp Asp Glu Ala Ala Trp Ala Asn
            595                 600                 605
```

```
Tyr Ser Glu Ala Gln Gly Ala Phe Glu Lys Ser Lys Thr Tyr Gly Phe
    610                 615                 620

His Tyr Val Asp His Thr Glu Tyr Ala Glu Val Gly Val Gln His Ile
625                 630                 635                 640

Val Pro Phe Ile Lys Ser Met Gly Gln Asn Leu Ser Val Ile Gly
                645                 650                 655

Ser Ile Val Asp Pro Asn Arg Ile Ile Ala Thr Tyr Ile Ser Asn Arg
                660                 665                 670

Gln Asp Ala Pro Thr Gly Asn Pro Asp Asn Ile Phe Asp Asn Asn Ala
            675                 680                 685

Ser Thr Glu Leu Val Tyr Lys Asn Pro Asn Arg Ile Asp Val Gly Thr
    690                 695                 700

Tyr Val Gly Val Lys Tyr Ser Asn Pro Ile Thr Leu Asn Asn Val Glu
705                 710                 715                 720

Phe Leu Met Gly Ala Asn Ser Asn Pro Asn Asp Thr Met Gln Lys Ala
                725                 730                 735

Lys Ile Gln Tyr Thr Val Asp Gly Arg Glu Trp Ile Asp Leu Glu Glu
                740                 745                 750

Gly Val Glu Tyr Thr Met Pro Gly Ala Ile Lys Val Glu Asn Leu Asp
            755                 760                 765

Leu Lys Val Arg Gly Val Arg Leu Ile Ala Thr Glu Ala Arg Glu Asn
    770                 775                 780

Thr Trp Leu Gly Val Arg Asp Ile Asn Val Asn Lys Lys Glu Asp Ser
785                 790                 795                 800

Asn Ser Gly Val Glu Phe Asn Pro Ser Leu Ile Arg Ser Glu Ser Trp
                805                 810                 815

Gln Val Tyr Glu Gly Asn Glu Ala Asn Leu Leu Asp Gly Asp Asp Asn
                820                 825                 830

Thr Gly Val Trp Tyr Lys Thr Leu Asn Gly Asp Thr Ser Leu Ala Gly
            835                 840                 845

Glu Phe Ile Gly Leu Asp Leu Gly Lys Glu Ile Lys Leu Asp Gly Ile
    850                 855                 860

Arg Phe Val Ile Gly Lys Asn Gly Gly Ser Ser Asp Lys Trp Asn
865                 870                 875                 880

Lys Phe Lys Leu Glu Tyr Ser Leu Asp Asn Glu Ser Trp Thr Thr Ile
                885                 890                 895

Lys Glu Tyr Asp Lys Thr Gly Ala Pro Ala Gly Lys Asp Val Ile Glu
                900                 905                 910

Glu Ser Phe Glu Thr Pro Ile Ser Ala Lys Tyr Ile Arg Leu Thr Asn
            915                 920                 925

Met Glu Asn Ile Asn Lys Trp Leu Thr Phe Ser Glu Phe Ala Ile Ile
930                 935                 940

Ser Asp Glu Leu Glu Asn Ala Gly Asn Lys Glu Asn Val Tyr Thr Asn
945                 950                 955                 960

Thr Glu Leu Asp Leu Leu Ser Leu Ala Lys Glu Asp Val Thr Lys Leu
                965                 970                 975

Ile Pro Thr Asp Asp Ile Ser Leu Asn His Gly Glu Tyr Ile Gly Val
            980                 985                 990

Lys Leu Asn Arg Ile Lys Asp Leu Ser Asn Ile Asn Leu Glu Ile Ser
        995                 1000                1005

Asn Asp Thr Gly Leu Lys Leu Gln Ser Ser Met Asn Gly Val Glu Trp
    1010                1015                1020
```

```
Thr Glu Ile Thr Asp Lys Asn Thr Leu Glu Asp Gly Arg Tyr Val Arg
1025                1030                1035                1040

Leu Ile Asn Thr Ser Asn Glu Ala Val Asn Phe Asn Leu Thr Lys Phe
                1045                1050                1055

Glu Val Asn Ser Asn Glu Val Tyr Glu Pro Ser Leu Val Asp Ala Tyr
            1060                1065                1070

Val Gly Asp Asp Gly Ala Lys Lys Ala Val Asp Gly Asp Leu Lys Thr
        1075                1080                1085

Arg Val Lys Phe Leu Gly Ala Pro Ser Thr Gly Asp Thr Ile Val Tyr
    1090                1095                1100

Asp Leu Gly Gln Glu Ile Leu Val Asp Asn Leu Lys Tyr Val Val Leu
1105                1110                1115                1120

Asp Thr Glu Val Asp His Val Arg Asp Gly Lys Ile Gln Leu Ser Leu
                1125                1130                1135

Asp Gly Glu Thr Trp Thr Asp Ala Ile Thr Ile Gly Asp Gly Val Glu
            1140                1145                1150

Asn Gly Val Asp Asp Met Phe Ser Thr Pro Leu Lys Asn Gly Tyr Lys
        1155                1160                1165

His Gly Asn Gln Ser Gly Gly Ile Val Pro Ile Asp Ser Ala Tyr Val
    1170                1175                1180

Glu Gly Asp Asn Leu Asn Gln Lys Ala Arg Tyr Val Arg Ile Leu Phe
1185                1190                1195                1200

Thr Ala Pro Tyr Arg His Arg Trp Thr Val Ile Asn Glu Leu Met Ile
                1205                1210                1215

Asn Asn Gly Glu Tyr Ile Ser Thr Val Asn Asp Pro Thr Tyr Ile Ser
            1220                1225                1230

Asn Pro Ile Glu Glu Arg Gly Phe Ala Pro Ser Asn Leu Arg Asp Gly
        1235                1240                1245

Asn Leu Thr Thr Ser Tyr Lys Pro Asn Thr Asn Asn Gly Glu Ile Ser
    1250                1255                1260

Glu Gly Ser Ile Thr Tyr Arg Leu Ser Glu Lys Thr Asp Val Arg Lys
1265                1270                1275                1280

Val Thr Ile Val Gln Ser Gly Ser Ser Ile Ser Asn Ala Lys Val Met
                1285                1290                1295

Ala Arg Val Gly Asp Gly Ser Glu Asn Val Thr Asp Gln Trp Val Gln
            1300                1305                1310

Leu Gly Thr Leu Ser Asn Ser Leu Asn Glu Phe Ile Asn Arg Asp Tyr
        1315                1320                1325

Asn Asn Ile Tyr Glu Ile Lys Ile Glu Trp Thr Asp Val Ala Pro Asn
    1330                1335                1340

Ile Tyr Glu Ile Ile Thr Leu Asn Gln Glu Phe Glu Phe Pro Val Asn
1345                1350                1355                1360

Asp Ser Leu Lys Ala Lys Tyr Asp Glu Leu Ile Asn Leu Ser Gly Asp
                1365                1370                1375

Glu Tyr Thr Leu Ser Ser Phe Glu Thr Leu Lys Glu Ala Leu Asn Glu
            1380                1385                1390

Ala Lys Ser Ile Leu Asp Asp Ser Asn Ser Ser Gln Lys Lys Ile Asp
        1395                1400                1405

Lys Ala Leu Glu Lys Leu Asn Lys Ala Glu Glu Arg Leu Asp Leu Arg
    1410                1415                1420

Ala Thr Asp Phe Glu Asp Phe Asn Lys Val Leu Thr Leu Gly Asn Ser
1425                1430                1435                1440

Leu Val Glu Glu Glu Tyr Thr Ala Glu Ser Trp Ala Leu Phe Ser Glu
```

```
                    1445            1450            1455

Val Leu Glu Ala Ala Asn Glu Ala Asn Lys Asn Lys Ala Asp Tyr Thr
            1460            1465            1470

Gln Asp Gln Ile Asn Gln Ile Val Ile Asp Leu Asp Ala Ser Ile Lys
        1475            1480            1485

Ala Leu Val Lys Glu Thr Pro Glu Val Asp Lys Thr Asn Leu Gly Glu
    1490            1495            1500

Leu Ile Asn Gln Gly Lys Ser Leu Leu Asp Glu Ser Val Glu Gly Phe
1505            1510            1515            1520

Asn Val Gly Glu Tyr His Lys Gly Ala Lys Asp Gly Leu Thr Val Glu
            1525            1530            1535

Ile Asn Lys Ala Glu Glu Val Phe Asn Lys Glu Asp Ala Thr Glu Glu
        1540            1545            1550

Glu Ile Asn Leu Ala Lys Glu Ser Leu Glu Gly Ala Ile Ala Arg Phe
    1555            1560            1565

Asn Ser Leu Leu Ile Glu Glu Ser Thr Gly Asp Phe Asn Gly Asn Gly
1570            1575            1580

Lys Ile Asp Ile Gly Asp Leu Ala Met Val Ser Lys Asn Ile Gly Ser
1585            1590            1595            1600

Thr Thr Asn Thr Ser Leu Asp Leu Asn Lys Asp Gly Ser Ile Asp Glu
            1605            1610            1615

Tyr Glu Ile Ser Phe Ile Asn His Arg Ile Leu Asn
            1620            1625

<210> SEQ ID NO 36
<211> LENGTH: 435
<212> TYPE: PRT
<213> ORGANISM: Homo sapiens
<220> FEATURE:
<223> OTHER INFORMATION: Hyaluronidase-1 [Precursor]

<400> SEQUENCE: 36

Met Ala Ala His Leu Leu Pro Ile Cys Ala Leu Phe Leu Thr Leu Leu
 1               5                  10                  15

Asp Met Ala Gln Gly Phe Arg Gly Pro Leu Leu Pro Asn Arg Pro Phe
            20                  25                  30

Thr Thr Val Trp Asn Ala Asn Thr Gln Trp Cys Leu Glu Arg His Gly
        35                  40                  45

Val Asp Val Asp Val Ser Val Phe Asp Val Val Ala Asn Pro Gly Gln
    50                  55                  60

Thr Phe Arg Gly Pro Asp Met Thr Ile Phe Tyr Ser Ser Gln Leu Gly
65                  70                  75                  80

Thr Tyr Pro Tyr Tyr Thr Pro Thr Gly Glu Pro Val Phe Gly Gly Leu
                85                  90                  95

Pro Gln Asn Ala Ser Leu Ile Ala His Leu Ala Arg Thr Phe Gln Asp
            100                 105                 110

Ile Leu Ala Ala Ile Pro Ala Pro Asp Phe Ser Gly Leu Ala Val Ile
        115                 120                 125

Asp Trp Glu Ala Trp Arg Pro Arg Trp Ala Phe Asn Trp Asp Thr Lys
    130                 135                 140

Asp Ile Tyr Arg Gln Arg Ser Arg Ala Leu Val Gln Ala Gln His Pro
145                 150                 155                 160

Asp Trp Pro Ala Pro Gln Val Glu Ala Val Ala Gln Asp Gln Phe Gln
                165                 170                 175

Gly Ala Ala Arg Ala Trp Met Ala Gly Thr Leu Gln Leu Gly Arg Ala
```

```
                180             185             190
Leu Arg Pro Arg Gly Leu Trp Gly Phe Tyr Gly Phe Pro Asp Cys Tyr
            195                 200             205

Asn Tyr Asp Phe Leu Ser Pro Asn Tyr Thr Gly Gln Cys Pro Ser Gly
        210                 215                 220

Ile Arg Ala Gln Asn Asp Gln Leu Gly Trp Leu Trp Gly Gln Ser Arg
225                 230                 235                 240

Ala Leu Tyr Pro Ser Ile Tyr Met Pro Ala Val Leu Glu Gly Thr Gly
                245                 250                 255

Lys Ser Gln Met Tyr Val Gln His Arg Val Ala Glu Ala Phe Arg Val
            260                 265                 270

Ala Val Ala Ala Gly Asp Pro Asn Leu Pro Val Leu Pro Tyr Val Gln
        275                 280                 285

Ile Phe Tyr Asp Thr Thr Asn His Phe Leu Pro Leu Asp Glu Leu Glu
        290                 295                 300

His Ser Leu Gly Glu Ser Ala Ala Gln Gly Ala Ala Gly Val Val Leu
305                 310                 315                 320

Trp Val Ser Trp Glu Asn Thr Arg Thr Lys Glu Ser Cys Gln Ala Ile
                325                 330                 335

Lys Glu Tyr Met Asp Thr Thr Leu Gly Pro Phe Ile Leu Asn Val Thr
            340                 345                 350

Ser Gly Ala Leu Leu Cys Ser Gln Ala Leu Cys Ser Gly His Gly Arg
        355                 360                 365

Cys Val Arg Arg Thr Ser His Pro Lys Ala Leu Leu Leu Leu Asn Pro
        370                 375                 380

Ala Ser Phe Ser Ile Gln Leu Thr Pro Gly Gly Gly Pro Leu Ser Leu
385                 390                 395                 400

Arg Gly Ala Leu Ser Leu Glu Asp Gln Ala Gln Met Ala Val Glu Phe
                405                 410                 415

Lys Cys Arg Cys Tyr Pro Gly Trp Gln Ala Pro Trp Cys Glu Arg Lys
            420                 425                 430

Ser Met Trp
        435

<210> SEQ ID NO 37
<211> LENGTH: 473
<212> TYPE: PRT
<213> ORGANISM: Homo sapiens
<220> FEATURE:
<223> OTHER INFORMATION: Hyaluronidase-2 [Precursor]

<400> SEQUENCE: 37

Met Arg Ala Gly Pro Gly Pro Thr Val Thr Leu Ala Leu Val Leu Ala
1               5                   10                  15

Val Ala Trp Ala Met Glu Leu Lys Pro Thr Ala Pro Pro Ile Phe Thr
            20                  25                  30

Gly Arg Pro Phe Val Val Ala Trp Asp Val Pro Thr Gln Asp Cys Gly
        35                  40                  45

Pro Arg Leu Lys Val Pro Leu Asp Leu Asn Ala Phe Asp Val Gln Ala
    50                  55                  60

Ser Pro Asn Glu Gly Phe Val Asn Gln Asn Ile Thr Ile Phe Tyr Arg
65                  70                  75                  80

Asp Arg Leu Gly Leu Tyr Pro Arg Phe Asp Ser Ala Gly Arg Ser Val
                85                  90                  95

His Gly Gly Val Pro Gln Asn Val Ser Leu Trp Ala His Arg Lys Met
```

```
                100             105              110
Leu Gln Lys Arg Val Glu His Tyr Ile Arg Thr Gln Glu Ser Ala Gly
            115                 120                 125
Leu Ala Val Ile Asp Trp Glu Asp Trp Arg Pro Val Trp Arg Asn
        130                 135                 140
Trp Gln Asp Lys Asp Val Tyr Arg Arg Leu Ser Arg Gln Leu Val Ala
145                 150                 155                 160
Ser Arg His Pro Asp Trp Pro Asp Arg Ile Val Lys Gln Ala Gln
                165                 170                 175
Tyr Glu Phe Glu Phe Ala Ala Gln Gln Phe Met Leu Glu Thr Leu Arg
            180                 185                 190
Tyr Val Lys Ala Val Arg Pro Arg His Leu Trp Gly Phe Tyr Leu Phe
            195                 200                 205
Pro Asp Cys Tyr Asn His Asp Tyr Val Gln Asn Trp Glu Ser Tyr Thr
            210                 215                 220
Gly Arg Cys Pro Asp Val Glu Val Ala Arg Asn Asp Gln Leu Ala Trp
225                 230                 235                 240
Leu Trp Ala Glu Ser Thr Ala Leu Phe Pro Ser Val Tyr Leu Asp Glu
                245                 250                 255
Thr Leu Ala Ser Ser Arg His Gly Arg Asn Phe Val Ser Phe Arg Val
                260                 265                 270
Gln Glu Ala Leu Arg Val Ala Arg Thr His His Ala Asn His Ala Leu
            275                 280                 285
Pro Val Tyr Val Phe Thr Arg Pro Thr Tyr Ser Arg Arg Leu Thr Gly
            290                 295                 300
Leu Ser Glu Met Asp Leu Ile Ser Thr Ile Gly Glu Ser Ala Ala Leu
305                 310                 315                 320
Gly Ala Ala Gly Val Ile Leu Trp Gly Asp Ala Gly Tyr Thr Thr Ser
                325                 330                 335
Thr Glu Thr Cys Gln Tyr Leu Lys Asp Tyr Leu Thr Arg Leu Leu Val
                340                 345                 350
Pro Tyr Val Val Asn Val Ser Trp Ala Thr Gln Tyr Cys Ser Arg Ala
            355                 360                 365
Gln Cys His Gly His Gly Arg Cys Val Arg Arg Asn Pro Ser Ala Ser
            370                 375                 380
Thr Phe Leu His Leu Ser Thr Asn Ser Phe Arg Leu Val Pro Gly His
385                 390                 395                 400
Ala Pro Gly Glu Pro Gln Leu Arg Pro Val Gly Glu Leu Ser Trp Ala
                405                 410                 415
Asp Ile Asp His Leu Gln Thr His Phe Arg Cys Gln Cys Tyr Leu Gly
            420                 425                 430
Trp Ser Gly Glu Gln Cys Gln Trp Asp His Arg Gln Ala Ala Gly Gly
            435                 440                 445
Ala Ser Glu Ala Trp Ala Gly Ser His Leu Thr Ser Leu Leu Ala Leu
            450                 455                 460
Ala Ala Leu Ala Phe Thr Trp Thr Leu
465                 470

<210> SEQ ID NO 38
<211> LENGTH: 417
<212> TYPE: PRT
<213> ORGANISM: Homo sapiens
<220> FEATURE:
<223> OTHER INFORMATION: Hyaluronidase-3 [Precursor]
```

```
<400> SEQUENCE: 38

Met Thr Thr Gln Leu Gly Pro Ala Leu Val Leu Gly Val Ala Leu Cys
1               5                   10                  15

Leu Gly Cys Gly Gln Pro Leu Pro Gln Val Pro Glu Arg Pro Phe Ser
            20                  25                  30

Val Leu Trp Asn Val Pro Ser Ala His Cys Glu Ala Arg Phe Gly Val
        35                  40                  45

His Leu Pro Leu Asn Ala Leu Gly Ile Ile Ala Asn Arg Gly Gln His
    50                  55                  60

Phe His Gly Gln Asn Met Thr Ile Phe Tyr Lys Asn Gln Leu Gly Leu
65                  70                  75                  80

Tyr Pro Tyr Phe Gly Pro Arg Gly Thr Ala His Asn Gly Gly Ile Pro
                85                  90                  95

Gln Ala Leu Pro Leu Asp Arg His Leu Ala Leu Ala Ala Tyr Gln Ile
            100                 105                 110

His His Ser Leu Arg Pro Gly Phe Ala Gly Pro Ala Val Leu Asp Trp
            115                 120                 125

Glu Glu Trp Cys Pro Leu Trp Ala Gly Asn Trp Gly Arg Arg Arg Ala
130                 135                 140

Tyr Gln Ala Ala Ser Trp Ala Trp Ala Gln Val Phe Pro Asp Leu
145                 150                 155                 160

Asp Pro Gln Glu Gln Leu Tyr Lys Ala Tyr Thr Gly Phe Glu Gln Ala
                165                 170                 175

Ala Arg Ala Leu Met Glu Asp Thr Leu Arg Val Ala Gln Ala Leu Arg
            180                 185                 190

Pro His Gly Leu Trp Gly Phe Tyr His Tyr Pro Ala Cys Gly Asn Gly
            195                 200                 205

Trp His Ser Met Ala Ser Asn Tyr Thr Gly Arg Cys His Ala Ala Thr
210                 215                 220

Leu Ala Arg Asn Thr Gln Leu His Trp Leu Trp Ala Ala Ser Ser Ala
225                 230                 235                 240

Leu Phe Pro Ser Ile Tyr Leu Pro Pro Arg Leu Pro Pro Ala His His
            245                 250                 255

Gln Ala Phe Val Arg His Arg Leu Glu Glu Ala Phe Arg Val Ala Leu
            260                 265                 270

Val Gly His Arg His Pro Leu Pro Val Leu Ala Tyr Val Arg Leu Thr
            275                 280                 285

His Arg Arg Ser Gly Arg Phe Leu Ser Gln Asp Asp Leu Val Gln Ser
290                 295                 300

Ile Gly Val Ser Ala Ala Leu Gly Ala Ala Gly Val Val Leu Trp Gly
305                 310                 315                 320

Asp Leu Ser Leu Ser Ser Glu Glu Glu Cys Trp His Leu His Asp
                325                 330                 335

Tyr Leu Val Asp Thr Leu Gly Pro Tyr Val Ile Asn Val Thr Arg Ala
                340                 345                 350

Ala Met Ala Cys Ser His Gln Arg Cys His Gly His Gly Arg Cys Ala
            355                 360                 365

Arg Arg Asp Pro Gly Gln Met Glu Ala Phe Leu His Leu Trp Pro Asp
370                 375                 380

Gly Ser Leu Gly Asp Trp Lys Ser Phe Ser Cys His Cys Tyr Trp Gly
385                 390                 395                 400

Trp Ala Gly Pro Thr Cys Gln Glu Pro Arg Pro Gly Pro Lys Glu Ala
                405                 410                 415
```

Val

<210> SEQ ID NO 39
<211> LENGTH: 481
<212> TYPE: PRT
<213> ORGANISM: Homo sapiens
<220> FEATURE:
<223> OTHER INFORMATION: Hyaluronidase-4

<400> SEQUENCE: 39

Met Lys Val Leu Ser Glu Gly Gln Leu Lys Leu Cys Val Val Gln Pro
 1               5                  10                  15

Val His Leu Thr Ser Trp Leu Leu Ile Phe Phe Ile Leu Lys Ser Ile
            20                  25                  30

Ser Cys Leu Lys Pro Ala Arg Leu Pro Ile Tyr Gln Arg Lys Pro Phe
        35                  40                  45

Ile Ala Ala Trp Asn Ala Pro Thr Asp Gln Cys Leu Ile Lys Tyr Asn
 50                  55                  60

Leu Arg Leu Asn Leu Lys Met Phe Pro Val Ile Gly Ser Pro Leu Ala
 65                  70                  75                  80

Lys Ala Arg Gly Gln Asn Val Thr Ile Phe Tyr Val Asn Arg Leu Gly
                85                  90                  95

Tyr Tyr Pro Trp Tyr Thr Ser Gln Gly Val Pro Ile Asn Gly Gly Leu
            100                 105                 110

Pro Gln Asn Ile Ser Leu Gln Val His Leu Glu Lys Ala Asp Gln Asp
        115                 120                 125

Ile Asn Tyr Tyr Ile Pro Ala Glu Asp Phe Ser Gly Leu Ala Val Ile
130                 135                 140

Asp Trp Glu Tyr Trp Arg Pro Gln Trp Ala Arg Asn Trp Asn Ser Lys
145                 150                 155                 160

Asp Val Tyr Arg Gln Lys Ser Arg Lys Leu Ile Ser Asp Met Gly Lys
                165                 170                 175

Asn Val Ser Ala Thr Asp Ile Glu Tyr Leu Ala Lys Val Thr Phe Glu
            180                 185                 190

Glu Ser Ala Lys Ala Phe Met Lys Glu Thr Ile Lys Leu Gly Ile Lys
        195                 200                 205

Ser Arg Pro Lys Gly Leu Trp Gly Tyr Leu Tyr Pro Asp Cys His
        210                 215                 220

Asn Tyr Asn Val Tyr Ala Pro Asn Tyr Ser Gly Ser Cys Pro Glu Asp
225                 230                 235                 240

Glu Val Leu Arg Asn Asn Glu Leu Ser Trp Leu Trp Asn Ser Ser Ala
                245                 250                 255

Ala Leu Tyr Pro Ser Ile Gly Val Trp Lys Ser Leu Gly Asp Ser Glu
            260                 265                 270

Asn Ile Leu Arg Phe Ser Lys Phe Arg Val His Glu Ser Met Arg Ile
        275                 280                 285

Ser Thr Met Thr Ser His Asp Tyr Ala Leu Pro Val Phe Val Tyr Thr
290                 295                 300

Arg Leu Gly Tyr Arg Asp Glu Pro Leu Phe Phe Leu Ser Lys Gln Asp
305                 310                 315                 320

Leu Val Ser Thr Ile Gly Glu Ser Ala Ala Leu Gly Ala Ala Gly Ile
                325                 330                 335

Val Ile Trp Gly Asp Met Asn Leu Thr Ala Ser Lys Ala Asn Cys Thr
            340                 345                 350

Lys Val Lys Gln Phe Val Ser Ser Asp Leu Gly Ser Tyr Ile Ala Asn
          355                 360                 365

Val Thr Arg Ala Ala Glu Val Cys Ser Leu His Leu Cys Arg Asn Asn
    370                 375                 380

Gly Arg Cys Ile Arg Lys Met Trp Asn Ala Pro Ser Tyr Leu His Leu
385                 390                 395                 400

Asn Pro Ala Ser Tyr His Ile Glu Ala Ser Glu Asp Gly Glu Phe Thr
                405                 410                 415

Val Lys Gly Lys Ala Ser Asp Thr Asp Leu Ala Val Met Ala Asp Thr
                420                 425                 430

Phe Ser Cys His Cys Tyr Gln Gly Tyr Glu Gly Ala Asp Cys Arg Glu
    435                 440                 445

Ile Lys Thr Ala Asp Gly Cys Ser Gly Val Ser Pro Ser Pro Gly Ser
    450                 455                 460

Leu Met Thr Leu Cys Leu Leu Leu Ala Ser Tyr Arg Ser Ile Gln
465                 470                 475                 480

Leu

<210> SEQ ID NO 40
<211> LENGTH: 467
<212> TYPE: PRT
<213> ORGANISM: Homo sapiens
<220> FEATURE:
<223> OTHER INFORMATION: sHuPH20 precursor 1-467

<400> SEQUENCE: 40

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
                20                  25                  30

Cys Leu Thr Leu Asn Phe Arg Ala Pro Pro Val Ile Pro Asn Val Pro
            35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
                100                 105                 110

Gly Ile Pro Gln Lys Ile Ser Leu Gln Asp His Leu Asp Lys Ala Lys
            115                 120                 125

Lys Asp Ile Thr Phe Tyr Met Pro Val Asp Asn Leu Gly Met Ala Val
130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
210                 215                 220

Tyr Asn His His Tyr Lys Lys Pro Gly Tyr Asn Gly Ser Cys Phe Asn

```
            225                 230                 235                 240
    Val Glu Ile Lys Arg Asn Asp Asp Leu Ser Trp Leu Trp Asn Glu Ser
                    245                 250                 255

Thr Ala Leu Tyr Pro Ser Ile Tyr Leu Asn Thr Gln Gln Ser Pro Val
                260                 265                 270

Ala Ala Thr Leu Tyr Val Arg Asn Arg Val Arg Glu Ala Ile Arg Val
                275                 280                 285

Ser Lys Ile Pro Asp Ala Lys Ser Pro Leu Pro Val Phe Ala Tyr Thr
        290                 295                 300

Arg Ile Val Phe Thr Asp Gln Val Leu Lys Phe Leu Ser Gln Asp Glu
    305                 310                 315                 320

Leu Val Tyr Thr Phe Gly Glu Thr Val Ala Leu Gly Ala Ser Gly Ile
                    325                 330                 335

Val Ile Trp Gly Thr Leu Ser Ile Met Arg Ser Met Lys Ser Cys Leu
                340                 345                 350

Leu Leu Asp Asn Tyr Met Glu Thr Ile Leu Asn Pro Tyr Ile Ile Asn
                355                 360                 365

Val Thr Leu Ala Ala Lys Met Cys Ser Gln Val Leu Cys Gln Glu Gln
        370                 375                 380

Gly Val Cys Ile Arg Lys Asn Trp Asn Ser Ser Asp Tyr Leu His Leu
    385                 390                 395                 400

Asn Pro Asp Asn Phe Ala Ile Gln Leu Glu Lys Gly Gly Lys Phe Thr
                    405                 410                 415

Val Arg Gly Lys Pro Thr Leu Glu Asp Leu Glu Gln Phe Ser Glu Lys
                420                 425                 430

Phe Tyr Cys Ser Cys Tyr Ser Thr Leu Ser Cys Lys Glu Lys Ala Asp
                435                 440                 445

Val Lys Asp Thr Asp Ala Val Asp Val Cys Ile Ala Asp Gly Val Cys
        450                 455                 460

Ile Asp Ala
    465

<210> SEQ ID NO 41
<211> LENGTH: 477
<212> TYPE: PRT
<213> ORGANISM: Homo sapiens
<220> FEATURE:
<223> OTHER INFORMATION: sHuPH20 precursor 1-477

<400> SEQUENCE: 41

Met Gly Val Leu Lys Phe Lys His Ile Phe Phe Arg Ser Phe Val Lys
    1               5                  10                  15

Ser Ser Gly Val Ser Gln Ile Val Phe Thr Phe Leu Leu Ile Pro Cys
                    20                  25                  30

Cys Leu Thr Leu Asn Phe Arg Ala Pro Pro Val Ile Pro Asn Val Pro
                35                  40                  45

Phe Leu Trp Ala Trp Asn Ala Pro Ser Glu Phe Cys Leu Gly Lys Phe
        50                  55                  60

Asp Glu Pro Leu Asp Met Ser Leu Phe Ser Phe Ile Gly Ser Pro Arg
    65                  70                  75                  80

Ile Asn Ala Thr Gly Gln Gly Val Thr Ile Phe Tyr Val Asp Arg Leu
                    85                  90                  95

Gly Tyr Tyr Pro Tyr Ile Asp Ser Ile Thr Gly Val Thr Val Asn Gly
                100                 105                 110

Gly Ile Pro Gln Lys Ile Ser Leu Gln Asp His Leu Asp Lys Ala Lys
```

```
            115                 120                 125
Lys Asp Ile Thr Phe Tyr Met Pro Val Asp Asn Leu Gly Met Ala Val
        130                 135                 140
Ile Asp Trp Glu Glu Trp Arg Pro Thr Trp Ala Arg Asn Trp Lys Pro
145                 150                 155                 160
Lys Asp Val Tyr Lys Asn Arg Ser Ile Glu Leu Val Gln Gln Gln Asn
                165                 170                 175
Val Gln Leu Ser Leu Thr Glu Ala Thr Glu Lys Ala Lys Gln Glu Phe
            180                 185                 190
Glu Lys Ala Gly Lys Asp Phe Leu Val Glu Thr Ile Lys Leu Gly Lys
        195                 200                 205
Leu Leu Arg Pro Asn His Leu Trp Gly Tyr Tyr Leu Phe Pro Asp Cys
210                 215                 220
Tyr Asn His His Tyr Lys Lys Pro Gly Tyr Asn Gly Ser Cys Phe Asn
225                 230                 235                 240
Val Glu Ile Lys Arg Asn Asp Asp Leu Ser Trp Leu Trp Asn Glu Ser
                245                 250                 255
Thr Ala Leu Tyr Pro Ser Ile Tyr Leu Asn Thr Gln Gln Ser Pro Val
            260                 265                 270
Ala Ala Thr Leu Tyr Val Arg Asn Arg Val Arg Glu Ala Ile Arg Val
        275                 280                 285
Ser Lys Ile Pro Asp Ala Lys Ser Pro Leu Pro Val Phe Ala Tyr Thr
290                 295                 300
Arg Ile Val Phe Thr Asp Gln Val Leu Lys Phe Leu Ser Gln Asp Glu
305                 310                 315                 320
Leu Val Tyr Thr Phe Gly Glu Thr Val Ala Leu Gly Ala Ser Gly Ile
                325                 330                 335
Val Ile Trp Gly Thr Leu Ser Ile Met Arg Ser Met Lys Ser Cys Leu
            340                 345                 350
Leu Leu Asp Asn Tyr Met Glu Thr Ile Leu Asn Pro Tyr Ile Ile Asn
        355                 360                 365
Val Thr Leu Ala Ala Lys Met Cys Ser Gln Val Leu Cys Gln Glu Gln
370                 375                 380
Gly Val Cys Ile Arg Lys Asn Trp Asn Ser Ser Asp Tyr Leu His Leu
385                 390                 395                 400
Asn Pro Asp Asn Phe Ala Ile Gln Leu Glu Lys Gly Gly Lys Phe Thr
                405                 410                 415
Val Arg Gly Lys Pro Thr Leu Glu Asp Leu Glu Gln Phe Ser Glu Lys
            420                 425                 430
Phe Tyr Cys Ser Cys Tyr Ser Thr Leu Ser Cys Lys Glu Lys Ala Asp
        435                 440                 445
Val Lys Asp Thr Asp Ala Val Asp Val Cys Ile Ala Asp Gly Val Cys
450                 455                 460
Ile Asp Ala Phe Leu Lys Pro Pro Met Glu Thr Glu Glu
465                 470                 475

<210> SEQ ID NO 42
<211> LENGTH: 478
<212> TYPE: PRT
<213> ORGANISM: Homo sapiens
<220> FEATURE:
<223> OTHER INFORMATION: sHuPH20 precursor 1-478

<400> SEQUENCE: 42

Met Gly Val Leu Lys Phe Lys His Ile Phe Phe Arg Ser Phe Val Lys
```

```
                1               5              10              15
         Ser Ser Gly Val Ser Gln Ile Val Phe Thr Phe Leu Leu Ile Pro Cys
                        20              25              30
         Cys Leu Thr Leu Asn Phe Arg Ala Pro Pro Val Ile Pro Asn Val Pro
                        35              40              45
         Phe Leu Trp Ala Trp Asn Ala Pro Ser Glu Phe Cys Leu Gly Lys Phe
                 50              55              60
         Asp Glu Pro Leu Asp Met Ser Leu Phe Ser Phe Ile Gly Ser Pro Arg
          65              70              75              80
         Ile Asn Ala Thr Gly Gln Gly Val Thr Ile Phe Tyr Val Asp Arg Leu
                        85              90              95
         Gly Tyr Tyr Pro Tyr Ile Asp Ser Ile Thr Gly Val Thr Val Asn Gly
                       100             105             110
         Gly Ile Pro Gln Lys Ile Ser Leu Gln Asp His Leu Asp Lys Ala Lys
                       115             120             125
         Lys Asp Ile Thr Phe Tyr Met Pro Val Asp Asn Leu Gly Met Ala Val
                       130             135             140
         Ile Asp Trp Glu Glu Trp Arg Pro Thr Trp Ala Arg Asn Trp Lys Pro
         145             150             155             160
         Lys Asp Val Tyr Lys Asn Arg Ser Ile Glu Leu Val Gln Gln Gln Asn
                       165             170             175
         Val Gln Leu Ser Leu Thr Glu Ala Thr Glu Lys Ala Lys Gln Glu Phe
                       180             185             190
         Glu Lys Ala Gly Lys Asp Phe Leu Val Glu Thr Ile Lys Leu Gly Lys
                       195             200             205
         Leu Leu Arg Pro Asn His Leu Trp Gly Tyr Tyr Leu Phe Pro Asp Cys
                       210             215             220
         Tyr Asn His His Tyr Lys Lys Pro Gly Tyr Asn Gly Ser Cys Phe Asn
         225             230             235             240
         Val Glu Ile Lys Arg Asn Asp Asp Leu Ser Trp Leu Trp Asn Glu Ser
                       245             250             255
         Thr Ala Leu Tyr Pro Ser Ile Tyr Leu Asn Thr Gln Gln Ser Pro Val
                       260             265             270
         Ala Ala Thr Leu Tyr Val Arg Asn Arg Val Arg Glu Ala Ile Arg Val
                       275             280             285
         Ser Lys Ile Pro Asp Ala Lys Ser Pro Leu Pro Val Phe Ala Tyr Thr
                       290             295             300
         Arg Ile Val Phe Thr Asp Gln Val Leu Lys Phe Leu Ser Gln Asp Glu
         305             310             315             320
         Leu Val Tyr Thr Phe Gly Glu Thr Val Ala Leu Gly Ala Ser Gly Ile
                       325             330             335
         Val Ile Trp Gly Thr Leu Ser Ile Met Arg Ser Met Lys Ser Cys Leu
                       340             345             350
         Leu Leu Asp Asn Tyr Met Glu Thr Ile Leu Asn Pro Tyr Ile Ile Asn
                       355             360             365
         Val Thr Leu Ala Ala Lys Met Cys Ser Gln Val Leu Cys Gln Glu Gln
                       370             375             380
         Gly Val Cys Ile Arg Lys Asn Trp Asn Ser Ser Asp Tyr Leu His Leu
         385             390             395             400
         Asn Pro Asp Asn Phe Ala Ile Gln Leu Glu Lys Gly Gly Lys Phe Thr
                       405             410             415
         Val Arg Gly Lys Pro Thr Leu Glu Asp Leu Glu Gln Phe Ser Glu Lys
                       420             425             430
```

```
Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Pro
465                 470                 475

<210> SEQ ID NO 43
<211> LENGTH: 479
<212> TYPE: PRT
<213> ORGANISM: Homo sapiens
<220> FEATURE:
<223> OTHER INFORMATION: sHuPH20 precursor 1-479

<400> SEQUENCE: 43

Met Gly Val Leu Lys Phe Lys His Ile Phe Phe Arg Ser Phe Val Lys
 1               5                  10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
    290                 295                 300

Arg Ile Val Phe Thr Asp Gln Val Leu Lys Phe Leu Ser Gln Asp Glu
305                 310                 315                 320
```

```
Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
                355                 360                 365

Val Thr Leu Ala Ala Lys Met Cys Ser Gln Val Leu Cys Gln Glu Gln
        370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
                435                 440                 445

Val Lys Asp Thr Asp Ala Val Asp Val Cys Ile Ala Asp Gly Val Cys
        450                 455                 460

Ile Asp Ala Phe Leu Lys Pro Pro Met Glu Thr Glu Glu Pro Gln
465                 470                 475
```

<210> SEQ ID NO 44
<211> LENGTH: 480
<212> TYPE: PRT
<213> ORGANISM: Homo sapiens
<220> FEATURE:
<223> OTHER INFORMATION: sHuPH20 precursor 1-480

<400> SEQUENCE: 44

```
Met Gly Val Leu Lys Phe Lys His Ile Phe Phe Arg Ser Phe Val Lys
 1               5                  10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
        115                 120                 125

Lys Asp Ile Thr Phe Tyr Met Pro Val Asp Asn Leu Gly Met Ala Val
    130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205
```

```
Leu Leu Arg Pro Asn His Leu Trp Gly Tyr Tyr Leu Phe Pro Asp Cys
    210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
    290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
    370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
    450                 455                 460

Ile Asp Ala Phe Leu Lys Pro Pro Met Glu Thr Glu Glu Pro Gln Ile
465                 470                 475                 480

<210> SEQ ID NO 45
<211> LENGTH: 481
<212> TYPE: PRT
<213> ORGANISM: Homo sapiens
<220> FEATURE:
<223> OTHER INFORMATION: sHuPH20 precursor 1-481

<400> SEQUENCE: 45

Met Gly Val Leu Lys Phe Lys His Ile Phe Phe Arg Ser Phe Val Lys
  1               5                  10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80

Ile Asn Ala Thr Gly Gln Gly Val Thr Ile Phe Tyr Val Asp Arg Leu
                85                  90                  95
```

Gly Tyr Tyr Pro Tyr Ile Asp Ser Ile Thr Gly Val Thr Val Asn Gly
                100                 105                 110

Gly Ile Pro Gln Lys Ile Ser Leu Gln Asp His Leu Asp Lys Ala Lys
            115                 120                 125

Lys Asp Ile Thr Phe Tyr Met Pro Val Asp Asn Leu Gly Met Ala Val
        130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
        275                 280                 285

Ser Lys Ile Pro Asp Ala Lys Ser Pro Leu Pro Val Phe Ala Tyr Thr
290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
        355                 360                 365

Val Thr Leu Ala Ala Lys Met Cys Ser Gln Val Leu Cys Gln Glu Gln
370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
            420                 425                 430

Phe Tyr Cys Ser Cys Tyr Ser Thr Leu Ser Cys Lys Glu Lys Ala Asp
        435                 440                 445

Val Lys Asp Thr Asp Ala Val Asp Val Cys Ile Ala Asp Gly Val Cys
450                 455                 460

Ile Asp Ala Phe Leu Lys Pro Pro Met Glu Thr Glu Glu Pro Gln Ile
465                 470                 475                 480

Phe

<210> SEQ ID NO 46
<211> LENGTH: 483
<212> TYPE: PRT

<213> ORGANISM: Homo sapiens
<220> FEATURE:
<223> OTHER INFORMATION: sHuPH20 precursor 1-483

<400> SEQUENCE: 46

```
Met Gly Val Leu Lys Phe Lys His Ile Phe Phe Arg Ser Phe Val Lys
 1               5                   10                  15

Ser Ser Gly Val Ser Gln Ile Val Phe Thr Phe Leu Leu Ile Pro Cys
             20                  25                  30

Cys Leu Thr Leu Asn Phe Arg Ala Pro Pro Val Ile Pro Asn Val Pro
         35                  40                  45

Phe Leu Trp Ala Trp Asn Ala Pro Ser Glu Phe Cys Leu Gly Lys Phe
 50                  55                  60

Asp Glu Pro Leu Asp Met Ser Leu Phe Ser Phe Ile Gly Ser Pro Arg
 65                  70                  75                  80

Ile Asn Ala Thr Gly Gln Gly Val Thr Ile Phe Tyr Val Asp Arg Leu
                 85                  90                  95

Gly Tyr Tyr Pro Tyr Ile Asp Ser Ile Thr Gly Val Thr Val Asn Gly
            100                 105                 110

Gly Ile Pro Gln Lys Ile Ser Leu Gln Asp His Leu Asp Lys Ala Lys
            115                 120                 125

Lys Asp Ile Thr Phe Tyr Met Pro Val Asp Asn Leu Gly Met Ala Val
130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
            195                 200                 205

Leu Leu Arg Pro Asn His Leu Trp Gly Tyr Tyr Leu Phe Pro Asp Cys
210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
            260                 265                 270

Ala Ala Thr Leu Tyr Val Arg Asn Arg Val Arg Glu Ala Ile Arg Val
            275                 280                 285

Ser Lys Ile Pro Asp Ala Lys Ser Pro Leu Pro Val Phe Ala Tyr Thr
290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
            340                 345                 350

Leu Leu Asp Asn Tyr Met Glu Thr Ile Leu Asn Pro Tyr Ile Ile Asn
            355                 360                 365

Val Thr Leu Ala Ala Lys Met Cys Ser Gln Val Leu Cys Gln Glu Gln
370                 375                 380

Gly Val Cys Ile Arg Lys Asn Trp Asn Ser Ser Asp Tyr Leu His Leu
```

```
385                 390                 395                 400
Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
                420                 425                 430

Phe Tyr Cys Ser Cys Tyr Ser Thr Leu Ser Cys Lys Glu Lys Ala Asp
                435                 440                 445

Val Lys Asp Thr Asp Ala Val Asp Val Cys Ile Ala Asp Gly Val Cys
        450                 455                 460

Ile Asp Ala Phe Leu Lys Pro Pro Met Glu Thr Glu Glu Pro Gln Ile
465                 470                 475                 480

Phe Tyr Asn

<210> SEQ ID NO 47
<211> LENGTH: 432
<212> TYPE: PRT
<213> ORGANISM: Homo sapiens
<220> FEATURE:
<223> OTHER INFORMATION: sHuPH20 mature 36-467

<400> SEQUENCE: 47

Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
                20                  25                  30

Leu Asp Met Ser Leu Phe Ser Phe Ile Gly Ser Pro Arg Ile Asn Ala
            35                  40                  45

Thr Gly Gln Gly Val Thr Ile Phe Tyr Val Asp Arg Leu Gly Tyr Tyr
        50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
                100                 105                 110

Glu Glu Trp Arg Pro Thr Trp Ala Arg Asn Trp Lys Pro Lys Asp Val
            115                 120                 125

Tyr Lys Asn Arg Ser Ile Glu Leu Val Gln Gln Asn Val Gln Leu
        130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
                180                 185                 190

His Tyr Lys Lys Pro Gly Tyr Asn Gly Ser Cys Phe Asn Val Glu Ile
            195                 200                 205

Lys Arg Asn Asp Asp Leu Ser Trp Leu Trp Asn Glu Ser Thr Ala Leu
        210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
                260                 265                 270
```

```
Phe Thr Asp Gln Val Leu Lys Phe Leu Ser Gln Asp Glu Leu Val Tyr
            275                 280                 285

Thr Phe Gly Glu Thr Val Ala Leu Gly Ala Ser Gly Ile Val Ile Trp
290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
            355                 360                 365

Asn Phe Ala Ile Gln Leu Glu Lys Gly Gly Lys Phe Thr Val Arg Gly
370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

<210> SEQ ID NO 48
<211> LENGTH: 448
<212> TYPE: PRT
<213> ORGANISM: Homo sapiens
<220> FEATURE:
<223> OTHER INFORMATION: sHuPH20 mature 36-483

<400> SEQUENCE: 48

Leu Asn Phe Arg Ala Pro Pro Val Ile Pro Asn Val Pro Phe Leu Trp
  1               5                  10                  15

Ala Trp Asn Ala Pro Ser Glu Phe Cys Leu Gly Lys Phe Asp Glu Pro
             20                  25                  30

Leu Asp Met Ser Leu Phe Ser Phe Ile Gly Ser Pro Arg Ile Asn Ala
         35                  40                  45

Thr Gly Gln Gly Val Thr Ile Phe Tyr Val Asp Arg Leu Gly Tyr Tyr
     50                  55                  60

Pro Tyr Ile Asp Ser Ile Thr Gly Val Thr Val Asn Gly Gly Ile Pro
 65                  70                  75                  80

Gln Lys Ile Ser Leu Gln Asp His Leu Asp Lys Ala Lys Lys Asp Ile
                 85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205
```

```
Lys Arg Asn Asp Asp Leu Ser Trp Leu Trp Asn Glu Ser Thr Ala Leu
            210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
        290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
            355                 360                 365

Asn Phe Ala Ile Gln Leu Glu Lys Gly Gly Lys Phe Thr Val Arg Gly
370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

<210> SEQ ID NO 49
<211> LENGTH: 1446
<212> TYPE: DNA
<213> ORGANISM: Homo sapiens
<220> FEATURE:
<223> OTHER INFORMATION: DNA encoding soluble rHuPH20 "precursor"

<400> SEQUENCE: 49
atgggagtgc taaaattcaa gcacatcttt ttcagaagct tgttaaaatc aagtggagta      60
tcccagatag ttttcacctt ccttctgatt ccatgttgct tgactctgaa tttcagagca    120
cctcctgtta ttccaaatgt gcctttcctc tgggcctgga atgccccaag tgaattttgt    180
cttggaaaat ttgatgagcc actagatatg agcctcttct ctttcatagg aagcccccga    240
ataaacgcca ccgggcaagg tgttacaata ttttatgttg atagacttgg ctactatcct    300
tacatagatt caatcacagg agtaactgtg aatggaggaa tcccccagaa gatttcctta    360
caagaccatc tggacaaagc taagaaagac attacatttt atatgccagt agacaatttg    420
ggaatggctg ttattgactg gaagaatgg agacccactt gggcaagaaa ctggaaacct    480
aaagatgttt acaagaatag gtctattgaa ttggttcagc aacaaaatgt acaacttagt    540
ctcacagagg ccactgagaa agcaaaacaa gaatttgaaa aggcagggaa ggatttcctg    600
gtagagacta aaaattggg aaaattactt cggccaaatc acttgtgggg ttattatctt    660
tttccggatt gttacaacca tcactataag aaacccggtt acaatggaag ttgcttcaat    720
```

```
gtagaaataa aaagaaatga tgatctcagc tggttgtgga atgaaagcac tgctctttac    780
ccatccattt atttgaacac tcagcagtct cctgtagctg ctacactcta tgtgcgcaat    840
cgagttcggg aagccatcag agtttccaaa atacctgatg caaaaagtcc acttccggtt    900
tttgcatata cccgcatagt ttttactgat caagttttga aattcctttc tcaagatgaa    960
cttgtgtata catttggcga aactgttgct ctgggtgctt ctggaattgt aatatgggga   1020
accctcagta taatgcgaag tatgaaatct tgcttgctcc tagacaatta catggagact   1080
atactgaatc cttacataat caacgtcaca ctagcagcca aaatgtgtag ccaagtgctt   1140
tgccaggagc aaggagtgtg tataaggaaa aactggaatt caagtgacta tcttcacctc   1200
aacccagata attttgctat tcaacttgag aaaggtggaa agttcacagt acgtggaaaa   1260
ccgacacttg aagacctgga gcaatttttct gaaaaatttt attgcagctg ttatagcacc   1320
ttgagttgta aggagaaagc tgatgtaaaa gacactgatg ctgttgatgt gtgtattgct   1380
gatggtgtct gtatagatgc ttttctaaaa cctcccatgg agacagaaga acctcaaatt   1440
ttctac                                                              1446

<210> SEQ ID NO 50
<211> LENGTH: 509
<212> TYPE: PRT
<213> ORGANISM: Homo sapiens
<220> FEATURE:
<223> OTHER INFORMATION: PH20 variant P48A

<400> SEQUENCE: 50

Met Gly Val Leu Lys Phe Lys His Ile Phe Phe Arg Ser Phe Val Lys
  1               5                  10                  15

Ser Ser Gly Val Ser Gln Ile Val Phe Thr Phe Leu Leu Ile Pro Cys
                 20                  25                  30

Cys Leu Thr Leu Asn Phe Arg Ala Pro Pro Val Ile Pro Asn Val Ala
             35                  40                  45

Phe Leu Trp Ala Trp Asn Ala Pro Ser Glu Phe Cys Leu Gly Lys Phe
 50                  55                  60

Asp Glu Pro Leu Asp Met Ser Leu Phe Ser Phe Ile Gly Ser Pro Arg
 65                  70                  75                  80

Ile Asn Ala Thr Gly Gln Gly Val Thr Ile Phe Tyr Val Asp Arg Leu
                 85                  90                  95

Gly Tyr Tyr Pro Tyr Ile Asp Ser Ile Thr Gly Val Thr Val Asn Gly
                100                 105                 110

Gly Ile Pro Gln Lys Ile Ser Leu Gln Asp His Leu Asp Lys Ala Lys
            115                 120                 125

Lys Asp Ile Thr Phe Tyr Met Pro Val Asp Asn Leu Gly Met Ala Val
130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
            180                 185                 190

Glu Lys Ala Gly Lys Asp Phe Leu Val Glu Thr Ile Lys Leu Gly Lys
        195                 200                 205

Leu Leu Arg Pro Asn His Leu Trp Gly Tyr Tyr Leu Phe Pro Asp Cys
    210                 215                 220
```

```
Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
            245                 250                 255

Thr Ala Leu Tyr Pro Ser Ile Tyr Leu Asn Thr Gln Gln Ser Pro Val
        260                 265                 270

Ala Ala Thr Leu Tyr Val Arg Asn Arg Val Arg Glu Ala Ile Arg Val
    275                 280                 285

Ser Lys Ile Pro Asp Ala Lys Ser Pro Leu Pro Val Phe Ala Tyr Thr
290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
            325                 330                 335

Val Ile Trp Gly Thr Leu Ser Ile Met Arg Ser Met Lys Ser Cys Leu
        340                 345                 350

Leu Leu Asp Asn Tyr Met Glu Thr Ile Leu Asn Pro Tyr Ile Ile Asn
    355                 360                 365

Val Thr Leu Ala Ala Lys Met Cys Ser Gln Val Leu Cys Gln Glu Gln
370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
            405                 410                 415

Val Arg Gly Lys Pro Thr Leu Glu Asp Leu Glu Gln Phe Ser Glu Lys
        420                 425                 430

Phe Tyr Cys Ser Cys Tyr Ser Thr Leu Ser Cys Lys Glu Lys Ala Asp
    435                 440                 445

Val Lys Asp Thr Asp Ala Val Asp Val Cys Ile Ala Asp Gly Val Cys
450                 455                 460

Ile Asp Ala Phe Leu Lys Pro Pro Met Glu Thr Glu Glu Pro Gln Ile
465                 470                 475                 480

Phe Tyr Asn Ala Ser Pro Ser Thr Leu Ser Ala Thr Met Phe Ile Val
            485                 490                 495

Ser Ile Leu Phe Leu Ile Ile Ser Ser Val Ala Ser Leu
        500                 505

<210> SEQ ID NO 51
<211> LENGTH: 509
<212> TYPE: PRT
<213> ORGANISM: Homo sapiens
<220> FEATURE:
<223> OTHER INFORMATION: precursor PH20 variant L499W

<400> SEQUENCE: 51

Met Gly Val Leu Lys Phe Lys His Ile Phe Phe Arg Ser Phe Val Lys
1               5                   10                  15

Ser Ser Gly Val Ser Gln Ile Val Phe Thr Phe Leu Leu Ile Pro Cys
            20                  25                  30

Cys Leu Thr Leu Asn Phe Arg Ala Pro Pro Val Ile Pro Asn Val Pro
        35                  40                  45

Phe Leu Trp Ala Trp Asn Ala Pro Ser Glu Phe Cys Leu Gly Lys Phe
    50                  55                  60

Asp Glu Pro Leu Asp Met Ser Leu Phe Ser Phe Ile Gly Ser Pro Arg
65                  70                  75                  80
```

Ile Asn Ala Thr Gly Gln Gly Val Thr Ile Phe Tyr Val Asp Arg Leu
              85                  90                  95

Gly Tyr Tyr Pro Tyr Ile Asp Ser Ile Thr Gly Val Thr Val Asn Gly
             100                 105                 110

Gly Ile Pro Gln Lys Ile Ser Leu Gln Asp His Leu Asp Lys Ala Lys
             115                 120                 125

Lys Asp Ile Thr Phe Tyr Met Pro Val Asp Asn Leu Gly Met Ala Val
             130                 135                 140

Ile Asp Trp Glu Glu Trp Arg Pro Thr Trp Ala Arg Asn Trp Lys Pro
145                 150                 155                 160

Lys Asp Val Tyr Lys Asn Arg Ser Ile Glu Leu Val Gln Gln Gln Asn
                165                 170                 175

Val Gln Leu Ser Leu Thr Glu Ala Thr Glu Lys Ala Lys Gln Glu Phe
             180                 185                 190

Glu Lys Ala Gly Lys Asp Phe Leu Val Glu Thr Ile Lys Leu Gly Lys
             195                 200                 205

Leu Leu Arg Pro Asn His Leu Trp Gly Tyr Tyr Leu Phe Pro Asp Cys
210                 215                 220

Tyr Asn His His Tyr Lys Lys Pro Gly Tyr Asn Gly Ser Cys Phe Asn
225                 230                 235                 240

Val Glu Ile Lys Arg Asn Asp Asp Leu Ser Trp Leu Trp Asn Glu Ser
                245                 250                 255

Thr Ala Leu Tyr Pro Ser Ile Tyr Leu Asn Thr Gln Gln Ser Pro Val
             260                 265                 270

Ala Ala Thr Leu Tyr Val Arg Asn Arg Val Arg Glu Ala Ile Arg Val
             275                 280                 285

Ser Lys Ile Pro Asp Ala Lys Ser Pro Leu Pro Val Phe Ala Tyr Thr
             290                 295                 300

Arg Ile Val Phe Thr Asp Gln Val Leu Lys Phe Leu Ser Gln Asp Glu
305                 310                 315                 320

Leu Val Tyr Thr Phe Gly Glu Thr Val Ala Leu Gly Ala Ser Gly Ile
                325                 330                 335

Val Ile Trp Gly Thr Leu Ser Ile Met Arg Ser Met Lys Ser Cys Leu
             340                 345                 350

Leu Leu Asp Asn Tyr Met Glu Thr Ile Leu Asn Pro Tyr Ile Ile Asn
             355                 360                 365

Val Thr Leu Ala Ala Lys Met Cys Ser Gln Val Leu Cys Gln Glu Gln
             370                 375                 380

Gly Val Cys Ile Arg Lys Asn Trp Asn Ser Ser Asp Tyr Leu His Leu
385                 390                 395                 400

Asn Pro Asp Asn Phe Ala Ile Gln Leu Glu Lys Gly Gly Lys Phe Thr
                405                 410                 415

Val Arg Gly Lys Pro Thr Leu Glu Asp Leu Glu Gln Phe Ser Glu Lys
             420                 425                 430

Phe Tyr Cys Ser Cys Tyr Ser Thr Leu Ser Cys Lys Glu Lys Ala Asp
             435                 440                 445

Val Lys Asp Thr Asp Ala Val Asp Val Cys Ile Ala Asp Gly Val Cys
             450                 455                 460

Ile Asp Ala Phe Leu Lys Pro Pro Met Glu Thr Glu Glu Pro Gln Ile
465                 470                 475                 480

Phe Tyr Asn Ala Ser Pro Ser Thr Leu Ser Ala Thr Met Phe Ile Val
                485                 490                 495

Ser Ile Trp Phe Leu Ile Ile Ser Ser Val Ala Ser Leu

<210> SEQ ID NO 52
<211> LENGTH: 6630
<212> TYPE: DNA
<213> ORGANISM: Artificial Sequence
<220> FEATURE:
<223> OTHER INFORMATION: HZ24 vector

<400> SEQUENCE: 52

```
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat      300
agtaacgcca atagggactt tccattgacg tcaatgggtg gagtatttac ggtaaactgc     360
ccacttggca gtacatcaag tgtatcatat gccaagtccg cccctattg acgtcaatga      420
cggtaaatgg cccgcctggc attatgccca gtacatgacc ttacgggact ttcctacttg     480
gcagtacatc tacgtattag tcatcgctat taccatggta tgcggtttt ggcagtacac      540
caatgggcgt ggatagcggt ttgactcacg ggatttcca gtctccacc ccattgacgt       600
caatgggagt ttgttttggc accaaaatca acgggacttt ccaaaatgtc gtaataaccc     660
cgccccgttg acgcaaatgg gcggtaggcg tgtacggtgg gaggtctata taagcagagc     720
tcgtttagtg aaccgtcaga tcactagaag ctttattgcg gtagttatc acagttaaat      780
tgctaacgca gtcagtgctt ctgacacaac agtctcgaac ttaagctgca gaagttggtc     840
gtgaggcact gggcaggtaa gatcaaggt tacaagacag gtttaaggag accaatagaa      900
actgggcttg tcgagacaga aagactctt gcgtttctga taggcaccta ttggtcttac      960
tgacatccac tttgcctttc tctccacagg tgtccactcc cagttcaatt acagctctta    1020
aggctagagt acttaatacg actcactata ggctagcatg ggagtgctaa aattcaagca    1080
catcttttc agaagctttg ttaaatcaag tggagtatcc cagatagttt tcaccttcct     1140
tctgattcca tgttgcttga ctctgaattt cagagcacct cctgttattc caaatgtgcc    1200
tttcctctgg gcctgaatg ccccaagtga attttgtctt ggaaaatttg atgagccact     1260
agatatgagc ctcttctctt tcataggaag cccccgaata aacgccaccg ggcaaggtgt    1320
tacaatattt tatgttgata gacttggcta ctatccttac atagattcaa tcacaggagt    1380
aactgtgaat ggaggaatcc cccagaagat ttccttacaa gaccatctgg acaaagctaa    1440
gaaagacatt acattttata tgccagtaga caatttggga atggctgtta ttgactggga    1500
agaatggaga cccacttggg caagaaactg gaaacctaaa gatgtttaca gaataggtc     1560
tattgaattg gttcagcaac aaaatgtaca acttagtctc acagaggcca ctgagaaagc    1620
aaaacaagaa tttgaaaagg cagggaagga tttcctggta gagactataa aattgggaaa    1680
attacttcgg ccaaatcact gtgggggtta ttatcttttt ccggattgtt acaaccatca    1740
ctataagaaa cccggttaca atggaagttg cttcaatgta gaaataaaaa gaatgatga    1800
tctcagctgg ttgtggaatg aaagcactgc tctttaccca tccattattt tgaacactca    1860
gcagtctcct gtagctgcta cactctatgt gcgcaatcga gttcgggaag ccatcagagt    1920
ttccaaaata cctgatgcaa aaagtccact tccggttttt gcatataccc gcatagtttt    1980
tactgatcaa gtttttgaaat tccttttctca agatgaactt gtgtatacat ttggcgaaac    2040
```

-continued

```
tgttgctctg ggtgcttctg gaattgtaat atggggaacc ctcagtataa tgcgaagtat      2100
gaaatcttgc ttgctcctag acaattacat ggagactata ctgaatcctt acataatcaa      2160
cgtcacacta gcagccaaaa tgtgtagcca agtgctttgc caggagcaag gagtgtgtat      2220
aaggaaaaac tggaattcaa gtgactatct tcacctcaac ccagataatt ttgctattca      2280
acttgagaaa ggtggaaagt tcacagtacg tggaaaaccg acacttgaag acctggagca      2340
attttctgaa aaatttttatt gcagctgtta tagcaccttg agttgtaagg agaaagctga      2400
tgtaaaagac actgatgctg ttgatgtgtg tattgctgat ggtgtctgta tagatgcttt      2460
tctaaaacct cccatggaga cagaagaacc tcaaattttc tactgaggat ccatagctaa      2520 cgccectctc cctccccccc ccctaacgtt actggccgaa gccgcttgga ataaggccgg      2580
tgtgcgtttg tctatatgtt attttccacc atattgccgt cttttggcaa tgtgagggcc      2640
cggaaacctg gccctgtctt cttgacgagc attcctaggg gtctttcccc tctcgccaaa      2700
ggaatgcaag gtctgttgaa tgtcgtgaag gaagcagttc ctctggaagc ttcttgaaga      2760
caaacaacgt ctgtagcgac cctttgcagg cagcggaacc ccccacctgg cgacaggtgc      2820
ctctgcggcc aaaagccacg tgtataagat acacctgcaa aggcggcaca accccagtgc      2880
cacgttgtga gttggatagt tgtggaaaga gtcaaatggc tctcctcaag cgtattcaac      2940
aaggggctga aggatgccca gaaggtaccc cattgtatgg gatctgatct ggggcctcgg      3000
tgcacatgct ttacatgtgt ttagtcgagg ttaaaaaaac gtctaggccc cccgaaccac      3060
ggggacgtgg ttttccttttg aaaaacacga tgataagctt gccacaaccc acagcggccg      3120
ctgccatcat ggttcgacca ttgaactgca tcgtcgccgt gtcccaaaat atggggattg      3180
gcaagaacgg agacctaccc tggcctccgc tcaggaacga gttcaagtac ttccaaagaa      3240
tgaccacaac ctcttcagtg gaaggtaaac agaatctggt gattatgggt aggaaaacct      3300
ggttctccat tcctgagaag aatcgacctt taaaggacag aattaatata gttctcagta      3360
gagaactcaa agaaccacca cgaggagctc attttcttgc caaaagtttg gatgatgcct      3420
taagacttat tgaacaaccg gaattggcaa gtaaagtaga catggtttgg atagtcggag      3480
gcagttctgt ttaccaggaa gccatgaatc aaccaggcca cctcagactc tttgtgacaa      3540
ggatcatgca ggaatttgaa agtgacacgt ttttcccaga aattgatttg gggaaatata      3600
aacttctccc agaatacccca ggcgtcctct ctgaggtcca ggaggaaaaa ggcatcaagt      3660
ataagtttga agtctacgag aagaaagact aaacgcgtgg tacctctaga gtcgacccgg      3720
gcggccgctt cgagcagaca tgataagata cattgatgag tttggacaaa ccacaactag      3780
aatgcagtga aaaaaatgct ttatttgtga aatttgtgat gctattgctt tatttgtaac      3840
cattataagc tgcaataaac aagttaacaa caacaattgc attcatttta tgtttcaggt      3900
tcaggggagt atgtgggagg ttttttaaag caagtaaaac ctctacaaat gtggtaaaat      3960
cgataaggat ccgggctggc gtaatagcga agaggcccgc accgatcgcc cttcccaaca      4020
gttgcgcagc ctgaatggcg aatggacgcg ccctgtagcg gcgcattaag cgcggcgggt      4080
gtggtggtta cgcgcagcgt gaccgctaca cttgccagcg ccctagcgcc cgctcctttc      4140
gctttcttcc cttcctttct cgccacgttc gccggctttc cccgtcaagc tctaaatcgg      4200
gggctccctt tagggttccg atttagtgct ttacggcacc tcgaccccaa aaaacttgat      4260
tagggtgatg gttcacgtag tgggccatcg ccctgataga cggttttttcg ccctttgacg      4320 ttggagtcca cgttctttaa tagtggactc ttgttccaaa ctggaacaac actcaaccct      4380
```

```
atctcggtct attcttttga tttataaggg attttgccga tttcggccta ttggttaaaa    4440
aatgagctga tttaacaaaa atttaacgcg aattttaaca aaatattaac gcttacaatt    4500
tcctgatgcg gtattttctc cttacgcatc tgtgcggtat ttcacaccgc atatggtgca    4560
ctctcagtac aatctgctct gatgccgcat agttaagcca gccccgacac ccgccaacac    4620
ccgctgacgc gccctgacgg gcttgtctgc tcccggcatc cgcttacaga caagctgtga    4680
ccgtctccgg gagctgcatg tgtcagaggt tttcaccgtc atccgaaa cgcgcgagac       4740
gaaagggcct cgtgatacgc ctattttat aggttaatgt catgataata atggtttctt     4800
agacgtcagg tggcactttt cggggaaatg tgcgcggaac ccctatttgt ttatttttct    4860
aaatacattc aaatatgtat ccgctcatga acaataacc ctgataaatg cttcaataat     4920
attgaaaaag gaagagtatg agtattcaac atttccgtgt cgcccttatt ccctttttg     4980
cggcattttg ccttcctgtt tttgctcacc cagaaacgct ggtgaaagta aaagatgctg    5040
aagatcagtt gggtgcacga gtgggttaca tcgaactgga tctcaacagc ggtaagatcc    5100
ttgagagttt tcgccccgaa gaacgttttc caatgatgag cacttttaaa gttctgctat    5160
gtggcgcggt attatcccgt attgacgccg ggcaagagca actcggtcgc cgcatacact    5220
attctcagaa tgacttggtt gagtactcac cagtcacaga aaagcatctt acggatggca    5280
tgacagtaag agaattatgc agtgctgcca taaccatgag tgataacact gcggccaact    5340
tacttctgac aacgatcgga ggaccgaagg agctaaccgc ttttttgcac aacatggggg    5400
atcatgtaac tcgccttgat cgttgggaac cggagctgaa tgaagccata ccaaacgacg    5460
agcgtgacac cacgatgcct gtagcaatgg caacaacgtt gcgcaaacta ttaactggcg    5520
aactacttac tctagcttcc cggcaacaat taatagactg gatggaggcg gataaagttg    5580
caggaccact tctgcgctcg gcccttccgg ctggctggtt tattgctgat aaatctggag    5640
ccggtgagcg tgggtctcgc ggtatcattg cagcactggg gccagatggt aagccctccc    5700
gtatcgtagt tatctacacg acggggagtc aggcaactat ggatgaacga atagacaga    5760
tcgctgagat aggtgcctca ctgattaagc attggtaact gtcagaccaa gtttactcat    5820
atatacttta gattgattta aaacttcatt tttaatttaa aaggatctag gtgaagatcc    5880
tttttgataa tctcatgacc aaaatccctt aacgtgagtt ttcgttccac tgagcgtcag    5940
accccgtaga aaagatcaaa ggatcttctt gagatccttt ttttctgcgc gtaatctgct    6000
gcttgcaaac aaaaaaacca ccgctaccag cggtggtttg tttgccggat caagagctac    6060
caactctttt tccgaaggta actggcttca gcagagcgca gataccaaat actgttcttc    6120
tagtgtagcc gtagttaggc caccacttca agaactctgt agcaccgcct acatacctcg    6180
ctctgctaat cctgttacca gtggctgctg ccagtggcga taagtcgtgt cttaccgggt    6240
tggactcaag acgatagtta ccggataagg cgcagcggtc gggctgaacg gggggttcgt    6300
gcacacagcc cagcttggag cgaacgacct acaccgaact gagataccta cagcgtgagc    6360
tatgagaaag cgccacgctt cccgaaggga gaaaggcgga caggtatccg gtaagcggca    6420
gggtcggaac aggagagcgc acgagggagc ttccaggggg aaacgcctgg tatctttata    6480
gtcctgtcgg gtttcgccac ctctgacttg agcgtcgatt tttgtgatgc tcgtcagggg    6540
ggcggagcct atggaaaaac gccagcaacg cggccttttt acggttcctg ccttttgct    6600
ggccttttgc tcacatggct cgacagatct                                     6630
```

<210> SEQ ID NO 53
<211> LENGTH: 186

```
<212> TYPE: PRT
<213> ORGANISM: Mus musculus
<220> FEATURE:
<223> OTHER INFORMATION: dihydrofolate reductase

<400> SEQUENCE: 53
```

Val Arg Pro Leu Asn Cys Ile Val Ala Val Ser Gln Asn Met Gly Ile
1               5                   10                  15

Gly Lys Asn Gly Asp Leu Pro Trp Pro Pro Leu Arg Asn Glu Phe Lys
            20                  25                  30

Tyr Phe Gln Arg Met Thr Thr Thr Ser Ser Val Glu Gly Lys Gln Asn
        35                  40                  45

Leu Val Ile Met Gly Arg Lys Thr Trp Phe Ser Ile Pro Glu Lys Asn
    50                  55                  60

Arg Pro Leu Lys Asp Arg Ile Asn Ile Val Leu Ser Arg Glu Leu Lys
65                  70                  75                  80

Glu Pro Pro Arg Gly Ala His Phe Leu Ala Lys Ser Leu Asp Asp Ala
                85                  90                  95

Leu Arg Leu Ile Glu Gln Pro Glu Leu Ala Ser Lys Val Asp Met Val
            100                 105                 110

Trp Ile Val Gly Gly Ser Ser Val Tyr Gln Glu Ala Met Asn Gln Pro
        115                 120                 125

Gly His Leu Arg Leu Phe Val Thr Arg Ile Met Gln Glu Phe Glu Ser
    130                 135                 140

Asp Thr Phe Phe Pro Glu Ile Asp Leu Gly Lys Tyr Lys Leu Leu Pro
145                 150                 155                 160

Glu Tyr Pro Gly Val Leu Ser Glu Val Gln Glu Lys Gly Ile Lys
                165                 170                 175

Tyr Lys Phe Glu Val Tyr Glu Lys Lys Asp
            180                 185

```
<210> SEQ ID NO 54
<211> LENGTH: 6
<212> TYPE: PRT
<213> ORGANISM: Artificial Sequence
<220> FEATURE:
<223> OTHER INFORMATION: His tag

<400> SEQUENCE: 54
```

His His His His His His
1               5

```
<210> SEQ ID NO 55
<211> LENGTH: 8
<212> TYPE: PRT
<213> ORGANISM: Artificial Sequence
<220> FEATURE:
<223> OTHER INFORMATION: Flag tag

<400> SEQUENCE: 55
```

Asp Tyr Lys Asp Asp Asp Asp Lys
1               5

```
<210> SEQ ID NO 56
<211> LENGTH: 1449
<212> TYPE: DNA
<213> ORGANISM: Homo sapiens
<220> FEATURE:
<223> OTHER INFORMATION: Gen2 mRNA sequence

<400> SEQUENCE: 56
```

-continued

```
atgggagtgc taaaattcaa gcacatcttt ttcagaagct ttgttaaatc aagtggagta         60
tcccagatag ttttcacctt ccttctgatt ccatgttgct tgactctgaa tttcagagca        120
cctcctgtta ttccaaatgt gcctttcctc tgggcctgga atgccccaag tgaattttgt        180
cttggaaaat ttgatgagcc actagatatg agcctcttct ctttcatagg aagccccga         240 ataaacgcca ccgggcaagg tgttacaata ttttatgttg atagacttgg ctactatcct        300
tacatagatt caatcacagg agtaactgtg aatggaggaa tcccccagaa gatttcctta        360
caagaccatc tggacaaagc taagaaagac attacatttt atatgccagt agacaatttg        420
ggaatggctg ttattgactg ggaagaatgg agacccactt gggcaagaaa ctggaaacct        480
aaagatgttt acaagaatag gtctattgaa ttggttcagc aacaaaatgt acaacttagt        540
ctcacagagg ccactgagaa agcaaaacaa gaatttgaaa aggcagggaa ggatttcctg        600
gtagagacta taaaattggg aaaattactt cggccaaatc acttgtgggg ttattatctt        660
tttccggatt gttacaacca tcactataag aaacccggtt acaatggaag ttgcttcaat        720
gtagaaataa aagaaatga tgatctcagc tggttgtgga atgaaagcac tgctctttac        780
ccatccattt atttgaacac tcagcagtct cctgtagctg ctacactcta tgtgcgcaat        840
cgagttcggg aagccatcag agtttccaaa atacctgatg caaaaagtcc acttccggtt        900
tttgcatata cccgcatagt ttttactgat caagttttga aattcctttc tcaagatgaa        960
cttgtgtata catttggcga aactgttgct ctgggtgctt ctggaattgt aatatgggga       1020
accctcagta taatgcgaag tatgaaatct tgcttgctcc tagacaatta catggagact       1080
atactgaatc cttacataat caacgtcaca ctagcagcca aaatgtgtag tcaagtgctt       1140
tgccaggagc aaggagtgtg tataaggaaa aactggaatt caagtgacta tcttcacctc       1200
aacccagata attttgctat tcaacttgag aaaggtggaa agttcacagt acgtggaaaa       1260
ccgacacttg aagacctgga gcaattttct gaaaaatttt attgcagctg ttatagcacc       1320
ttgagttgta aggagaaagc tgatgtaaaa gacactgatg ctgttgatgt gtgtattgct       1380
gatggtgtct gtatagatgc ttttctaaaa cctcccatgg agacagaaga acctcaaatt       1440
ttctactga                                                              1449
```

STABLE CO-FORMULATION OF HYALURONIDASE AND IMMUNOGLOBULIN, AND METHODS OF USE THEREOF

RELATED APPLICATIONS

Benefit of priority is claimed to U.S. Provisional Application Ser. No. 61/277,045, entitled "STABLE CO-FORMULATION OF HYALURONIDASE AND IMMUNOGLOBULIN, AND METHODS OF USE THEREOF," filed on Sep. 17, 2009.

This application also is related to corresponding International Application No. PCT/US2010/002545, filed the same day herewith, entitled "STABLE CO-FORMULATION OF HYALURONIDASE AND IMMUNOGLOBULIN, AND METHODS OF USE THEREOF," which also claims priority to U.S. Provisional Application Ser. No. 61/277,045.

The subject matter of each of the above-referenced applications is incorporated by reference in its entirety.

FIELD OF THE INVENTION

Provided herein are stable co-formulations of immunoglobulin and hyaluronidase that are stable to storage in liquid form at room temperature for at least 6 months and at standard refrigerator temperatures for 1-2 years. Such co-formulations can be used in methods of treating IG-treatable diseases or conditions by subcutaneous administration.

BACKGROUND

Immune globulin (IG) products from human plasma were first used in 1952 to treat immune deficiency. Initially, intramuscular or subcutaneous administrations of IG were the methods of choice. For injecting larger amounts of IG necessary for effective treatment of various diseases, however, intravenous administrable products with lower concentrated IG (50 mg/mL) were developed. The intravenous (IV) administration of immune globulin (IVIG) is the primary treatment of individuals with immune deficiencies. Although the initial IVIG preparations caused severe side effects, the IVIG preparations available at the present time are well tolerated in the majority of immune deficient patients. Nonetheless, a small proportion of patients continue to have unpleasant, even disabling, reactions such as headache, fatigue, and myalgia. Fever and chills remains a problem, especially when patients have intercurrent infections. The reactions often persist despite trying other IVIG preparations or pre-medicating with acetaminophen, diphenhydramine, and corticosteroids. Further, due to the requirement for IV administration, there are issues with patient compliance.

Subcutaneous (SQ) administration of immune globulin is an alternative to intravenous administration. Compared to IV infusions, SQ administration of immune globulin has several advantages. For example, it reduces the incidence of systemic reactions, does not require sometimes-difficult IV access, improves trough levels, and gives patients more independence.

For therapeutic use of any IG preparation, another important consideration in IG products is their stability during storage. Safe handling and administration of formulations containing proteins represent significant challenges to pharmaceutical formulators. Proteins possess unique chemical and physical properties that present stability problems: a variety of degradation pathways exist for proteins, implicating both chemical and physical instability. Chemical instability includes deamination, aggregation, clipping of the peptide backbone, and oxidation of methionine residues. Physical instability encompasses many phenomena, including, for example, aggregation. Hence, there is a need for stable formulations of immune globulin preparations.

SUMMARY

Provided herein are compositions, methods and kits for subcutaneous administration of stable, liquid co-formulations for treating IG-treatable diseases and conditions. Provided are stable, liquid co-formulation compositions formulated for subcutaneous administration, containing immune globulin (IG) at a concentration that is at least 10% w/v, a soluble hyaluronidase at a concentration that is at least 50 U/mL and is present at a ratio of at least 100 Units/gram (U/g) IG, NaCl at a concentration of at least 50 mM and a pH of between 4 to 5. The co-formulation is stable at 28° C.-32° C. for at least 6 months.

Further, an amino acid stabilizer can be present, for example, alanine, histidine, arginine, lysine, ornithine, isoleucine, valine, methionine, glycine or proline. In some examples, the amino acid is present in an amount that is at least 100 mM. In one example, the amino acid is glycine and is present in an amount that is or is at least 100 mM, 150 mM, 200 mM, 250 mM, 300 mM, 350 mM, 400 mM, 450 mM, 500 mM or more. In another example, the glycine is in an amount that is 250 mM.

The stable, liquid co-formulations provided herein contain IG at least 10% to 22%, for example 10% w/v, 11% w/v, 12% w/v, 13% w/v, 14% w/v, 15% w/v, 16% w/v, 17% w/v, 18% w/v, 19% w/v, 20% w/v, 21% w/v, 22% w/v or more. In some examples, the IG is 10% w/v or 20% w/v. The IG used in the co-formulations is from human plasma, for example, it can be purified from human plasma such as by alcohol fractionation. In some examples, the IG is further purified by any one or more of a chemical modification, incubation at pH 4.0 with or without pepsin, polyethylene glycol (PEG) precipitation, ion-exchange chromatography, enzymatic cleavage, solvent/detergent treatment, diafiltration or ultrafiltration. The co-formulations provided herein can employ IG that contains IgG, IgA and IgM. In some examples, the IG contains greater than 95% IgG.

Further, the co-formulations can contain NaCl. In some examples, the NaCl is at a concentration of 50 mM to 220 mM, for example, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, 200 mM, 210 mM, 220 mM or more. In one example, the NaCl is at a concentration of 150 mM.

The co-formulations provided herein contain a soluble hyaluronidase that can be PH20, or a truncated form thereof. For example, the soluble hyaluronidase can be an ovine, bovine or truncated human PH20. In some examples where the PH20 is a truncated human PH20, the truncated human PH20 can be selected from among polypeptides having a sequence of amino acids set forth in any of SEQ ID NOS: 4-9, or allelic variants or other variants thereof. In one example, the soluble hyaluronidase is rHuPH20.

Further, the soluble hyaluronidase can be at a concentration that is 50 U/mL to 500 U/mL, for example 50 U/mL, 100 U/mL, 200 U/mL, 300 U/mL, 400 U/mL, 500 U/mL or more. For example, the soluble hyaluronidase can be at a concentration that is 100 U/mL or 300 U/mL. In the co-formulations provided herein, the soluble hyaluronidase can be present at a ratio of 100 U/g IG to 5000 U/g IG, for example, 100 U/g IG, 150 U/g IG, 200 U/g IG, 250 U/g IG, 300 U/g IG, 400 U/g IG, 500 U/g IG, 600 U/g IG, 700 U/g IG, 800 U/g IG, 900 U/g IG, 1000 U/g IG, 1200 U/g IG, 1500 U/g IG, 1800 U/g IG, 2000 U/g IG, 3000 U/g IG, 4000 U/g IG, 5000 U/g IG or more. In some examples the soluble hyaluronidase is at a ratio of 500 U/g IG, 1000 U/g IG, 1500 U/g IG or 3000 U/g IG. The pH of the co-formulations can be 4.4 to 4.9 in concentrated form.

The co-formulations provided herein can be formulated for multiple dosage administration or single dosage administration. Further, in examples where the co-formulation is for single dosage administration, the IG is in an amount sufficient to treat an IG-treatable disease or condition. The IG can be administered daily, weekly, biweekly, every 2-3 weeks, every 3-4 weeks or monthly for treatment of an IG-treatable disease or condition. The administration of the co-formulation is effected such that the amount of IG administered is substantially the same as the amount in a single dosage administration when administered intravenously for treatment of an IG-treatable disease or condition. In some examples the amount of IG in the co-formulation can be about 1 gram (g) to 200 g, for example, 1 gram (g), 2 g, 3 g, 4 g, 5 g, 10 g, 20 g, 30 g, 40 g, 50 g, 60 g, 70 g, 80 g, 90 g, 100 g or 200 g. Further, the amount of hyaluronidase in the composition can be about 500 Units to 100,000 Units, for example, 500 Units, 1000 Units, 2000 Units, 5000 Units, 10,000 Units, 30,000 Units, 40,000 Units, 50,000 Units, 60,000 Units, 70,000 Units, 80,000 Units, 90,000 Units, 100,000 Units or more.

The liquid co-formulations provided herein are stable at 28° C.-32° C. for at least 6 months to a year, for example, 6 months, 7 months, 8 months, 9 months, 10 months, 11 months, 12 months or more. The liquid co-formulations are further stable at 0° C.-10° C. for at least 6 months to 2 years, for example, 6 months, 1 year, 2 years or more.

Also provided herein is a kit containing any of the stable, liquid co-formulations provided herein, and optionally instructions for use.

Provided herein are containers that contain the stable, liquid co-formulations provided herein. The container can be a tube, bottle, vial or syringe. In examples where the container is a syringe, the container further comprises a needle for injection. Thus, the containers provided herein contain the stable, liquid co-formulations for single dosage administration or multiple dosage administration.

Provided herein are methods of treating IG-treatable diseases or conditions, by subcutaneously administering to a subject a stable, liquid co-formulation containing a soluble hyaluronidase and IG. The co-formulation is administered such that the amount of IG administered is substantially the same as the amount when administered intravenously for treatment of an IG-treatable disease or condition.

Further, the methods provided herein are for treating an IG-treatable disease or condition, selected from among primary immune deficiency diseases, secondary immune deficiency diseases, inflammatory diseases, autoimmune diseases and acute infections.

In some examples, the co-formulations can be administered using the methods provided herein to treat a primary immune deficiency disease. The primary immune deficiency disease can be common variable immunodeficiency (CVID), selective IgA deficiency, IgG subclass deficiency, specific antibody deficiency, complement disorders, congenital agammaglobulinemia, ataxia telangiectasia, hyper IgM, Wiskott-Aldrich syndrome, severe combined immunodeficiency (SCID), primary hypogammaglobulinemia, primary immunodeficiency diseases with antibody deficiency, X-linked agammaglobulinemia (XLA), or hypogammaglobulinemia of infancy.

In other examples, the IG-treatable disease or condition is an acquired immune deficiency disease secondary to hematological malignancies. The hematological malignancy can be selected from among chronic lymphocytic leukemia (CLL), multiple myeloma (MM) and non-Hodgkin's lymphoma (NHL).

In instances where the IG-treatable disease or condition is an inflammatory or autoimmune disease, the inflammatory or autoimmune disease can be selected from among Kawasaki's disease, chronic inflammatory demyelinating polyneuropathy, Guillain-Barre syndrome, idiopathic thrombocytopenic purpura, polymyositis, dermatomyositis, inclusion body myositis, Lambert-Eaton myasthenic syndrome, multifocal motor neuropathy, myasthenia gravis and Moersch-Woltman syndrome.

In some examples the co-formulation is administered to treat an acute bacterial, viral or fungal infection, such as, for example, Haemophilus influenzae type B; *Pseudomonas aeruginosa* types A and B; *Staphylococcus aureus*; group B streptococcus; *Streptococcus pneumoniae* types 1, 3, 4, 6, 7, 8, 9, 12, 14, 18, 19, and 23; adenovirus types 2 and 5; cytomegalovirus; Epstein-Barr virus VCA; hepatitis A virus; hepatitis B virus; herpes simplex virus-1; herpes simplex virus-2; influenza A; measles; parainfluenza types 1, 2 and 3; polio; varicella zoster virus; *Aspergillus*; and *Candida albicans*.

Further, the IG-treatable disease or condition can be selected from among iatrogenic immunodeficiency; acute disseminated encephalomyelitis; ANCA-positive systemic necrotizing vasculitis; autoimmune haemolytic anaemia; bullous pemphigoid; cicatricial pemphigoid; Evans syndrome (including autoimmune haemolytic anaemia with immune thrombocytopenia); foeto-maternal/neonatal alloimmune thrombocytopenia (FMAIT/NAIT); haemophagocytic syndrome; high-risk allogeneic haemopoietic stem cell transplantation; IgM paraproteinaemic neuropathy; kidney transplantation; multiple sclerosis; opsoclonus myoclonus ataxia; pemphigus foliaceus; pemphigus vulgaris; post-transfusion purpura; toxic epidermal necrolysis/Steven Johnson syndrome (TEN/SJS); toxic shock syndrome; Alzheimer's Disease; systemic lupus erythematosus; multiple myeloma; sepsis; B cell tumors; paraneoplastic cerebellar degeneration with no antibodies; and bone marrow transplantation.

DETAILED DESCRIPTION

Outline
  A. Definitions
  B. Stable co-formulations of Immune Globulin (IG) and hyaluronidase
    1. Immune Globulin Therapy
    2. Subcutaneous Administration of Immune Globulin and Hyaluronidase Formulations
    3. Stable Co-Formulations
  C. Immune Globulin and Preparation of Immune Globulin
    1. Preparation and Purification
      a. Cohn-Oncley Method
      b. Modified Cohn-Oncley Procedures
      c. Viral Processing
      d. Protein concentration
      e. Exemplary IG Preparations
        i. 10% IG
        ii. High Concentration IG Preparations (e.g. 20% IG)
    2. Storage Stability
      a. Protein-stabilizing excipients
      b. pH D. Hyaluronidase
1. PH20
2. Soluble Hyaluronidase
   a. Soluble Human PH20
   b. Soluble Recombinant Human PH20 (rHuPH20)
3. Glycosylation
4. Modification of hyaluronidases to improve their pharmacokinetic properties
E. Methods of Producing Nucleic Acids encoding a soluble Hyaluronidase and Polypeptides Thereof
1. Vectors and Cells
2. Expression
   a. Prokaryotic Cells
   b. Yeast Cells
   c. Insect Cells
   d. Mammalian Cells
   e. Plants
3. Purification Techniques
F. Preparation, Formulation and Administration of Immune Globulins and Soluble Hyaluronidase Polypeptides
1. Formulations and Dosages
   a. Immune Globulin
   b. Hyaluronidase
   c. Sodium Chloride
   d. Amino acid Stabilizer
   e. Other Agents
2. Dosage Forms
3. Administration
G. Methods of Assessing Activity, Stability, Bioavailability and Pharmacokinetics
1. Molecular Size
2. Biological Activity
   a. Immune globulin
   b. Hyaluronidase
1. Pharmacokinetics and tolerability
H. Methods of Treatment and Therapeutic Uses
1. Primary and Secondary Immune Deficiency
   a. Primary immune deficiency
   b. Secondary Immune Deficiency
2. Inflammatory and Autoimmune diseases
   a. Kawasaki's disease
   b. Chronic inflammatory demyelinating polyneuropathy
   c. Guillain-Barre Syndrome
   d. Idiopathic thrombocytopenic purpura
   e. Inflammatory myopathies
      i. Dermatomyositis
      ii. polymyositis
      iii. inclusion body myositis
   f. Lambert-Eaton myasthenic syndrome
   g. Multifocal motor neuropathy
   h. Myasthenia Gravis
   i. Moersch-Woltmann syndrome
3. Acute Infections
4. Other Disease and Conditions
I. Articles of manufacture and kits
J. Examples
A. Definitions Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the interne can come and go, but equivalent information can be found by searching the interne. Reference thereto evidences the availability and public dissemination of such information.

As used herein, "immunoglobulin," "immune globulin," "gamma globulin" refer to preparations of plasma proteins derived from the pooled plasma of adult donors. IgG antibodies predominate; other antibody subclasses, such as IgA and IgM are present. Therapeutic immune globulin can provide passive immunization by increasing a recipient's serum levels of circulating antibodies. IgG antibodies can, for example, bind to and neutralize bacterial toxins; opsonize pathogens; activate complement; and suppress pathogenic cytokines and phagocytes through interaction with cytokines and receptors thereof, such as CD5, interleukin-1a (IL-1a), interleukin 6 (IL-6), tumor necrosis factor-alpha (TNF-alpha), and T-cell receptors. Therapeutic immune globulin can inhibit the activity of autoantibodies. Immune globulin preparations also include, but are not limited to, immune globulin intravenous (IGIV), immune globulin IV, therapeutic immunoglobulin. Immune globulin preparation are well known, and include brand names, such as BayGam®, Gamimune® N, Gammagard® S/D, Gammar®-P, Iveegam® EN, Panglobulin®, Polygam® S/D, Sandoglobulin®, Venoglobulin®-I, Venoglobulin®-S, WinRho® SDF and others. Immune globulin preparations can be derived from human plasma, or are recombinantly produced.

As used herein, "intravenous IgG" or "IVIG" treatment refers generally to a therapeutic method of intravenously administering a composition of IgG immunoglobulins to a patient for treating a number of conditions such as immune deficiencies, inflammatory diseases, and autoimmune diseases. The IgG immunoglobulins are typically pooled and prepared from plasma. Whole antibodies or fragments can be used.

As used herein, IG-treatable diseases or conditions refer to any disease or condition for which immune globulin preparations are used. Such diseases and conditions, include, but are not limited to, any disease in which an increase in circulating antibodies is ameliorative, such as, for example, immunodeficiency; acquired hypogammaglobulinemia secondary to hematological malignancies; Kawasaki's disease; chronic inflammatory demyelinating polyneuropathy (CIDP); Guillain-Barre Syndrome; Idiopathic thrombocytopenic purpura; inflammatory myopathies; Lambert-Eaton myasthenic syndrome; multifocal motor neuropathy; Myasthenia Gravis; Moersch-Woltmann syndrome; secondary hypogammaglobulinemia (including iatrogenic immunodeficiency); specific antibody deficiency; Acute disseminated encephalomyelitis; ANCA-positive systemic necrotizing vasculitis; Autoimmune haemolytic anaemia; Bullous pemphigoid; Cicatricial pemphigoid; Evans syndrome (including autoimmune haemolytic anaemia with immune thrombocytopenia); Foeto-maternal/neonatal alloimmune thrombocytopenia (FMAIT/NAIT); Haemophagocytic syndrome; High-risk allogeneic haemopoietic stem cell transplantation; IgM paraproteinaemic neuropathy; kidney transplantation; multiple sclerosis; Opsoclonus myoclonus ataxia; Pemphigus foliaceus; Pemphigus vulgaris; Post-transfusion purpura; Toxic epidermal necrolysis/Steven Johnson syndrome (TEN/SJS); Toxic shock syndrome; Alzheimer's Disease; Systemic lupus erythematosus; multiple myeloma; sepsis; B cell tumors; trauma; and a bacterial viral or fugal infection.

As used herein, room temperature refers to a range generally from about or at to 18° C. to about or at 32° C. Those of skill in the art appreciate that room temperature varies by location and prevailing conditions. For example, room temperatures can be higher in warmer climates such as Italy or Texas.

As used herein, "stable" or "stability" with reference to a co-formulation provided herein refers to one in which the protein(s) (IG and hyaluronidase) therein essentially retains their physical and chemical stability and integrity upon storage for at least six months at temperatures up to 32° C. For purposes herein, "stability at room temperature" means stability at the upper range of typical room temperatures for warmer locales (i.e. 28-32° C. for Italy or Texas). The formulations are stable over the range of refrigerated and room temperatures, i.e., 0-32° C., or up to 32° C. for at least six months. Each of the IG and hyaluronidase exhibit stability in the co-formulation upon storage for at least six months at room temperature, including temperatures up to at or about 32° C. Assays for assessing the stability of each are well known to one of skill in the art and described herein.

As used herein, stability of IG means that the IG does not substantially aggregate, denature or fragment such that at least 90% of the IG is present as monomers or oligo-/dimers, with a molecular weight of IG of between at or about greater than 70 kDa and less than <450 kDa. Thus, less than about 10%, for example, less than about 5%, less than about 4%, less than about 3%, less than about 2%, less than about 1% of the IG protein is present as an aggregate (i.e. has a molecular size greater than or equal to 450 kDa in size) in the formulation. Similarly, no more than 5% to 7%, for example, 7%, 6%, 5%, 4%, 3%, 2%, 1% or 0.5% or less of the IG in the co-formulation is fragmented (i.e., i.e. has a molecular size less than 70 kDa).

As used herein, stability of the hyaluronidase means that it retains at least 50%, 60%, 70%, 80%, 90% or more of the original hyaluronidase activity prior to storage. Assays to assess hyaluronidase activity are known to one of skill in the art and described herein.

As used herein, "storage" means that a formulation is not immediately administered to a subject once prepared, but is kept for a period of time under particular conditions (e.g. particular temperature; liquid or lyophilized form) prior to use. For example, a liquid formulation can be kept for days, weeks, months or years, generally at least six months, prior to administration to a subject under varied temperatures such as refrigerated (0° to 10° C.) or room temperature (e.g. temperature up to 32° C.).

As used herein, dosing regime refers to the amount of immune globulin administered and the frequency of administration. The dosing regime is a function of the disease or condition to be treated, and thus can vary.

As used herein, "substantially the same as an intravenous IG (IVIG) dosing regime" refers to a regimen in which the dose and/or frequency is within an amount that is effective for treating a particular disease or condition, typically is about or 10%, of the IV dose or frequency. Amounts of IVIG that are effective for treating a particular disease or condition are known or can be empirically determined by one of skill in the art. For example, as exemplified below, 300 mg/kg (i.e. 21 grams assuming the average adult weighs 70 kg) to 600 mg/kg (i.e. 42 grams) is the typical monthly dose of IVIG administered to patients having primary immunodeficiency diseases. Hence, IG, when administered in combination with hyaluronidase, is administered subcutaneously at doses that are or are about 300 mg/kg to 600 mg/kg for treatment of primary immunodeficiency diseases.

As used herein, frequency of administration refers to the time between successive doses of immune globulin. For example, frequency can be one, two, three, four weeks, and is a function of the particular disease or condition treated. Generally, frequency is a least every two or three weeks, and typically no more than once a month.

As used herein, hyaluronidase refers to an enzyme that degrades hyaluronic acid. Hyaluronidases include bacterial hyaluronidases (EC 4.2.99.1), hyaluronidases from leeches, other parasites, and crustaceans (EC 3.2.1.36), and mammalian-type hyaluronidases (EC 3.2.1.35). Hyaluronidases also include any of non-human origin including, but not limited to, murine, canine, feline, leporine, avian, bovine, ovine, porcine, equine, piscine, ranine, bacterial, and any from leeches, other parasites, and crustaceans. Exemplary non-human hyaluronidases include, hyaluronidases from cows (SEQ ID NOS:10 and 11), yellow jacket wasp (SEQ ID NOS:12 and 13), honey bee (SEQ ID NO:14), white-face hornet (SEQ ID NO:15), paper wasp (SEQ ID NO:16), mouse (SEQ ID NOS: 17-19, 32), pig (SEQ ID NOS:20-21), rat (SEQ ID NOS:22-24, 31), rabbit (SEQ ID NO:25), sheep (SEQ ID NOS:26 and 27), orangutan (SEQ ID NO:28), cynomolgus monkey (SEQ ID NO:29), guinea pig (SEQ ID NO:30), Staphylococcus aureus (SEQ ID NO:33), *Streptococcus pyogenes* (SEQ ID NO:34), and *Clostridium perfringens* (SEQ ID NO:35). Hyaluronidases also include those of human origin. Exemplary human hyaluronidases include HYAL1 (SEQ ID NO:36), HYAL2 (SEQ ID NO:37), HYAL3 (SEQ ID NO:38), HYAL4 (SEQ ID NO:39), and PH20 (SEQ ID NO:1). Also included amongst hyaluronidases are soluble hyaluronidases, including, ovine and bovine PH20, soluble human PH20 and soluble rHuPH20.

Reference to hyaluronidases includes precursor hyaluronidase polypeptides and mature hyaluronidase polypeptides (such as those in which a signal sequence has been removed), truncated forms thereof that have activity, and includes allelic variants and species variants, variants encoded by splice variants, and other variants, including polypeptides that have at least 40 %, 45 %, 50 %, 55 %, 65 %, 70 %, 75 %, 80 %, 85 %, 90 %, 95 %, 96 %, 97 %, 98 %, 99 % or more sequence identity to the precursor polypeptides set forth in SEQ ID NOS: 1 and 10-39, or the mature form thereof. For example, reference to hyaluronidase also includes the human PH20 precursor polypeptide variants set forth in SEQ ID NOS:50-51. Hyaluronidases also include those that contain chemical or posttranslational modifications and those that do not contain chemical or posttranslational modifications. Such modifications include, but are not limited to, PEGylation, albumination, glycosylation, farnesylation, carboxylation, hydroxylation, phosphorylation, and other polypeptide modifications known in the art.

As used herein, a soluble hyaluronidase refers to a polypeptide characterized by its solubility under physiologic conditions. Generally, a soluble hyaluronidase lacks all or a portion of a glycophosphatidyl anchor (GPI), or does not otherwise sufficiently anchor to the cell membrane. Hence, upon expression from a cell, a soluble hyaluronidase is secreted into the medium. Soluble hyaluronidases can be distinguished, for example, by its partitioning into the aqueous phase of a Triton X-114 solution warmed to 37 ° C. (Bordier et al., (1981)*J Biol. Chem.*, 256:1604-7). Membrane-anchored, such as lipid anchored hyaluronidases, will partition into the detergent rich phase, but will partition into the detergent-poor or aqueous phase following treatment with Phospholipase-C. Included among soluble hyaluronidases are membrane anchored hyaluronidases in which one or more regions associated with anchoring of the hyaluronidase to the membrane has been removed or modified, where the soluble form retains hyaluronidase activity. Soluble hyaluronidases include recombinant soluble hyaluronidases and those contained in or purified from natural sources, such as, for example, testes extracts from sheep or cows. Exemplary of such soluble hyaluronidases are soluble human PH20. Other soluble hyaluronidases include ovine (SEQ ID NO:27) and bovine (SEQ ID NO:11) PH20.

As used herein, soluble human PH20 or sHuPH20 include mature polypeptides lacking all or a portion of the glycosylphosphatidylinositol (GPI) attachment site at the C-terminus such that upon expression, the polypeptides are soluble. Exemplary sHuPH20 polypeptides include mature polypeptides having an amino acid sequence set forth in any one of SEQ ID NOS:4-9 and 47-48. The precursor polypeptides for such exemplary sHuPH20 polypeptides include a signal sequence. Exemplary of the precursors are those set forth in SEQ ID NOS:3 and 40-46, each of which contains a 35 amino acid signal sequence at amino acid positions 1-35. Soluble HuPH20 polypeptides also include those degraded during or after the production and purification methods described herein.

As used herein, soluble recombinant human PH20 (rHuPH20) refers to a soluble form of human PH20 that is recombinantly expressed in Chinese Hamster Ovary (CHO) cells. Soluble rHuPH20 is encoded by nucleic acid that includes the signal sequence and is set forth in SEQ ID NO:49. Also included are DNA molecules that are allelic variants thereof and other soluble variants. The nucleic acid encoding soluble rHuPH20 is expressed in CHO cells which secrete the mature polypeptide. As produced in the culture medium there is heterogeneity at the C-terminus so that the product includes a mixture of species that can include any one or more of SEQ ID NOS: 4-9 in various abundance. Corresponding allelic variants and other variants also are included, including those corresponding to the precursor human PH20 polypeptides set forth in SEQ ID NOS:50-51. Other variants can have 60%, 70%, 80%, 85%, 90%, 91%, 92%, 93%, 94%, 95%, 96%, 97%, 98%, 99% or more sequence identity with any of SEQ ID NOS:4-9 and 47-48 as long they retain a hyaluronidase activity and are soluble.

As used herein, activity refers to a functional activity or activities of a polypeptide or portion thereof associated with a full-length (complete) protein. Functional activities include, but are not limited to, biological activity, catalytic or enzymatic activity, antigenicity (ability to bind or compete with a polypeptide for binding to an anti-polypeptide antibody), immunogenicity, ability to form multimers, and the ability to specifically bind to a receptor or ligand for the polypeptide.

As used herein, hyaluronidase activity refers to the ability of hyaluronidase to cleave hyaluronic acid. In vitro assays to determine the hyaluronidase activity of hyaluronidases, such as soluble rHuPH20, are known in the art and described herein. Exemplary assays include the microturbidity assay described below (see e.g. Example 3) that measures cleavage of hyaluronic acid by hyaluronidase indirectly by detecting the insoluble precipitate formed when the uncleaved hyaluronic acid binds with serum albumin.

As used herein, the term "ultrafiltration (UF)" encompasses a variety of membrane filtration methods in which hydrostatic pressure forces a liquid against a semi-permeable membrane. Suspended solids and solutes of high molecular weight are retained, while water and low molecular weight solutes pass through the membrane. This separation process is often used for purifying and concentrating macromolecular ($10^3$-$10^6$ Da) solutions, especially protein solutions. A number of ultrafiltration membranes are available depending on the size of the molecules they retain. Ultrafiltration is typically characterized by a membrane pore size between 1 and 1000 kDa and operating pressures between 0.01 and 10 bar, and is particularly useful for separating colloids like proteins from small molecules like sugars and salts.

As used herein, the term "diafiltration" is performed with the same membranes as ultrafiltration and is a tangential flow filtration. During diafiltration, buffer is introduced into the recycle tank while filtrate is removed from the unit operation. In processes where the product is in the retentate (for example IgG), diafiltration washes components out of the product pool into the filtrate, thereby exchanging buffers and reducing the concentration of undesirable species.

As used herein, the term "mixing" describes an act of causing equal distribution of two or more distinct compounds or substances in a solution or suspension by any form of agitation. Complete equal distribution of all ingredients in a solution or suspension is not required as a result of "mixing" as the term is used in this application.

As used herein, the term "solvent" encompasses any liquid substance capable of dissolving or dispersing one or more other substances. A solvent may be inorganic in nature, such as water, or it may be an organic liquid, such as ethanol, acetone, methyl acetate, ethyl acetate, hexane, petrol ether, etc. As used in the term "solvent detergent treatment," solvent denotes an organic solvent (e.g., tri-N-butyl phosphate), which is part of the solvent detergent mixture used to inactivate lipid-enveloped viruses in solution.

As used herein, the term "detergent" is used in this application interchangeably with the term "surfactant" or "surface acting agent." Surfactants are typically organic compounds that are amphiphilic, i.e., containing both hydrophobic groups ("tails") and hydrophilic groups ("heads"), which render surfactants soluble in both organic solvents and water. A surfactant can be classified by the presence of formally charged groups in its head. A non-ionic surfactant has no charge groups in its head, whereas an ionic surfactant carries a net charge in its head. A zwitterionic surfactant contains a head with two oppositely charged groups. Some examples of common surfactants include: Anionic (based on sulfate, sulfonate or carboxylate anions): perfluorooctanoate (PFOA or PFO), perfluorooctanesulfonate (PFOS), sodium dodecyl sulfate (SDS), ammonium lauryl sulfate, and other alkyl sulfate salts, sodium laureth sulfate (also known as sodium lauryl ether sulfate, or SLES), alkyl benzene sulfonate; cationic (based on quaternary ammonium cations): cetyl trimethylammonium bromide (CTAB) a.k.a. hexadecyl trimethyl ammonium bromide, and other alkyltrimethylammonium salts, cetylpyridinium chloride (CPC), polyethoxylated tallow amine (POEA), benzalkonium chloride (BAC), benzethonium chloride (BZT); Zwitterionic (amphoteric): dodecyl betaine; cocamidopropyl betaine; coco ampho glycinate; nonionic: alkyl poly(ethylene oxide), alkylphenol poly(ethylene oxide), copolymers of poly(ethylene oxide) and poly (propylene oxide) (commercially known as Poloxamers or Poloxamines), alkyl polyglucosides, including octyl glucoside, decyl maltoside, fatty alcohols (e.g., cetyl alcohol and oleyl alcohol), cocamide MEA, cocamide DEA, polysorbates (Tween 20, Tween 80, etc.), Triton detergents, and dodecyl dimethylamine oxide.

As used herein, the residues of naturally occurring α-amino acids are the residues of those 20 α-amino acids found in nature which are incorporated into protein by the specific recognition of the charged tRNA molecule with its cognate mRNA codon in humans.

As used herein, nucleic acids include DNA, RNA and analogs thereof, including peptide nucleic acids (PNA) and mixtures thereof. Nucleic acids can be single or double-stranded. When referring to probes or primers, which are optionally labeled, such as with a detectable label, such as a fluorescent or radiolabel, single-stranded molecules are contemplated. Such molecules are typically of a length such that their target is statistically unique or of low copy number (typically less than 5, generally less than 3) for probing or priming a library. Generally a probe or primer contains at least 14, 16 or 30 contiguous nucleotides of sequence complementary to or identical to a gene of interest. Probes and primers can be 10, 20, 30, 50, 100 or more nucleic acids long.

As used herein, a peptide refers to a polypeptide that is from 2 to 40 amino acids in length.

As used herein, the amino acids which occur in the various sequences of amino acids provided herein are identified according to their known, three-letter or one-letter abbreviations (Table 1). The nucleotides which occur in the various nucleic acid fragments are designated with the standard single-letter designations used routinely in the art.

As used herein, an "amino acid" is an organic compound containing an amino group and a carboxylic acid group. A polypeptide contains two or more amino acids. For purposes herein, amino acids include the twenty naturally-occurring amino acids, non-natural amino acids and amino acid analogs (i.e., amino acids wherein the a-carbon has a side chain).

As used herein, "amino acid residue" refers to an amino acid formed upon chemical digestion (hydrolysis) of a polypeptide at its peptide linkages. The amino acid residues described herein are presumed to be in the "L" isomeric form. Residues in the "D" isomeric form, which are so designated, can be substituted for any L-amino acid residue as long as the desired functional property is retained by the polypeptide. $NH_2$ refers to the free amino group present at the amino terminus of a polypeptide. COOH refers to the free carboxy group present at the carboxyl terminus of a polypeptide. In keeping with standard polypeptide nomenclature described in J. Biol. Chem., 243: 3557-3559 (1968), and adopted 37 C.F.R. §§1.821-1.822, abbreviations for amino acid residues are shown in Table 1:

TABLE 1

Table of Correspondence

SYMBOL

| 1-Letter | 3-Letter | AMINO ACID |
|---|---|---|
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | proline |
| K | Lys | Lysine |
| H | His | Histidine |
| Q | Gln | Glutamine |
| E | Glu | glutamic acid |
| Z | Glx | Glu and/or Gln |
| W | Trp | Tryptophan |
| R | Arg | Arginine |
| D | Asp | aspartic acid |
| N | Asn | asparagine |
| B | Asx | Asn and/or Asp |
| C | Cys | Cysteine |
| X | Xaa | Unknown or other |

It should be noted that all amino acid residue sequences represented herein by formulae have a left to right orientation in the conventional direction of amino-terminus to carboxyl-terminus. In addition, the phrase "amino acid residue" is broadly defined to include the amino acids listed in the Table of Correspondence (Table 1) and modified and unusual amino acids, such as those referred to in 37 C.F.R. §§1.821-1.822, and incorporated herein by reference. Furthermore, it should be noted that a dash at the beginning or end of an amino acid residue sequence indicates a peptide bond to a further sequence of one or more amino acid residues, to an amino-terminal group such as $NH_2$ or to a carboxyl-terminal group such as COOH.

As used herein, "naturally occurring amino acids" refer to the 20 L-amino acids that occur in polypeptides.

As used herein, "non-natural amino acid" refers to an organic compound that has a structure similar to a natural amino acid but has been modified structurally to mimic the structure and reactivity of a natural amino acid. Non-naturally occurring amino acids thus include, for example, amino acids or analogs of amino acids other than the 20 naturally-occurring amino acids and include, but are not limited to, the D-isostereomers of amino acids. Exemplary non-natural amino acids are described herein and are known to those of skill in the art.

As used herein, an isokinetic mixture is one in which the molar ratios of amino acids has been adjusted based on their reported reaction rates (see, e.g., Ostresh et al., (1994) Biopolymers 34:1681).

As used herein, modification is in reference to modification of a sequence of amino acids of a polypeptide or a sequence of nucleotides in a nucleic acid molecule and includes deletions, insertions, and replacements of amino acids and nucleotides, respectively. Methods of modifying a polypeptide are routine to those of skill in the art, such as by using recombinant DNA methodologies.

As used herein, suitable conservative substitutions of amino acids are known to those of skill in this art and can be made generally without altering the biological activity of the resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. co., p. 224). Such substitutions can be made in accordance with those set forth in TABLE 1A as follows:

TABLE 1A

| Original residue | Exemplary conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions also are permissible and can be determined empirically or in accord with known conservative substitutions.

As used herein, a DNA construct is a single or double stranded, linear or circular DNA molecule that contains segments of DNA combined and juxtaposed in a manner not found in nature. DNA constructs exist as a result of human manipulation, and include clones and other copies of manipulated molecules.

As used herein, a DNA segment is a portion of a larger DNA molecule having specified attributes. For example, a DNA segment encoding a specified polypeptide is a portion of a longer DNA molecule, such as a plasmid or plasmid fragment, which, when read from the 5' to 3' direction, encodes the sequence of amino acids of the specified polypeptide.

As used herein, the term polynucleotide means a single- or double-stranded polymer of deoxyribonucleotides or ribonucleotide bases read from the 5' to the 3' end. Polynucleotides include RNA and DNA, and can be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term nucleotides is used for single- and double-stranded molecules where the context permits. When the term is applied to double-stranded molecules it is used to denote overall length and will be understood to be equivalent to the term base pairs. It will be recognized by those skilled in the art that the two strands of a double-stranded polynucleotide can differ slightly in length and that the ends thereof can be staggered; thus all nucleotides within a double-stranded polynucleotide molecule can not be paired. Such unpaired ends will, in general, not exceed 20 nucleotides in length.

As used herein, "similarity" between two proteins or nucleic acids refers to the relatedness between the sequence of amino acids of the proteins or the nucleotide sequences of the nucleic acids. Similarity can be based on the degree of identity and/or homology of sequences of residues and the residues contained therein. Methods for assessing the degree of similarity between proteins or nucleic acids are known to those of skill in the art. For example, in one method of assessing sequence similarity, two amino acid or nucleotide sequences are aligned in a manner that yields a maximal level of identity between the sequences. "Identity" refers to the extent to which the amino acid or nucleotide sequences are invariant. Alignment of amino acid sequences, and to some extent nucleotide sequences, also can take into account conservative differences and/or frequent substitutions in amino acids (or nucleotides). Conservative differences are those that preserve the physico-chemical properties of the residues involved. Alignments can be global (alignment of the compared sequences over the entire length of the sequences and including all residues) or local (the alignment of a portion of the sequences that includes only the most similar region or regions).

"Identity" per se has an art-recognized meaning and can be calculated using published techniques. (See, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and Sequence Analysis Primer, Gribskov, M. and Devereux, J., eds., M Stockton Press, New York, 1991). While there exists a number of methods to measure identity between two polynucleotide or polypeptides, the term "identity" is well known to skilled artisans (Carillo, H. & Lipton, D., *SIAM J Applied Math* 48:1073 (1988)).

As used herein, homologous (with respect to nucleic acid and/or amino acid sequences) means about greater than or equal to 25% sequence homology, typically greater than or equal to 25%, 40%, 50%, 60%, 70%, 80%, 85%, 90% or 95% sequence homology; the precise percentage can be specified if necessary. For purposes herein the terms "homology" and "identity" are often used interchangeably, unless otherwise indicated. In general, for determination of the percentage homology or identity, sequences are aligned so that the highest order match is obtained (see, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; Carillo et al. (1988) *SIAM J Applied Math* 48:1073). By sequence homology, the number of conserved amino acids is determined by standard alignment algorithms programs, and can be used with default gap penalties established by each supplier. Substantially homologous nucleic acid molecules would hybridize typically at moderate stringency or at high stringency all along the length of the nucleic acid of interest. Also contemplated are nucleic acid molecules that contain degenerate codons in place of codons in the hybridizing nucleic acid molecule.

Whether any two molecules have nucleotide sequences or amino acid sequences that are at least 60%, 70%, 80%, 85%, 90%, 95%, 96%, 97%, 98% or 99% "identical" or "homologous" can be determined using known computer algorithms such as the "FASTA" program, using for example, the default parameters as in Pearson et al. (1988) *Proc. Natl. Acad. Sci. USA* 85:2444 (other programs include the GCG program package (Devereux, J., et al., *Nucleic Acids Research* 12(I): 387 (1984)), BLASTP, BLASTN, FASTA (Atschul, S. F., et al., *J Molec Biol* 215:403 (1990)); *Guide to Huge Computers*, Martin J. Bishop, ed., Academic Press, San Diego, 1994, and Carillo et al. (1988) *SIAM J Applied Math* 48:1073). For example, the BLAST function of the National Center for Biotechnology Information database can be used to determine identity. Other commercially or publicly available programs include, DNAStar "MegAlign" program (Madison, Wis.) and the University of Wisconsin Genetics Computer Group (UWG) "Gap" program (Madison Wis.). Percent homology or identity of proteins and/or nucleic acid molecules can be determined, for example, by comparing sequence information using a GAP computer program (e.g., Needleman et al. (1970) *J. Mol. Biol.* 48:443, as revised by Smith and Waterman ((1981) *Adv. Appl. Math.* 2:482). Briefly, the GAP program defines similarity as the number of aligned symbols (i.e., nucleotides or amino acids), which are similar, divided by the total number of symbols in the shorter of the two sequences. Default parameters for the GAP program can include: (1) a unary comparison matrix (containing a value of 1 for identities and 0 for non-identities) and the weighted comparison matrix of Gribskov et al. (1986) *Nucl. Acids Res.* 14:6745, as described by Schwartz and Dayhoff, eds., *ATLAS OF PROTEIN SEQUENCE AND STRUCTURE*, National Biomedical Research Foundation, pp. 353-358

(1979); (2) a penalty of 3.0 for each gap and an additional 0.10 penalty for each symbol in each gap; and (3) no penalty for end gaps.

Therefore, as used herein, the term "identity" or "homology" represents a comparison between a test and a reference polypeptide or polynucleotide. As used herein, the term at least "90% identical to" refers to percent identities from 90 to 99.99 relative to the reference nucleic acid or amino acid sequence of the polypeptide. Identity at a level of 90% or more is indicative of the fact that, assuming for exemplification purposes a test and reference polypeptide length of 100 amino acids are compared. No more than 10% (i.e., 10 out of 100) of the amino acids in the test polypeptide differs from that of the reference polypeptide. Similar comparisons can be made between test and reference polynucleotides. Such differences can be represented as point mutations randomly distributed over the entire length of a polypeptide or they can be clustered in one or more locations of varying length up to the maximum allowable, e.g. 10/100 amino acid difference (approximately 90% identity). Differences are defined as nucleic acid or amino acid substitutions, insertions or deletions. At the level of homologies or identities above about 85-90%, the result should be independent of the program and gap parameters set; such high levels of identity can be assessed readily, often by manual alignment without relying on software.

As used herein, an aligned sequence refers to the use of homology (similarity and/or identity) to align corresponding positions in a sequence of nucleotides or amino acids. Typically, two or more sequences that are related by 50% or more identity are aligned. An aligned set of sequences refers to 2 or more sequences that are aligned at corresponding positions and can include aligning sequences derived from RNAs, such as ESTs and other cDNAs, aligned with genomic DNA sequence.

As used herein, "primer" refers to a nucleic acid molecule that can act as a point of initiation of template-directed DNA synthesis under appropriate conditions (e.g., in the presence of four different nucleoside triphosphates and a polymerization agent, such as DNA polymerase, RNA polymerase or reverse transcriptase) in an appropriate buffer and at a suitable temperature. It will be appreciated that a certain nucleic acid molecules can serve as a "probe" and as a "primer." A primer, however, has a 3' hydroxyl group for extension. A primer can be used in a variety of methods, including, for example, polymerase chain reaction (PCR), reverse-transcriptase (RT)-PCR, RNA PCR, LCR, multiplex PCR, panhandle PCR, capture PCR, expression PCR, 3' and 5' RACE, in situ PCR, ligation-mediated PCR and other amplification protocols.

As used herein, "primer pair" refers to a set of primers that includes a 5' (upstream) primer that hybridizes with the 5' end of a sequence to be amplified (e.g. by PCR) and a 3' (downstream) primer that hybridizes with the complement of the 3' end of the sequence to be amplified.

As used herein, "specifically hybridizes" refers to annealing, by complementary base-pairing, of a nucleic acid molecule (e.g. an oligonucleotide) to a target nucleic acid molecule. Those of skill in the art are familiar with in vitro and in vivo parameters that affect specific hybridization, such as length and composition of the particular molecule. Parameters particularly relevant to in vitro hybridization further include annealing and washing temperature, buffer composition and salt concentration. Exemplary washing conditions for removing non-specifically bound nucleic acid molecules at high stringency are 0.1×SSPE, 0.1% SDS, 65° C., and at medium stringency are 0.2×SSPE, 0.1% SDS, 50° C. Equivalent stringency conditions are known in the art. The skilled person can readily adjust these parameters to achieve specific hybridization of a nucleic acid molecule to a target nucleic acid molecule appropriate for a particular application. Complementary, when referring to two nucleotide sequences, means that the two sequences of nucleotides are capable of hybridizing, typically with less than 25%, 15% or 5% mismatches between opposed nucleotides. If necessary, the percentage of complementarity will be specified. Typically the two molecules are selected such that they will hybridize under conditions of high stringency.

As used herein, substantially identical to a product means sufficiently similar so that the property of interest is sufficiently unchanged so that the substantially identical product can be used in place of the product.

As used herein, it also is understood that the terms "substantially identical" or "similar" varies with the context as understood by those skilled in the relevant art.

As used herein, an allelic variant or allelic variation references any of two or more alternative forms of a gene occupying the same chromosomal locus. Allelic variation arises naturally through mutation, and can result in phenotypic polymorphism within populations. Gene mutations can be silent (no change in the encoded polypeptide) mean encode polypeptides having altered amino acid sequence. The term "allelic variant" also is used herein to denote a protein encoded by an allelic variant of a gene. Typically the reference form of the gene encodes a wildtype form and/or predominant form of a polypeptide from a population or single reference member of a species. Typically, allelic variants, which include variants between and among species typically have at least 80%, 90% or greater amino acid identity with a wildtype and/or predominant form from the same species; the degree of identity depends upon the gene and whether comparison is interspecies or intraspecies. Generally, intraspecies allelic variants have at least about 80%, 85%, 90% or 95% identity or greater with a wildtype and/or predominant form, including 96%, 97%, 98%, 99% or greater identity with a wildtype and/or predominant form of a polypeptide. Reference to an allelic variant herein generally refers to variations n proteins among members of the same species.

As used herein, "allele," which is used interchangeably herein with "allelic variant" refers to alternative forms of a gene or portions thereof. Alleles occupy the same locus or position on homologous chromosomes. When a subject has two identical alleles of a gene, the subject is said to be homozygous for that gene or allele. When a subject has two different alleles of a gene, the subject is said to be heterozygous for the gene. Alleles of a specific gene can differ from each other in a single nucleotide or several nucleotides, and can include substitutions, deletions and insertions of nucleotides. An allele of a gene also can be a form of a gene containing a mutation.

As used herein, species variants refer to variants in polypeptides among different species, including different mammalian species, such as mouse and human.

As used herein, a splice variant refers to a variant produced by differential processing of a primary transcript of genomic DNA that results in more than one type of mRNA.

As used herein, the term promoter means a portion of a gene containing DNA sequences that provide for the binding of RNA polymerase and initiation of transcription. Promoter sequences are commonly, but not always, found in the 5' non-coding region of genes.

As used herein, isolated or purified polypeptide or protein or biologically-active portion thereof is substantially free of cellular material or other contaminating proteins from the cell or tissue from which the protein is derived, or substantially free from chemical precursors or other chemicals when chemically synthesized. Preparations can be determined to be substantially free if they appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound, however, can be a mixture of stereoisomers. In such instances, further purification might increase the specific activity of the compound.

The term substantially free of cellular material includes preparations of proteins in which the protein is separated from cellular components of the cells from which it is isolated or recombinantly-produced. In one embodiment, the term substantially free of cellular material includes preparations of enzyme proteins having less that about 30% (by dry weight) of non-enzyme proteins (also referred to herein as a contaminating protein), generally less than about 20% of non-enzyme proteins or 10% of non-enzyme proteins or less that about 5% of non-enzyme proteins. When the enzyme protein is recombinantly produced, it also is substantially free of culture medium, i.e., culture medium represents less than about or at 20%, 10% or 5% of the volume of the enzyme protein preparation.

As used herein, the term substantially free of chemical precursors or other chemicals includes preparations of enzyme proteins in which the protein is separated from chemical precursors or other chemicals that are involved in the synthesis of the protein. The term includes preparations of enzyme proteins having less than about 30% (by dry weight) 20%, 10%, 5% or less of chemical precursors or non-enzyme chemicals or components.

As used herein, synthetic, with reference to, for example, a synthetic nucleic acid molecule or a synthetic gene or a synthetic peptide refers to a nucleic acid molecule or polypeptide molecule that is produced by recombinant methods and/or by chemical synthesis methods.

As used herein, production by recombinant means by using recombinant DNA methods means the use of the well known methods of molecular biology for expressing proteins encoded by cloned DNA.

As used herein, vector (or plasmid) refers to discrete elements that are used to introduce a heterologous nucleic acid into cells for either expression or replication thereof. The vectors typically remain episomal, but can be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well known to those of skill in the art.

As used herein, an expression vector includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, vector also includes "virus vectors" or "viral vectors." Viral vectors are engineered viruses that are operatively linked to exogenous genes to transfer (as vehicles or shuttles) the exogenous genes into cells.

As used herein, operably or operatively linked when referring to DNA segments means that the segments are arranged so that they function in concert for their intended purposes, e.g., transcription initiates in the promoter and proceeds through the coding segment to the terminator.

As used herein the term assessing is intended to include quantitative and qualitative determination in the sense of obtaining an absolute value for the activity of a protein, such as an enzyme or protease, or a domain thereof, present in the sample, and also of obtaining an index, ratio, percentage, visual or other value indicative of the level of the activity. Assessment can be direct or indirect and the chemical species actually detected need not of course be the endproduct of a reaction, such as a proteolysis product itself, but can for example be a derivative thereof or some further substance. For example, assessment can be detection of a cleavage product of a protein, such as by SDS-PAGE and protein staining with Coomasie blue.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures. Biological activities can be observed in in vitro systems designed to test or use such activities. Thus, for purposes herein a biological activity of a protease is its catalytic activity in which a polypeptide is hydrolyzed.

As used herein equivalent, when referring to two sequences of nucleic acids, means that the two sequences in question encode the same sequence of amino acids or equivalent proteins. When equivalent is used in referring to two proteins or peptides, it means that the two proteins or peptides have substantially the same amino acid sequence with only amino acid substitutions that do not substantially alter the activity or function of the protein or peptide. When equivalent refers to a property, the property does not need to be present to the same extent (e.g., two peptides can exhibit different rates of the same type of enzymatic activity), but the activities are usually substantially the same.

As used herein, "modulate" and "modulation" or "alter" refer to a change of an activity of a molecule, such as a protein. Exemplary activities include, but are not limited to, biological activities, such as signal transduction. Modulation can include an increase in the activity (i.e., up-regulation or agonist activity) a decrease in activity (i.e., down-regulation or inhibition) or any other alteration in an activity (such as a change in periodicity, frequency, duration, kinetics or other parameter). Modulation can be context dependent and typically modulation is compared to a designated state, for example, the wildtype protein, the protein in a constitutive state, or the protein as expressed in a designated cell type or condition.

As used herein, a composition refers to any mixture. It can be a solution, suspension, liquid, powder, paste, aqueous, non-aqueous or any combination thereof.

As used herein, a combination refers to any association between or among two or more items. The combination can be two or more separate items, such as two compositions or two collections, can be a mixture thereof, such as a single mixture of the two or more items, or any variation thereof. The elements of a combination are generally functionally associated or related.

As used herein, a kit is a packaged combination that optionally includes other elements, such as additional reagents and instructions for use of the combination or elements thereof.

As used herein, "disease or disorder" refers to a pathological condition in an organism resulting from cause or condition including, but not limited to, infections, acquired conditions, genetic conditions, and characterized by identifiable symptoms. Diseases and disorders of interest herein are those that are treatable by immune globulin.

As used herein, "treating" a subject with a disease or condition means that the subject's symptoms are partially or totally alleviated, or remain static following treatment. Hence treatment encompasses prophylaxis, therapy and/or cure. Prophylaxis refers to prevention of a potential disease and/or a prevention of worsening of symptoms or progression of a disease. Treatment also encompasses any pharmaceutical use of an immune globulin preparation and compositions provided herein.

As used herein, a pharmaceutically effective agent, includes any therapeutic agent or bioactive agents, including, but not limited to, for example, anesthetics, vasoconstrictors, dispersing agents, conventional therapeutic drugs, including small molecule drugs and therapeutic proteins.

As used herein, treatment means any manner in which the symptoms of a condition, disorder or disease or other indication, are ameliorated or otherwise beneficially altered.

As used herein therapeutic effect means an effect resulting from treatment of a subject that alters, typically improves or ameliorates the symptoms of a disease or condition or that cures a disease or condition. A therapeutically effective amount refers to the amount of a composition, molecule or compound which results in a therapeutic effect following administration to a subject.

As used herein, the term "subject" refers to an animal, including a mammal, such as a human being.

As used herein, a patient refers to a human subject.

As used herein, amelioration of the symptoms of a particular disease or disorder by a treatment, such as by administration of a pharmaceutical composition or other therapeutic, refers to any lessening, whether permanent or temporary, lasting or transient, of the symptoms that can be attributed to or associated with administration of the composition or therapeutic.

As used herein, prevention or prophylaxis refers to methods in which the risk of developing disease or condition is reduced.

As used herein, a "therapeutically effective amount" or a "therapeutically effective dose" refers to the quantity of an agent, compound, material, or composition containing a compound that is at least sufficient to produce a therapeutic effect. Hence, it is the quantity necessary for preventing, curing, ameliorating, arresting or partially arresting a symptom of a disease or disorder.

As used herein, unit dose form refers to physically discrete units suitable for human and animal subjects and packaged individually as is known in the art.

As used herein, a single dosage formulation refers to a formulation for direct administration.

As used herein, an "article of manufacture" is a product that is made and sold.

As used throughout this application, the term is intended to encompass IG and hyaluronidase compositions contained in articles of packaging.

As used herein, fluid refers to any composition that can flow. Fluids thus encompass compositions that are in the form of semi-solids, pastes, solutions, aqueous mixtures, gels, lotions, creams and other such compositions.

As used herein, a "kit" refers to a combination of compositions provided herein and another item for a purpose including, but not limited to, activation, administration, diagnosis, and assessment of a biological activity or property. Kits optionally include instructions for use.

As used herein, a cellular extract or lysate refers to a preparation or fraction which is made from a lysed or disrupted cell.

As used herein, animal includes any animal, such as, but are not limited to primates including humans, gorillas and monkeys; rodents, such as mice and rats; fowl, such as chickens; ruminants, such as goats, cows, deer, sheep; ovine, such as pigs and other animals. Non-human animals exclude humans as the contemplated animal. The enzymes provided herein are from any source, animal, plant, prokaryotic and fungal. Most enzymes are of animal origin, including mammalian origin.

As used herein, a control refers to a sample that is substantially identical to the test sample, except that it is not treated with a test parameter, or, if it is a plasma sample, it can be from a normal volunteer not affected with the condition of interest. A control also can be an internal control.

As used herein, the singular forms "a," "an" and "the" include plural referents unless the context clearly dictates otherwise. Thus, for example, reference to a compound, comprising "an extracellular domain" includes compounds with one or a plurality of extracellular domains.

As used herein, ranges and amounts can be expressed as "about" a particular value or range. About also includes the exact amount. Hence "about 5 bases" means "about 5 bases" and also "5 bases."

As used herein, "optional" or "optionally" means that the subsequently described event or circumstance does or does not occur, and that the description includes instances where said event or circumstance occurs and instances where it does not. For example, an optionally substituted group means that the group is unsubstituted or is substituted.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

B. STABLE CO-FORMULATIONS OF IMMUNE GLOBULIN (IG) AND HYALURONIDASE

Provided herein are stable co-formulations containing immune globulin (IG) and hyaluronidase. The co-formulations retain IG molecular size distribution and hyaluronidase activity after extended storage in liquid form at room temperature (e.g. 28 to 32° C.) for at least six months. Generally, the co-formulations also retain IG molecular size distribution and hyaluronidase activity at standard refrigerator temperatures for at least 1-2 years. The co-formulations can be used for treating IG-treatable diseases and conditions. In particular, the stable co-formulations provided herein are formulated for subcutaneous administration.

1. Immune Globulin Therapy

Immune globulin is a therapeutic that is primarily given to treat individuals with immune deficiencies. Immunoglobulin deficiency disorders are a subset of immunodeficiency diseases characterized by missing or reduced levels of serum immunoglobulins, leading to increased susceptibility to bacterial infections, especially of the sinopulmonary tract. Immunodeficiency diseases are either primary (genetic) or secondary (acquired). Primary immunodeficiency diseases are rare and include X-linked agammaglobulinemia, immunoglobulin heavy chain deletion, selective immunoglobulin G (IgG) subclass deficiency, common variable immunodeficiency, or X-linked hyperimmunoglobulin M syndrome. Decreased immunoglobulin levels also are found in individuals having combined immunodeficiencies due to defects in T and B cells, such as, but not limited to, severe combined immunodeficiency or Wiskott Aldrich Syndrome (IUIS Scientific Committee, 1999). More common are secondary immunodeficiencies, induced by factors including, but not limited to, malnutrition, viruses, aging and leukemia. Individuals with these diseases require replacement therapy with immunoglobulin products to prevent or reduce the severity of infections.

Immunoglobulin replacement therapy was first used in 1952 and was administered intramuscularly and subcutaneously. However, to effectively treat disease, larger amounts of IG are necessary, which led to the development of intravenously administrable products with lower IG concentrations (50-100 mg/mL). Since 1981, the majority of immunoglobulin products available in the United States are administered intravenously. Generally, IG preparations are sterile, purified products that contain immunoglobulin G (IgG, IgM, IgA or a combination of those). Typically, IG products contain 95-99% IgG and only trace amounts of immunoglobulins A (IgA), M (IgM), D (IgD) and E (IgE). IG preparations for IV administration are generally formulated at 3 to 12% IG.

More recently, immunoglobulin preparations have been developed for subcutaneous administration (Gardulf et al. (2006) *Curr. Opin. Allergy Clin. Immunol.* 6: 434-42; Gardulf et al. (2006) *J. Clin. Immunol.* 26: 177-85; Ochs et al. (2006) *J. Clin. Immunol.* 26:265-73), and at least one product, Vivaglobin®, is licensed for subcutaneous administration in the United States. A subcutaneous route of administration of IG has several advantages compared to the IV route such as better tolerability and the possibility of home care treatment.

The bioavailability of immunoglobulin administered subcutaneously generally is less than that infused intravenously. Following IV administration, immunoglobulin is immediately available in the blood, and slowly equilibrates to the extra-vascular compartment over 3 to 5 days (Schiff et al. (1986) *J. Clin. Immunol.* 6:256-64). Subcutaneously administered immunoglobulin is slowly absorbed from the subcutaneous space into the blood and at the same time equilibrates with the extra-vascular compartment; there is no high IV spike. The bioavailability has not been extensively studied, but in a recent trial of the ZLB-Behring preparation (i.e., Vivaglobin®), it was determined by measuring the area under the curve (AUC) that only 67% of the immunoglobulin was absorbed, and thus, the recommended dose was 137% of the IV dose (Ochs et al. (2006) *J. Clin. Immunol.* 26:265-73). Despite the technical difficulties of comparing the AUC for two different routes and frequency of administration, studies of intradermally administered immunoglobulin in rabbits suggests there is decreased bioavailability through the subcutaneous route. This may be due to the mode of absorption of large protein molecules, which cannot readily diffuse through the capillary walls and must be absorbed via the lymphatics (Supersaxo et al. (1990) *Pharm. Res.* 7:167-9).

All of the immunoglobulin preparations presently used for subcutaneous administration are formulated at 16% IG, compared to IVIG preparations formulated at 5 to 12% IG. The higher concentration of IG in subcutaneous preparations relative to IV preparations allows smaller infusion volumes; such preparations cannot be infused intravenously. Such subcutaneous methods of immunoglobulin replacement therapy are considered to be effective, safe and also highly appreciated by patients, as it has a low risk of systemic adverse reactions and leads to higher trough serum IgG concentrations compared to monthly IV infusions (Gardulf et al. (1995) *J. Adv. Nurs.*, 21:917-27; Gardulf et al. (1993) *Clin. Exp. Immunol.*, 92:200-4; Gardulf et al. (1991) *Lancet*, 338:162-6).

In addition to the decreased bioavailability associated with subcutaneous administration of IG, another distinction between SC and IV administration is that only small volumes can be infused subcutaneously at each site, necessitating the use of multiple sites on a weekly or biweekly (ever other week) basis. In general, however, adults can only be infused with 20-40 mL at a single subcutaneous site, with lower volumes per site for children. Currently, the accepted practice for IG administration is 300-600 mg/kg intravenously once every 3-4 weeks or 100-200 mg/kg/wk subcutaneously (Berger (2008) *Immunol. Allergy Clin. North Am.* 28(2):413-438). Thus, up to 15 g of IG is administered per week subcutaneously. This means that administration of a 16-20% IG preparation at least 3 sites per week is required. Even though weekly or biweekly administration has the added advantage of maintaining better trough levels than monthly IV infusions, the requirement of multiple needle insertions has been a deterrent for many patients.

Nevertheless, subcutaneous methods of immunoglobulin replacement therapy are becoming an increasingly popular alternative to IVIG therapy. Patients having severe reactions to IVIG infusions can often tolerate subcutaneously administered IG. Subcutaneous administration is considered to be effective, safe and also highly appreciated by patients, as it has a low risk of systemic adverse reactions and can be administered at home or in the hospital (Gardulf et al. (1995) *J Adv. Nurs.* 21: 917-27; Gardulf et al. (1993) *Clin. Exp. Immunol.* 92: 200-4; Gardulf et al. (1991) *Lancet* 338: 162-6).

2. Subcutaneous Administration of Immune Globulin and Hyaluronidase Formulations The bioavailability of subcutaneously administered IG is increased in combination with hyaluronidase administration, thereby permitting subcutaneous administration of immune globulin at dosages and frequencies similar to IVIG treatment (see e.g. U.S. Patent Application No. 2010-0074885 and International PCT No. WO 2009-117085, each incorporated by reference herein). The subcutaneous (SC) space, formed by a collagen network filled with hyaluronic acid, a gel-like substance, is largely responsible for the resistance to fluid flow through the tissues. Hyaluronidase is a family of naturally occurring enzymes that break down hyaluronic acid, which is a space-filling "gel"-like substance found in the extracellular matrix and in tissues throughout the body such as the skin and eye. Hyaluronidase acts by splitting the glucosaminidic bond in hyaluronic acid between the $C_1$ of an N-acetylglucosamine moiety and $C_4$ of a glucuronic moiety. This temporarily decreases the viscosity of the cellular cement and promotes diffusion of injected fluids, thus facilitating their absorption. Afterwards, hyaluronic acid is regenerated naturally within 24 hours. Accordingly, the bioavailability, pharmacokinetics and/or pharmacodynamic characteristics of co-formulations containing hyaluronidase are improved. Based on experiments in animals, the increased fluid dispersion permits administration of up to 1 L per hour via the subcutaneous route, which is an IV-like flow rate.

In the presence of hyaluronidase, the bioavailability of subcutaneously administered IG is increased, typically to more than 90% of the bioavailability of IG following IVIG treatment. Further, co-administration with a soluble hyaluronidase permits infusion of large volumes at a single subcutaneous site. For example, volumes up to 600 mL or greater of IG can be administered at a single site in a single sitting, for example 200 mL, 300 mL, 400 mL, 500 mL, 600 mL or more can be administered at a single site in a single administration. For example, an IG preparation formulated at or between 5-12%, for example at 10% protein, which typically are used only for IVIG therapy can be co-administered subcutaneously with a soluble hyaluronidase at dosages equivalent to once monthly IVIG doses, for example, at or about 100 mg/kg, 200 mg/kg, 300 mg/kg, 400 mg/kg, 500 mg/kg, 600 mg/kg or more. IG preparations at higher concentrations of protein, for example, 12-25% IG such as 15%, 16%, 17%, 18%, 19%, 20%, 21%, 22% or more also can be administered subcutaneously in the presence of hyaluronidase. The dosages can be administered as a single dose or can be divided into multiple doses given daily or weekly, such as once a week or every two, three or four weeks or combinations thereof. Thus, IG, when administered subcutaneously in the presence of hyaluronidase, can be administered once monthly at prevailing IVIG doses for the particular indication. Further, because hyaluronidase acts to open flow channels in the skin, it can speed infusion rates. Hence, subcutaneously administering IG administered with hyaluronidase increases infusion rates and thereby decreases time of delivery of IG therapy.

By administering IG subcutaneously in the presence of a hyaluronidase, one or all of the considerations and problems associated with subcutaneous administration of IG are addressed. Thus, by virtue of the dispersion properties of hyaluronidase, subcutaneously administering IG in the presence of a soluble hyaluronidase permits administration of IVIG doses at once monthly IVIG frequencies, while maintaining IVIG bioavailability.

3. Stable Co-Formulations

Since subcutaneously administrable immune globulin preparations have the advantages of home-care treatment, a stable, ready-for-use preparation of IG and hyaluronidase is contemplated. Proteins used for therapy are typically subjected to a range of conditions during processing and storage, including low pH, fluctuations in temperature, various buffer components and ionic strengths, and, often, high protein concentration in the final preparation. To be effective, however, the co-formulation should retain sufficient activity of the IG and hyaluronidase. Thus, a co-formulation of IG and hyaluronidase must be provided as a stable solution for storage as an aqueous solution without deteriorating for prolonged periods of time. Hence, provided herein is a stable liquid co-formulation of IG and hyaluronidase. The co-formulation is such that it is provided as a dosage form that can be used for direct injection, i.e. not diluted before use.

It was found herein that a co-formulated product prepared by the addition of a hyaluronidase designated rHuPH20 to a preparation of IG before administration was not stable at room temperature. The addition of salt improves the stability of the formulation, in particular, by maintaining the activity of the hyaluronidase in the formulation. Thus, in addition to containing an effective amount of IG and hyaluronidase, the stable co-formulations provided herein also contain at least 50 mM of an alkali metal chloride salt, for example, NaCl or KCl. Typically, the stable co-formulations also contain an amino acid, for example glycine, as a stabilizer and are provided at a pH of about or at 4 to 5. In general, the ratio of hyaluronidase to IG in a co-formulated product is greater than the ratio when the same products (IG and hyaluronidase) and the same amount of IG are subcutaneously administered separately, for example, in a leading edge administration.

Generally, the stable co-formulation is a liquid formulation. Storage of the co-formulation directly in a liquid form takes advantage of the convenience of having storage stability in the liquid form, ease of administration without reconstitution, and ability to supply the formulation in prefilled, ready-to-use syringes or as multidose preparations. Hence the liquid co-formulations provide a ready-to-use preparation of IG and hyaluronidase for subcutaneous administration to a subject without having to reconstitute the preparation accurately and aseptically and waiting for a period of time until the solution clarifies before administering the formulation to the subject. It simplifies the procedure of administering the formulation to a subject for a healthcare professional. In addition, the manufacturing process of the liquid formulations is simplified and more efficient than the manufacturing process for the lyophilized version because all stages of the manufacturing of the liquid formulations are carried out in an aqueous solution, involving no drying process, such as lyophilization and freeze-drying. Accordingly, it is more cost effective as well. The stable co-formulation can be provided as a liquid solution in a container or syringe. Such a co-formulation can be conveniently dispensed to humans or other mammalian species as a pharmaceutical without further re-constitution by the physician or patient.

Furthermore, due to its high stability during the storage, the co-formulations can contain high protein concentrations in the range of about 10% to 22% IG, such as 10% to 20% IG without causing an adverse effect on the biological activity (ies) of IG due to protein aggregation and/or fragmentation during a prolonged storage. Such stability not only ensures the efficacy of the IG co-formulation, but also reduces possible risks of causing adverse effects on a subject. Hence, the stable co-formulations provided herein retain hyaluronidase enzymatic activity and IG activity while minimizing IG self-association and aggregation. Generally, the activity is retained at a temperature that is up to 32° C., for example at or about 0° C. to 32° C., generally at or about 28° C. to 32° C. The stability of the co-formulation is maintained over prolonged periods of time, for example, daily, weekly, monthly, yearly or more. The co-formulations have the advantage that they are stable in liquid form during storage for prolonged periods of time of at least 6 months. In one example, the stable co-formulations are stable in liquid for at least 1 year or longer, for example, 1 year to 2 years, such as 1 year, 2 years, or more at standard refrigerator temperatures (approximately 4±2° C., or about 2-8° C., or, more generally, ranging from about 0-10° C.). In another example, the co-formulations are stable in liquid form during storage at room temperature (in the range of 18-32° C., for example, 28° C. to 32° C.) for at least six months. For example, the stable co-formulations generally have a shelf-life of at least or about 6 months to 18 months, for example 6 months, 12 months, 18 months, or more when stored at room temperature.

The following sections describe the formulations provided herein, including exemplary immunoglobulins and hyaluronidases in the formulations, methods of making them, and methods of using the stable co-formulations to treat IG-treatable diseases and conditions.

C. IMMUNE GLOBULIN AND PREPARATION OF IMMUNE GLOBULIN

Provided herein are immune globulins (IG, also referred to as immunoglobulin, gamma globulin or IgG) that can be formulated in stable compositions with hyaluronidase. The stable co-formulations can be used for use in treating IG-treatable diseases and conditions.

Immunoglobulins are gamma globulin proteins produced by the humoral immune system and found in the plasma of higher animals. IG acts to strengthen the immune system by modulating the activity of complement, suppressing autoantibody production, saturating or blocking Fc receptors on macrophages and B lymphocytes, and suppressing the production of inflammatory mediators such as cytokines, chemokines and metalloproteinases. IG is composed of five classes, or isotypes, of antibodies (IgG, IgA, IgM, IgD and IgE) and various subclasses, each with varying specificities. IgG is the most predominate class of IG found in the blood and is important in secondary immune responses and protecting tissues against infection. Table 2 illustrates typical amounts of immunoglobulins found in the serum, although preparations of IG for treatment can employ purification steps to alter ratios of a particular immunoglobulin class or classes. For example, protein A, protein G or protein H sepharose chromatography can be used to enrich a mixture of immunoglobulins for IgG, or for specific IgG subtypes (see, e.g., Harlow and Lane (1999) *Using Antibodies*, Cold Spring Harbor Laboratory Press; Harlow and Lane (1988) *Antibodies, A Laboratory Manual*, Cold Spring Harbor Laboratory Press; U.S. Pat. No. 5,180,810).

TABLE 2

Serum Immunoglobulin

| Ig Class | Serum Level mg/mL (%) | Function |
|---|---|---|
| IgG | 1200 (77) | Major IG class in humans; secondary immune response; protects against infection |
| IgA | 200 (13) | Protects mucosa |
| IgM | 150 (9) | Major IG for primary immune responses |
| IgD | 2 (<1) | Regulates B cells |
| IgE | <1 (trace) | Major IG in allergic response |

1. Preparation and Purification

The immunoglobulin preparations provided herein can be prepared from any suitable starting materials. For example, immune globulins can be isolated from human or animal blood, for example, from human donor serum, or produced by other means, for example, by recombinant DNA technology or hybridoma technology. Hence, immunoglobulin preparations can include monoclonal or recombinant immunoglobulins. For example, immune globulin can be obtained from tissues, lymphocyte hybridoma cultures, blood plasma or serum, or recombinant cell cultures using any suitable procedure, such as, for example, precipitation (Cohn alcohol fractionation or polyethylene glycol fractionation); chromatographic methods (ion exchange chromatography, affinity chromatography, immunoaffinity chromatography); ultra-centrifugation; or electrophoretic preparation (see, e.g., Cohn et al. (1946) *J. Am. Chem. Soc.* 68:459-75; Oncley et al. (1949) *J. Am. Chem. Soc.*, 71:541-50; Barandern et al. (1962) *Vox Sang.*, 7:157-74; Koblet et al. (1967) *Vox Sang.*, 13:93-102; U.S. Pat. Nos. 5,122,373 and 5,177,194). Typically, immunoglobulin is prepared from gamma globulin-containing products produced by alcohol fractionation and/or ion exchange and affinity chromatography methods well known to those of skill in the art.

Preparative steps can be used to enrich a particular isotype or subtype of immunoglobulin. For example, protein A, protein G or protein H sepharose chromatography can be used to enrich a mixture of immunoglobulins for IgG, or for specific IgG subtypes. (See generally Harlow and Lane, *Using Antibodies*, Cold Spring Harbor Laboratory Press (1999); Harlow and Lane, *Antibodies, A Laboratory Manual*, Cold Spring Harbor Laboratory Press (1988); U.S. Pat. No. 5,180,810).

a. Cohn-Oncley Method

Conventional industrial methods of immune globulin purification from blood plasma are based on cold ethanol fractionation, which co-precipitates groups of proteins based on their isoelectric points at given alcohol concentrations at sub-zero temperatures, originally employed by Cohn and modified by Oncley (see, e.g., Cohn et al. (1946) *J. Am. Chem. Soc.* 68:459-75; Oncley et al. (1949) *J. Am. Chem. Soc.* 71:541-50). The use of alcohol in the purification process can inactivate potentially contaminating viruses, however, with increasing temperature and alcohol concentration, the Cohn-Oncley method can result in denatured and aggregated proteins. These high molecular weight forms can act as antibody-antigen complexes having the capacity to freely fix complement.

b. Modified Cohn-Oncley Procedures

To prevent the unwanted effects of the Cohn-Oncley method, modified Cohn-Oncley methods have been developed for the preparation and purification of IG. Various such procedures are known and can be adapted and modified for producing the IG preparations herein. It is within the skill of the art to prepare IG preparations in view of the detailed methods known and available in the art.

Typically, IG is manufactured using a primary cold ethanol fractionation and a secondary fractionation that can include, for example, any one or more of the following steps to obtain a product having a low anti-complementary activity (ACA): separation of IG aggregates by conventional techniques, such as ultra-centrifuging or exclusion chromatography; chemical modification of the IG molecules by alcoholization, alkylation, sulfonation and treatment with reducing agents (see e.g., U.S. Pat. No. 6,875,848); incubation at a moderately acidic pH (pH 4.0) with or without pepsin, plasmin and immobilized trypsin; fractionating human plasma by means of ethyleneglycol polymers (Polson et al. (1964) *Biochim. Biophys. Acta.* 82: 463-475), incorporation of polyethyleneglycol (PEG) as a purification agent for material separated from the Cohn fractionation (fraction II or II+III, see e.g., U.S. Pat. Nos. 4,093, 606 and 4,165,370), fractionation methods which use polyethylene glycol as a precipitating agent, and other techniques described in U.S. Pat. Nos. 4,093,606, 4,126,605, 3,966,906, and 4,124,576, and other similar methods of purification processes with polyethyleneglycol (EP 0246579); B-propiolactone treatment; ion exchange chromatography to eliminate undesirable contaminants from the starting materials used to obtain the IG preparations (see e.g., U.S. Pat. No. 3,869,436, EP 91300790 and WO 94/29334). EP 0440483 describes a combination of techniques useful for facilitating the intravenous preparation of the product based on ion exchange chromatography and diafiltration at a weakly acidic pH; enzymatic cleavage; solvent/detergent treatment; and diafiltration and ultrafiltration. Other methods also are described in the art and are known to one of skill in the art (see e.g., U.S. Pat. Nos. 5,177,194 and 6,875,848).

Purified Cohn Fraction II is commonly used. The starting Cohn Fraction II paste is typically about 95 percent IgG and also contains the four IG subtypes. The different subtypes are present in Fraction II in approximately the same ratio as they are found in the pooled human plasma from which they are obtained. The Fraction II is further purified before formulation into an administrable product. For example, the Fraction II can be dissolved in cold purified aqueous alcohol solution and impurities removed via precipitation and filtration. Following the final filtration, the immunoglobulin suspension can be dialyzed or diafiltered (e.g. using ultrafiltration membranes having a nominal molecular weight limit of less than or equal to 100,000 daltons) to remove alcohol. The solution can be concentrated or diluted to obtain the desired protein concentration and can be further purified by techniques well known to those skilled in the art.

c. Viral Processing

The IG preparations should be treated to remove viral load. There are two methods of viral processing: viral inactivation and viral partitioning or removal. Viral inactivation renders viruses inactive by, for example, chemically altering the lipid or protein coat, or by completely denaturing the virus. Exemplary of viral inactivation methods include, but are not limited to, heating (pasteurization), solvent/detergent (S/D) treatment and exposure to an acidic environment (low pH). The S/D process is the most widely used viral inactivation method in the blood plasma industry, used to inactivate viruses containing a lipid coat. For example, the S/D process has been demonstrated to have virucidal action against VSV (vesicular stomatitits virus), Sindbis virus, HIV, HBV (hepatitis B virus) and HCV (hepatitis C virus).

Viral removal is a method that completely removes all viruses from the sample. Exemplary of viral partitioning or removal include, but are not limited to, cold ethanol fractionation, phase partitioning or PEG precipitation, affinity chromatography, ion exchange or gel exclusion chromatography and nanofiltration.

d. Protein concentration

Immunoglobulins can be prepared at varying concentrations. For example, IG can be prepared at protein concentrations ranging from at or about 3-25 % IG, typically at or about 10% to 22%, such as 10 % - 20 % w/v. For example, IG preparations can be at or about 18% to 22% IG w/v. The IG preparations provided herein generally are prepared at IG concentrations of at or about 10 %, 11 %, 12 %, 13 %, 14 %, 15 %, 16 %, 17 %, 18 %, 19 %, 20 %, 21 %, 22 % or more. The final protein concentration depends largely on the method of generation and purification. It is contemplated herein that any immune globulin preparation can be used herein for stable co-formulations with hyaluronidase. It is within the level of one of skill in the art to empirically determine the appropriate concentration of IG for inclusion in the stable co-formulations herein. The choice of IG preparation will depend on a variety of factors such as the administration route, the patient to be treated and the type of condition to be treated.

For example, any known or existing preparation of IG can be used. These include preparations of IG typically used for IV administration (IVIG). In general, final IG preparations for intravenous administration have a protein concentration of about 3 to 12% w/v, or typically 10% w/v. For example, WIG is commercially available as Carimune® NF, Flebogamma® 5%, Gammagard® Liquid, Gammagard® S/D, Gamunex®, Iveegam® EN, Octagam® and Polygam® S/D. Typically, such preparations use a method of cold alcohol fractionation, but differ in the methods used to isolate and purify the immune globulin and methods to reduce potential virus contamination.

Further, other preparations presently formulated for intramuscular or subcutaneous administration can be used in the compositions and methods provided herein. For example, IG preparations for intramuscular administration and subcutaneous administration are commercially available as GamaSTAN® S/D and Vivaglobin®, respectively. Typically, such preparations use cold ethanol fractionation from human plasma and have an IgG concentration of about 15 to 18% or 10 to 22%, respectively. U.S. Provisional Application No. 61/181,606 describes the generation of a highly purified and concentrated immunoglobulin composition from pooled plasma for subcutaneous administration.

e. Exemplary IG Preparations i. 10% IG

Exemplary of an IG preparation is Immune Globulin Intravenous (Human), 10% (IVIG, 10%, marketed as Gammagard® liquid, Baxter Healthcare Corporation), which is a liquid unmodified IgG preparation, with a distribution of IgG subclasses similar to that of normal plasma. The preparation contains intact fragment crystallizable (Fc) and fragment antigen binding (Fab) regions. The preparations contain 100 mg/mL protein, with at least 98% being IgG; IgA is present at a concentration of 37 µg/mL, and IgM is present only in trace amounts. It has an osmolality that is similar to physiologic osmolality, and contains no added sugars, sodium or preservatives. It is formulated with glycine for stabilization at a pH of 4.6 to 5.1. The manufacturing process employs a modified Cohn-Oncley cold alcohol fractionation procedure and further purifications by a continuous process through the use of weak cation exchange chromatography and weak anion exchange chromatography. The manufacturing process also includes 3 independent viral inactivation or removal steps: solvent/detergent (S/D) treatment, nanofiltration and incubation at a low pH and elevated temperature. Preparation of a 10% IVIG preparation is described in Example 1.

ii. High Concentration IG Preparations (e.g. 20% IG)

The generation of high concentration immunoglobulin preparations are described in U.S. Provisional Application No. 61/181,606. Exemplary of preparations containing 18-22% IG are highly purified, isotonic liquid formulations of immunoglobulin (at least 95% IgG) formulated in 0.25 mM glycine at pH 4.4 to 4.9, represented in the Examples below.

The high concentration IgG products described herein are produced by a process having many of the same or similar steps as in the process of producing traditional IVIG preparations (e.g. 10% IG). The additional steps, ultrafiltration/diafiltration using open channel membranes with a specifically designed post-wash and formulation near the end of the production process, render the resulting IG compositions about twice as high in protein concentration (200 mg/mL) compared to state of the art IVIGs (e.g., Gammagard Liquid), without affecting yield and storage stability. With most commercially available ultrafiltration membranes, a concentration of 200 mg/mL IgG cannot be reached without major protein losses. These membranes become blocked early, consequently adequate post-wash is difficult to achieve. Therefore, open channel membrane configurations have to be used. Further, a specifically designed post-wash procedure is employed to obtain the required IG concentration without significant protein loss (less than 2% loss); the higher protein concentration of 200 mg/mL does not affect the virus inactivation capacity of the low pH storage step.

The general process of producing the high concentration IG composition includes the following steps which are described in further detail in Example 2. First, the cryoprecipitates are separated from previously frozen plasma to yield a liquid "cryo-poor plasma," which is processed in the next step to obtain the supernatant (or Fractionation I). Adjustment of pH and ethanol concentration, typically to 7 and 20 to 25% v/v, respectively, followed by subsequent centrifugation while decreasing temperature, separates the liquid and solid. The precipitate from this step is then extracted, mixed with fumed silica, and filtered, all steps performed at low temperatures, typically 2 to 8° C. The filtrate is then mixed with polysorbate-80 and sodium citrate dehydrate while stirring at 2 to 8° C. Precipitate G is then obtained, in a manner similar to the precipitation step of Cohn II, in which the pH and alcohol concentration is adjusted. Precipitate G is dissolved and filtered with a depth filter of a nominal pore size of 0.2 µm (e.g., Cuno VR06 filter or equivalent) to obtain a clear filtrate. Subsequent solvent/detergent treatment, typically using 1.0% (v/v) Triton X-100, 0.3% (v/v) Tween-80, and 0.3% (v/v) TNBP, at 18 to 25° C. for at least 60 minutes, followed by cation exchange chromatography, anion exchange chromatography and nanofiltration using, e.g., an Asahi Planova 35N filter or equivalent. Subsequent to nanofiltration, the filtrate is concentrated to a protein concentration of 5±1% w/v by ultrafiltration. In some examples, the ultrafiltration is carried out in a cassette with an open channel screen and the ultrafiltration membrane has a nominal molecular weight cut off (NMWCO) of 50 kDa or less. Upon completion of the ultrafiltration step, the concentrate is diafiltered against a 0.25 M glycine solution with a low pH. Typically, the minimum exchange volume is 6 times the original concentrate volume, and the solution is concentrated to a protein concentration of more than 20% w/v. At the end of the diafiltration and concentration process, the pH of the solution is typically between 4.4 to 4.9. For formulation, the protein concentration of the solution is then adjusted to just over 20% w/v, e.g., 20.4±04% w/v, with the diafiltration buffer. The formulated bulk solution is further sterilized by first filtering through a membrane filter with an absolute pore size of 0.2 micron or less. Then the solution is aseptically dispensed into final containers for proper sealing, with samples taken for testing. The final step is storing the sealed containers at 30 to 32° C. for an extended time period, e.g., 21 to 22 days.

Incorporating ultrafiltration and formulations steps in the manufacturing process is an improvement over previously used IG purification and concentration methods, resulting in preparations with higher IG concentrations without significant IG activity loss while maintaining a low pH in the final formulation. Typically, the products have a protein concentration of at least 18% weight/volume (w/v), of which the vast majority (typically no less than 95%) is IgG, and a pH in the range of pH 3-6, which facilitates inactivation of pathogens such as viruses that may be present in the plasma. Due to the high IG concentration and therefore reduced volume in administration, the high concentration preparations are suitable for subcutaneous administration. In some embodiments, the IG products have a viscosity no greater than 18 mPascal·second and may therefore be suitable for intravenous administration as well. Simple dilution can also permit intravenous administration.

2. Storage Stability

Final, purified IG formulations must be prepared to retain activity of the IG and avoid excessive aggregation. Upon storage of the IG preparations, aggregation can be minimized and stability improved by, for example, the addition of protein-stabilizing excipients or adjusting the pH of the solution.

a. Protein-Stabilizing Excipients

A way to increase the stability of IG preparations that is well known in the art is to add protein-stabilizing excipients to the IG preparation. Known excipients include, but are not limited to, sugars, polyols, amino acids, amines, salts, polymers and surfactants. For example, U.S. Pat. No. 4,499,073 describes stabilization as a result of ionic strength and pH of the storage solution; JP Patent 54020124 discloses the addition of an amino acid to an intramuscular preparation to render the preparation stable and safe for storage; JP 57031623 and JP 57128635 disclose the use of arginine and/or lysine with NaCl in 5 to 15% IG preparations to achieve long-term stability in an intramuscular preparation; JP 4346934 discloses the use of low conductivity (less than 1 mmho), pH 5.3 to 5.7 and optionally one or more stabilizers, including PEG, human serum albumin and mannitol; U.S. Pat. No. 4,439,421 teaches the addition of a hydrophilic macromolecule, a polyol and another protein to stabilize against anti-complement generation; U.S. Pat. No. 5,945,098 discloses the stabilization of isotonic solutions by the addition of amino acids (0.1 to 0.3 M glycine) and non-ionic detergents (polysorbate and PEG); U.S. Pat. No. 4,186,192 discloses various additives, including amino acids; WO 2005/049078 discloses the stabilization with maltose, and additionally, glycine to 0.1 M; U.S. Pat. No. 4,362,661 discloses the use of neutral and basic amino acids to impart stability on a 5% IG preparation. Stable liquid formulations can also be prepared using carbohydrates in an aqueous medium with very low ionic strength and a pH of 4.25 (U.S. Pat. No. 4,396,608) or a weakly acidic pH of 5-6 (EP 0278422).

Dimer formation of IG preparations also can be controlled. For example, U.S. Pat. No. 5,871,736 discloses IG preparations, particularly liquid preparations, containing one or more amphiphilic stabilizers against dimer formation. The amphiphilic stabilizers include nicotinic acid and its derivatives, in particular nicotinamide, and mainly in conjunction with amino acids having uncharged lipophilic side chains, e.g., phenylalanine, methionine, leucine, isoleucine, proline and valine.

b. pH

The IG preparations can be prepared by methods known in the art, such as any described herein. Generally, however, the pH of the final preparation is adjusted to a relatively high pH, namely in the range of about pH 4.0 to 7.4. It has been found that the pH of the immune globulin preparation is an important factor relative to the IgG monomer content of the final product. Generally, a 5 percent immune globulin preparation has a pH of 4.2±0.5. Ten percent preparations are most stable at a pH of 5.2±0.2. Optimal pH is obtained by formulation techniques well known to those skilled in the art. For example, optimal pH can be determined from size exclusion chromatography determinations as well as heat stability data and anticomplement titers of the various preparations under differing pH conditions.

D. Hyaluronidase

Provided herein are stable co-formulations containing immunoglobulin and a hyaluronidase, typically a soluble hyaluronidase. Hyaluronidases are members of a large family of enzymes that degrade hyaluronic acid, which is an essential component of the extracellular matrix and a major constituent of the interstitial barrier. By catalyzing the hydrolysis of hyaluronic acid, a major constituent of the interstitial barrier, hyaluronidase lowers the viscosity of hyaluronic acid, thereby increasing tissue permeability. As such, hyaluronidases have been used, for example, as a spreading or dispersing agent in conjunction with other agents, drugs and proteins to enhance their dispersion and delivery. Exemplary of hyaluronidases in the co-formulations provided herein are soluble hyaluronidases.

There are three general classes of hyaluronidases: mammalian hyaluronidase, bacterial hyaluronidase and hyaluronidase from leeches, other parasites and crustaceans.

Mammalian-type hyaluronidases (EC 3.2.1.35) are endo-β-N-acetyl-hexosaminidases that hydrolyze the β1-4 glycosidic bond of hyaluronan into various oligosaccharide lengths such as tetrasaccharides and hexasaccharides. They have both hydrolytic and transglycosidase activities, and can degrade hyaluronan and chondroitin sulfates (CS), generally C4-S and C6-S. Hyaluronidases of this type include, but are not limited to, hyaluronidases from cows (bovine) (SEQ ID NOS:10 and 11), mouse (SEQ ID NOS:17-19, 32), pig (SEQ ID NOS:20-21), rat (SEQ ID NOS:22-24, 31), rabbit (SEQ ID NO:25), sheep (ovine) (SEQ ID NOS:26 and 27), orangutan (SEQ ID NO:28), cynomolgus monkey (SEQ ID NO:29), guinea pig (SEQ ID NO:30), and human hyaluronidases.

Mammalian hyaluronidases can be further subdivided into those that are neutral active, predominantly found in testes extracts, and acid active, predominantly found in organs such as the liver. Exemplary neutral active hyaluronidases include PH20, including but not limited to, PH20 derived from different species such as ovine (SEQ ID NO:27), bovine (SEQ ID NO:11) and human (SEQ ID NO:1). Human PH20 (also known as SPAM1 or sperm surface protein PH20), is generally attached to the plasma membrane via a glycosylphosphatidyl inositol (GPI) anchor. It is naturally involved in sperm-egg adhesion and aids penetration by sperm of the layer of cumulus cells by digesting hyaluronic acid.

Besides human PH20 (also termed SPAM1), five hyaluronidase-like genes have been identified in the human genome, HYAL1, HYAL2, HYAL3, HYAL4 and HYALP1. HYALP1 is a pseudogene, and HYAL3 (SEQ ID NO:38) has not been shown to possess enzyme activity toward any known substrates. HYAL4 (precursor polypeptide set forth in SEQ ID NO:39) is a chondroitinase and exhibits little activity towards hyaluronan. HYAL1 (precursor polypeptide set forth in SEQ ID NO:36) is the prototypical acid-active enzyme and PH20 (precursor polypeptide set forth in SEQ ID NO:1) is the prototypical neutral-active enzyme. Acid-active hyaluronidases, such as HYAL1 and HYAL2 (precursor polypeptide set forth in SEQ ID NO:37) generally lack catalytic activity at neutral pH (i.e. pH 7). For example, HYAL1 has little catalytic activity in vitro over pH 4.5 (Frost et al. (1997) *Anal. Biochemistry*, 251:263-269). HYAL2 is an acid-active enzyme with a very low specific activity in vitro. The hyaluronidase-like enzymes can also be characterized by those which are generally attached to the plasma membrane via a glycosylphosphatidyl inositol anchor such as human HYAL2 and human PH20 (Danilkovitch-Miagkova et al. (2003) *Proc Natl Acad Sci USA*. 100(8):4580-5), and those which are generally soluble such as human HYAL1 (Frost et al., (1997) *Biochem Biophys Res Commun.* 236(1):10-5).

1. PH20

PH20, like other mammalian hyaluronidases, is an endo-β-N-acetyl-hexosaminidase that hydrolyzes the β1→4 glycosidic bond of hyaluronic acid into various oligosaccharide lengths such as tetrasaccharides and hexasaccharides. They have both hydrolytic and transglycosidase activities and can degrade hyaluronic acid and chondroitin sulfates, such as C4-S and C6-S. PH20 is naturally involved in sperm-egg adhesion and aids penetration by sperm of the layer of cumulus cells by digesting hyaluronic acid. PH20 is located on the sperm surface, and in the lysosome-derived acrosome, where it is bound to the inner acrosomal membrane. Plasma membrane PH20 has hyaluronidase activity only at neutral pH, while inner acrosomal membrane PH20 has activity at both neutral and acid pH. In addition to being a hyaluronidase, PH20 also appears to be a receptor for HA-induced cell signaling, and a receptor for the zona pellucida surrounding the oocyte.

Exemplary PH20 proteins include, but are not limited to, human (precursor polypeptide set forth in SEQ ID NO:1, mature polypeptide set forth in SEQ ID NO: 2), bovine (SEQ ID NOS: 11), rabbit (SEQ ID NO: 25), ovine PH20 (SEQ ID NOS: 27), Cynomolgus monkey (SEQ ID NO: 29), guinea pig (SEQ ID NO: 30), rat (SEQ ID NO: 31) and mouse (SEQ ID NO: 32) PH20 polypeptides.

Bovine PH20 is a 553 amino acid precursor polypeptide (SEQ ID NO:11). Alignment of bovine PH20 with the human PH20 shows only weak homology, with multiple gaps existing from amino acid 470 through to the respective carboxy termini due to the absence of a GPI anchor in the bovine polypeptide (see e.g., Frost GI (2007) *Expert Opin. Drug. Deliv.* 4: 427-440). In fact, clear GPI anchors are not predicted in many other PH20 species besides humans. Thus, PH20 polypeptides produced from ovine and bovine naturally exist as soluble forms. Though bovine PH20 exists very loosely attached to the plasma membrane, it is not anchored via a phospholipase sensitive anchor (Lalancette et al. (2001) *Biol Reprod.* 65(2):628-36). This unique feature of bovine hyaluronidase has permitted the use of the soluble bovine testes hyaluronidase enzyme as an extract for clinical use (Wydase®, Hyalase®).

The human PH20 mRNA transcript is normally translated to generate a 509 amino acid precursor polypeptide (SEQ ID NO:1) containing a 35 amino acid signal sequence at the N-terminus (amino acid residue positions 1-35) and a 19 amino acid glycosylphosphatidylinositol (GPI) anchor attachment signal sequence at the C-terminus (amino acid residue positions 491-509). The mature PH20 is, therefore, a 474 amino acid polypeptide set forth in SEQ ID NO:2. Following transport of the precursor polypeptide to the ER and removal of the signal peptide, the C-terminal GPI-attachment signal peptide is cleaved to facilitate covalent attachment of a GPI anchor to the newly-formed C-terminal amino acid at the amino acid position corresponding to position 490 of the precursor polypeptide set forth in SEQ ID NO:1. Thus, a 474 amino acid GPI-anchored mature polypeptide with an amino acid sequence set forth in SEQ ID NO:2 is produced.

Compared to other hyaluronidases, including bee and honey venom hyaluronidase and mouse, monkey and guinea pig PH20, human PH20 contains a common region of 340 amino acids with 57 conserved amino acids (see e.g. Arming et al. (1997) *Eur. I Biochem.,* 247:810-814). The conserved amino acids include four cysteine residues that form disulfide bridges at amino acid residues 25, 189, 203 and 316 in the sequence of amino acids set forth in SEQ ID NO:2 (corresponding to residues 60, 224, 238 and 351 in the sequence of amino acids set forth in SEQ ID NO:1). Disulfide bonds form between the cysteine residues C60 and C351 and between C224 and C238 to form the core hyaluronidase domain. However, additional cysteines are required in the carboxy terminus for neutral enzyme catalytic activity such that amino acids 36 to 464 of SEQ ID NO:1 contains the minimally active human PH20 hyaluronidase domain. A further four disulfide bonds are formed between the cysteine residues C376 and C387; between C381 and C435; between C437 and C443; and between C458 and C464 of the polypeptide exemplified in SEQ ID NO: 1 (corresponding to residues C341 and C352; between C346 and C400; between C402 and C408; and between C423 and C429 of the mature polypeptide set forth in SEQ ID NO:2, respectively).

In addition, other conserved residues are likely involved in substrate binding and catalysis. Amino acid residues at amino acid positions 111, 113, 176, 249 and 252 corresponding to residues in SEQ ID NO:2 appear to be involved in the activity of PH20, since mutation at these position renders the enzyme devoid of enzymatic activity or leave only residual activity compared to wild-type PH20 not containing the mutations (see e.g. Arming et al. (1997) *Eur. J. Biochem.,* 247:810-814).

There are seven potential N-linked glycosylation sites at N82, N166, N235, N254, N368, N393, N490 of human PH20 exemplified in SEQ ID NO: 1. Disulfide bonds form between the cysteine residues C60 and C351 and between C224 and C238 to form the core hyaluronidase domain. Since amino acids 36 to 464 of SEQ ID NO:1 contain the minimally active human PH20 hyaluronidase domain, N-linked glycosylation site N-490 is not required for proper hyaluronidase activity.

2. Soluble Hyaluronidase

Generally, the hyaluronidase in the stable co-formulations provided herein are soluble hyaluronidases. Soluble hyaluronidases, when expressed in cells, are secreted into the media. Solubility can be demonstrated by partitioning of the protein into the aqueous phase of Triton X-114 solution. Accordingly, it is understood that a soluble hyaluronidase does not include any hyaluronidase that contains a GPI anchor, rendering the polypeptide attached to the cell membrane. For example, full-length human PH20 (set forth in its mature form as SEQ ID NO:2) contains a GPI anchor and is not soluble. In contrast, bovine and ovine PH20 polypeptides do not contain a GPI anchor that is sufficient for attachment to the GPI anchor, and thus are considered to be soluble proteins. Further, the soluble hyaluronidase that are included in the co-formulations provided herein generally are substantially purified proteins. Also, soluble hyaluronidases retain hyaluronidase activity. For example, soluble human PH20 retains neutral activity.

Soluble hyaluronidases include hyaluronidases that do not naturally include a GPI anchor or an anchor sufficient for attachment to the membrane, including, but not limited to, Hyal1, bovine PH20 and ovine PH20, allelic variants thereof and other variants. Also included among soluble hyaluronidase are any hyaluronidase that has been modified to be soluble. For example, human PH20, which is normally membrane anchored via a GPI anchor, can be made soluble by truncation of and removal of all or a portion of the GPI anchor at the C-terminus. Soluble hyaluronidases also include neutral active and acid active hyaluronidases, however, neutral active hyaluronidases are contemplated for use herein for purposes of subcutaneous administration.

Thus, exemplary of a soluble hyaluronidase is PH20 from any species, such as any set forth in any of SEQ ID NOS: 1, 2, 11, 25, 27, 30, 31 and 32, or truncated forms thereof lacking all or a portion of the C-terminal GPI anchor, so long as the hyaluronidase is soluble and retains hyaluronidase activity. Also included among soluble hyaluronidases are allelic variants or other variants of soluble forms of any of SEQ ID NOS: 1, 2, 11, 25, 27, 30, 31 and 32, such as truncated forms thereof. Allelic variants and other variants are known to one of skill in the art, and include polypeptides having 60%, 70%, 80%, 90%, 91%, 92%, 93%, 94%, 95% or more sequence identify to any of SEQ ID NOS: 1, 2, 11, 25, 27, 30 and 31, or truncated forms thereof.

Typically, co-formulations herein contain a soluble human PH20. Although PH20 from other animals can be utilized, such preparations are potentially immunogenic, since they are animal proteins. For example, a significant proportion of patients demonstrate prior sensitization secondary to ingested foods, and since these are animal proteins, all patients have a risk of subsequent sensitization. Thus, non-human preparations may not be suitable for chronic use. If non-human preparations are desired, it is contemplated herein that such polypeptides can be prepared to have reduced immunogenicity. Such modifications are within the level of one of skill in the art.

a. Soluble Human PH20

Exemplary of a soluble hyaluronidase is soluble human PH20, Soluble forms of recombinant human PH20 have been produced and can be included in the co-formulations described herein. The production of such soluble forms of PH20 is described in U.S. Patent Application Nos. 2005-0260186 and 2006-0104968. Soluble forms include, but are not limited to, any having C-terminal truncations to generate polypeptides containing amino acid 1 to amino acid 464 or of the sequence of amino acids set forth in SEQ ID NOS 1. For example, soluble forms include, but are not limited to, any having C-terminal truncations to generate polypeptides containing amino acid 1 to amino acid 467 to 483, for example, 467, 477, 478, 479, 480, 481, 482 and 483. When expressed in mammalian cells, the 35 amino acid N-terminal signal sequence is cleaved during processing, and the mature form of the protein is secreted. Thus, the mature soluble polypeptides contain at least amino acids 36 to 464 of SEQ ID NO:1. For example, mature soluble polypeptides contain amino acids 36 to 467 to 36 to 483 of SEQ ID NO:1, for example 36 to 467, 477, 478, 479, 480, 481, 482 and 483 of SEQ ID NO:1. Deletion mutants ending at amino acid position 477 to 483 (corresponding to the precursor polypeptide set forth in SEQ ID NO:1) exhibit higher secreted hyaluronidase activity than the full length GPI-anchored form. Hence, exemplary of soluble hyaluronidases are those that are 442, 443, 444, 445, 446 or 447 amino acids in length, such as set forth in any of SEQ ID NOS:4-9, or allelic or species variants or other variants thereof.

b. Recombinant Soluble Human PH20 (rHuPH20)

Recombinant soluble forms of human PH20 designated as rHuPH20 have been generated and can be produced and purified using the methods described herein. The generation of such soluble forms of rHuPH20 are described in U.S. Patent Application Ser. Nos. 11/065,716 and 11/238,171 (published as U.S. published patent application Nos. US20050260186 and US 20060104968), and in Examples 3 below. Exemplary of such polypeptides are those generated from a nucleic acid molecule encoding amino acids 1-482 set forth in SEQ ID NO:3. Post translational processing removes the 35 amino acid signal sequence, resulting in the secretion of a 447 amino acid soluble rHuPH20 (SEQ ID NO:4). Resulting purified rHuPH20 can be heterogenous due to peptidases present in the culture medium upon production and purification. Typically, rHuPH20 is produced in cells that facilitate correct N-glycosylation to retain activity, such as CHO cells (e.g. DG44 CHO cells).

3. Glycosylation

Glycosylation, including N- and O-linked glycosylation, of some hyaluronidases can be very important for their catalytic activity and stability. While altering the type of glycan modifying a glycoprotein can have dramatic affects on a protein's antigenicity, structural folding, solubility, and stability, most enzymes are not thought to require glycosylation for optimal enzyme activity. Such hyaluronidases are unique in this regard, in that removal of N-linked glycosylation can result in near complete inactivation of the hyaluronidase activity. For such hyaluronidases, the presence of N-linked glycans is critical for generating an active enzyme.

N-linked oligosaccharides fall into several major types (oligomannose, complex, hybrid, sulfated), all of which have (Man) 3-GlcNAc-GlcNAc-cores attached via the amide nitrogen of Asn residues that fall within-Asn-Xaa-Thr/Ser-sequences (where Xaa is not Pro). Glycosylation at an-Asn-Xaa-Cys-site has been reported for coagulation protein C. In some instances, the hyaluronidase can contain both N-glycosidic and O-glycosidic linkages. For example, PH20 has O-linked oligosaccharides as well as N-linked oligosaccharides. There are seven potential N-linked glycosylation sites at N82, N166, N235, N254, N368, N393, N490 of human PH20 exemplified in SEQ ID NO: 1. As noted above, N-linked glycosylation at N490 is not required for hyaluronidase activity.

4. Modifications of Hyaluronidases to Improve their Pharmacokinetic Properties Hyaluronidases provided in the co-formulations can be modified to improve their pharmacokinetic properties, such as increasing their half-life in vivo and/or activities. The modification of hyaluronidases for use in co-formulations provided herein can include attaching, directly or indirectly via a linker, such as covalently to or by other stable linkage, a polymer, such as dextran, a polyethylene glycol (PEGylation (PEG)) or sialyl moiety, or other such polymers, such as natural or sugar polymers.

PEGylation of therapeutics is known to increase resistance to proteolysis, increase plasma half-life, and decrease antigenicity and immunogenicity. Covalent or other stable attachment (conjugation) of polymeric molecules, such as polyethylene glycol moiety (PEG), to the hyaluronidase thus can impart beneficial properties to the resulting enzyme-polymer composition. Such properties include improved biocompatibility, extension of protein (and enzymatic activity) half-life in the blood, cells and/or in other tissues within a subject, effective shielding of the protein from proteases and hydrolysis, improved biodistribution, enhanced pharmacokinetics and/or pharmacodynamics, and increased water solubility.

Exemplary polymers that can be conjugated to the hyaluronidase, include natural and synthetic homopolymers, such as polyols (i.e. poly-OH), polyamines (i.e. poly-NH2) and polycarboxyl acids (i.e. poly-COOH), and further heteropolymers i.e. polymers containing one or more different coupling groups e.g. a hydroxyl group and amine groups. Examples of suitable polymeric molecules include polymeric molecules selected from among polyalkylene oxides (PAO), such as polyalkylene glycols (PAG), including polypropylene glycols (PEG), methoxypolyethylene glycols (mPEG) and polypropylene glycols, PEG-glycidyl ethers (Epox-PEG), PEG-oxycarbonylimidazole (CDI-PEG) branched polyethylene glycols (PEGs), polyvinyl alcohol (PVA), polycarboxylates, polyvinylpyrrolidone, poly-D,L-amino acids, polyethylene-co-maleic acid anhydride, polystyrene-co-maleic acid anhydride, dextrans including carboxymethyl-dextrans, heparin, homologous albumin, celluloses, including methylcellulose, carboxymethylcellulose, ethylcellulose, hydroxyethylcellulose carboxyethylcellulose and hydroxypropylcellulose, hydrolysates of chitosan, starches such as hydroxyethyl-starches and hydroxypropyl-starches, glycogen, agaroses and derivatives thereof, guar gum, pullulan, inulin, xanthan gum, carrageenan, pectin, alginic acid hydrolysates and bio-polymers.

Typically, the polymers are polyalkylene oxides (PAO), such as polyethylene oxides, such as PEG, typically mPEG, which, in comparison to polysaccharides such as dextran, pullulan and the like, have few reactive groups capable of cross-linking. Typically, the polymers are non-toxic polymeric molecules such as (m)polyethylene glycol (mPEG) which can be covalently conjugated to the hyaluronan degrading enzyme (e.g., to attachment groups on the protein surface) using a relatively simple chemistry.

Suitable polymeric molecules for attachment to the hyaluronan degrading enzyme include, but are not limited to, polyethylene glycol (PEG) and PEG derivatives such as methoxypolyethylene glycols (mPEG), PEG-glycidyl ethers (Epox-PEG), PEG-oxycarbonylimidazole (CDI-PEG), branched PEGs, and polyethylene oxide (PEO) (see e.g. Roberts et al., Advanced Drug Delivery Review 2002, 54: 459-476; Harris and Zalipsky, S (eds.) "Poly(ethyl ene glycol), Chemistry and Biological Applications" ACS Symposium Series 680, 1997; Mehvar et al., J. Pharm. Pharmaceut. Sci., 3(1):125-136, 2000; Harris, Nature Reviews 2:215 et seq. (2003); and Tsubery, J Biol. Chem. 279(37):38118-24, 2004). The polymeric molecule can be of a molecular weight typically ranging from about 3 kDa to about 60 kDa. In some embodiments the polymeric molecule that is conjugated to a protein, such as rHuPH20, has a molecular weight of 5, 10, 15, 20, 25, 30, 35, 40, 45, 50, 55, 60 or more than 60 kDa.

Various methods of modifying polypeptides by covalently attaching (conjugating) a PEG or PEG derivative (i.e. "PEGylation") are known in the art (see e.g., U.S. 2006/0104968; U.S. Pat. No. 5,672,662; U.S. Pat. No. 6,737,505; and U.S. 2004/0235734). Techniques for PEGylation include, but are not limited to, specialized linkers and coupling chemistries (see e.g., Harris, Adv. Drug Deliv. Rev. 54:459-476, 2002), attachment of multiple PEG moieties to a single conjugation site (such as via use of branched PEGs; see e.g., Veronese et al., Bioorg. Med. Chem. Lett. 12:177-180, 2002), site-specific PEGylation and/or mono-PEGylation (see e.g., Chapman et al., Nature Biotech. 17:780-783, 1999), and site-directed enzymatic PEGylation (see e.g., Sato, Adv. Drug Deliv. Rev., 54:487-504, 2002) (see, also, for example, Lu and Felix (1994) Int. J. Peptide Protein Res. 43:127-138; Lu and Felix (1993) Peptide Res. 6:142-6, 1993; Felix et al. (1995) Int. J. Peptide Res. 46:253-64; Benhar et al. (1994) J. Biol. Chem. 269:13398-404; Brumeanu et al. (1995) J Immunol. 154: 3088-95; see also, Caliceti et al. (2003) Adv. Drug Deliv. Rev. 55(10):1261-77 and Molineux (2003) Pharmacotherapy 23 (8 Pt 2):3S-8S). Methods and techniques described in the art can produce proteins having 1, 2, 3, 4, 5, 6, 7, 8, 9, 10 or more than 10 PEG or PEG derivatives attached to a single protein molecule (see e.g., U.S. 2006/0104968).

Numerous reagents for PEGylation have been described in the art. Such reagents include, but are not limited to, N-hydroxysuccinimidyl (NHS) activated PEG, succinimidyl mPEG, mPEG2-N-hydroxysuccinimide, mPEG succinimidyl alpha-methylbutanoate, mPEG succinimidyl propionate, mPEG succinimidyl butanoate, mPEG carboxymethyl 3-hydroxybutanoic acid succinimidyl ester, homobifunctional PEG-succinimidyl propionate, homobifunctional PEG propionaldehyde, homobifunctional PEG butyraldehyde, PEG maleimide, PEG hydrazide, p-nitrophenyl-carbonate PEG, mPEG-benzotriazole carbonate, propionaldehyde PEG, mPEG butyraldehyde, branched mPEG2 butyraldehyde, mPEG acetyl, mPEG piperidone, mPEG methylketone, mPEG "linkerless" maleimide, mPEG vinyl sulfone, mPEG thiol, mPEG orthopyridylthioester, mPEG orthopyridyl disulfide, Fmoc-PEG-NHS, Boc-PEG-NHS, vinylsulfone PEG-NHS, acrylate PEG-NHS, fluorescein PEG-NHS, and biotin PEG-NHS (see e.g., Monfardini et al., Bioconjugate Chem. 6:62-69, 1995; Veronese et al., J. Bioactive Compatible Polymers 12:197-207, 1997; U.S. Pat. Nos. 5,672,662; 5,932,462; 6,495,659; 6,737,505; 4,002,531; 4,179,337; 5,122,614; 5,183,550; 5,324,844; 5,446,090; 5,612,460; 5,643,575; 5,766,581; 5,795,569; 5,808,096; 5,900,461; 5,919,455; 5,985,263; 5,990,237; 6,113,906; 6,214,966; 6,258,351; 6,340,742; 6,413,507; 6,420,339; 6,437,025; 6,448,369; 6,461,802; 6,828,401; 6,858,736; U.S. 2001/0021763; U.S. 2001/0044526; U.S. 2001/0046481; U.S. 2002/0052430; U.S. 2002/0072573; U.S. 2002/0156047; U.S. 2003/ 0114647; U.S. 2003/0143596; U.S. 2003/0158333; U.S. 2003/0220447; U.S. 2004/0013637; US 2004/0235734; U.S. 2005/000360; U.S. 2005/0114037; U.S. 2005/0171328; U.S. 2005/0209416; EP 01064951; EP 0822199; WO 00176640; WO 0002017; WO 0249673; WO 9428024; and WO 0187925).

E. Methods of producing nucleic acids encoding a soluble Hyaluronidase and polypeptides thereof Polypeptides of a soluble hyaluronidase set forth herein, can be obtained by methods well known in the art for protein purification and recombinant protein expression. Any method known to those of skill in the art for identification of nucleic acids that encode desired genes can be used. Any method available in the art can be used to obtain a full length (i.e., encompassing the entire coding region) cDNA or genomic DNA clone encoding a hyaluronidase, such as from a cell or tissue source. Modified or variant soluble hyaluronidases, can be engineered from a wildtype polypeptide, such as by site-directed mutagenesis. Typically, hyaluronidases, including soluble hyaluronidases such as rHuPH20, used in the co-formulations provided herein can be recombinantly produced or can be purified or partially-purified from natural sources, such as, for example, from testes extracts.

Polypeptides can be cloned or isolated using any available methods known in the art for cloning and isolating nucleic acid molecules. Such methods include PCR amplification of nucleic acids and screening of libraries, including nucleic acid hybridization screening, antibody-based screening and activity-based screening.

Methods for amplification of nucleic acids can be used to isolate nucleic acid molecules encoding a desired polypeptide, including for example, polymerase chain reaction (PCR) methods. A nucleic acid containing material can be used as a starting material from which a desired polypeptide-encoding nucleic acid molecule can be isolated. For example, DNA and mRNA preparations, cell extracts, tissue extracts, fluid samples (e.g. blood, serum, saliva), samples from healthy and/or diseased subjects can be used in amplification methods. Nucleic acid libraries also can be used as a source of starting material. Primers can be designed to amplify a desired polypeptide. For example, primers can be designed based on expressed sequences from which a desired polypeptide is generated. Primers can be designed based on back-translation of a polypeptide amino acid sequence. Nucleic acid molecules generated by amplification can be sequenced and confirmed to encode a desired polypeptide.

Additional nucleotide sequences can be joined to a polypeptide-encoding nucleic acid molecule, including linker sequences containing restriction endonuclease sites for the purpose of cloning the synthetic gene into a vector, for example, a protein expression vector or a vector designed for the amplification of the core protein coding DNA sequences. Furthermore, additional nucleotide sequences specifying functional DNA elements can be operatively linked to a polypeptide-encoding nucleic acid molecule. Examples of such sequences include, but are not limited to, promoter sequences designed to facilitate intracellular protein expression, and secretion sequences, for example heterologous signal sequences, designed to facilitate protein secretion. Such sequences are known to those of skill in the art. Additional nucleotide residues sequences such as sequences of bases specifying protein binding regions also can be linked to enzyme-encoding nucleic acid molecules. Such regions include, but are not limited to, sequences of residues that facilitate or encode proteins that facilitate uptake of an enzyme into specific target cells, or otherwise alter pharmacokinetics of a product of a synthetic gene. For example, enzymes can be linked to PEG moieties.

In addition, tags or other moieties can be added, for example, to aid in detection or affinity purification of the polypeptide. For example, additional nucleotide residues sequences such as sequences of bases specifying an epitope tag or other detectable marker also can be linked to enzyme-encoding nucleic acid molecules. Exemplary of such sequences include nucleic acid sequences encoding a His tag (e.g., 6×His, HHHHHH; SEQ ID NO:54) or Flag Tag (DYKDDDDK; SEQ ID NO:55).

The identified and isolated nucleic acids can then be inserted into an appropriate cloning vector. A large number of vector-host systems known in the art can be used. Possible vectors include, but are not limited to, plasmids or modified viruses, but the vector system must be compatible with the host cell used. Such vectors include, but are not limited to, bacteriophages such as lambda derivatives, or plasmids such as pCMV4, pBR322 or pUC plasmid derivatives or the Bluescript vector (Stratagene, La Jolla, Calif.). Other expression vectors include the HZ24 expression vector exemplified herein. The insertion into a cloning vector can, for example, be accomplished by ligating the DNA fragment into a cloning vector which has complementary cohesive termini. Insertion can be effected using TOPO cloning vectors (INVITROGEN, Carlsbad, Calif.). If the complementary restriction sites used to fragment the DNA are not present in the cloning vector, the ends of the DNA molecules can be enzymatically modified. Alternatively, any site desired can be produced by ligating nucleotide sequences (linkers) onto the DNA termini; these ligated linkers can contain specific chemically synthesized oligonucleotides encoding restriction endonuclease recognition sequences. In an alternative method, the cleaved vector and protein gene can be modified by homopolymeric tailing. Recombinant molecules can be introduced into host cells via, for example, transformation, transfection, infection, electroporation and sonoporation, so that many copies of the gene sequence are generated.

In specific embodiments, transformation of host cells with recombinant DNA molecules that incorporate the isolated protein gene, cDNA, or synthesized DNA sequence enables generation of multiple copies of the gene. Thus, the gene can be obtained in large quantities by growing transformants, isolating the recombinant DNA molecules from the transformants and, when necessary, retrieving the inserted gene from the isolated recombinant DNA. Generally, hyaluronidases, including soluble forms of PH20, are produced using protein expression systems that facilitate correct N-glycosylation to ensure the polypeptide retains activity, since glycosylation is important for the catalytic activity and stability of hyaluronidases. Such cells include, for example Chinese Hamster Ovary (CHO) cells (e.g. DG44 CHO cells).

1. Vectors and Cells

For recombinant expression of one or more of the desired proteins, such as any described herein, the nucleic acid containing all or a portion of the nucleotide sequence encoding the protein can be inserted into an appropriate expression vector, i.e., a vector that contains the necessary elements for the transcription and translation of the inserted protein coding sequence. The necessary transcriptional and translational signals also can be supplied by the native promoter for enzyme genes, and/or their flanking regions.

Also provided are vectors that contain a nucleic acid encoding the enzyme. Cells containing the vectors also are provided. The cells include eukaryotic and prokaryotic cells, and the vectors are any suitable for use therein.

Prokaryotic and eukaryotic cells, including endothelial cells, containing the vectors are provided. Such cells include bacterial cells, yeast cells, fungal cells, Archea, plant cells, insect cells and animal cells. The cells are used to produce a protein thereof by growing the above-described cells under conditions whereby the encoded protein is expressed by the cell, and recovering the expressed protein. For purposes herein, for example, the enzyme can be secreted into the medium.

Provided are vectors that contain a sequence of nucleotides that encodes the soluble hyaluronidase polypeptide coupled to the native or heterologous signal sequence, as well as multiple copies thereof. The vectors can be selected for expression of the enzyme protein in the cell or such that the enzyme protein is expressed as a secreted protein.

A variety of host-vector systems can be used to express the protein coding sequence. These include but are not limited to mammalian cell systems infected with virus (e.g. vaccinia virus, adenovirus and other viruses); insect cell systems infected with virus (e.g. baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system used, any one of a number of suitable transcription and translation elements can be used.

Any methods known to those of skill in the art for the insertion of DNA fragments into a vector can be used to construct expression vectors containing a chimeric gene containing appropriate transcriptional/translational control signals and protein coding sequences. These methods can include in vitro recombinant DNA and synthetic techniques and in vivo recombinants (genetic recombination). Expression of nucleic acid sequences encoding protein, or domains, derivatives, fragments or homologs thereof, can be regulated by a second nucleic acid sequence so that the genes or fragments thereof are expressed in a host transformed with the recombinant DNA molecule(s). For example, expression of the proteins can be controlled by any promoter/enhancer known in the art. In a specific embodiment, the promoter is not native to the genes for a desired protein. Promoters which can be used include but are not limited to the SV40 early promoter (Bernoist and Chambon, *Nature* 290:304-310 (1981)), the promoter contained in the 3' long terminal repeat of Rous sarcoma virus (Yamamoto et al. *Cell* 22:787-797 (1980)), the herpes thymidine kinase promoter (Wagner et al., *Proc. Natl. Acad. Sci. USA* 78:1441-1445 (1981)), the regulatory sequences of the metallothionein gene (Brinster et al., *Nature* 296:39-42 (1982)); prokaryotic expression vectors such as the β-lactamase promoter (Jay et al., (1981) *Proc. Natl. Acad. Sci. USA* 78:5543) or the tac promoter (DeBoer et al., *Proc. Natl. Acad. Sci. USA* 80:21-25 (1983)); see also "Useful Proteins from Recombinant Bacteria": in Scientific American 242:79-94 (1980)); plant expression vectors containing the nopaline synthetase promoter (Herrara-Estrella et al., *Nature* 303:209-213 (1984)) or the cauliflower mosaic virus 35S RNA promoter (Garder et al., *Nucleic Acids Res.* 9:2871 (1981)), and the promoter of the photosynthetic enzyme ribulose bisphosphate carboxylase (Herrera-Estrella et al., *Nature* 310:115-120 (1984)); promoter elements from yeast and other fungi such as the Gal4 promoter, the alcohol dehydrogenase promoter, the phosphoglycerol kinase promoter, the alkaline phosphatase promoter, and the following animal transcriptional control regions that exhibit tissue specificity and have been used in transgenic animals: elastase I gene control region which is active in pancreatic acinar cells (Swift et al., *Cell* 38:639-646 (1984); Ornitz et al., *Cold Spring Harbor Symp. Quant. Biol.* 50:399-409 (1986); MacDonald, *Hepatology* 7:425-515 (1987)); insulin gene control region which is active in pancreatic beta cells (Hanahan et al., *Nature* 315:115-122 (1985)), immunoglobulin gene control region which is active in lymphoid cells (Grosschedl et al., *Cell* 38:647-658 (1984); Adams et al., *Nature* 318:533-538 (1985); Alexander et al., *Mol. Cell. Biol.* 7:1436-1444 (1987)), mouse mammary tumor virus control region which is active in testicular, breast, lymphoid and mast cells (Leder et al., *Cell* 45:485-495 (1986)), albumin gene control region which is active in liver (Pinckert et al., *Genes and Devel.* 1:268-276 (1987)), alpha-fetoprotein gene control region which is active in liver (Krumlauf et al., *Mol. Cell. Biol.* 5:1639-1648 (1985); Hammer et al., *Science* 235:53-58 1987)), alpha-1 antitrypsin gene control region which is active in liver (Kelsey et al., *Genes and Devel.* 1:161-171 (1987)), beta globin gene control region which is active in myeloid cells (Magram et al., *Nature* 315:338-340 (1985); Kollias et al., *Cell* 46:89-94 (1986)), myelin basic protein gene control region which is active in oligodendrocyte cells of the brain (Readhead et al., *Cell* 48:703-712 (1987)), myosin light chain-2 gene control region which is active in skeletal muscle (Shani, *Nature* 314:283-286 (1985)), and gonadotrophic releasing hormone gene control region which is active in gonadotrophs of the hypothalamus (Mason et al., *Science* 234:1372-1378 (1986)).

In a specific embodiment, a vector is used that contains a promoter operably linked to nucleic acids encoding a desired protein, or a domain, fragment, derivative or homolog, thereof, one or more origins of replication, and optionally, one or more selectable markers (e.g., an antibiotic resistance gene). Exemplary plasmid vectors for transformation of *E. coli* cells, include, for example, the pQE expression vectors (available from Qiagen, Valencia, Calif.; see also literature published by Qiagen describing the system). pQE vectors have a phage T5 promoter (recognized by *E. coli* RNA polymerase) and a double lac operator repression module to provide tightly regulated, high-level expression of recombinant proteins in *E. coli*, a synthetic ribosomal binding site (RBS II) for efficient translation, a 6×His tag coding sequence, $t_0$ and T1 transcriptional terminators, ColE1 origin of replication, and a beta-lactamase gene for conferring ampicillin resistance. The pQE vectors enable placement of a 6×His tag at either the N- or C-terminus of the recombinant protein. Such plasmids include pQE 32, pQE 30, and pQE 31 which provide multiple cloning sites for all three reading frames and provide for the expression of N-terminally 6×His-tagged proteins. Other exemplary plasmid vectors for transformation of *E. coli* cells, include, for example, the pET expression vectors (see, U.S. Pat. No. 4,952,496; available from NOVAGEN, Madison, Wis.; see, also literature published by Novagen describing the system). Such plasmids include pET 11a, which contains the T7lac promoter, T7 terminator, the inducible *E. coli* lac operator, and the lac repressor gene; pET 12a-c, which contains the T7 promoter, T7 terminator, and the *E. coli* ompT secretion signal; and pET 15b and pET19b (NOVAGEN, Madison, Wis.), which contain a His-Tag™ leader sequence for use in purification with a His column and a thrombin cleavage site that permits cleavage following purification over the column, the T7-lac promoter region and the T7 terminator. Exemplary of a vector for mammalian cell expression is the HZ24 expression vector. The HZ24 expression vector was derived from the pCI vector backbone (Promega). It contains DNA encoding the Beta-lactamase resistance gene (AmpR), an F1 origin of replication, a Cytomegalovirus immediate-early enhancer/promoter region (CMV), and an SV40 late polyadenylation signal (SV40). The expression vector also has an internal ribosome entry site (IRES) from the ECMV virus (Clontech) and the mouse dihydrofolate reductase (DHFR) gene.

2. Expression

Soluble hyaluronidase polypeptides can be produced by any method known to those of skill in the art including in vivo and in vitro methods. Desired proteins can be expressed in any organism suitable to produce the required amounts and forms of the proteins, such as for example, needed for administration and treatment. Expression hosts include prokaryotic and eukaryotic organisms such as *E. coli*, yeast, plants, insect cells, mammalian cells, including human cell lines and transgenic animals. Expression hosts can differ in their protein production levels as well as the types of post-translational modifications that are present on the expressed proteins. The choice of expression host can be made based on these and other factors, such as regulatory and safety considerations, production costs and the need and methods for purification.

Many expression vectors are available and known to those of skill in the art and can be used for expression of proteins. The choice of expression vector will be influenced by the choice of host expression system. In general, expression vectors can include transcriptional promoters and optionally enhancers, translational signals, and transcriptional and translational termination signals. Expression vectors that are used for stable transformation typically have a selectable marker which allows selection and maintenance of the transformed cells. In some cases, an origin of replication can be used to amplify the copy number of the vector.

Soluble hyaluronidase polypeptides also can be utilized or expressed as protein fusions. For example, an enzyme fusion can be generated to add additional functionality to an enzyme. Examples of enzyme fusion proteins include, but are not limited to, fusions of a signal sequence, a tag such as for localization, e.g. a $his_6$ tag or a myc tag, or a tag for purification, for example, a GST fusion, and a sequence for directing protein secretion and/or membrane association.

a. Prokaryotic Cells

Prokaryotes, especially *E. coli*, provide a system for producing large amounts of proteins. Transformation of *E. coli* is simple and rapid technique well known to those of skill in the art. Expression vectors for *E. coli* can contain inducible promoters, such promoters are useful for inducing high levels of protein expression and for expressing proteins that exhibit some toxicity to the host cells. Examples of inducible promoters include the lac promoter, the trp promoter, the hybrid tac promoter, the T7 and SP6 RNA promoters and the temperature regulated λPL promoter.

Proteins, such as any provided herein, can be expressed in the cytoplasmic environment of *E. coli*. The cytoplasm is a reducing environment and for some molecules, this can result in the formation of insoluble inclusion bodies. Reducing agents such as dithiothreitol and β-mercaptoethanol and denaturants, such as guanidine-HCl and urea can be used to resolubilize the proteins. An alternative approach is the expression of proteins in the periplasmic space of bacteria which provides an oxidizing environment and chaperonin-like and disulfide isomerases and can lead to the production of soluble protein. Typically, a leader sequence is fused to the protein to be expressed which directs the protein to the periplasm. The leader is then removed by signal peptidases inside the periplasm. Examples of periplasmic-targeting leader sequences include the pelB leader from the pectate lyase gene and the leader derived from the alkaline phosphatase gene. In some cases, periplasmic expression allows leakage of the expressed protein into the culture medium. The secretion of proteins allows quick and simple purification from the culture supernatant. Proteins that are not secreted can be obtained from the periplasm by osmotic lysis. Similar to cytoplasmic expression, in some cases proteins can become insoluble and denaturants and reducing agents can be used to facilitate solubilization and refolding. Temperature of induction and growth also can influence expression levels and solubility, typically temperatures between 25° C. and 37° C. are used. Typically, bacteria produce aglycosylated proteins. Thus, if proteins require glycosylation for function, glycosylation can be added in vitro after purification from host cells.

b. Yeast Cells

Yeasts such as *Saccharomyces cerevisae, Schizosaccharomyces pombe, Yarrowia lipolytica, Kluyveromyces lactis* and *Pichia pastoris* are well known yeast expression hosts that can be used for production of proteins, such as any described herein. Yeast can be transformed with episomal replicating vectors or by stable chromosomal integration by homologous recombination. Typically, inducible promoters are used to regulate gene expression. Examples of such promoters include GAL1, GAL7 and GAL5 and metallothionein promoters, such as CUP1, AOX1 or other *Pichia* or other yeast promoter. Expression vectors often include a selectable marker such as LEU2, TRP1, HIS3 and URA3 for selection and maintenance of the transformed DNA. Proteins expressed in yeast are often soluble. Co-expression with chaperonins such as Bip and protein disulfide isomerase can improve expression levels and solubility. Additionally, proteins expressed in yeast can be directed for secretion using secretion signal peptide fusions such as the yeast mating type alpha-factor secretion signal from *Saccharomyces cerevisae* and fusions with yeast cell surface proteins such as the Aga2p mating adhesion receptor or the *Arxula adeninivorans* glucoamylase. A protease cleavage site such as for the Kex-2 protease, can be engineered to remove the fused sequences from the expressed polypeptides as they exit the secretion pathway. Yeast also is capable of glycosylation at Asn-X-Ser/Thr motifs.

c. Insect Cells

Insect cells, particularly using baculovirus expression, are useful for expressing polypeptides such as hyaluronidase polypeptides. Insect cells express high levels of protein and are capable of most of the post-translational modifications used by higher eukaryotes. Baculovirus have a restrictive host range which improves the safety and reduces regulatory concerns of eukaryotic expression. Typical expression vectors use a promoter for high level expression such as the polyhedrin promoter of baculovirus. Commonly used baculovirus systems include the baculoviruses such as *Autographa californica* nuclear polyhedrosis virus (AcNPV), and the *Bombyx mori* nuclear polyhedrosis virus (BmNPV) and an insect cell line such as Sf9 derived from *Spodoptera frugiperda, Pseudaletia unipuncta* (A7S) and *Danaus plexippus* (DpN1). For high-level expression, the nucleotide sequence of the molecule to be expressed is fused immediately downstream of the polyhedrin initiation codon of the virus. Mammalian secretion signals are accurately processed in insect cells and can be used to secrete the expressed protein into the culture medium. In addition, the cell lines *Pseudaletia unipuncta* (A7S) and *Danaus plexippus* (DpN1) produce proteins with glycosylation patterns similar to mammalian cell systems.

An alternative expression system in insect cells is the use of stably transformed cells. Cell lines such as the Schneider 2 (S2) and Kc cells (*Drosophila melanogaster*) and C7 cells (*Aedes albopictus*) can be used for expression. The *Drosophila* metallothionein promoter can be used to induce high levels of expression in the presence of heavy metal induction with cadmium or copper. Expression vectors are typically maintained by the use of selectable markers such as neomycin and hygromycin.

d. Mammalian Cells

Mammalian expression systems can be used to express proteins including soluble hyaluronidase polypeptides. Expression constructs can be transferred to mammalian cells by viral infection such as adenovirus or by direct DNA transfer such as liposomes, calcium phosphate, DEAE-dextran and by physical means such as electroporation and microinjection. Expression vectors for mammalian cells typically include an mRNA cap site, a TATA box, a translational initiation sequence (Kozak consensus sequence) and polyadenylation elements. IRES elements also can be added to permit bicistronic expression with another gene, such as a selectable marker. Such vectors often include transcriptional promoter-enhancers for high-level expression, for example the SV40 promoter-enhancer, the human cytomegalovirus (CMV) promoter and the long terminal repeat of Rous sarcoma virus (RSV). These promoter-enhancers are active in many cell types. Tissue and cell-type promoters and enhancer regions also can be used for expression. Exemplary promoter/enhancer regions include, but are not limited to, those from genes such as elastase I, insulin, immunoglobulin, mouse mammary tumor virus, albumin, alpha fetoprotein, alpha 1 antitrypsin, beta globin, myelin basic protein, myosin light chain 2, and gonadotropic releasing hormone gene control. Selectable markers can be used to select for and maintain cells with the expression construct. Examples of selectable marker genes include, but are not limited to, hygromycin B phosphotransferase, adenosine deaminase, xanthine-guanine phosphoribosyl transferase, aminoglycoside phosphotransferase, dihydrofolate reductase (DHFR) and thymidine kinase. For example, expression can be performed in the presence of methotrexate to select for only those cells expressing the DHFR gene. Fusion with cell surface signaling molecules such as TCR-ζ and $Fc_\varepsilon RI$-γ can direct expression of the proteins in an active state on the cell surface.

Many cell lines are available for mammalian expression including mouse, rat human, monkey, chicken and hamster cells. Exemplary cell lines include but are not limited to CHO, Balb/3T3, HeLa, MT2, mouse NS0 (nonsecreting) and other myeloma cell lines, hybridoma and heterohybridoma cell lines, lymphocytes, fibroblasts, Sp2/0, COS, NIH3T3, HEK293, 293S, 2B8, and HKB cells. Cell lines also are available adapted to serum-free media which facilitates purification of secreted proteins from the cell culture media. Examples include CHO—S cells (Invitrogen, Carlsbad, Calif., cat #11619-012) and the serum free EBNA-1 cell line (Pham et al., (2003) *Biotechnol. Bioeng.* 84:332-42.). Cell lines also are available that are adapted to grow in special mediums optimized for maximal expression. For example, DG44 CHO cells are adapted to grow in suspension culture in a chemically defined, animal product-free medium.

e. Plants

Transgenic plant cells and plants can be used to express proteins such as any described herein. Expression constructs are typically transferred to plants using direct DNA transfer such as microprojectile bombardment and PEG-mediated transfer into protoplasts, and with *agrobacterium*-mediated transformation. Expression vectors can include promoter and enhancer sequences, transcriptional termination elements and translational control elements. Expression vectors and transformation techniques are usually divided between dicot hosts, such as *Arabidopsis* and tobacco, and monocot hosts, such as corn and rice. Examples of plant promoters used for expression include the cauliflower mosaic virus promoter, the nopaline syntase promoter, the ribose bisphosphate carboxylase promoter and the ubiquitin and UBQ3 promoters. Selectable markers such as hygromycin, phosphomannose isomerase and neomycin phosphotransferase are often used to facilitate selection and maintenance of transformed cells. Transformed plant cells can be maintained in culture as cells, aggregates (callus tissue) or regenerated into whole plants. Transgenic plant cells also can include algae engineered to produce hyaluronidase polypeptides. Because plants have different glycosylation patterns than mammalian cells, this can influence the choice of protein produced in these hosts.

3. Purification Techniques

Method for purification of polypeptides, including soluble hyaluronidase polypeptides or other proteins, from host cells will depend on the chosen host cells and expression systems.

For secreted molecules, proteins are generally purified from the culture media after removing the cells. For intracellular expression, cells can be lysed and the proteins purified from the extract. When transgenic organisms such as transgenic plants and animals are used for expression, tissues or organs can be used as starting material to make a lysed cell extract. Additionally, transgenic animal production can include the production of polypeptides in milk or eggs, which can be collected, and if necessary, the proteins can be extracted and further purified using standard methods in the art.

Proteins, such as soluble hyaluronidase polypeptides, can be purified using standard protein purification techniques known in the art including but not limited to, SDS-PAGE, size fraction and size exclusion chromatography, ammonium sulfate precipitation and ionic exchange chromatography, such as anion exchange. Affinity purification techniques also can be utilized to improve the efficiency and purity of the preparations. For example, antibodies, receptors and other molecules that bind hyaluronidase enzymes can be used in affinity purification. Expression constructs also can be engineered to add an affinity tag to a protein such as a myc epitope, GST fusion or $His_6$ and affinity purified with myc antibody, glutathione resin and Ni-resin, respectively. Purity can be assessed by any method known in the art including gel electrophoresis and staining and spectrophotometric techniques.

F. Preparation, Formulation and Administration of Immune Globulins and Soluble Hyaluronidase Polypeptides Provided herein are co-formulations of IG and hyaluronidase that are stable as a liquid formulation for prolonged periods of time of at least 6 months at temperatures up to 32° C., for example, ranging from at or about 0° C. to 32° C. The increased stability is characterized by improved storage time, decreased fragmentation, decreased aggregate formation, decreased dimer formation or/and decreased discoloring, while retaining activity of the IG and hyaluronidase. Such co-formulations can be provided as "ready-to-use" liquid formulation without further reconstitution and/or without any requirement for further dilution. The resulting stable co-formulations can be conveniently dispensed to physicians or patients in dosage forms for direct injection or administration. For example, the co-formulations can be infused or injected at home or anywhere.

Soluble hyaluronidases that are co-formulated with immune globulin permit enhanced delivery of immune globulin to desired sites within the body by increasing the bioavailability of the immune globulin. Thus, the co-formulations achieve elevated and/or more rapidly achieved concentrations of the immune globulin following subcutaneous administration compared to conventional methods of subcutaneous administration, to provide, for example, a more potent and/or more rapid response for a given dose. In addition, co-formulations of IG containing soluble hyaluronidases also permit lower doses of IG to be administered achieving a given response with a lower dose of administered IG. Finally, the ability of a soluble hyaluronidase to enhance bulk fluid flow at and near a site of injection or infusion also can improve other aspects of associated pharmacologic delivery. For example, the increase in bulk fluid flow can help to allow the volume of fluid injected to be more readily dispersed from the site of injection (reducing potentially painful or other adverse consequences of injection). This is particularly important for subcutaneous infusions to permit higher doses to be administered. In addition to increased bioavailability, co-formulation of IG with hyaluronidase provides for a safer or more convenient route of administration compared to conventional intravenous routes of administration.

The co-formulations provided herein are stable for prolonged periods of time, including at varied temperatures. For example, the co-formulations are provided herein are stable and retain activity of the IG and hyaluronidase temperatures up to 32° C. for at least 6 months. For example, the co-formulations are stable at "refrigerator" temperatures, for example at 2° C. to 8° C., such as at or about 4° C., for at least 6 months to 4 years, such as 1 year to 2 years, for example 6 months, at least 1 year, at least 2 years, at least 3 years or at least 4 years or more. In another example, the co-formulations are stable and retain activity at room temperature, for example at 18° C. to 32° C., generally 20° C. to 32° C., such as 28° C. to 32° C., for at least 6 months to 1 year, for example 6 months, at least 7 months, at least 8 months, at least 9 months, or at least 1 year or more.

In particular, the stable co-formulations exhibit low to undetectable levels of aggregation and/or fragmentation of IG after storage for defined periods of time. Methods to assess aggregation and fragmentation are known to one of skill in the art, and are exemplified in Section G below. Generally, no more than 0.5% to 5% of IG, for example, no more than 5%, no more than 4%, no more than 3%, no more than 2%, no more than 1% and generally no more than 0.5% of IG in the co-formulation forms an aggregate, as measured by HPSEC or other methods, after storage for the defined periods of time as set forth above.

In addition, the IG and hyaluronidase in the stable co-formulations provided herein retain one or more activities of the initial activity of the IG and hyaluronidase prior to storage. One of skill in the art is familiar with activities of IG and hyaluronidase and can assess such activities. Section G provides exemplary activities and assays to assess activity. Typically, the stable liquid co-formulations provided herein retain after storage at least 50%, 60%, 70%, 80%, 90%, 100%, or more of the initial activity of the protein prior to storage, generally at least 70% to 95% of the initial activity. For example the stable liquid co-formulations retain after storage more than 70%, more than 80%, more than 85%, more than 90%, more than 95%, more than 98%, more than 99%, or more than 99.5% of the initial activity of the respective protein prior to storage.

1. Formulations and Dosages

The co-formulations provided herein are formulated as liquids. The co-formulations contain immune globulin, hyaluronidase, at least 0.05 M of an alkali metal chloride salt, for example, at least 0.05 M sodium chloride (NaCl or salt) or 0.05 M potassium chloride (KCl). The co-formulations also are adjusted in pH to limit aggregation and retain activity of the IG and hyaluronidase. In some examples, the co-formulations do not contain other ingredients except water or suitable solvents. In other examples, the co-formulations further contain diluents, carriers or other excipients.

Typically, the compounds are formulated into pharmaceutical compositions using techniques and procedures well known in the art (see e.g., Ansel *Introduction to Pharmaceutical Dosage Forms*, Fourth Edition, 1985, 126). Pharmaceutically acceptable compositions are prepared in view of approvals for a regulatory agency or other agency prepared in accordance with generally recognized pharmacopeia for use in animals and in humans. The formulation should suit the mode of administration.

The co-formulations can be provided as a pharmaceutical preparation in liquid form as solutions, syrups or suspensions. In liquid form, the pharmaceutical preparations can be provided as a concentrated preparation to be diluted to a therapeutically effective concentration before use. Generally, the preparations are provided in a dosage form that does not require dilution for use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). In another example, pharmaceutical preparations can be presented in lyophilized form for reconstitution with water or other suitable vehicle before use.

The pH of the stable co-formulations provided herein is such that the IG in the co-formulation does not aggregate and/or the IG and hyaluronidase retain activity as described in Section G. Optimal pH can be obtained by formulation techniques known to those skilled in the art. For example, optimal pH can be determined by assessing aggregation and activity under differing pH conditions using various methods known to one of skill in the art, for example, as described in Section G. Such assays or assessment include, but are not limited to, size exclusion chromatography, HSPEC determinations, heat stability data, anticomplement titers of the various preparations and/or hyaluronidase activity assays. Typically, in the co-formulations provided herein the pH can range from 4.0 to 8.0 as measured in the concentrated solution of the co-formulation. Generally, within this range, a lower pH is desired, however, to ensure maximum monomer content. Accordingly, the co-formulations provided herein typically have a pH that is at least or about 4.0 to 7.4, generally at least or about 4.0 to 6.0, and typically 4.4 to 4.9. As noted, the indicated pH is measured in the concentrated solution of the formulation. pH can be adjusted using acidifying agents to lower the pH or alkalizing agents to increase the pH. Exemplary acidifying agents include, but are not limited to, acetic acid, citric acid, sulfuric acid, hydrochloric acid, monobasic sodium phosphate solution, and phosphoric acid. Exemplary alkalizing agents include, but are not limited to, dibasic sodium phosphate solution, sodium carbonate, or sodium hydroxide.

Any buffer can be used in the preparation of the liquid formulation provided herein so long as it does not adversely affect the stability of the co-formulation, and supports the requisite pH range required. Examples of particularly suitable buffers include succinate, acetate, phosphate buffers, citrate, aconitate, malate and carbonate. Those of skill in the art, however, will recognize that formulations provided herein are not limited to a particular buffer, so long as the buffer provides an acceptable degree of pH stability, or "buffer capacity" in the range indicated. Generally, a buffer has an adequate buffer capacity within about 1 pH unit of its pK (Lachman et al. 1986). Buffer suitability can be estimated based on published pK tabulations or can be determined empirically by methods well known in the art. The pH of the solution can be adjusted to the desired endpoint within the range as described above, for example, using any acceptable acid or base.

a. Immune Globulin

The IG in the co-formulations is provided at a concentration that is or is about 5% to 22% w/v, for example, that is or is about 50 mg/mL, 60 mg/mL, 70 mg/mL, 80 mg/mL, 90 mg/mL, 100 mg/mL, 120 mg/mL, 150 mg/mL, 180 mg/mL, 200 mg/mL, 220 mg/mL, 250 mg/mL or more. Generally, the IG in the co-formulation is provided in an amount that is at least 10% (100 mg/mL) to 20% (200 mg/mL), for example, 10%, 11%, 12%, 13%, 14%, 15%, 16%, 17%, 18%, 19%, 20% or more.

The immune globulin preparations provided herein can be formulated as pharmaceutical compositions for single or multiple dosage use. Typically, as noted elsewhere herein, the IG in the co-formulation is formulated in an amount such that it is ready to use and that no further dilution is necessary. Depending on whether the co-formulation is provided as a single or multiple dosage formulation, one of skill in the art can empirically determine the exact amount of IG in the co-formulation.

Generally, the immune globulin is provided in a therapeutically effective amount for the particular dosage regime. Therapeutically effective concentration can be determined empirically by testing the compounds in known in vitro and in vivo systems, such as the assays provided herein. The concentration of a selected immune globulin in the composition depends on absorption, inactivation and excretion rates of the complex, the physicochemical characteristics of the complex, the dosage schedule, and amount administered as well as other factors known to those of skill in the art. For example, it is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope thereof. The amount of a selected immune globulin preparation to be administered for the treatment of a disease or condition, for example an IG-treatable disease or condition, can be determined by standard clinical techniques. In addition, in vitro assays and animal models can be employed to help identify optimal dosage ranges. Hence, the precise dosage, which can be determined empirically, can depend on the particular immune globulin preparation, the regime and dosing schedule with the soluble hyaluronidase, the route of administration, the type of disease to be treated and the seriousness of the disease.

For example, IG preparations can be formulated in pharmaceutical compositions to achieve dosage regimes (doses and frequencies) for which current intravenous (IVIG) preparations are prepared and administered for particular IG-treatable diseases or conditions. One of skill in the art is familiar with dosage regimes for IVIG administration of particular diseases or conditions. For example, Section H below provides exemplary dosage regimes (doses and frequencies) of IG for particular diseases and conditions. Other dosage regimes are well known to those of skill in the art. If necessary, a particular dosage and duration and treatment protocol can be empirically determined or extrapolated.

For example, exemplary doses of intravenously administered immune globulin can be used as a starting point to determine appropriate dosages. Dosage levels can be determined based on a variety of factors, such as body weight of the individual, general health, age, the activity of the specific compound employed, sex, diet, time of administration, rate of excretion, drug combination, the severity and course of the disease, and the patient's disposition to the disease and the judgment of the treating physician. Generally, dosages of immune globulin are from or about 100 mg per kg body weight (i.e. 100 mg/kg BW) to 2 g/kg BW. It is understood that the amount to administer will be a function of the indication treated, and possibly side effects that will be tolerated. Dosages can be empirically determined using recognized models for each disorder.

In one example, IG is provided in an amount that permits subcutaneous administration of a dose equivalent to a once monthly IV dose for the particular indication being treated. In such an example, immune globulin preparations can be formulated for single dose administration in an amount sufficient to provide a once monthly dose, but can be provided in lesser amounts for multiple dosage administrations. For example, once monthly doses of IG preparations can be administered daily, weekly, biweekly or once a month. Dosage regimes can be continued for months or years. The particular once monthly IV dose is a function of the disease to be treated, and thus can vary.

Exemplary single dosages ranges, in particular for subcutaneous administration of IG, are from at or about 1 gram (g) to 200 g, for example, 1 gram (g), 5 g, 10 g, 20 g, 30 g, 40 g, 50 g, 60 g, 70 g, 80 g, 90 g, 100 g or 200 g. The particular dosage and formulation thereof depends upon the indication and individual. For example, dosages can be administered at 50 mg/kg body weight (BW) to 600 mg/kg, BW, for example 50 mg/kg body weight (BW), 100 mg/kg BW, 200 mg/kg BW, 300 mg/kg BW, 400 mg/kg BW, 500 mg/kg BW, 600 mg/kg BW, or more. If necessary dosage can be empirically determined. To achieve such dosages, volumes of IG-containing co-formulations administered subcutaneously can be at or about 10 mL to 700 mL, for example, 100 mL to 500 mL, such as 200 mL to 400 mL. For example, volumes of IG-containing co-formulations administered subcutaneously can be at or about 10 mL, 20 mL, 30 mL, 40 mL, 50 ml, 100 ml, 200 ml, 300 ml, 400 ml, 500 ml, 600 ml, 700 ml or more for single dosage administration. For example, a 10% liquid IG co-formulation (100 mg/ml) for indications described herein can be administered in a volume of 200 ml to 700 ml to achieve a single dosage of 20 g to 70 g of IG. In another example, a 20% liquid IG co-formulation (200 mg/mL) for indications described herein can be administered in a volume of 100 mL to 350 mL to achieve a similar single dosage of 20 g to 70 g of IG. As noted, IG can be provided in lesser amounts in the co-formulation for multiple dosage administrations.

b. Hyaluronidase

The selected hyaluronidase, in particular a soluble hyaluronidase, for example, rHuPH20, is included in the co-formulation at a concentration that is at or about 50 U/mL to 300 U/mL, for example 50 U/ml, 75 U/mL, 100 U/ml, 150 U/ml, 200 U/ml, 300 U/mL, 400 U/ml or 500 U/ml, typically at least 100 U/mL to 300 U/mL, generally at a concentration that is 75 U/mL to 350 U/mL. If desired, the hyaluronidase can be provided in a more concentrated form, for example at or about 1000 U/mL to 5000 U/mL, such as 1000 U/ml, 1500 Units/ml, 2000 U/ml, 4000 U/ml or 5000 U/ml.

The hyaluronidase in the co-formulation can be formulated as a pharmaceutical compositions for single or multiple dosage administration. As noted above for IG, the hyaluronidase in the co-formulation typically is formulated in an amount that is ready to use such that no further dilution is necessary. Depending on whether the formulation is provided as a single or multiple dosage form, one of skill in the art can empirically determine the exact amount of hyaluronidase to include in the co-formulation.

Generally, the selected hyaluronidase, in particular a soluble hyaluronidase, for example, rHuPH20, is included in the co-formulation in an amount sufficient to exert a therapeutically useful effect of the IG in the absence of undesirable side effects on the patient treated. The therapeutically effective concentration can be determined empirically by testing the polypeptides in known in vitro and in vivo systems such as by using the assays provided herein or known in the art (see e.g., Taliani et al. (1996) *Anal. Biochem.*, 240: 60-67; Filocamo et al. (1997) *J Virology,* 71: 1417-1427; Sudo et al. (1996) *Antiviral Res.* 32: 9-18; Buffard et al. (1995) *Virology,*

209:52-59; Bianchi et al. (1996) *Anal. Biochem.*, 237: 239-244; Hamatake et al. (1996) *Intervirology* 39:249-258; Steinkuhler et al. (1998) *Biochem.*, 37:8899-8905; D'Souza et al. (1995) *J. Gen. Virol.*, 76:1729-1736; Takeshita et al. (1997) *Anal. Biochem.* 247:242-246; see also e.g., Shimizu et al. (1994) *J Virol.* 68:8406-8408; Mizutani et al. (1996) *J. Virol.* 70:7219-7223; Mizutani et al. (1996) *Biochem. Biophys. Res. Commun.*, 227:822-826; Lu et al. (1996) *Proc. Natl. Acad. Sci.* (USA), 93:1412-1417; Hahm et al., (1996) *Virology*, 226:318-326; Ito et al. (1996) *J Gen. Virol.*, 77:1043-1054; Mizutani et al. (1995) *Biochem. Biophys. Res. Commun.*, 212:906-911; Cho et al. (1997) *J. Virol. Meth.* 65:201-207 and then extrapolated therefrom for dosages for humans.

For example, a therapeutically effective dose of hyaluronidase for single dosage administration is at or about 500 Units to 500,000 Units, for example, 1000 Units to 100,000 Units of hyaluronidase. For example, hyaluronidase can be administered, in particular for subcutaneous administration, at or about 500 Units, 1000 Units, 2000 Units, 5000 Units, 10,000 Units, 30,000 Units, 40,000 Units, 50,000 Units, 60,000 Units, 70,000 Units, 80,000 Units, 90,000 Units, 100,000 Units or more. As noted, hyaluronidase can be provided in lesser amounts in the co-formulation for multiple dosage administrations.

In some examples, dosages can be provided as a ratio IG administered. For example, hyaluronidase can be administered at 10 U/gram (g) to 2000 U/g or more of IG, for example, at or about 10 U/g, 20 U/g, 30 U/g, 40 U/g, 50 U/g, 60 U/g, 70 U/g, 80 U/g, 90 U/g, 100 U/g, 150 U/g, 200 U/g, 250 U/g, 300 U/g, 400 U/g, 500 U/g, 1000 U/g, 1500 U/g, 2000 U/g, 3000 U/g IG or more. In general, the ratio of hyaluronidase to IG in a co-formulated product is greater than the ratio when the same products (IG and hyaluronidase) and the same amount of IG are subcutaneously administered separately, for example, in a leading edge administration. Thus, generally the ratio is at least 100 U/g, and generally 250 U/g or more, for example 100 U/g to 3000 U/g IG, such as 250 U/g to 1000 U/g, and in particular 250 U/g to 750 U/g, such as 500 U/g IG. For example, a co-formulation containing 100 U/mL hyaluronidase, when co-formulated with a 20% IG (200 mg/mL), is provided at a ratio that is or is about 500 U/g of IG. Typically, volumes administered subcutaneously can be at or about 10 mL to 700 mL, such as 50 mL to 500 mL, for example 100 mL to 400 mL for a single dosage administration. For example, volumes administered subcutaneously can be at or about 10 mL, 20 mL, 30 mL, 40 mL, 50 ml, 100 ml, 200 ml, 300 ml, 400 ml, 500 ml, 600 ml, 700 ml or more for single dosage administration.

c. Alkali metal Chloride Salt

The co-formulation provided herein contain an alkali metal chloride salt that is at least 0.05 M. The alkali metal chloride salt includes, but is not limited to, sodium chloride (NaCl) or potassium chloride (KCl). Typically, the alkali metal chloride salt, for example NaCl or KCl, is provided to retain the stability and activity of the hyaluronidase. The exact amount of salt can be empirically determined by one of skill in the art. For example, the amount of salt in the formulations can be determined by assessing aggregation and activity under differing salt conditions using various methods known to one of skill in the art, for example, as described in Section G.

Typically, in the co-formulations provided herein, sodium chloride is provided in an amount that is or is about 0.05 M to 0.3 M, for example, at or about 0.05M, 0.06 M, 0.07 M, 0.08 M, 0.09 M, 0.1 M, 0.15 M, 0.2 M, 0.25 M or more. Typically, the amount of salt is between 0.05 M to 0.25 M, for example 0.15 M.

d. Amino Acid Stabilizer

The co-formulation provided herein contains an amino acid stabilizer, which contributes to the stability of the preparation. The stabilizer can be a non-polar and basic amino acids. Exemplary non-polar and basic amino acids include, but are not limited to, alanine, histidine, arginine, lysine, ornithine, isoleucine, valine, methionine, glycine and proline. For example, the amino acid stabilizer is glycine or proline, typically glycine. The stabilizer can be a single amino acid or it can be a combination of 2 or more such amino acids. The amino acid stabilizers can be natural amino acids, amino acid analogues, modified amino acids or amino acid equivalents. Generally, the amino acid is an L-amino acid. For example, when proline is used as the stabilizer, it is generally L-proline. It is also possible to use amino acid equivalents, for example, proline analogues.

Generally, an amount of one or more amino acids effective to maintain the immune globulin in monomeric form is added to the solution. The concentration of amino acid stabilizer, for example glycine, included in the liquid co-formulation ranges from 0.1 M to 1 M amino acid, typically 0.1 M to 0.75 M, generally 0.2M to 0.5M, for example, at least at or about 0.1 M, 0.15 M, 0.2 M, 0.25 M, 0.3 M, 0.35 M, 0.4 M, 0.45 M, 0.5 M, 0.6 M, 0.7 M, 0.75 M or more. The amino acid, for example glycine, can be used in a form of a pharmaceutically acceptable salt, such as hydrochloride, hydrobromide, sulfate, acetate, etc. The purity of the amino acid, for example glycine, should be at least 98%, at least 99%, or at least 99.5% or more.

e. Other Agents

Optionally, the co-formulations can include carriers such as a diluent, adjuvant, excipient, or vehicle with which a hyaluronidase or IG is administered. Examples of suitable pharmaceutical carriers are described in "Remington's Pharmaceutical Sciences" by E. W. Martin. Such compositions will contain a therapeutically effective amount of the compound, generally in purified form or partially purified form, together with a suitable amount of carrier so as to provide the form for proper administration to the patient. Such pharmaceutical carriers can be sterile liquids, such as water and oils, including those of petroleum, animal, vegetable or synthetic origin, such as peanut oil, soybean oil, mineral oil, and sesame oil. Water is a typical carrier when the pharmaceutical composition is administered intravenously. Saline solutions and aqueous dextrose and glycerol solutions also can be employed as liquid carriers, particularly for injectable solutions.

For example, pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers, which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEENs 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

Compositions can contain along with an active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyvinylpyrrolidone, celluloses and derivatives thereof, povidone, crospovidones and other such binders known to those of skill in the art.

For example, an excipient protein can be added to the co-formulation that can be any of a number of pharmaceutically acceptable proteins or peptides. Generally, the excipient protein is selected for its ability to be administered to a mammalian subject without provoking an immune response. For example, human serum albumin is well-suited for use in pharmaceutical formulations. Other known pharmaceutical protein excipients include, but are not limited to, starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol. The excipient is included in the formulation at a sufficient concentration to prevent adsorption of the protein to the holding vessel or vial. The concentration of the excipient will vary according to the nature of the excipient and the concentration of the protein in the co-formulation.

A composition, if desired, also can contain minor amounts of wetting or emulsifying agents, or pH buffering agents, for example, acetate, sodium citrate, cyclodextrine derivatives, sorbitan monolaurate, triethanolamine sodium acetate, triethanolamine oleate, and other such agents.

2. Dosage Forms

The co-formulations provided herein can be formulated as single or multiple dosage forms. For example, since the co-formulation provided herein is stable over prolonged periods of time, the co-formulation can be provided in multiple dosage form for administration over an interval of days, weeks, months or years. Thus, the liquid co-formulation can be prepared as unit dosage forms. The concentration of the pharmaceutically active compound is adjusted so that an injection provides an effective amount to produce the desired pharmacological effect. For example, each unit dose contains a predetermined quantity of therapeutically active compound sufficient to produce the desired therapeutic effect, in association with the required pharmaceutical carrier, vehicle or diluent. The exact dose depends on the age, weight and condition of the patient or animal as is known in the art.

Unit dose forms can be administered in fractions or multiples thereof. A multiple dose form is a plurality of identical unit dosage forms packaged in a single container to be administered in segregated unit dose form. Hence, multiple dose form is a multiple of unit doses that are not segregated in packaging.

The unit-dose parenteral preparations are packaged in an ampoule, a vial or a syringe with a needle. The volume of liquid solution containing the pharmaceutically active compound is a function of the disease to be treated and the particular article of manufacture chosen for package. All preparations for parenteral administration must be sterile, as is known and practiced in the art. When provided as a multidose preparation, the formulation can contain a bacteriostatic agent.

3. Administration

Co-formulated compositions provided herein typically are formulated for parenteral administration, for example, by subcutaneous route. Due to the increased bioavailability of IG in co-formulations with hyaluronidase, immune globulins can be administered subcutaneously at dosages and frequencies for which current intravenous (IVIG) preparations are prepared and administered. The advantages over current subcutaneous formulations of IG is that co-formulated hyaluronidase/IG can result in more favorable dosing regimens, for example, less frequent dosing. By less frequent or lower dosing, side effects associated with toxicity can be reduced. Generally, the pharmacokinetic and/or pharmacodynamics of subcutaneous IG therapy is improved. In addition, subcutaneous administrations of IG also has advantages over current intravenous infusions. For example, subcutaneous infusion permits infusion by the patient or family as opposed to a skilled nurse; infusion can be achieved at higher rates such that IG is infused in 1-3 hours compared to 5-10 hours for conventional IVIG therapies; there is no requirement for functional veins; there is no infusion related side effects such as thrombosis, headache, thrombophlebitis, and nausea and less probability of adverse events; and infusion can be performed at home or anywhere.

Subcutaneous administration also is desired to ensure that hyaluronidases are administered so that they reach the interstitium of skin or tissues, thereby degrading the interstitial space for subsequent delivery of immunoglobulin. Thus, direct administration under the skin, such as by subcutaneous administration methods, is contemplated.

Administration can be local, topical or systemic depending upon the locus of treatment. Local administration to an area in need of treatment can be achieved by, for example, but not limited to, local infusion, topical application, e.g., in conjunction with a wound dressing after surgery, by injection, by means of a catheter, by means of a suppository, or by means of an implant. Generally, local administration is achieved by injection, such as from a syringe or other article of manufacture containing a injection device such as a needle. In another example, local administration can be achieved by infusion, which can be facilitated by the use of a pump or other similar device.

Other modes of administration also are contemplated. Pharmaceutical composition can be formulated in dosage forms appropriate for each route of administration. The most suitable route in any given case depends on a variety of factors, such as the nature of the disease, the progress of the disease, the severity of the disease the particular composition which is used. Other routes of administration, such as any route known to those of skill in the art, include but are not limited to intramuscular, intravenous, intradermal, intralesional, intraperitoneal injection, epidural, nasal, oral, vaginal, rectal, topical, local, otic, inhalational, buccal (e.g., sublingual), and transdermal administration or any route. Formulations suited for such routes are known to one of skill in the art.

Compositions also can be administered with other biologically active agents, either sequentially, intermittently or in the same composition. Administration also can include controlled release systems including controlled release formulations and device controlled release, such as by means of a pump.

Subcutaneous administration, generally characterized by injection or infusion, is contemplated herein. Injectables can be prepared in conventional forms, either as liquid solutions or suspensions, solid forms suitable for solution or suspension in liquid prior to injection, or as emulsions. Generally, the co-formulations provided herein are prepared as liquids. Injectables are designed for local and systemic administration. For purposes herein, local administration is desired for direct administration to the affected interstitium. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous. If administered intravenously, suitable carriers include physiological saline or phosphate buffered saline (PBS), and solutions containing thickening and solubilizing agents, such as glucose, polyethylene glycol, and polypropylene glycol and mixtures thereof.

Administration methods can be employed to decrease the exposure of selected compounds to degradative processes, such as proteolytic degradation and immunological intervention via antigenic and immunogenic responses. Examples of such methods include local administration at the site of treatment. PEGylation of therapeutics has been reported to increase resistance to proteolysis, increase plasma half-life, and decrease antigenicity and immunogenicity. Examples of PEGylation methodologies are known in the art (see for example, Lu and Felix, *Int. J. Peptide Protein Res.*, 43: 127-138, 1994; Lu and Felix, *Peptide Res.*, 6: 142-6, 1993; Felix et al., *Int. J. Peptide Res.*, 46 : 253-64, 1995; Benhar et al., *J. Biol. Chem.*, 269: 13398-404, 1994; Brumeanu et al., *J Immunol.*, 154: 3088-95, 1995; see also, Caliceti et al. (2003) *Adv. Drug Deliv. Rev.* 55(10):1261-77 and Molineux (2003) *Pharmacotherapy* 23 (8 Pt 2):3S-8S). Pegylation also can be used in the delivery of nucleic acid molecules in vivo. For example, pegylation of adenovirus can increase stability and gene transfer (see, e.g., Cheng et al. (2003) *Pharm. Res.* 20(9): 1444-51).

Where large volumes are administered, administration is typically by infusion. Subjects can be dosed at rates of infusion at or about 0.5 ml/kg/BW/h to 5 ml/kg/BW/h, for example at or about 0.5 ml/kg/BW/h, 1 ml/kg/BW/h, 2 ml/kg/BW/h, 3 ml/kg/BW/h, 4 ml/kg/BW/h, or 5 ml/kg/BW/h. The infusion rate can be empirically determined, and typically is a function of the tolerability of the subject. If an adverse reaction occurs during the infusion, the rate of infusion can be slowed to the rate immediately below that at which the adverse event occurred. If the adverse event resolves in response to the reduction in rate, the infusion rate can be slowly increased at the discretion of the physician. Subcutaneous infusion of IG co-formulations can be facilitated by gravity, pump infusion or injection of a desired dose, for example, a full 20-30 gram dose. Generally, for infusions intravenous infusion pumps can be employed. IG/hyaluronidase co-formulations can be infused at rates at or about 5 ml/h, 10 ml/h, 30 ml/h, 60 ml/h, 120 ml/h, 240 ml/h or 300 ml/h. Infusion rates can be increased during the course of treatment so long as the infusion is tolerated by the patient. Generally, time of administration of infusion is at or about 0.5 h, 1 h, 1.5 h, 2 h, 2.5 h, 3 h, 4 h or more. Due to the high rate of infusion achieved by subcutaneous administration of IG co-formulated with hyaluronidase, the time of infusion is significantly less than for conventional IVIG therapies. Where infusion time exceeds the desired limit, a second infusion site can be started at the physician and subject's discretion. The second site typically is started at least 10 cm from the initial site.

Techniques for infusion are known to one of skill in the art, and are within the skill of a treating physician. Generally, the appropriate dose of IG/hyaluronidase co-formulation can be pooled into a standard IV bag. For example, a non-vented infusion set can be used that has a Y-port near its terminus. A 24-gauge subcutaneous infusion needle can be inserted at a site of the subject's preferences, but the abdomen and secondarily the thighs are recommended because of the volume of solution to be infused. The hyaluronidase and IG can be provided in the same Y port apparatus. Other articles of manufacture also can be used herein for purposes of infusion by gravity or a pump, and include, but are not limited to tubes, bottles, syringes or other containers.

In the event that an infusion is not tolerated (e.g., it causes moderate to severe local reactions), a second infusion site can be started so that the subject receives the full dosage.

Further, it is understood that the stable co-formulations provided herein are amenable to dosage regimes involving a periodic frequency of administration. For example, the dosage frequency can be daily over an interval of time given over consecutive or alternate days, for example, 1, 2, 3, 4, 5, 6, 7, 8, 9, 10 or more days. In other examples, the dosage regime is weekly, for example, once every week, every two weeks, every three weeks, every four weeks, every five weeks, every six weeks or more. Thus, an IG/hyaluronidase preparation can be administered at once, or can be divided into a number of smaller doses to be administered at intervals of time.

Selected IG/hyaluronidase preparations can be administered in one or more doses over the course of a treatment time for example over several hours, days, weeks, or months. In some cases, continuous administration is useful. It is understood that the precise dosage and course of administration depends on the indication and patient's tolerability.

Also, it is understood that the precise dosage and duration of treatment is a function of the disease being treated and can be determined empirically using known testing protocols or by extrapolation from in vivo or in vitro test data. It is to be noted that concentrations and dosage values also can vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or use of compositions and combinations containing them. The compositions can be administered hourly, daily, weekly, monthly, yearly or once. Generally, dosage regimens are chosen to limit toxicity. It should be noted that the attending physician would know how to and when to terminate, interrupt or adjust therapy to lower dosage due to toxicity, or bone marrow, liver or kidney or other tissue dysfunctions. Conversely, the attending physician would also know how to and when to adjust treatment to higher levels if the clinical response is not adequate (precluding toxic side effects).

G. Methods of Assessing Stability, Activity, Bioavailability and Pharmacokinetics The stability and activity of IG and hyaluronidase in the formulations can be assessed using various in vitro and in vivo assays that are known to one of skill in the art. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993). Stability can be measured at a selected temperature for a selected time period.

Assays to assess molecular size (e.g. caused by aggregation, denaturation and/or fragmentation) of the IG is an important consideration for assessing stability of the co-formulation. In addition, the stability of the liquid formulations also can be assessed by any assays which measure the biological activity of IG and hyaluronidase in the formulation. Such assays are well known in the art. In addition to assessing the stability of the co-formulation, such assays can be used, for example, to determine appropriate dosages of immune globulin and hyaluronidase, and the frequency of dosing, for treatment. Further, assays known to one of skill in the art also can be performed to assess the pharmacokinetic properties of subcutaneously-administered immune globulin, including bioavailability, and tolerability.

1. Molecular Size

The main stability indicating parameter is molecular size, and a change in size may be the result of degradation by denaturation, aggregation or fragmentation. Aggregation of IG is a common problem during storage of IG products. The aggregates are problematic because they can combine with complement in the patient's blood and produce an anti-complement reaction. The ability of IG to bind complement is greatly increased as a result of denaturation, in particular by aggregation to high molecular weight species. The complement binding mechanism of these aggregates appears to be identical to that of antigen-antibody complexes. Marcus, D. M., (1960) *J. Immunol.* 84:273-284. In the case of IgG, it is known that the complement binding site requires two molecules close together. It is therefore possible that critical packing of the molecules is required, rather than any necessary conformational change.

Methods for monitoring stability of IG are available in the art, including those methods described herein and in the examples disclosed herein. There are various methods available for assessing the stability of protein formulations, including antibody or immuno globulin formulations, based on the physical and chemical structures of the proteins as well as on their biological activities. For example, to study aggregation, fragmentation and denaturation of proteins, methods such as charge-transfer absorption, thermal analysis, fluorescence spectroscopy, circular dichroism, NMR, reduced capillary gel electrophoresis (rCGE), and high performance size exclusion chromatography (HPSEC), are available. See, for example, Wang et al., 1988, *J. of Parenteral Science & Technology* 42(supp):S4-S26. The rCGE, and HPSEC are the most common and simplest methods to assess the molecular size due to formation of protein aggregates, protein degradation and protein fragmentation. Further, the anticomplement activity (ACA) can be directly determined.

For example, the stability of the liquid formulations can be evaluated by HPSEC or rCGE, where the percentage area of the peaks represents the non-degraded protein. In one example, protein is injected onto a TosoH Biosep TSK G3000 SW 600×7.5 mm column. The protein is eluted. Eluted protein is detected using UV absorbance at 280 nm. A reference standard is run in the assay as a control, and the results are reported as the area percent of the product monomer peak compared to all other peaks excluding the included volume peak. Peaks eluting earlier than the monomer peak are recorded as percent aggregate.

ACA titer also can be determined as described in the European Pharmacopoeia (European Pharmacopeia, 1997, $2^{nd}$ ed. Part II. Maisonneuve, S. A., Saint Ruffine, France). Generally, ACA titer is a specification indicator for intravenous (IV) administration and is not relevant for subcutaneous administration of the co-formulations. Thus, for purposes herein, ACA titer is not generally a determinative indicator for co-formulations that are formulated for subcutaneous administration.

Generally, the ACA assay measures the amount of complement that is bound by the mixture of standardized amounts of complement and protein (see e.g., Palmer, D. F. and Whaley, S. D., *Complement Fixation Test*, in Manual of Clinical Laboratory Immunology (Ed. N. R. Rose, et al., American Society for Microbiology, Washington, D.C., 1986) pp. 57-66; Mayer, M. M., *Quantitative C' Fixation Analysis, Complement and Complement Fixation*, in Experimental Immunochemistry (Ed. E. A. Kabat and M. M. Meyer, Thomas, Springfield, Ill., 1961), pp. 214-216, 227-228.) Briefly, red blood cells that have been sensitized by preincubation with red blood cell antibodies are added to the complement/protein mixture. In the presence of free complement (not already bound by the protein) these sensitized cells will lyse, releasing hemoglobin which can be quantitated as a measure of the degree of lysis. In parallel, sensitized red blood cells are also added to a buffer control-complement mixture, whose degree of lysis is defined as 100%. The difference between the actual amount of complement needed to give 100% lysis and the amount of complement remaining unbound in the presence of protein equals the amount of complement actually bound by the protein, or anticomplement activity. One unit of ACA activity (one $CH_{50}$ unit) is the amount of protein capable of activating 50% of the complement in an optimally titered complement and red blood cell/hemolysin system. Generally, an acceptable ACA titer is less than 50% CH50 units consumed per mg protein.

In another example, molecular size distribution, for example due to aggregate formation, during storage of a liquid co-formulation can be readily determined by measuring the change in soluble protein in solution over time. Amount of soluble polypeptide in solution can be quantified by a number of analytical assays. Such assays include, for example, reverse phase (RP)-HPLC and UV absorption spectroscopy. Determination of both soluble and insoluble aggregates during storage in liquid formulations can be achieved, for example, using analytical ultracentrifugation to distinguish between that portion of the soluble polypeptide that is present as soluble aggregates and that portion that is present in the nonaggregate, biologically active molecular form.

In a further example, the stability of co-formulations can be assessed by heating the finished product to a temperature of 57° C. and holding it at that temperature for four hours while examining the product for visual precipitates. (See e.g., Code of Federal Regulations 21, Food and Drugs, 640. 101a (revised Apr. 1978)). In a modification of the method (see e.g., Fernandes and Lundblad, *Vox Sang* 39:101-112 (1980)), approximately 2 milliliters of the test product is heated at 57° C. for four hours and then the percent change in degree of opalescence as measured by recording the transmittance at 580 nm with a laboratory spectrophotometer is evaluated (see also U.S. Pat. No. 4,597,966).

SDS-PAGE also can be used to assess aggregation and/or fragmentation. The density or the radioactivity of each band stained or labeled with radioisotope can be measured and the % density or % radioactivity of the band representing non-degraded protein can be obtained.

Generally, the co-formulations exhibit low to undetectable levels of aggregation as measured by any of the above assays, for example HPSEC or rCGE. For example, the aggregation is, no more than 5%, no more than 4%, no more than 3%, no more than 2%, no more than 1%, and generally no more than 0.5% aggregate by weight protein, and low to undetectable levels of fragmentation, that is, 80% or higher, 85% or higher, 90% or higher, 95% or higher, 98% or higher, or 99% or higher, or 99.5% or higher of the total peak area in the peak(s) representing intact antibodies or fragments thereof. For example, typically, an acceptable aggregation includes >90% monomers and oligo-/dimers; <5% aggregates, and <5% fragments.

2. Biological Activity a. Immune Globulin

The ability of immune globulin to act as a therapeutic agent can be assessed in vitro or in vivo. For example, in vitro assays can be performed to assess the ability of immune globulin to neutralize viral or bacterial infectivity (Hiemstra et al., (1994) *J Lab Clin Med* 123:241-6). Other in vitro assays can be utilized to assess other biological activities of immune globulin. For example, the ability of immune globulin preparations to interact with and modulate complement activation products, bind idiotypic antibody, bind Fc receptors on macrophages, and suppress various inflammatory mediators including cytokines, chemokines, and metalloproteinases, can be assessed using any method known in the art, including, but not limited to, ELISA, Western blot, Northern blot, and flow cytometry to assess marker expression. For example, the effect of immune globulin on the expression of chemokine receptors on peripheral blood mononuclear cells can be assessed using flow cytomtery (Trebst et al., (2006) *Eur J Neurology* 13(12):1359-63). In another example, the effect of immune globulin on metalloproteinase expression in macrophages can be assessed using Northern blot analysis (Shapiro et al., (2002) *Cancer* 95:2032-2037).

In vivo studies using animal models also can be performed to assess the therapeutic activity of immune globulin. Immune globulin can be administered to animal models infected with one or more microorganisms and the effect on progression of infection can be assessed, such as by measuring the number of microorganisms or measuring weight as a marker of morbidity. The therapeutic effect of immune globulin also can be assessed using animal models of the diseases and conditions for which therapy using immune globulin is considered. Such animal models are known in the art, and include, but are not limited to, small animal models for X-linked agammaglobulinemia (XLA), SCID, Wiskott-Aldrich syndrome, Kawasaki disease, Guillain-Barré syndrome, ITP, polymyositis, Lambert-Eaton myasthenic syndrome, Myasthenia gravis and Moersch-Woltmann syndrome (Czitrom et al. (1985) *J Immunol* 134:2276-2280, Ellmeier et al., (2000) *J Exp Med.* 192: 1611-1624, Ohno (2006) *Drug Discovery Today: Disease Models* 3:83-89, Oyaizu et al. (1988) *J Exp Med* 2017-2022, Hansen et al., (2002) *Blood* 100:2087-2093, Strongwater et al., (1984) *Arthritis Rheum.* 27:433-42, Kim et al. (1998) *Annals NY Acad Sci* 841:670-676, Christadoss et al. (2000) *Clin. Immunol.* 94:75-87, Sommer et al., (2005) *Lancet* 365:1406-1411 and U.S. Pat. No. 7,309,810)

b. Hyaluronidase

Hyaluronidase activity can be assessed using methods well known in the art. In one example, activity is measured using a microturbidity assay. This is based on the formation of an insoluble precipitate when hyaluronic acid binds with serum albumin. The activity is measured by incubating hyaluronidase with sodium hyaluronate (hyaluronic acid) for a set period of time (e.g. 10 minutes) and then precipitating the undigested sodium hyaluronate with the addition of acidified serum albumin. The turbidity of the resulting sample is measured at 640 nm after an additional development period. The decrease in turbidity resulting from hyaluronidase activity on the sodium hyaluronate substrate is a measure of hyaluronidase enzymatic activity. In another example, hyaluronidase activity is measured using a microtiter assay in which residual biotinylated hyaluronic acid is measured following incubation with hyaluronidase (see e.g. Frost and Stern (1997) *Anal. Biochem.* 251:263-269, U.S. Patent Publication No. 20050260186). The free carboxyl groups on the glucuronic acid residues of hyaluronic acid are biotinylated, and the biotinylated hyaluronic acid substrate is covalently couple to a microtiter plate. Following incubation with hyaluronidase, the residual biotinylated hyaluronic acid substrate is detected using an avidin-peroxidase reaction, and compared to that obtained following reaction with hyaluronidase standards of known activity. Other assays to measure hyaluronidase activity also are known in the art and can be used in the methods herein (see e.g. Delpech et al., (1995) *Anal. Biochem.* 229:35-41; Takahashi et al., (2003) *Anal. Biochem.* 322:257-263).

The ability of hyaluronidase to act as a spreading or diffusing agent also can be assessed. For example, trypan blue dye can be injected subcutaneously with or without hyaluronidase into the lateral skin on each side of nude mice. The dye area is then measured, such as with a microcaliper, to determine the ability of hyaluronidase to act as a spreading agent (U.S. Patent No. 20060104968).

3. Pharmacokinetics and Tolerability

Pharmacokinetic and tolerability studies can be performed using animal models or can be performed during clinical studies with patients. Animal models include, but are not limited to, mice, rats, rabbits, dogs, guinea pigs and non-human primate models, such as cynomolgus monkeys or rhesus macaques. In some instances, pharmacokinetic and tolerability studies are performed using healthy animals. In other examples, the studies are performed using animal models of a disease for which therapy with immune globulin is considered, such as animal models of any of the diseases and conditions described below.

The pharmacokinetics of subcutaneously administered immune globulin can be assessed by measuring such parameters as the maximum (peak) plasma immune globulin concentration ($C_{max}$), the peak time (i.e. when maximum plasma immune globulin concentration occurs; $T_{max}$), the minimum plasma immune globulin concentration (i.e. the minimum plasma concentration between doses of immune globulin; $C_{min}$), the elimination half-life ($T_{1/2}$) and area under the curve (i.e. the area under the curve generated by plotting time versus plasma immune globulin concentration; AUC), following administration. The absolute bioavailability of subcutaneously administered immune globulin is determined by comparing the area under the curve of immune globulin following subcutaneous delivery ($AUC_{sc}$) with the AUC of immune globulin following intravenous delivery ($AUC_{iv}$). Absolute bioavailability (F), can be calculated using the formula: $F=([AUC]_{sc} \times dose_{sc})/([AUC]_{iv} \times dose_{iv})$. The concentration of immune globulin in the plasma following subcutaneous administration can be measured using any method known in the art suitable for assessing concentrations of immune globulin in samples of blood. Exemplary methods include, but are not limited to, ELISA and nephelometry.

A range of doses and different dosing frequency of dosing can be administered in the pharmacokinetic studies to assess the effect of increasing or decreasing concentrations of immune globulin and/or hyaluronidase in the dose. Pharmacokinetic properties of subcutaneously administered immune globulin, such as bioavailability, also can be assessed with or without co-administration of hyaluronidase. For example, dogs, such as beagles, can be administered immune globulin subcutaneously in combination with hyaluronidase, or alone. Intravenous doses of immune globulin also are given to another group of beagles. Blood samples can then be taken at various time points and the amount of immune globulin in the plasma determine, such as by nephelometry. The AUC can then be measured and the bioavailability of subcutaneously administered immune globulin administered with or without hyaluronidase can be determined. Such studies can be performed to assess the effect of co-administration with hyaluronidase on pharmacokinetic properties, such as bioavailability, of subcutaneously administered immune globulin.

Studies to assess safety and tolerability also are known in the art and can be used herein. Following subcutaneous administration of immune globulin, with or without co-administration of hyaluronidase, the development of any adverse reactions can be monitored. Adverse reactions can include, but are not limited to, injection site reactions, such as edema or swelling, headache, fever, fatigue, chills, flushing, dizziness, urticaria, wheezing or chest tightness, nausea, vomiting, rigors, back pain, chest pain, muscle cramps, seizures or convulsions, changes in blood pressure and anaphylactic or severe hypersensitivity responses. Typically, a range of doses and different dosing frequencies are be administered in the safety and tolerability studies to assess the effect of increasing or decreasing concentrations of immune globulin and/or hyaluronidase in the dose.

H. Methods of Treatment and Therapeutic Uses

The IG/hyaluronidase co-formulations described herein can be used for treatment of any condition for which immune globulin is employed. Immune globulin (IG) can be administered subcutaneously in co-formulations with hyaluronidase, to treat any condition that is amendable to treatment with immune globulin. This section provides exemplary therapeutic uses of IG/hyaluronidase co-formulations. It is understood that the IG/hyaluronidase co-formulations provided herein can be used in methods, processes or uses to treat any of the diseases and conditions described below and other diseases and conditions known to one of skill in the art that are treatable by IG. In particular, subcutaneous administration of the co-formulations is contemplated. Dosages of IG administered is the same or similar to the dosage administered intravenously and known to one of skill in the art. The dosage regime and frequency can vary from intravenous regimes as described elsewhere herein. The therapeutic uses described below are exemplary and do not limit the applications of the methods described herein.

For example, co-formulations provided herein can be used to treat immune deficiencies such as primary immune deficiencies, such as X-linked agammaglobulinemia, hypogammaglobulinemia, and acquired compromised immunity conditions (secondary immune deficiencies), such as those featuring low antibody levels; inflammatory and autoimmune diseases; and acute infections. Therapeutic uses include, but are not limited to, immunoglobulin replacement therapy and immunomodulation therapy for various immunological, hematological, neurological, inflammatory, dermatological and/or infectious diseases and conditions. In some examples, immune globulin is administered to augment the immune response in healthy patients, such as following possible exposure to infectious disease (e.g. accidental needle stick injury). IG co-formulations provided herein also can be used for treating multiple sclerosis (especially relapsing-remitting multiple sclerosis or RRMS), Alzheimer's disease, and Parkinson's disease. It is within the skill of a treating physician to identify such diseases or conditions.

Immune globulin/hyaluronidase co-formulations can be administered in combination with other agents used in the treatment of these diseases and conditions. For example, other agents that can be administered include, but are not limited to, antibiotics, chemotherapeutics, steroidal anti-inflammatories, non-steroidal anti-inflammatories, and other immunomodulatory agents such as cytokines, chemokines and growth factors.

If necessary, a particular dosage and duration and treatment protocol can be empirically determined or extrapolated. For example, exemplary doses of intravenously administered immune globulin can be used as a starting point to determine appropriate dosages. Dosage levels can be determined based on a variety of factors, such as body weight of the individual, general health, age, the activity of the specific compound employed, sex, diet, time of administration, rate of excretion, drug combination, the severity and course of the disease, and the patient's disposition to the disease and the judgment of the treating physician. Exemplary dosages of immune globulin and hyaluronidase are provided elsewhere herein. It is understood that the amount to administer will be a function of the indication treated, and possibly side effects that will be tolerated. Dosages can be empirically determined using recognized models for each disorder.

Upon improvement of a patient's condition, a maintenance dose of immune globulin can be administered subcutaneously in combination with hyaluronidase, if necessary, and the dosage, the dosage form, or frequency of administration, or a combination thereof can be modified. In some cases, a subject can require intermittent treatment on a long-term basis upon any recurrence of disease symptoms.

1. Primary and Secondary Immune Deficiency a. Primary Immune Deficiency

More than 80 primary immune deficiency diseases are recognized by the World Health Organization and occur in about 1 out of 10,000 individuals. These diseases are characterized by an intrinsic defect in the immune system in which, in some cases, the body is unable to produce any or enough antibodies against infection. In other cases, cellular defenses to fight infection fail to work properly. Immune globulin can be used to treat primary immune deficiency with antibody deficiency. Thus, immune globulin can be administered as immunoglobulin replacement therapy to patients presenting with such diseases.

Typically, primary immune deficiencies are inherited disorders. Exemplary of primary immune deficiencies include, but are not limited to, common variable immune deficiency (CVID), selective IgA deficiency, IgG subclass deficiency, X-linked agammaglobulinemia (XLA), severe combined immune deficiency (SCID), complement disorders, ataxia telangiectasia, hyper IgM, and Wiskott-Aldridge syndrome. Immune globulin/hyaluronidase co-formulations can be administered subcutaneously to patients with primary immune deficiency diseases with antibody deficiency at doses similar to the doses used for intravenous administration of immune globulin. Exemplary doses include, for example, between 100 mg/kg BW and 800 mg/kg BW immune globulin, at four-week intervals. The dose can be increased or decreased, as can the frequency of the doses, depending on the clinical response.

b. Secondary Immune Deficiency

Secondary, or acquired, immune deficiency is not the result of inherited genetic abnormalities, but rather occurs in individuals in which the immune system is compromised by factors outside the immune system. Examples include, but are not limited to, trauma, viruses, chemotherapy, toxins, and pollution. Acquired immunodeficiency syndrome (AIDS) is an example of a secondary immune deficiency disorder caused by a virus, the human immunodeficiency virus (HIV), in which a depletion of T lymphocytes renders the body unable to fight infection.

Another example, hypogammaglobulinemia, is caused by a lack of B-lymphocytes, is characterized by low levels of antibodies in the blood, and can occur in patients with chronic lymphocytic leukemia (CLL), multiple myeloma (MM), non-Hodgkin's lymphoma (NHL) and other relevant malignancies as a result of both leukemia-related immune dysfunction and therapy-related immunosuppression. Patients with acquired hypogammaglobulinemia secondary to such hematological malignancies, and those patients receiving post-hematopoietic stem cell transplantation are susceptible to bacterial infections. The deficiency in humoral immunity is largely responsible for the increased risk of infection-related morbidity and mortality in these patients, especially by encapsulated microorganisms. For example, *Streptococcus pneumoniae, Haemophilus influenzae*, and *Staphylococcus aureus*, as well as *Legionella* and *Nocardia* spp. are frequent bacterial pathogens that cause pneumonia in patients with CLL. Opportunistic infections such as *Pneumocystis carinii*, fungi, viruses, and mycobacteria also have been observed. The number and severity of infections in these patients can be significantly reduced by administration of immune globulin (Griffiths et al. (1989) *Blood* 73:366-368; Chapel et al. (1994) *Lancet* 343:1059-1063).

Therefore, immune globulin/hyaluronidase co-formulations can be administered subcutaneously in such patients to prevent recurrent infections. Exemplary dosages include those used for intravenous administration of immune globulin to patients with acquired hypogammaglobulinemia secondary to hematological malignancies. For example, co-formulations containing about 400 mg/kg BW immune globulin can be administered subcutaneously every 3 to 4 weeks. In a further example, an additional dose of 400 mg/kg BW can be administered in the first month of therapy in cases where the patient's serum IgG is less than 4 g/L. The amount of immune globulin administered, and the frequency of the doses, can be increased or decreased as appropriate.

2. Inflammatory and Autoimmune Diseases a. Kawasaki Disease

Kawasaki disease is an acute, febrile, multi-system disease of children and young infants, often involving the coronary arteries. It also is known as lymph node syndrome, mucocutaneous node disease, infantile polyarteritis and Kawasaki syndrome. Kawasaki disease is a poorly understood, self-limited vasculitis that affects many organs, including the skin, mucous membranes, lymph nodes, blood vessel walls, and the heart. Coronary artery aneurysms can occur from the second week of illness during the convalescent stage. Although the cause of the condition is unknown, there is evidence that the characteristic vasculitis results from an immune reaction characterized by T-cell and macrophage activation to an unknown antigen, secretion of cytokines, polyclonal B-cell hyperactivity, and the formation of autoantibodies to endothelial cells and smooth muscle cells. In genetically susceptible individuals, one or more uncharacterized common infectious agents, possibly with super-antigen activity, may trigger the disease.

Immune globulin administered early in Kawasaki disease can prevent coronary artery pathology. Subcutaneous administration of immune globulin/hyaluronidase co-formulations to patients with ongoing inflammation associated with Kawasaki disease can ameliorate symptoms. Exemplary dosages include those used for intravenous administration of immune globulin to patients with Kawasaki disease. For example, a patient with Kawasaki disease can be administered about 1-2 g/kg patient body weight of immune globulin. This can be administered, for example, in four doses of 400 mg/kg BW for four consecutive days. In another example, 1 g/kg BW immune globulin is administered as a single dose over a 10 hour period. The amount of immune globulin administered can be increased or decreased as appropriate.

b. Chronic Inflammatory Demyelinating Polyneuropathy

Chronic inflammatory demyelinating polyneuropathy (CIDP) is a neurological disorder characterized by progressive weakness and impaired sensory function in the legs and arms. The disorder, which is sometimes called chronic relapsing polyneuropathy, is caused by damage to the myelin sheath of the peripheral nerves. Although it can occur at any age and in both genders, CIDP is more common in young adults, and in men more so than women. It often presents with symptoms that include tingling or numbness (beginning in the toes and fingers), weakness of the arms and legs, loss of deep tendon reflexes (areflexia), fatigue, and abnormal sensations. CIDP is closely related to Guillain-Barré syndrome and is considered the chronic counterpart of that acute disease. There is no specific diagnostic test, but characteristic clinical and laboratory findings help distinguish this disorder from other immune mediated neuropathic syndromes.

Studies indicate that treatment with immune globulin reduces symptoms (van Schaik et al. (2002) *Lancet Neurol.* 1:497-498). Thus, immune globulin/hyaluronidase co-formulations can be administered subcutaneously to patients presenting with CIDP using the methods described herein. Exemplary dosages include those used for intravenous administration of immune globulin to patients with CIDP. In one example, a patient with, CIDP is administered about 2 g/kg BW of immune globulin subcutaneously, in combination with hyaluronidase. This can be administered, for example, in five doses of 400 mg/kg BW for five consecutive days. The amount of immune globulin administered can be increased or decreased as appropriate.

c. Guillain-Barré Syndrome

Guillain-Barré syndrome is a neurologic autoimmune disorder involving inflammatory demyelination of peripheral nerves. The first symptoms include varying degrees of weakness or tingling sensations in the legs, which can spread to the arms and upper body. These symptoms can increase in intensity until the muscles cannot be used at all and the patient is almost totally paralyzed, resulting in a life-threatening condition. Although recovery is generally good or complete in the majority of patients, persistent disability has been reported in about 20% of all patients and death in 4 to 15% of patients. Guillain-Barré syndrome can occur a few days or weeks after symptoms of a respiratory or gastrointestinal viral infection. In some instances, surgery or vaccinations can trigger the syndrome. The disorder can develop over the course of hours or days, or it may take up to 3 to 4 weeks. A nerve conduction velocity (NCV) test can give a doctor clues to aid the diagnosis. In some instances, a spinal tap can be used in diagnosis, as the cerebrospinal fluid in Guillain-Barré syndrome patients typically contains more protein than normal subjects. Although there is no known cure for Guillain-Barré syndrome, treatment with immune globulin can lessen the severity of the illness and accelerate recovery. Immune globulin/hyaluronidase co-formulations can be administered subcutaneously to patients at an appropriate dose of IG, such as, for example, a dose similar to the dose used to administer immune globulin intravenously to patients with Guillain-Barré syndrome. For example, a patient with Guillain-Barré syndrome can be administered about 2 g/kg BW of immune globulin, in combination with hyaluronidase, subcutaneously. This can be administered, for example, in five doses of 400 mg/kg BW for five consecutive days. The amount of immune globulin administered can be increased or decreased depending on, for example, the severity of the disease and the clinical response to therapy, which can be readily evaluated by one of skill in the art.

d. Idiopathic Thrombocytopenic Purpura

Idiopathic thrombocytopenic purpura (ITP), also known as primary immune thrombocytopenic purpura and autoimmune thrombocytopenic purpura, is a reduction in platelet count (thrombocytopenia) resulting from shortened platelet survival due to anti-platelet antibodies. When platelet counts are very low (e.g., <30×10$^9$/L), bleeding into the skin (purpura) and mucous membranes can occur. Bone marrow platelet production (megakaryopoiesis) in patients with ITP is morphologically normal. In some instances, there is additional impairment of platelet function related to antibody binding to glycoproteins on the platelet surface. ITP can present as chronic and acute forms. Approximately 80% of adults with ITP have the chronic form of the disease. The highest incidence of chronic ITP is in women aged 15-50 years, although some reports suggest increasing incidence with age. ITP is relatively common in patients with HIV. While ITP can be found at any stage of the infection, its prevalence increases as HIV disease advances.

Studies have demonstrated that immune globulin can be used to treat patients with ITP (Godeau et al. (1993) *Blood* 82(5):1415-21; Godeau et al. (1999) *Br. J. Haematol.* 107(4): 716-9). Immune globulin/hyaluronidase co-formulations can be administered subcutaneously to patients at an IG dose similar to the dose used to administer immune globulin intravenously to treat patients with ITP. For example, a patient with ITP can be administered about 1 to 2 g/kg BW of immune globulin, in combination with hyaluronidase, subcutaneously. This can be administered over several days, or can be administered in one dose. In some examples, five doses of 400 mg/kg BW immune globulin on consecutive days is administered. In another example, 1 g/kg BW is administered for 1-2 consecutive days, depending on platelet count and clinical response. The amount of immune globulin administered, and the frequency of the doses, can be increased or decreased depending on, for example, platelet count and the clinical response to therapy, which can be readily evaluated by one of skill in the art.

e. Inflammatory Myopathies

Inflammatory myopathies are a group of muscle diseases involving the inflammation and degeneration of skeletal muscle tissues. These acquired disorders all present with significant muscle weakness and the presence of an inflammatory response within the muscle.

i. Dermatomyositis

Dermatomyositis (DM) is the most easily recognized of the inflammatory myopathies due to its distinctive rash, which occurs as a patchy, dusky, reddish or lilac rash on the eyelids, cheeks, and bridge of the nose, and on the back or upper chest, elbows, knees and knuckles. In some patients, calcified nodules or hardened bumps develop under the skin. The rash often precedes muscle weakness, which typically develops over a period of weeks, but may develop over months or even days. Dermatomyositis can occur at any age from childhood to adulthood, and is more common in females than males. Approximately one-third of DM patients report difficulty swallowing. More than 50% of children with DM complain of muscle pain and tenderness, while this generally occurs in less than 25% of adults with DM.

ii. Polymyositis

Polymyositis (PM) does not have the characteristic rash of dermatomyositis, and the onset of muscle weakness usually progresses slower than DM. Many PM patients present with difficulty in swallowing. In some instances, the patients also have difficulty breathing due to muscle failure. As many as one-third of PM patients have muscle pain. The disease affects more women than men, and rarely affects people under the age of 20, although cases of childhood and infant polymyositis have been reported.

iii. Inclusion Body Myositis

Inclusion body myositis (IBM) is very similar to polymyositis. Onset of muscle weakness in IBM is usually very gradual, taking place over months or years. It differs from PM in that both proximal and distal muscles are affected, while generally only the proximal muscles are affected in PM. Typical findings include weakness of the wrist flexors and finger flexors. Atrophy of the forearms and the quadriceps muscle is characteristic of the disease, with varying degrees of weakness in other muscles. Approximately half of the patients afflicted with IBM have difficulty swallowing. Symptoms of IBM usually begin after age 50, although no age group is excluded. IBM occurs more frequently in men than women. About one in ten cases of IBM may be hereditary.

Studies indicate that administration of immune globulin can benefit patients with these inflammatory myopathies. Immune globulin can improve muscle strength, reduce inflammation and reduce disease progression and severity (Dalakas et al. (1993) *N. Engl. J. Med.* 329(27):1993-2000; Dalakas et al. (2001) *Neurology* 56(3):323-7; Dalakas (2004) *Pharmacol. Ther.* 102(3):177-93; Walter et al. (2000) *J. Neurol.* 247(1):22-8). Immune globulin/hyaluronidase co-formulations can be administered subcutaneously to patients with DM, PM or IBM at a dose of IG similar to the dose used to administer immune globulin intravenously. For example, 2 g/kg BW of immune globulin can be administered, typically over several days, such as, for example, five doses of 400 mg/kg BW on consecutive days.

f. Lambert-Eaton Myasthenic Syndrome

Lambert-Eaton myasthenic syndrome (LEMS) is a rare autoimmune disorder of neuromuscular transmission first recognized clinically in association with lung cancer, and subsequently in cases in which no neoplasm was detected. Patients with LEMS have a presynaptic neuromuscular junction defect. The disease is characterized clinically by proximal muscle weakness, with augmentation of strength after exercise, mild oculomotor signs, depressed deep tendon reflexes and autonomic dysfunction (dry mouth, constipation, erectile failure).

Subcutaneous administration of immune globulin/hyaluronidase co-formulations to patients with LEMS can ameliorate symptoms. Exemplary dosages of IG in the co-formulations include those used for intravenous administration of immune globulin to patients with LEMS. For example, a patient with LEMS can be administered 2 g/kg BW of immune globulin over several doses. For example, five doses of 400 mg/kg BW immune globulin can be administered on five consecutive days. The amount of immune globulin administered can be increased or decreased as appropriate.

g. Multifocal Motor Neuropathy

Multifocal motor neuropathy (MMN) with conduction block is an acquired immune-mediated demyelinating neuropathy with slowly progressive weakness, fasciculations and cramping, without significant sensory involvement. The duration of disease prior to diagnosis ranges from several months to more than 15 years. The precise cause of MMN is unknown. Histopathologic and electrodiagnostic studies demonstrate the presence of both demyelinating and axonal injury. Motor nerves are primarily affected, although mild demyelination has been demonstrated in sensory nerves as well. Efficacy of immunomodulatory and immunosuppressive treatment further supports the immune nature of MMN.

Titers of anti-GM1 antibodies are elevated in over half of the patients with MMN. Although the role of the anti-GM1 antibodies in the disease in unknown, their presence can be used as a diagnostic marker for MMN.

Subcutaneous administration of immune globulin/hyaluronidase co-formulations to patients with MMN can ameliorate symptoms. Exemplary dosages of IG in the co-formulations include those used for intravenous administration of immune globulin to patients with MMN. For example, a patient with MMN can be administered 2 g/kg BW of immune globulin over several doses. For example, five doses of 400 mg/kg BW immune globulin can be administered on five consecutive days. In another example, 1 g/kg BW can be administered on 2 consecutive days. Some patients can be given maintenance therapy, which can include, for example, doses of 400 mg/kg BW to 2 g/kg BW, given every 2-6 weeks. The amount of immune globulin administered can be increased or decreased as appropriate, taking into account the patient's response.

h. Myasthenia Gravis

Myasthenia gravis (MG) is a chronic autoimmune neuromuscular disease characterized by varying degrees of weakness of the skeletal muscles of the body. It is associated with the presence of antibodies to acetylcholine receptors (AChR) or muscle-specific tyrosine kinase (MuSK) at the neuromuscular junction, although some patients are antibody negative. The clinical features of MG include fluctuating weakness and fatigability of voluntary muscles, particularly levator palpebrae, extraocular, bulbar, limb and respiratory muscles. Patients usually present with unilateral or bilateral drooping of the eyelid (ptosis), double vision (diplopia), difficulty in swallowing (dysphagia) and proximal muscle weakness. Weakness of respiratory muscles can result in respiratory failure in severe cases, or in acute severe exacerbations (myasthenic crisis). Myasthenia gravis occurs in all ethnic groups and both genders. It most commonly affects young adult women under 40 and older men over 60, but it can occur at any age. In some instances, thymectomy is performed to reduce symptoms.

Immune globulin can be used, for example, as maintenance therapy for patients with moderate to severe MG, typically when other treatments have been ineffective or caused severe side effects, and also can be administered prior to thymectomy or during an acute exacerbation of the disease (myasthenic crisis). Immune globulin/hyaluronidase co-formulations can be administered subcutaneously to patients with MG using the methods described herein. Exemplary dosages of IG in the co-formulations include those used for intravenous administration of immune globulin to patients with MG. For example, a patient with MG can be administered doses of 400 mg/kg BW to 2 g/kg BW every 4-6 weeks for maintenance therapy. Prior to thymectomy or during myasthenic crisis, 1-2 g/kg BW can be administered over several doses, such as, for example, five doses of 400 mg/kg BW on five consecutive days. In another example, 1 g/kg BW can be administered on 2 consecutive days.

i. Moersch-Woltmann Syndrome

Moersch-Woltmann syndrome, also known as stiff person syndrome (SPS) or stiff man syndrome, is a rare neurological disorder with features of an autoimmune disease. Patients present with symptoms related to muscular rigidity and superimposed episodic spasms. Muscle rigidity spreads to involve axial muscles, primarily abdominal and thoracolumbar, as well as proximal limb muscles. Typically, co-contraction of truncal agonist and antagonist muscles leads to a board-like appearance with hyperlordosis. Less frequently, respiratory muscle involvement leads to breathing difficulty and facial muscle involvement to a mask-like face.

Treatment with immune globulin can effect decreased stiffness and heightened sensitivity scores in patients with Moersch-Woltmann syndrome (Dalakas et al. (2001) *N. Engl. J. Med.* 345(26):1870-6). Immune globulin/hyaluronidase co-formulations can be administered subcutaneously to patients with Moersch-Woltmann syndrome using the methods described herein. Exemplary dosages of IG in the co-formulations include those used for intravenous administration of immune globulin to patients with Moersch-Woltmann syndrome. For example; immune globulin can be administered at doses of 400 mg/kg BW on five consecutive days. Some patients can be given maintenance therapy, which can include, for example, 1-2 g/kg BW immune globulin every 4-6 weeks. The amount of immune globulin administered can be increased or decreased as appropriate.

3. Acute Infections

Immune globulin also has been shown to have antimicrobial activity against a number of bacterial, viral and fungal infections, including, but not limited to, *Haemophilus influenzae* type B; *Pseudomonas aeruginosa* types A and B; *Staphylococcus aureus*; group B streptococcus; *Streptococcus pneumoniae* types 1, 3, 4, 6, 7, 8, 9, 12, 14, 18, 19, and 23; adenovirus types 2 and 5; cytomegalovirus; Epstein-Barr virus VCA; hepatitis A virus; hepatitis B virus; herpes simplex virus-1; herpes simplex virus-2; influenza A; measles; parainfluenza types 1, 2 and 3; polio; varicella zoster virus; *Aspergillus*; and *Candida albicans*. Thus, immune globulin/hyaluronidase co-formulations can be administered subcutaneously to patients with bacterial, viral and fungal infections to augment the patient's immune system and treat the disease. In some examples, antibiotics or other antimicrobials also are administered.

4. Other Diseases and Conditions

Exemplary of other diseases and conditions treatable by IG therapy and not described above include, but are not limited to, iatrogenic immunodeficiency; specific antibody deficiency; acute disseminated encephalomyelitis; ANCA-positive systemic necrotizing vasculitis; autoimmune haemolytic anaemia; bullous pemphigoid; cicatricial pemphigoid; Evans syndrome (including autoimmune haemolytic anaemia with immune thrombocytopenia); feto-maternal/neonatal alloimmune thrombocytopenia (FMAIT/NAIT); haemophagocytic syndrome; high-risk allogeneic haemopoietic stem cell transplantation; IgM paraproteinaemic neuropathy; kidney transplantation; multiple sclerosis; opsoclonus myoclonus ataxia; pemphigus foliaceus; pemphigus vulgaris; post-transfusion purpura; toxic epidermal necrolysis/Steven Johnson syndrome (TEN/SJS); toxic shock syndrome; systemic lupus erythematosus; multiple myeloma; sepsis; bone marrow transplantation; B cell tumors; and Alzheimer's disease.

Alzheimer's disease, for example, includes treatment with intravenous immunoglobulin (see e.g., Dodel et al. (2004) *J Neurol. Neurosurg. Psychiatry* 75:1472-4; Solomon et al. (2007) *Curr. Opin. Mol. Ther.* 9:79-85; Relkin et al. (2008) *Neurobiol Aging*). IG contains antibodies that bind to beta amyloid (AB), which is a central component of the plaque in the brains of Alzheimer's patients. Thus, IG can help to promote the clearance of AB from the brain and block AB's toxic effects on brain cells. Hence, immune globulin/hyaluronidase co-formulations can be administered subcutaneously to patients with Alzheimer's disease using the methods described herein. Subjects to be treated include patients having mild, moderate or advanced Alzheimer's disease. It is within the level of skill of a treating physician to identify patients for treatment. Immune globulin/hyaluronidase co-formulations can be administered every week, every two weeks, or once a month. Treatment can continue over the course of months or years. The co-formulations can be administered at IG doses at or between 200 mg/kg BW to 2 g/kg BW every week or every two weeks, and generally at least 200 mg/kg to 2 g/kg BW at least once a month. Treatment with immune globulin can effect an increase in a patient's anti-amyloid beta antibody levels compared to levels before treatment.

I. Articles Of Manufacture And Kits

Pharmaceutical compositions of immune globulin and hyaluronidase co-formulations can be packaged as articles of manufacture containing packaging material, a pharmaceutical composition which is effective for treating a IG-treatable disease or condition, and a label that indicates that the composition is to be used for treating an IG-treatable diseases and conditions. Exemplary of articles of manufacture are containers including single chamber and dual chamber containers. The containers include, but are not limited to, tubes, bottles and syringes. The containers can further include a needle for subcutaneous administration.

The articles of manufacture provided herein contain packaging materials. Packaging materials for use in packaging pharmaceutical products are well known to those of skill in the art. See, for example, U.S. Pat. Nos. 5,323,907, 5,033,252 and 5,052,558, each of which is incorporated herein in its entirety. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any IG-treatable disease or condition.

Compositions of immune globulin and a soluble hyaluronidase co-formulations also can be provided as kits. Kits can include a pharmaceutical composition described herein and an item for administration. For example compositions can be supplied with a device for administration, such as a syringe, an inhaler, a dosage cup, a dropper, or an applicator. The kit can, optionally, include instructions for application including dosages, dosing regimens and instructions for modes of administration. Kits also can include a pharmaceutical composition described herein and an item for diagnosis. For example, such kits can include an item for measuring the concentration, amount or activity of IG.

J. EXAMPLES

The following examples are included for illustrative purposes only and are not intended to limit the scope of the invention.

Example 1

Preparation of Gammagard Liquid (10% Immunoglobulin (IG) Formulations)

Gammagard Liquid (10% IG) was manufactured from large pools of human plasma, screened throughout for infectious agents. Immune globulins were purified from plasma pools using a modified Cohn-Oncley cold ethanol fractionation process (Cohn et al. (1946) *J. Am. Chem. Soc.* 68:459-467), as well as cation and anion exchange chromatography (Teschner et al. (2007) *Vox Sang.* 92:42-55). The purified protein was further subjected to three independent viral inactivation/removal steps: solvent/detergent (S/D) treatment (Horowitz et al. (1994) *Blood Coagul. Fibrin.* 5(3):S21-S28; Kreil et al. (2003) *Transfusion* 43:1023-1038), 35 nm nanofiltration (Hamamoto et al. (1989) *Vox Sang.* 56:230-236; Yuasa et al. (1991) *J. Gen. Virol.* 72:2021-2024), and a low pH incubation at elevated temperatures (Kempf et al. (1991) *Transfusion* 31:423-427; Louie et al. (1994) *Biologicals* 22:13-19). The S/D procedure included treatment with an organic mixture of tri-n-butyl phosphate, octoxynol-9 and polysorbate-80 at 18 to 25° C. for a minimum of 60 minutes (Polsler et al., (2008) *Vox Sang.* 94:184-192).

The final preparations used in the studies were 10% liquid preparations of highly purified and concentrated immunoglobulin G (IG) antibodies formulated in 0.25 mM glycine at pH 4.6 to 5.1 (as measured in the concentrated solution). Glycine serves as a stabilizing and buffering agent, and there were no added sugars, sodium or preservatives. All lots of 10% IG (e.g. lots LE12H020, LE12H062, LE12H173, LE12F047) were substantially similar. The osmolality was 240 to 300 mOsmol/kg, which is similar to physiological osmolality. The distribution of the IG subclasses of the product manufactured according to the process described above was similar to that of normal plasma: at least 98% of the protein preparation being IgG, the average IgA concentration was 37 μg/mL (none of these lots had an IgA concentration of >140 μg/mL) and IgM was present only in trace amounts. The Fc and Fab functions were maintained. Pre-kalikrein activator activity was not detectable.

Example 2

Preparation of SUBQ NG 20% (20% IG)

A. Producing a Concentrated, Purified IG Composition
  a. Summary

Previously frozen pooled plasma from blood donors was separated into a cryo-poor plasma sample for isolation of various crude coagulation factors and inhibitors prior to subsequent cold alcohol fractionation using a modified Cohn fractionation procedure as described by Teschner et al. (2007) *Vox Sang.* 92:42-55. The alcohol fractionation procedure gave a principal intermediate IG fraction, referred to as Precipitate G, which was further processed to the final product using chromatographic purification. The downstream manufacturing involved cation exchange (CM-Sepharose fast flow) and anion exchange chromatography (ANX-Sepharose fast flow). To provide a high safety margin with respect to potential virus transmission, three dedicated virus inactivation/removal steps, which complement each other in their mode of action, were integrated in the manufacturing process, namely: solvent/detergent treatment (mixture of 1% Triton X-100, 0.3% tri-n-butyl phosphate and 0.3% polysorbate-80), nanofiltration (Asahi Planova 35 nm), and low pH (4.7) storage for 3 weeks at elevated temperature.

b. Separation of Cryoprecipitates

Previously frozen pooled plasma from blood donors, already checked for safety and quality considerations, was thawed at a temperature no higher than 6° C. Centrifugation in the cold was performed to separate solid and liquid, which formed upon the plasma thawing. The liquid portion (also referred to as "cryo-poor plasma," after cold-insoluble proteins were removed by centrifugation from fresh thawed plasma) was then cooled to 0±1° C., and its pH was adjusted to 7. The cryo-poor plasma was used for isolation of various crude coagulation factors and inhibitors prior to subsequent cold alcohol fractionation. Seven pathways were chosen for batch adsorption of crude coagulation factors and inhibitors from the cryo-poor plasma prior to SUBQ NG 20% purification and are referred to as pathways 1 to 7 in Table 3.

TABLE 3

Pathways for batch adsorption of coagulation factors and inhibitors from cryo-poor plasma

| Step | Gel | Heparin | Adsorption Pathways | | | | | | |
|---|---|---|---|---|---|---|---|---|---|
| | | | 1 | 2 | 3 | 4 | 5 | 6 | 7 |
| Cryoprecipitation | — | — | X | X | X | X | X | X | X |
| FEIBA | 0.5 g DEAE-Sephadex/L | — | | X | X | | | | |
| Factor IX | 0.5 g DEAE-Sephadex/L | 2000 IU/mL | | | | X | X | X | X |
| Factor VII | 120 mg Al(OH)$_3$/L | 750 IU/mL | | | | | | X | X |
| Antithrombin | 1 g DEAE-Sephadex/L | 80000 IU/mL | | | X | | X | X | |

For pre-clinical SUBQ NG 20% production, Cohn starting materials derived from pathways 1 (US source plasma without adsorption steps), 3 (US source plasma after FEIBA, AT-III adsorption) and 6 (US source plasma after F-IX, F-VII, AT-III adsorption) were chosen to cover a broad variety of different adsorption steps prior to alcohol fractionation. Various adsorption processes are described in Teschner et al. (2007) *Vox Sang.* 92:42-55; Polsler et al. (2008) *Vox Sang.* 94:184-192; U.S. Pat. Nos. 6,395,880 and 5,409,990; and *Prothrombin complex: Brummelhuis in Methods of Plasma Protein Fractionation* (J. M. Curling Editor, Academic Press, 1980).

c. Fractionation i. Obtain Supernatant of Fractionation I

While the plasma was being stirred, pre-cooled ethanol was added, to a target concentration of 8% v/v ethanol, and the temperature was further lowered to −2 to 0° C. to allow precipitation. Supernatant (or Fractionation I) was collected after centrifugation.

ii. Precipitate of Fractionations II and III

Fractionation I was adjusted to pH 7 and 20 to 25% v/v ethanol concentration, while the temperature was further lowered. Subsequently, centrifugation was performed to separate liquid (Fractionation II+III supernatant) and solid.

iii. Extraction From Fractionations II and III Precipitate

A cold extraction buffer (5 mM monobasic sodium phosphate, 5 mM acetate, pH 4.5±0.2, conductivity of 0.7 to 0.9 mS/cm) was used to re-suspend Fractionations II+III at a ratio of 1:15 precipitate:extraction buffer. The extraction process was performed at 2 to 8° C.

iV. Fumed Silica Treatment and Filtration

Fumed silica (e.g., Aerosil 380 or equivalent) was added to the suspension to a concentration of about 40 g/kg of suspension (or equivalent to 1.8 g/L of cryo-poor plasma) and was mixed at 2 to 8° C. for 50 to 70 minutes. Liquids and solids were separated by filtration at 2 to 8° C. using a filter aid (Hyflo Super-Cel, World Minerals Inc., 0.5 kg/kg of suspension), followed by post-washing of the filter press with extraction buffer.

v. Fractionation of Precipitate G

The filtrate was mixed with polysorbate-80 to a concentration of about 0.2% w/v with stirring for at least 30 minutes at 2 to 8° C. Sodium citrate dehydrate was then mixed into the solution at 8 g/L for another 30 minutes of stirring at 2 to 8° C. The pH was then adjusted to 7.0±0.1 with either 1M sodium hydroxide or 1M acetic acid. Cold alcohol was then added to the solution to a concentration of about 25% v/v, and a precipitation step similar to Cohn II was performed (Cohn et al. (1946) *J. Am. Chem. Soc.* 68:459-467).

vi. Suspension of Precipitate G and Solvent/Detergent Treatment

The precipitate was dissolved and filtered with a depth filter of a nominal pore size of 0.2 μm (e.g., Cuno VR06 filter or equivalent) to obtain a clear filtrate which was used for the solvent/detergent (S/D) treatment.

The first of the steps in viral inactivation is S/D treatment of the re-suspended Precipitate G. The S/D treatment mixture contained 1.0% (v/v) Triton X-100, 0.3% (v/v) Tween-80, and 0.3% (v/v) tri-n-butyl phosphate, and the mixture was held at 18 to 25° C. for at least 60 minutes.

d. Cation Exchange Chromatography

The S/D-containing protein solution was then passed through a cation exchange column (Carboxymethyl (CM)-Sepharose fast flow) to remove the solvent and detergent. After washing out of S/D reagents, the absorbed proteins were then eluted with high pH elution buffer (pH 8.5±0.1).

e. Anion Exchange Chromatography

The eluate was then adjusted to pH 6 and diluted to the appropriate conductivity before the solution was passed through the equilibrated anion exchange column (ANX-Sepharose fast flow). The column flow-through during loading and washing was collected for further processing.

f. Nanofiltration

In the second of three virus inactivation steps, the column effluent from the last step was nanofiltered (Asahi Planova 35 nm filter) to generate a nanofiltrate.

g. Ultrafiltration and Diafiltration

The glycine concentration of the nanofiltrate was adjusted to 0.25 M and the nanofiltrate was further concentrated to a protein concentration of 5±1% w/v by ultrafiltration and pH was adjusted to 5.2±0.2. In order to reach a higher protein concentration for subcutaneous application, the ultrafiltration was carried out in a cassette with an open channel screen and ultrafiltration membrane (Millipore Pellicon Biomax) with a nominal molecular weight cut off (NMWCO) of 50 kDa or less that was especially designed for high viscosity products.

The concentrate was diafiltered against a 0.25 M glycine solution with a pH of 4.2±0.2. The minimum exchange volume was 10× the original concentrate volume. Throughout the ultrafiltration/diafiltration operation, the solution was maintained at 4 to 20° C. After diafiltration, the solution was concentrated to a protein concentration of minimum 22% w/v and adjusted to 2 to 8° C.

In order to recover the complete residual protein in the system, thereby increasing the protein concentration, the post-wash of the first bigger ultrafiltration system was done with at least 2× the dead volume in re-circulation mode to assure that all protein was washed out. Then the post-wash of the first ultrafiltration system was concentrated to a protein concentration of at least 22% w/v with a second ultra-/diafiltration system equipped with the same type of membrane which was dimensioned a tenth or less of the first one. The post-wash concentrate was added to the bulk solution. The second ultrafiltration system was then post-washed and the solution temperature was adjusted to 2 to 8° C.

h. Formulation

For formulation, the protein concentration of the solution was adjusted to 20.4±0.4% w/v with post-wash of the second smaller ultrafiltration system and/or with diafiltration buffer. The pH was adjusted to 4.4 to 4.9, if necessary.

i. Further Sterilization

The formulated bulk solution was further sterilized by first filtering through a membrane filter with an absolute pore size of 0.2 micron or less, then was aseptically dispensed into final containers for proper sealing, with samples taken for testing. The final virus inactivation/removal step was performed by storing the sealed containers at 30 to 32° C. for 21 to 22 days.

Thus, the resulting 20% IG formulations were highly purified, isotonic liquid formulations of immunoglobulin (at least 95% gamma globulin) formulated in 0.25 mM glycine at pH 4.4 to 4.9. The final preparations used in the studies were lots SC00107NG, SC00207NG, and SC00307NG.

B. Characterization of Pre-Clinical Batches

Pre-clinical lots SC00107NG, SC00207NG, and SC00307NG were manufactured on the 200 L scale and characterized according to Table 4. At the final bulk level, the purity of the preparation was illustrated by the low levels of the main impurities, which were well below 0.1% of the total IgG. The molecular size distribution (MSD) in the 20% IG product at the final stage of the process was similar to the MSD of a 10% IG (Gammagard Liquid) final container. This indicated that increasing the concentration to 20% protein did not have a negative impact on the integrity of the IgG molecule.

TABLE 4

Characterization of SUBQ NG 20% lots

| | | Sterile Bulk | | |
|---|---|---|---|---|
| Test/Method | Lot | SC00107NG | SC00207NG | SC00307NG |
| Total protein/UV | g/L Plasma | 3.4 | 3.7 | 3.7 |
| IgG/Nephelometric | g/L Plasma | 3.0 | 3.0 | 3.0 |
| IgA/ELISA | g/L Plasma | <0.001 | <0.001 | <0.001 |
| IgM/ELISA | g/L Plasma | <0.001 | <0.001 | <0.001 |
| MSD (HPLC) | % Aggregates | 0.1 | 0.1 | 0.1 |
| | % Oligo/Dimers | 4.6 | 4.5 | 3.2 |
| | % Monomers | 95.2 | 95.4 | 96.6 |
| | % Fragments | 0.1 | 0 | 0.1 |
| Lot number of starting material | | Precipitate G VNELG171 | Precipitate G VNELG173 | Precipitate G LB0790301 |

The preliminary final container release criteria were defined on the basis of the requirements from the U.S. and European authorities (FDA and EMEA) for subcutaneous human immunoglobulins, the final container specifications of the current product for subcutaneous administration (SUBCUVIA, licensed for subcutaneous administration in Europe) and the Gammagard Liquid specifications. Characterization of the relevant antibody spectrum of the three final containers was completed and compared to the results from the pre-clinical 10% IG Triple Virally Reduced (TVR) lots. Table 5 compares the results of the antibody titers and the enrichment factors of the three pre-clinical SUBQ NG 20% final containers and pre-clinical Gammagard Liquid lots. The results are in the same order of magnitude for both lots.

TABLE 5

Comparison of SUBQ NG 20% and 10% IG TVR release data

| | | | SUBQ NG 20% | | | 10% IG TVR | | |
|---|---|---|---|---|---|---|---|---|
| Test | System | Unit | SC00107NG | SC00207NG | SC00307NG | P0010ING 01C21AN11 | P00201NG 0IC21AN21 | P0030ING 01D05AN11 |
| Bacteria: | | | | | | | | |
| Corynebacterium diphtheriae EUR | Guinea pigs | IU/mL | 6.0 | 6.0 | 6.0 | 5.0 | 5.0 | 5.0 |

TABLE 5-continued

Comparison of SUBQ NG 20% and 10% IG TVR release data

| Test | | | SUBQ NG 20% | | | 10% IG TVR | | |
|---|---|---|---|---|---|---|---|---|
| | | | | | | P0010ING | P00201NG | P0030ING |
| | System | Unit | SC00107NG | SC00207NG | SC00307NG | 01C21AN11 | 0IC21AN21 | 01D05AN11 |
| Viruses | | | | | | | | |
| HAV | ELISA | IU/mL | 14.0 | 14.0 | 27.0 | 14 | 9 | 16 |
| HBV (antibody to hep Bs Ag) | ELISA | IU/mg TP | 40.0 | 47.0 | 43.0 | 35.9 | 40.1 | 40.0 |
| Measles virus EUR Enrich. Factor | Hemagglut. | | 41.0 | 41.0 | 24.0 | n/a | n/a | n/a |
| Measles virus US | Hemagglut. | NIH 176 | 0.8 | 0.8 | 0 | 1.001 | 1.0 | 1.001 |
| Parvo 619 | ELISA | IU/mL | 718 | 78 | 71 | 567 | 442 | 36 |
| Poliomyelitis virus type I | | NIHU/ mL | 1.4 | 1.711 | 1.5 | 1.01 | 1.11 | 1.21 |

Additional quality control tests were performed to evaluate the level of product and/or process-related impurities. Table 6 shows the quality control data of the three SUBQ NG 20% final containers. The removal of product and process related impurities is satisfactory, and all product-related preliminary specifications are met for all three lots.

TABLE 6

Quality control tests of SUBQ NG 20% final container

| | Test System | Unit | SC00107NG | SC00207NG | SC00307NG |
|---|---|---|---|---|---|
| Fc functional integrity | Bc-binding | % of BPR lot 3 | 15.8 | 138 | 164 |
| Anti-complementary activity | EP method | % | 41.1 | 41.5 | 41.2 |
| Anti-complementary activity | EP method | CH50 U/mg | 41.4 | 41.8 | 41.6 |
| Prekallikrein activator activity, EUR | chromogenic | IU/mL | <0.6 | 1.004 | 1.237 |
| Anti-A hemagglutinins, pH. Eur. | hemagglut. | Dilution: 1 | 8 | 16 | 8 |
| Anti-B hemagglutinins, pH. Eur. | hemagglut. | Dilution: 1 | 4 | 4 | 2 |
| Anti-D | hemagglut. | | complies | complies | Complies |
| Exclusion of pyrogenicity, pH. Eur. and CFR | rabbit | ° C. rise | pyrogen free | pyrogen free | pyrogen free |
| Bacterial Endotoxins | Chromogenic | IU/mL | <1.2 | 1.8 | <1.2 |
| Purity by cellulose acetate electrophoresis | CAE | % | 99.6 | 99.8 | 99.5 |
| Molecular size distribution (Monomer + Dimers) | SE-HPLC | % | 99.2 | 99.3 | 99.2 |
| Molecular size distribution (Polymers) | SE-HPLC | % | 0.2 | 0.2 | 0.3 |
| Molecular size distribution (Fragments) | SE-HPLC | % | 0.6 | 0.5 | 0.5 |
| IgA-EUR | ELISA | µg/mL | 20 | 20 | 30 |
| IgM | ELISA | µg/mL | 1.1 | 1.0 | 1.2 |
| IgG | Nephelometry | mg/mL | 177 | 165 | 163 |
| Protein (Bulk) | UV | mg/mL | 201 | 203 | 202 |
| Protein | Autom.N2 | mg/mL | 202 | 208 | 203 |
| Glycine | HPLC | mg/mL | 14.7 | 14.5 | 14.7 |
| Polysorbate 80 | Spectrophot. | µg/mL | <250 | <250 | <250 |
| TNBP | Gas-chromat. | µg/mL | <0.3 | <0.3 | <0.3 |
| Octoxynol 9 | Ion-chromat. | µg/mL | <3 | <3 | <3 |
| Sterility | Membrane filtr. | n/a | sterile | sterile | sterile |
| Osmolality | | mOsmol/kg | 298 | 298 | 299 |
| pH, undiluted | Potentiometry | | 5.1 | 5.2 | 5.3 |
| Appearance | Visual Inspec. | | satisfied | satisfied | satisfied |
| Ethanol | Gas-chromat. | µg/mL | <20 | <20 | <20 |
| Isopropanol | Gas-chromat. | µg/mL | <20 | <20 | <20 |
| Aluminum AAS | Photometry | µg/L | <50 | <50 | <50 |

TABLE 6-continued

| Quality control tests of SUBQ NG 20% final container | | | | | |
|---|---|---|---|---|---|
|  | Test System | Unit | SC00107NG | SC00207NG | SC00307NG |
| Silicium ICP OES | Ion Electr. | µg/L | 3466 | 17270 | 21180 |
| Heparin |  | IU/mL | <0.0075 | <0.0075 | <0.0075 |

In-process parameters monitored during the pre-clinical production and the characterization of intermediates and the final product showed that there were no obvious differences detectable between the three lots. All final containers met the product related preliminary specifications regardless of which kind of starting material (Precipitate G VNELG171, VNELG173, or LB0790301) was chosen.

C. Storage Study of 20% IG Formulations

In order to evaluate the storage stability of the 20% IG final containers, the 3 pre-clinical lots described above (SC00107NG, SC00207NG, SC00307NG) and one feasibility lot (IgGSC 62/1) were stored at 2 to 8° C. and 28 to 30° C. (feasibility lot only) for up to 18 months. High performance size exclusion chromatography was used to determine the molecular size distribution (MSD) and stability of the samples. The main stability indicating parameter is molecular size, and a change in size can be the result of degradation by denaturation, aggregation or fragmentation.

The MSD of the pre-clinical final containers after storage at 2 to 8° C. up to 12 months are shown in Table 7. Table 8 gives the MSD of the feasibility lot, IgGSC 62/1, at 2 to 8° C. and 28 to 30° C., after storage up to 18 months. The data confirmed that the product complies to the pre-defined specifications for the parameters investigated for up to 18 months storage at 2 to 8° C. and 28 to 30° C.

TABLE 7

| MSD of pre-clinical 20% IG batches at 2 to 8° C. | | | | |
|---|---|---|---|---|
|  |  | MSD (HP-SEC) (%) | | |
| Lot | Month | Aggregates (>450 KDa) | Olig/Dimers + Monomers | Fragments (<70 Kda) |
| SC00107NG | 0 | 0.3 | 99.5 | 0.2 |
|  | 3 | 0.4 | 99.5 | 0.2 |
|  | 4 | 0.5 | 99.4 | 0.2 |
|  | 6 | 0.5 | 99.3 | 0.2 |
|  | 12 | 0.7 | 99.1 | 0.3 |
| SC00207NG | 0 | 0.3 | 99.5 | 0.2 |
|  | 3 | 0.4 | 99.5 | 0.1 |
|  | 4 | 0.5 | 99.3 | 0.2 |
|  | 6 | 0.6 | 99.2 | 0.2 |
|  | 12 | 0.8 | 99.0 | 0.2 |
| SC00307NG | 0 | 0.3 | 99.6 | 0.1 |
|  | 3 | 0.5 | 99.3 | 0.2 |
|  | 4 | 0.6 | 99.2 | 0.1 |
|  | 6 | 0.7 | 99.1 | 0.2 |
|  | 12 | 0.9 | 98.8 | 0.2 |
| Release criteria |  | <5 | >90 | <5 |

TABLE 8

| MSD of the feasibility lot IgGSC 62/1 at 2 to 8° C. and 28 to 30° C. | | | | | |
|---|---|---|---|---|---|
|  |  |  | MSD (HP-SEC) (%) | | |
| Lot | ° C. | Month | Aggregates (>450 KDa) | Olig/Dimers + Monomers | Fragments (<70 Kda) |
| IgGSC 62/1 | 2 to 8 | 0 | 0.2 | 99.5 | 0.3 |
|  |  | 1 | 0.1 | 99.7 | 0.2 |
|  |  | 3 | 0.2 | 99.6 | 0.2 |
|  |  | 6 | 0.3 | 99.4 | 0.3 |
|  |  | 12 | 0.4 | 99.3 | 0.3 |
|  |  | 18 | 0.4 | 99.2 | 0.4 |
|  | 28 to 30 | 0 | 0.2 | 99.5 | 0.3 |
|  |  | 1 | 0.2 | 99.2 | 0.6 |
|  |  | 3 | 0.3 | 98.7 | 1.0 |
|  |  | 6 | 0.6 | 98.0 | 1.4 |
|  |  | 12 | 1.2 | 95.6 | 3.2 |
|  |  | 18 | 1.9 | 93.5 | 3.8 |
| Release criteria |  |  | <5 | >90 | <5 |

D. Stability Study of Various IG Concentrations and Formulations

The storage stability of high protein concentration formulations (14-20%) with low pH (0.25 M glycine pH 4.4-4.9) was compared to high protein concentration formulations with neutral pH (22.5 g/L glycine, 3 g/L NaCl, pH 7.0), which are currently used for intramuscularly and subcutaneously injectable immunoglobulins.

All runs started with concentration of the nanofiltrate to 5% protein. A 10× buffer exchange against 0.15 M glycine (lowest glycine concentration investigated) was performed, followed by the final concentration to a target value above 20% protein using a 0.5 m² polyethersulfone Millipore membrane with a molecular cut-off of 30K (standard screen). The final containers were either formulated and stored at low pH (4.7) or the low pH storage was done in bulk and afterwards they were formulated at neutral pH (7.0) prior to storage at either 2 to 8° C. or 28 to 30° C. for 3 months. After 3 months, molecular size distribution was determined by high performance size exclusion chromatography in order to determine aggregate and fragment content. Acceptance criteria was defined as: monomers and oligo-/dimers, ≥90%; aggregates, ≤5%, fragments, ≤5%. ACA titer was tested as described in the European Pharmacopoeia. Acceptable ACA titer was defined as less than 50% CH50 units consumed per mg protein.

Tables 9 and 10 show aggregate and fragment content as well as ACA titer after 3 months storage at 28 to 30° C. and 2 to 8° C., respectively, for the standard formulations (pH 4.7, 0.25 M glycine; or pH 7.0, 22.5 g/L glycine, 3 g/L NaCl) at different protein concentrations. The data clearly show that the low pH formulation had lower aggregates and lower ACA titer after 3 months storage at 28 to 30° C. All ACA titers of the pH 7.0 formulations were above the acceptance criterion defined for this test.

The results at 2 to 8° C. confirm the trend seen at 28 to 30° C. The ACA titers were all below the limit defined as acceptance criterion, although the pH 7.0 formulations seem to have higher values. The protein value does not influence the results of the parameters tested.

TABLE 9

Fragment, aggregate and ACA values after 3 months storage at 28 to 30° C. at pH 4.7 and pH 7.0 at different protein concentrations

| Protein | Fragments % | | Aggregates % | | ACA titer % | |
|---|---|---|---|---|---|---|
| | pH 4.7 | pH 7.0 | pH 4.7 | pH 7.0 | pH 4.7 | pH 7.0 |
| 14% | 1.35 | 1.50 | 0.10 | 0.92 | 44.1 | 52.0 |
| 16% | 1.24 | 1.38 | 0.08 | 0.91 | 40.5 | 53.1 |
| 18% | 1.24 | 1.60 | 0.11 | 0.93 | 40.3 | 52.4 |
| 20% | 1.35 | 1.52 | 0.12 | 0.93 | 37.5 | 62.7 |

TABLE 10

Fragment, aggregate and ACA values after 3 months storage at 2 to 8° C. at pH 4.7 and pH 7.0 at different protein concentrations

| Protein | Fragments % | | Aggregates % | | ACA titer | |
|---|---|---|---|---|---|---|
| | pH 4.7 | pH 7.0 | pH 4.7 | pH 7.0 | pH 4.7 | pH 7.0 |
| 14% | 0.36 | 1.80 | 0.16 | 1.09 | 38.3 | 46.5 |
| 16% | 0.30 | 0.51 | 0.11 | 1.01 | 37.4 | 44.7 |
| 18% | 0.33 | 1.10 | 0.17 | 0.86 | 35.8 | 39.8 |
| 20% | 0.33 | 1.98 | 0.20 | 1.06 | 36.1 | 46.0 |

The influence of different concentration procedures on MSD and ACA titer was investigated. The first procedure used a 0.5 m² polyethersulfone Millipore membrane with a molecular cut-off of 30K (standard screen), as described above, and the second procedure used a 0.5 m² polyethersulfone Millipore membrane with an open screen, suitable for solutions with higher viscosity. The post-wash fractions were concentrated by a second ultra-/diafiltration device with a lower membrane surface (0.1 m², open screen) in order to reduce yield losses.

Tables 11 and 12 show MSD and ACA titer after 3 months storage at 28 to 30° C. or 2 to 8° C., respectively, for the low pH (4.7) formulations at various protein concentrations. The data showed similar results after 3 months storage for both concentration modes. The values obtained at 2 to 8° C. confirmed the results obtained at 28 to 30° C. The concentration method does not influence the stability of the product, though adequate post-wash can only be obtained with open-screen membranes.

TABLE 11

Fragment, aggregate and ACA values after 3 months storage at 28 to 30° C. at pH 4.7 with different protein concentration methods

| Protein | Fragments (%) | | Aggregates (%) | | ACA titer | |
|---|---|---|---|---|---|---|
| | standard-screen | open-screen | standard-screen | open-screen | standard-screen | open-screen |
| 14% | 1.35 | 0.92 | 0.10 | 0.21 | 44.1 | 42.6 |
| 16% | 1.24 | 1.09 | 0.08 | 0.20 | 40.5 | 40.9 |
| 18% | 1.24 | 0.96 | 0.11 | 0.23 | 40.3 | 40.7 |
| 20% | 1.35 | 0.98 | 0.12 | 0.30 | 37.5 | 41.6 |

TABLE 12

Fragment, aggregate and ACA values after 3 months storage at 2 to 8° C. at pH 4.7 with different protein concentration methods

| Protein | Fragments (%) | | Aggregates (%) | | ACA titer (%) | |
|---|---|---|---|---|---|---|
| | standard-screen | open-screen | standard-screen | open-screen | standard-screen | open-screen |
| 14% | 0.36 | 0.27 | 0.16 | 0.17 | 38.3 | 39.6 |
| 16% | 0.30 | 0.22 | 0.11 | 0.14 | 37.4 | 38.3 |
| 18% | 0.33 | 0.23 | 0.17 | 0.18 | 35.8 | 39.6 |
| 20% | 0.33 | 0.22 | 0.20 | 0.20 | 36.1 | 39.9 |

Example 3

Preparation of Soluble Recombinant Human PH20 (rHuPH20)

A. Generation of a Soluble rHuPH20 -Expressing Cell Line

The HZ24 plasmid (set forth in SEQ ID NO:52) was used to transfect Chinese Hamster Ovary (CHO cells) (see e.g. application Nos. 10/795,095, 11/065,716 and 11/238,171). The HZ24 plasmid vector for expression of soluble rHuPH20 contains a pCI vector backbone (Promega), DNA encoding amino acids 1-482 of human PH20 hyaluronidase (SEQ ID NO:49, an internal ribosomal entry site (IRES) from the ECMV virus (Clontech), and the mouse dihydrofolate reductase (DHFR) gene. The pCI vector backbone also includes DNA encoding the Beta-lactamase resistance gene (AmpR), an f1 origin of replication, a Cytomegalovirus immediate-early enhancer/promoter region (CMV), a chimeric intron, and an SV40 late polyadenylation signal (SV40). The DNA encoding the soluble rHuPH20 construct contains an NheI site and a Kozak consensus sequence prior to the DNA encoding the methionine at amino acid position 1 of the native 35 amino acid signal sequence of human PH20, and a stop codon following the DNA encoding the tyrosine corresponding to amino acid position 482 of the human PH20 hyaluronidase (set forth in SEQ ID NO:1), followed by a BamHI restriction site. The construct pCI-PH20-IRES-DHFR-SV40pa (HZ24), therefore, results in a single mRNA species driven by the CMV promoter that encodes amino acids 1-482 of human PH20 (set forth in SEQ ID NO:3) and amino acids 1-186 of mouse dihydrofolate reductase (set forth in SEQ ID NO:53), separated by the internal ribosomal entry site (IRES).

Non-transfected DG44 CHO cells growing in GIBCO Modified CD-CHO media for DHFR(−) cells, supplemented with 4 mM glutamine and 18 mL/L Pluronic F68/L (Gibco), were seeded at $0.5 \times 10^6$ cells/mL in a shake flask in preparation for transfection. Cells were grown at 37° C. in 5% $CO_2$ in a humidified incubator, shaking at 120 rpm. Exponentially growing non-transfected DG44 CHO cells were tested for viability prior to transfection.

Sixty million viable cells of the non-transfected DG44 CHO cell culture were pelleted and re-suspended to a density of $2 \times 10^7$ cells in 0.7 mL of 2× transfection buffer (2×HeBS: 40 mM Hepes, pH 7.0, 274 mM NaCl, 10 mM KCl, 1.4 mM $Na_2HPO_4$, 12 mM dextrose). To each aliquot of re-suspended cells, 0.09 mL (250 μg) of the linear HZ24 plasmid (linearized by overnight digestion with Cla I (New England Biolabs)) was added, and the cell/DNA solutions were transferred into 0.4 cm gap BTX (Gentronics) electroporation cuvettes at room temperature. A negative control electroporation was performed with no plasmid DNA mixed with the cells. The cell/plasmid mixes were electroporated with a capacitor discharge of 330 V and 960 μF or at 350 V and 960 g.

The cells were removed from the cuvettes after electroporation and transferred into 5 mL of Modified CD-CHO media for DHFR(−) cells, supplemented with 4 mM glutamine and 18 mL/L Pluronic F68/L (Gibco), and allowed to grow in a well of a E-well tissue culture plate without selection for 2 days at 37° C. in 5% $CO_2$ in a humidified incubator.

Two days post-electroporation, 0.5 mL of tissue culture media was removed from each well and tested for the presence of hyaluronidase activity, using the microturbidity assay described in Example 4.

TABLE 13

Initial hyaluronidase activity of HZ24 transfected DG44 CHO cells at 40 hours post-transfection

| | Dilution | Activity (Units/mL) |
|---|---|---|
| Transfection 1 (330 V) | 1 to 10 | 0.25 |
| Transfection 2 (350 V) | 1 to 10 | 0.52 |
| Negative Control | 1 to 10 | 0.015 |

Cells from Transfection 2 (350V) were collected from the tissue culture well, counted and diluted to $1\times10^4$ to $2\times10^4$ viable cells per mL. A 0.1 mL aliquot of the cell suspension was transferred to each well of five, 96-well round bottom tissue culture plates. One hundred microliters of CD-CHO media (GIBCO) containing 4 mM GlutaMAX™-1 supplement (GIBCO™, Invitrogen Corporation) and without hypoxanthine and thymidine supplements were added to the wells containing cells (final volume 0.2 mL).

Ten clones were identified from the 5 plates grown without methotrexate.

TABLE 14

Hyaluronidase activity of identified clones

| Plate/Well ID | Relative Hyaluronidase |
|---|---|
| 1C3 | 261 |
| 2C2 | 261 |
| 3D3 | 261 |
| 3E5 | 243 |
| 3C6 | 174 |
| 2G8 | 103 |
| 1B9 | 304 |
| 2D9 | 273 |
| 4D10 | 302 |

Six HZ24 clones were expanded in culture and transferred into shake flasks as single cell suspensions. Clones 3D3, 3E5, 2G8, 2D9, 1E11, and 4D10 were plated into 96-well round bottom tissue culture plates using a two-dimensional infinite dilution strategy in which cells were diluted 1:2 down the plate, and 1:3 across the plate, starting at 5000 cells in the top left hand well. Diluted clones were grown in a background of 500 non-transfected DG44 CHO cells per well, to provide necessary growth factors for the initial days in culture. Ten plates were made per subclone, with 5 plates containing 50 nM methotrexate and 5 plates without methotrexate.

Clone 3D3 produced 24 visual subclones (13 from the no methotrexate treatment, and 11 from the 50 nM methotrexate treatment). Significant hyaluronidase activity was measured in the supernatants from 8 of the 24 subclones (>50 Units/mL), and these 8 subclones were expanded into T-25 tissue culture flasks. Clones isolated from the methotrexate treatment protocol were expanded in the presence of 50 nM methotrexate. Clone 3D35M was further expanded in 500 nM methotrexate giving rise to clones producing in excess of 1,000 Units/mL in shake flasks (clone 3D35M; or Gen1 3D35M). A master cell bank (MCB) of the 3D35M cells was then prepared.

B. Production and Purification of Gen1 Human PH20 a. 5 L Bioreactor Process

A vial of 3D35M was thawed and expanded from shake flasks through 1 L spinner flasks in CD-CHO media (Invitrogen, Carlsbad Calif.) supplemented with 100 nM methotrexate and GlutaMAX™-1 (Invitrogen). Cells were transferred from spinner flasks to a 5 L bioreactor (Braun) at an inoculation density of $4\times10^5$ viable cells/mL. Parameters were: temperature setpoint: 37° C.; pH: 7.2 (starting setpoint); dissolved oxygen setpoint: 25%; and air overlay: 0-100 cc/min. At 168 hrs, 250 mL of Feed #1 Medium (CD CHO with 50 g/L glucose) was added. At 216 hours, 250 mL of Feed #2 Medium (CD CHO with 50 g/L glucose and 10 mM sodium butyrate) was added, and at 264 hours 250 mL of Feed #2 Medium was added. This process resulted in a final productivity of 1600 Units/mL with a maximal cell density of $6\times10^6$ cells/mL. The addition of sodium butyrate was to dramatically enhance the production of soluble rHuPH20 in the final stages of production.

Conditioned media from the 3D35M clone was clarified by depth filtration and tangential flow diafiltration into 10 mM Hepes pH 7.0. Soluble rHuPH20 was then purified by sequential chromatography on Q Sepharose (Pharmacia) ion exchange, Phenyl Sepharose (Pharmacia) hydrophobic interaction chromatography, phenyl boronate (Prometics) and hydroxyapatite chromatography (Bio-Rad, Richmond, Calif.).

Soluble rHuPH20 bound to Q Sepharose and eluted at 400 mM NaCl in the same buffer. The eluate was diluted with 2M ammonium sulfate to a final concentration of 500 mM ammonium sulfate and passed through a Phenyl Sepharose (low sub) column, followed by binding under the same conditions to a phenyl boronate resin. The soluble rHuPH20 was eluted from the Phenyl Sepharose resin in Hepes pH 6.9 after washing at pH 9.0 in 50 mM bicine without ammonium sulfate. The eluate was loaded onto a ceramic hydroxyapatite resin at pH 6.9 in 5 mM potassium phosphate and 1 mM $CaCl_2$ and eluted with 80 mM potassium phosphate, pH 7.4 with 0.1 mM $CaCl_2$.

The resultant purified soluble rHuPH20 possessed a specific activity in excess of 65,000 USP Units/mg protein by way of the microturbidity assay (Example 4) using the USP reference standard. Purified soluble rHuPH20 eluted as a single peak from 24 to 26 minutes from a Pharmacia 5RPC styrene divinylbenzene column with a gradient between 0.1% TFA/$H_2O$ and 0.1% TFA/90% acetonitrile/10% $H_2O$ and resolved as a single broad 61 kDa band by SDS electrophoresis that reduced to a sharp 51 kDa band upon treatment with PNGASE-F. N-terminal amino acid sequencing revealed that the leader peptide had been efficiently removed.

b. Upstream Cell Culture Expansion process Into 100 L Bioreactor Cell Culture

A scaled-up process was used to separately purify soluble rHuPH20 from four different vials of 3D35M cell to produce 4 separate batches of soluble rHuPH20 ; HUA0406C, HUA0410C, HUA0415C and HUA0420C. Each vial was separately expanded and cultured through a 125 L bioreactor, then purified using column chromatography. Samples were taken throughout the process to assess such parameters as enzyme yield. The description of the process provided below sets forth representative specifications for such things as bioreactor starting and feed media volumes, transfer cell densities, and wash and elution volumes. The exact numbers vary slightly with each batch, and are detailed in Tables 15 to 22.

Four vials of 3D35M cells were thawed in a 37° C. water bath, CD CHO containing 100 nM methotrexate and 40 mL/L GlutaMAX™-1 was added and the cells were centrifuged. The cells were re-suspended in a 125 mL shake flask with 20 mL of fresh media and placed in a 37° C., 7% $CO_2$ incubator. The cells were expanded up to 40 mL in the 125 mL shake flask. When the cell density reached $1.5-2.5\times10^6$ cells/mL, the culture was expanded into a 125 mL spinner flask in a 100 mL culture volume. The flask was incubated at 37° C., 7% $CO_2$. When the cell density reached $1.5-2.5\times10^6$ cells/mL, the culture was expanded into a 250 mL spinner flask in 200 mL culture volume, and the flask was incubated at 37° C., 7% $CO_2$. When the cell density reached $1.5-2.5\times10^6$ cells/mL, the culture was expanded into a 1 L spinner flask in 800 mL culture volume and incubated at 37° C., 7% $CO_2$. When the cell density reached $1.5-2.5\times10^6$ cells/mL, the culture was expanded into a 6 L spinner flask in 5 L culture volume and incubated at 37° C., 7% $CO_2$. When the cell density reached $1.5-2.5\times10^6$ cells/mL, the culture was expanded into a 36 L spinner flask in 20 L culture volume and incubated at 37° C., 7% $CO_2$.

A 125 L reactor was sterilized with steam at 121° C., 20 psi and 65 L of CD CHO media was added. Before use, the reactor was checked for contamination. When the cell density in the 36 L spinner flasks reached $1.8-2.5\times10^6$ cells/mL, 20 L of cell culture was transferred from the 36 L spinner flasks to the 125 L bioreactor (Braun), resulting in a final volume of 85 L and a seeding density of approximately $4\times10^5$ cells/mL. Parameters were: temperature setpoint: 37° C.; pH: 7.2; dissolved oxygen: 25%±10%; impeller speed: 50 rpm; vessel pressure: 3 psi; air sparge: 1 L/min.; air overlay: 1 L/min. The reactor was sampled daily for cell counts, pH verification, media analysis, protein production and retention. Nutrient feeds were added during the run. At Day 6, 3.4 L of Feed #1 Medium (CD CHO+50 g/L glucose+40 mL/L GlutaMAX™-1) was added, and culture temperature was changed to 36.5° C. At day 9, 3.5 L of Feed #2 (CD CHO+50 g/L glucose+40 mL/L GlutaMAX™-1+1.2 g/L sodium butyrate) was added, and culture temperature was changed to 36° C. At day 11, 3.7 L of Feed #3 (CD CHO+50 g/L glucose+40 mL/L GlutaMAX™-1+1.1 g/L sodium butyrate) was added, and the culture temperature was changed to 35.5° C. The reactor was harvested at 14 days, or when the viability of the cells dropped below 50%. The process resulted in production of soluble rHuPH20 with an enzymatic activity of 1600 Units/mL with a maximal cell density of 8 million cells/mL. At harvest, the culture was sampled for mycoplasma, bioburden, endotoxin, and virus in vitro and in vivo, transmission electron microscopy (TEM) for viral particles, and enzyme activity.

The 100 L bioreactor cell culture harvest was filtered through a series of disposable capsule filters having a polyethersulfone medium (Sartorius): first through a 8.0 μm depth capsule, a 0.65 μm depth capsule, a 0.22 μm capsule, and finally through a 0.22 μm Sartopore 2000 $cm^2$ filter and into a 100 L sterile storage bag. The culture was concentrated 10× using two TFF with Spiral Polyethersulfone 30 kDa MWCO filters (Millipore), followed by a 6× buffer exchange with 10 mM HEPES, 25 mM $Na_2SO_4$, pH 7.0, into a 0.22 μm final filter into a 20 L sterile storage bag. Table 15 provides monitoring data related to the cell culture, harvest, concentration and buffer exchange steps.

TABLE 15

Monitoring data for cell culture, harvest, concentration and buffer exchange steps

| Parameter | HUA0406C | HUA0410C | HUA0415C | HUA0420C |
|---|---|---|---|---|
| Time from thaw to inoculate 100 L bioreactor (days) | 21 | 19 | 17 | 18 |
| 100 L inoculation density (×10$^6$ cells/mL) | 0.45 | 0.33 | 0.44 | 0.46 |
| Doubling time in logarithmic growth (hr) | 29.8 | 27.3 | 29.2 | 23.5 |
| Max. cell density (×10$^6$ cells/mL) | 5.65 | 8.70 | 6.07 | 9.70 |
| Harvest viability (%) | 41 | 48 | 41 | 41 |
| Harvest titer (U/mL) | 1964 | 1670 | 991 | 1319 |
| Time in 100-L bioreactor (days) | 13 | 13 | 12 | 13 |
| Clarified harvest volume (mL) | 81800 | 93300 | 91800 | 89100 |
| Clarified harvest enzyme assay (U/mL) | 2385 | 1768 | 1039 | 1425 |
| Concentrate enzyme assay (U/mL) | 22954 | 17091 | 8561 | 17785 |
| Buffer exchanged concentrate enzyme assay (U/mL) | 15829 | 11649 | 9915 | 8679 |
| Filtered buffer exchanged concentrate enzyme assay (U/mL) | 21550 | 10882 | 9471 | 8527 |
| Buffer exchanged concentrate volume(mL) | 10699 | 13578 | 12727 | 20500 |
| Ratio enzyme units concentration/harvest | 0.87 | 0.96 | 1.32 | 1.4 |

A Q Sepharose (Pharmacia) ion exchange column (3 L resin, Height=20 cm, Diameter=14 cm) was prepared. Wash samples were collected for a determination of pH, conductivity and endotoxin (LAL) assay. The column was equilibrated with 5 column volumes of 10 mM Tris, 20 mM $Na_2SO_4$, pH 7.5. The concentrated, diafiltered harvest was loaded onto the Q column at a flow rate of 100 cm/hr. The column was washed with 5 column volumes of 10 mM Tris, 20 mM $Na_2SO_4$, pH 7.5 and 10 mM Hepes, 50 mM NaCl, pH 7.0. The protein was eluted with 10 mM Hepes, 400 mM NaCl, pH 7.0, and filtered through a 0.22 μm final filter into a sterile bag.

Phenyl Sepharose (Pharmacia) hydrophobic interaction chromatography was next performed. A Phenyl Sepharose (PS) column (9.1 L resin, Height=29 cm, Diameter=20 cm) was prepared. The column was equilibrated with 5 column volumes of 5 mM potassium phosphate, 0.5 M ammonium sulfate, 0.1 mM CaCl$_2$, pH 7.0. The protein eluate from above was supplemented with 2M ammonium sulfate, 1 M potassium phosphate and 1 M CaCl$_2$ stock solutions to final concentrations of 5 mM, 0.5 M and 0.1 mM, respectively. The protein was loaded onto the PS column at a flow rate of 100 cm/hr. 5 mM potassium phosphate, 0.5 M ammonium sulfate and 0.1 mM CaCl$_2$, pH 7.0, was added at 100 cm/hr. The flow-through was passed through a 0.22 µm final filter into a sterile bag.

The PS-purified protein was then loaded onto an aminophenyl boronate column (ProMedics) (6.3 L resin, Height=20 cm, Diameter=20 cm) that had been equilibrated with 5 column volumes of 5 mM potassium phosphate, 0.5 M ammonium sulfate. The protein was passed through the column at a flow rate of 100 cm/hr, and the column was washed with 5 mM potassium phosphate, 0.5 M ammonium sulfate, pH 7.0. The column was then washed with 20 mM bicine, 100 mM NaCl, pH 9.0, and the protein eluted with 50 mM Hepes, 100 mM NaCl, pH 6.9, through a sterile filter and into a 20 L sterile bag. The eluate was tested for bioburden, protein concentration and enzyme activity.

A hydroxyapatite (HAP) column (Bio-Rad) (1.6 L resin, Height=10 cm, Diameter=14 cm) was equilibrated with 5 mM potassium phosphate, 100 mM NaCl, 0.1 mM CaCl$_2$, pH 7.0. Wash samples were collected and tested for pH, conductivity and endotoxin (LAL assay). The aminophenyl boronate-purified protein was supplemented with potassium phosphate and CaCl$_2$ to yield final concentrations of 5 mM potassium phosphate and 0.1 mM CaCl$_2$, then was loaded onto the HAP column at a flow rate of 100 cm/hr. The column was washed with 5 mM potassium phosphate, pH 7.0, 100 mM NaCl, 0.1 mM CaCl$_2$, then 10 mM potassium phosphate, pH 7.0, 100 mM NaCl, 0.1 mM CaCl$_2$ pH. The protein was eluted with 70 mM potassium phosphate, pH 7.0, and filtered through a 0.22 µm filter into a 5 L sterile storage bag. The eluate was tested for bioburden, protein concentration and enzyme activity.

The HAP-purified protein was then pumped through a 20 nM viral removal filter via a pressure tank. The protein was added to the DV20 pressure tank and filter (Pall Corporation), passing through an Ultipor DV20 Filter with 20 nm pores (Pall Corporation) into a sterile 20 L storage bag. The filtrate was tested for protein concentration, enzyme activity, oligosaccharide, monosaccharide and sialic acid profiling, and process-related impurities. The protein in the filtrate was then concentrated to 1 mg/mL using a 10 kDa molecular weight cut off (MWCO) Sartocon Slice tangential flow filtration (TFF) system (Sartorius). The filter was first prepared by washing with a Hepes/saline solution (10 mM Hepes, 130 mM NaCl, pH 7.0) and the permeate was sampled for pH and conductivity. Following concentration, the concentrated protein was sampled and tested for protein concentration and enzyme activity. A 6× buffer exchange was performed on the concentrated protein into the final buffer: 10 mM Hepes, 130 mM NaCl, pH 7.0. The concentrated protein was passed though a 0.22 µm filter into a 20 L sterile storage bag. The protein was sampled and tested for protein concentration, enzyme activity, free sulfhydryl groups, oligosaccharide profiling and osmolarity.

Tables 16 through 22-provide monitoring data related to each of the purification steps described above, for each 3D35M cell lot.

TABLE 16

Q Sepharose column data

| Parameter | HUA0406C | HUA0410C | HUA0415C | HUA0420C |
|---|---|---|---|---|
| Load volume (mL) | 10647 | 13524 | 12852 | 20418 |
| Load Volume/ Resin Volume ratio | 3.1 | 4.9 | 4.5 | 7.3 |
| Column Volume (mL) | 2770 | 3840 | 2850 | 2880 |
| Eluate volume (mL) | 6108 | 5923 | 5759 | 6284 |
| Protein Conc. of Eluate (mg/mL) | 2.8 | 3.05 | 2.80 | 2.86 |
| Eluate Enzyme Assay (U/mL) | 24493 | 26683 | 18321 | 21052 |
| Enzyme Yield (%) | 65 | 107 | 87 | 76 |

TABLE 17

Phenyl Sepharose column data

| Parameter | HUA0406C | HUA0410C | HUA0415C | HUA0420C |
|---|---|---|---|---|
| Volume Before Stock Solution Addition (mL) | 5670 | 5015 | 5694 | 6251 |
| Load Volume (mL) | 7599 | 6693 | 7631 | 8360 |
| Column Volume (mL) | 9106 | 9420 | 9340 | 9420 |
| Load Volume/ Resin Volume ratio | 0.8 | 0.71 | 0.82 | 0.89 |
| Eluate volume (mL) | 16144 | 18010 | 16960 | 17328 |
| Protein Conc of Eluate (mg/mL) | 0.4 | 0.33 | 0.33 | 0.38 |
| Eluate Enzyme Assay (U/mL) | 8806 | 6585 | 4472 | 7509 |
| Protein Yield (%) | 41 | 40 | 36 | 37 |
| Enzyme Yield (%) | 102 | 88 | 82 | 96 |

TABLE 18

Amino phenyl boronate column data

| Parameter | HUA0406C | HUA0410C | HUA0415C | HUA0420C |
|---|---|---|---|---|
| Load Volume (mL) | 16136 | 17958 | 16931 | 17884 |
| Load Volume/Resin Volume ratio | 2.99 | 3.15 | 3.08 | 2.98 |
| Column Volume (mL) | 5400 | 5700 | 5500 | 5300 |
| Eluate volume (mL) | 17595 | 22084 | 20686 | 19145 |
| Protein Conc. of Eluate (mg/mL) | 0.0 | 0.03 | 0.03 | 0.04 |

TABLE 18-continued

Amino phenyl boronate column data

| Parameter | HUA0406C | HUA0410C | HUA0415C | HUA0420C |
|---|---|---|---|---|
| Protein Conc. of Filtered Eluate (mg/mL) | Not tested | 0.03 | 0.00 | 0.04 |
| Eluate Enzyme Assay (U/mL) | 4050 | 2410 | 1523 | 4721 |
| Protein Yield (%) | 0 | 11 | 11 | 12 |
| Enzyme Yield (%) | Not determined | 41 | 40 | 69 |

TABLE 19

Hydroxyapatite column data

| Parameter | HUA0406C | HUA0410C | HUA0415C | HUA0420C |
|---|---|---|---|---|
| Volume Before Stock Solution Addition (mL) | 16345 | 20799 | 20640 | 19103 |
| Load Volume/Resin Volume ratio | 10.95 | 13.58 | 14.19 | 12.81 |
| Column Volume (mL) | 1500 | 1540 | 1462 | 1500 |
| Load volume (mL) | 16429 | 20917 | 20746 | 19213 |
| Eluate volume (mL) | 4100 | 2415 | 1936 | 2419 |
| Protein Conc. of Eluate (mg/mL) | Not tested | 0.24 | 0.17 | 0.23 |
| Protein Conc. of Filtered Eluate (mg/mL) | NA | NA | 0.17 | NA |
| Eluate Enzyme Assay (U/mL) | 14051 | 29089 | 20424 | 29826 |
| Protein Yield (%) | Not tested | 93 | 53 | 73 |
| Enzyme Yield (%) | 87 | 118 | 140 | 104 |

TABLE 20

DV20 filtration data

| Parameter | HUA0406C | HUA0410C | HUA0415C | HUA0420C |
|---|---|---|---|---|
| Start volume (mL) | 4077 | 2233 | 1917 | 2419 |
| Filtrate Volume (mL) | 4602 | 3334 | 2963 | 3504 |
| Protein Conc. of Filtrate (mg/mL) | 0.1 | NA | 0.09 | NA |
| Protein Conc. of Filtered Eluate (mg/mL) | NA | 0.15 | 0.09 | 0.16 |
| Protein Yield (%) | Not tested | 93 | 82 | 101 |

TABLE 21

Final concentration data

| Parameter | HUA0406C | HUA0410C | HUA0415C | HUA0420C |
|---|---|---|---|---|
| Start volume (mL) | 4575 | 3298 | 2963 | 3492 |
| Concentrate Volume (mL) | 562 | 407 | 237 | 316 |
| Protein Conc. of Concentrate (mg/mL) | 0.9 | 1.24 | 1.16 | 1.73 |
| Protein Yield (%) | 111 | 102 | 103 | 98 |

TABLE 22

Buffer exchange into final formulation data

| Parameter | HUA0406C | HUA0410C | HUA0415C | HUA0420C |
|---|---|---|---|---|
| Start Volume (mL) | 562 | 407 | 237 | 316 |
| Final Volume Buffer Exchanged Concentrate (mL) | 594 | 516 | 310 | 554 |

TABLE 22-continued

Buffer exchange into final formulation data

| Parameter | HUA0406C | HUA0410C | HUA0415C | HUA0420C |
|---|---|---|---|---|
| Protein Conc. of Concentrate (mg/mL) | 1.00 | 0.97 | 0.98 | 1.00 |
| Protein Conc. of Filtered Concentrate (mg/mL) | 0.95 | 0.92 | 0.95 | 1.02 |
| Protein Yield (%) | 118 | 99 | 110 | 101 |

The purified and concentrated soluble rHuPH20 protein was aseptically filled into sterile vials with 5 mL and 1 mL fill volumes. The protein was passed though a 0.22 μm filter to an operator controlled pump that was used to fill the vials using a gravimetric readout. The vials were closed with stoppers and secured with crimped caps. The closed vials were visually inspected for foreign particles and then labeled. Following labeling, the vials were flash-frozen by submersion in liquid nitrogen for no longer than 1 minute and stored at ≤−15° C. (−20±5° C.).

C. Production Gen2 Cells Containing Soluble Human PH20 (rHuPH20)

The Gen1 3D35M cell line described above was adapted to higher methotrexate levels to produce generation 2 (Gen2) clones. 3D35M cells were seeded from established methotrexate-containing cultures into CD CHO medium containing 4 mM GlutaMAX™-1 and 1.0 μM methotrexate. The cells were adapted to a higher methotrexate level by growing and passaging them 9 times over a period of 46 days in a 37° C., 7% $CO_2$ humidified incubator. The amplified population of cells was cloned out by limiting dilution in 96-well tissue culture plates containing medium with 2.0 μM methotrexate. After approximately 4 weeks, clones were identified and clone 3E10B was selected for expansion. 3E10B cells were grown in CD CHO medium containing 4 mM GlutaMAX™-1 and 2.0 μM methotrexate for 20 passages. A master cell bank (MCB) of the 3E10B cell line was created and frozen and used for subsequent studies.

Amplification of the cell line continued by culturing 3E10B cells in CD CHO medium containing 4 mM GlutaMAX™-1 and 4.0 μM methotrexate. After the twelfth passage, cells were frozen in vials as a research cell bank (RCB). One vial of the RCB was thawed and cultured in medium containing 8.0 μM methotrexate. After 5 days, the methotrexate concentration in the medium was increased to 16.0 μM, then 20.0 μM 18 days later. Cells from the eighth passage in medium containing 20.0 μM methotrexate were cloned out by limiting dilution in 96-well tissue culture plates containing CD CHO medium containing 4 mM GlutaMAX™-1 and 20.0 μM methotrexate. Clones were identified 5-6 weeks later and clone 2B2 was selected for expansion in medium containing 20.0 μM methotrexate. After the eleventh passage, 2B2 cells were frozen in vials as a research cell bank (RCB).

The resultant 2B2 cells are dihydrofolate reductase deficient (dhfr-) DG44 CHO cells that express soluble recombinant human PH20 (rHuPH20). The soluble rHuPH20 is present in 2B2 cells at a copy number of approximately 206 copies/cell. Southern blot analysis of Spe I-, Xba I- and BamH I/Hind III-digested genomic 2B2 cell DNA using a rHuPH20-specific probe revealed the following restriction digest profile: one major hybridizing band of ~7.7 kb and four minor hybridizing bands (~13.9, ~6.6, ~5.7 and ~4.6 kb) with DNA digested with Spe I; one major hybridizing band of ~5.0 kb and two minor hybridizing bands (~13.9 and ~6.5 kb) with DNA digested with Xba I; and one single hybridizing band of ~1.4 kb observed using 2B2 DNA digested with BamH I/Hind III. Sequence analysis of the mRNA transcript indicated that the derived cDNA (SEQ ID NO:56) was identical to the reference sequence (SEQ ID NO:49) except for one base pair difference at position 1131, which was observed to be a thymidine (T) instead of the expected cytosine (C). This is a silent mutation, with no effect on the amino acid sequence.

D. Production of Gent Soluble rHuPH20 in 300 L Bioreactor Cell Culture

A vial of HZ24-2B2 was thawed and expanded from shake flasks through 36 L spinner flasks in CD-CHO media (Invitrogen, Carlsbad, Calif.) supplemented with 20 methotrexate and GlutaMAX™-1 (Invitrogen). Briefly, the vial of cells was thawed in a 37° C. water bath, media was added and the cells were centrifuged. The cells were re-suspended in a 125 mL shake flask with 20 mL of fresh media and placed in a 37° C., 7% $CO_2$ incubator. The cells were expanded up to 40 mL in the 125 mL shake flask. When the cell density reached greater than $1.5 \times 10^6$ cells/mL, the culture was expanded into a 125 mL spinner flask in a 100 mL culture volume. The flask was incubated at 37° C., 7% $CO_2$. When the cell density reached greater than $1.5 \times 10^6$ cells/mL, the culture was expanded into a 250 mL spinner flask in 200 mL culture volume, and the flask was incubated at 37° C., 7% $CO_2$. When the cell density reached greater than $1.5 \times 10^6$ cells/mL, the culture was expanded into a 1 L spinner flask in 800 mL culture volume and incubated at 37° C., 7% $CO_2$. When the cell density reached greater than $1.5 \times 10^6$ cells/mL the culture was expanded into a 6 L spinner flask in 5000 mL culture volume and incubated at 37° C., 7% $CO_2$. When the cell density reached greater than $1.5 \times 10^6$ cells/mL the culture was expanded into a 36 L spinner flask in 32 L culture volume and incubated at 37° C., 7% $CO_2$.

A 400 L reactor was sterilized and 230 mL of CD CHO media was added. Before use, the reactor was checked for contamination. Approximately 30 L cells were transferred from the 36L spinner flasks to the 400 L bioreactor (Braun) at an inoculation density of $4.0 \times 10^5$ viable cells per mL and a total volume of 260L. Parameters were: temperature setpoint: 37° C.; impeller speed 40-55 rpm; vessel pressure: 3 psi; air sparge: 0.5-1.5 L/Min.; air overlay: 3 L/min. The reactor was sampled daily for cell counts, pH verification, media analysis, protein production and retention. Also, during the run nutrient feeds were added. At 120 hrs (day 5), 10.4 L of Feed #1 Medium (4×CD CHO+33 g/L glucose+160 mL/L GlutaMAX™-1mL/L yeastolate+33 mg/L rHuInsulin) was added. At 168 hours (day 7), 10.8 L of Feed #2 (2×CD CHO+33 g/L glucose+80 mL/L GlutaMAX™-1+167 mL/L yeastolate+0.92 g/L sodium butyrate) was added, and culture temperature was changed to 36.5° C. At 216 hours (day 9), 10.8 L of Feed #3 (1× CD CHO+50 g/L glucose+50 mL/L GlutaMAX™-1+250 mL/L yeastolate+1.80 g/L sodium butyrate) was added, and culture temperature was changed to 36° C. At 264 hours (day 11), 10.8 L of Feed #4 (1× CD CHO+33 g/L glucose+33 mL/L GlutaMAX™-1+250 mL/L yeastolate+0.92 g/L sodium butyrate) was added, and culture temperature was changed to 35.5° C. The addition of the feed media was observed to dramatically enhance the production of soluble rHuPH20 in the final stages of production. The reactor was harvested at 14 or 15 days or when the viability of the cells dropped below 40%. The process resulted in a final productivity of 17,000 Units/mL with a maximal cell density of 12 million cells/mL. At harvest, the culture was sampled for mycoplasma, bioburden, endotoxin and viral in vitro and in vivo, transmission electron microscopy (TEM) and enzyme activity.

The culture was pumped by a peristaltic pump through four Millistak filtration system modules (Millipore) in parallel, each containing a layer of diatomaceous earth graded to 4-8 µm and a layer of diatomaceous earth graded to 1.4-1.1 µm, followed by a cellulose membrane, then through a second single Millistak filtration system (Millipore) containing a layer of diatomaceous earth graded to 0.4-0.11 µm and a layer of diatomaceous earth graded to <0.1 µm, followed by a cellulose membrane, and then through a 0.22 µm final filter into a sterile single use flexible bag with a 350 L capacity. The harvested cell culture fluid was supplemented with 10 mM EDTA and 10 mM Tris to a pH of 7.5. The culture was concentrated 10× with a tangential flow filtration (TFF) apparatus using four Sartoslice TFF 30 kDa molecular weight cut-off (MWCO) polyether sulfone (PES) filter (Sartorious), followed by a 10× buffer exchange with 10 mM Tris, 20 mM $Na_2SO_4$, pH 7.5, into a 0.22 µm final filter into a 50 L sterile storage bag.

The concentrated, diafiltered harvest was inactivated for virus. Prior to viral inactivation, a solution of 10% Triton X-100, 3% tri-n-butyl phosphate (TNBP) was prepared. The concentrated, diafiltered harvest was exposed to 1% Triton X-100, 0.3% TNBP for 1 hour in a 36 L glass reaction vessel immediately prior to purification on the Q column.

E. Purification of Gen2 Soluble rHuPH20

A Q Sepharose (Pharmacia) ion exchange column (9 L resin, H=29 cm, D=20 cm) was prepared. Wash samples were collected for a determination of pH, conductivity and endotoxin (LAL) assay. The column was equilibrated with 5 column volumes of 10 mM Tris, 20 mM $Na_2SO_4$, pH 7.5. Following viral inactivation, the concentrated, diafiltered harvest was loaded onto the Q column at a flow rate of 100 cm/hr. The column was washed with 5 column volumes of 10 mM Tris, 20 mM $Na_2SO_4$, pH 7.5, and 10 mM Hepes, 50 mM NaCl, pH 7.0. The protein was eluted with 10 mM Hepes, 400 mM NaCl, pH 7.0, into a 0.22 µm final filter into sterile bag. The eluate sample was tested for bioburden, protein concentration and hyaluronidase activity. A280 absorbance readings were taken at the beginning and end of the exchange.

Phenyl Sepharose (Pharmacia) hydrophobic interaction chromatography was next performed. A Phenyl Sepharose (PS) column (19-21 L resin, H=29 cm, D=30 cm) was prepared. The wash was collected and sampled for pH, conductivity and endotoxin (LAL assay). The column was equilibrated with 5 column volumes of 5 mM potassium phosphate, 0.5 M ammonium sulfate, 0.1 mM $CaCl_2$, pH 7.0. The protein eluate from the Q Sepharose column was supplemented with 2M ammonium sulfate, 1 M potassium phosphate and 1 M $CaCl_2$ stock solutions to yield final concentrations of 5 mM, 0.5 M and 0.1 mM, respectively. The protein was loaded onto the PS column at a flow rate of 100 cm/hr and the column flow-through collected. The column was washed with 5 mM potassium phosphate, 0.5 M ammonium sulfate and 0.1 mM $CaCl_2$, pH 7.0, at 100 cm/hr and the wash was added to the collected flow-through. Combined with the column wash, the flow-through was passed through a 0.22 µm final filter into a sterile bag. The flow-through was sampled for bioburden, protein concentration and enzyme activity.

An aminophenyl boronate column (ProMetic) was prepared. The wash was collected and sampled for pH, conductivity and endotoxin (LAL assay). The column was equilibrated with 5 column volumes of 5 mM potassium phosphate, 0.5 M ammonium sulfate. The PS flow-through containing purified protein was loaded onto the aminophenyl boronate column at a flow rate of 100 cm/hr. The column was washed with 5 mM potassium phosphate, 0.5 M ammonium sulfate, pH 7.0. The column was washed with 20 mM bicine, 0.5 M ammonium sulfate, pH 9.0. The column was washed with 20 mM bicine, 100 mM NaCl, pH 9.0. The protein was eluted with 50 mM Hepes, 100 mM NaCl, pH 6.9, and passed through a sterile filter into a sterile bag. The eluted sample was tested for bioburden, protein concentration and enzyme activity.

The hydroxyapatite (HAP) column (Bio-Rad) was prepared. The wash was collected and tested for pH, conductivity and endotoxin (LAL assay). The column was equilibrated with 5 mM potassium phosphate, 100 mM NaCl, 0.1 mM $CaCl_2$, pH 7.0. The aminophenyl boronate-purified protein was supplemented to final concentrations of 5 mM potassium phosphate and 0.1 mM $CaCl_2$ and loaded onto the HAP column at a flow rate of 100 cm/hr. The column was washed with 5 mM potassium phosphate, pH 7.0, 100 mM NaCl, 0.1 mM $CaCl_2$. The column was next washed with 10 mM potassium phosphate, pH 7.0, 100 mM NaCl, 0.1 mM $CaCl_2$. The protein was eluted with 70 mM potassium phosphate, pH 7.0, and passed through a 0.24 µm sterile filter into a sterile bag. The eluted sample was tested for bioburden, protein concentration and enzyme activity.

The HAP-purified protein was then passed through a viral removal filter. The sterilized Viosart filter (Sartorius) was first prepared by washing with 2 L of 70 mM potassium phosphate, pH 7.0. Before use, the filtered buffer was sampled for pH and conductivity. The HAP-purified protein was pumped via a peristaltic pump through the 20 nM viral removal filter. The filtered protein in 70 mM potassium phosphate, pH 7.0, was passed through a 0.22 µm final filter into a sterile bag. The viral filtered sample was tested for protein concentration, enzyme activity, oligosaccharide, monosaccharide and sialic acid profiling. The sample also was tested for process-related impurities.

The protein in the filtrate was then concentrated to 10 mg/mL using a 10 kD molecular weight cut off (MWCO) Sartocon Slice tangential flow filtration (TFF) system (Sartorius). The filter was first prepared by washing with 10 mM histidine, 130 mM NaCl, pH 6.0, and the permeate was sampled for pH and conductivity. Following concentration, the concentrated protein was sampled and tested for protein concentration and enzyme activity. A 6× buffer exchange was performed on the concentrated protein into the final buffer: 10 mM histidine, 130 mM NaCl, pH 6.0. Following buffer exchange, the concentrated protein was passed though a 0.22 µm filter into a 20 L sterile storage bag. The protein was sampled and tested for protein concentration, enzyme activity, free sulfhydryl groups, oligosaccharide profiling and osmolarity.

The sterile filtered bulk protein was then aseptically dispensed at 20 mL into 30 mL sterile Teflon vials (Nalgene). The vials were then flash frozen and stored at −20±5° C.

F. Comparison of Production and Purification of Gen1 Soluble rHuPH20 and Gen2 Soluble rHuPH20

The production and purification of Gen2 soluble rHuPH20 in a 300L bioreactor cell culture contained some changes in the protocols compared to the production and purification of Gen1 soluble rHuPH20 in a 100 L bioreactor cell culture. Table 23 sets forth exemplary differences, in addition to simple scale-up changes, between the methods.

TABLE 23

Comparison of Gen1 and Gen2 methods

| Process Difference | Gen1 soluble rHuPH20 | Gen2 soluble rHuPH20 |
|---|---|---|
| Cell line | 3D35M | 2B2 |
| Media used to expand cell inoculum | Contains 0.10 µM methotrexate (0.045 mg/L) | Contains 20 µM methotrexate (9 mg/L) |
| Media in 6 L cultures onwards | Contains 0.10 µM methotrexate | Contains no methotrexate |
| 36 L spinner flask | No instrumentation 20 L operating volume | Equipped with instrumentation that monitors and controls pH, dissolved oxygen, sparge and overlay gas flow rate. 32 L operating volume |
| Final operating volume in bioreactor | Approx. 100 L in a 125 L bioreactor (initial culture volume + 65 L) | Approx. 300 L in a 400 L bioreactor (initial culture volume + 260 L) |
| Culture media in final bioreactor | No rHuInsulin | 5.0 mg/L rHuInsulin |
| Media feed volume | Scaled at 4% of the bioreactor cell culture volume i.e. 3.4, 3.5 and 3.7 L, resulting in a target bioreactor volume of ~92 L | Scaled at 4% of the bioreactor cell culture volume i.e. 10.4, 10.8, 11.2 and 11.7 L, resulting in a target bioreactor volume of ~303 L |
| Media feed | Feed #1 Medium: CD CHO + 50 g/L glucose + 8 mM GlutaMAX™-1 Feed #2 (CD CHO + 50 g/L glucose + 8 mM GlutaMAX™-1 + 1.1 g/L sodium butyrate Feed #3: CD CHO + 50 g/L glucose + 8 mM GlutaMAX™-1 + 1.1 g/L sodium butyrate | Feed #1 Medium: 4 × CD CHO + 33 g/L glucose + 32 mM GlutaMAX™-1 + 16.6 g/L yeastolate + 33 mg/L rHuInsulin Feed #2: 2 x CD CHO + 33 g/L glucose + 16 mM GlutaMAX™-1 + 33.4 g/L yeastolate + 0.92 g/L sodium butyrate Feed #3: 1 x CD CHO + 50 g/L glucose + 10 mM GlutaMAX™-1 + 50 g/L yeastolate + 1.80 g/L sodium butyrate Feed #4: 1 x CD CHO + 33 g/L glucose + 6.6 mM GlutaMAX™-1 + 50 g/L yeastolate + 0.92 g/L sodium butyrate |
| Filtration of bioreactor cell culture | Four polyethersulfone filters (8.0 µm, 0.65 µm, 0.22 µm and 0.22 µm) in series 100 L storage bag | $1^{st}$ stage - Four modules in parallel, each with a layer of diatomaceous earth graded to 4-8 µm and a layer of diatomaceous earth graded to 1.4-1.1 µm, followed by a cellulose membrane. $2^{nd}$ stage - single module containing a layer of diatomaceous earth graded to 0.4-0.11 µm and a layer of diatomaceous earth graded to <0.1 µm, followed by a cellulose membrane. $3^{rd}$ stage - 0.22 µm polyethersulfone filter 300 L storage bag Harvested cell culture is supplemented with 10 mM EDTA, 10 mM Tris to a pH of 7.5 |
| Concentration and buffer exchange prior to chromatography | Concentrate with 2 TFF with Millipore Spiral Polyethersulfone 30K MWCO Filter Buffer Exchange the Concentrate 6x with 10 mM Hepes, 25 mM NaCl, pH 7.0 20 L sterile storage bag | Concentrate using four Sartorius Sartoslice TFF 30K MWCO Filter Buffer Exchange the Concentrate 10x with 10 mM Tris, 20 mM Na$_2$SO$_4$, pH 7.5 50 L sterile storage bag |
| Viral inactivation prior to chromatography | None | Viral inactivation performed with the addition of a 1% |

TABLE 23-continued

Comparison of Gen1 and Gen2 methods

| Process Difference | Gen1 soluble rHuPH20 | Gen2 soluble rHuPH20 |
|---|---|---|
| 1st purification step (Q Sepharose) | No absorbance reading | Triton X-100, 0.3% tri-n-butyl phosphate, pH 7.5 A280 measurements at the beginning and end |
| Viral filtration after chromatography | Pall DV-20 filter (20 nm) | Sartorius Virosart filter (20 nm) |
| Concentration and buffer exchange after chromatography | Hepes/saline, pH 7.0 buffer Protein concentrated to 1 mg/mL | Histidine/saline, pH 6.0 buffer Protein concentrated to 10 mg/mL |

Example 4

Determination of Hyaluronidase Activity of Soluble rHuPH20 Using a Microturbidity Assay Hyaluronidase activity of soluble recombinant human PH20 (rHuPH20) in samples such as cell cultures, purification fractions and purified solutions was determined using a turbidometric assay, which is based on the formation of an insoluble precipitate when hyaluronic acid binds with serum albumin. The activity is measured by incubating soluble rHuPH20 with sodium hyaluronate (hyaluronic acid) for a set period of time (10 minutes) and then precipitating the undigested sodium hyaluronate with the addition of acidified serum albumin. The turbidity of the resulting sample is measured at 640 nm after a 30 minute development period. The decrease in turbidity resulting from enzyme activity on the sodium hyaluronate substrate is a measure of the soluble rHuPH20 hyaluronidase activity. The method is performed using a calibration curve generated with dilutions of a soluble rHuPH20 assay working reference standard, and sample activity measurements are made relative to this calibration curve.

Dilutions of the sample were prepared in Enzyme Diluent Solutions. The Enzyme Diluent Solution (EDS) was prepared by dissolving 33.0±0.05 mg of hydrolyzed gelatin in 25.0 mL of the 50 mM PIPES Reaction Buffer (140 mM NaCl, 50 mM PIPES, pH 5.5) and 25.0 mL of Sterile Water for Irrigation (SWFI), and diluting 0.2 mL of 25% human serum albumin solution into the mixture and vortexing for 30 seconds. This was performed within 2 hours of use and stored on ice until needed. The samples were diluted with EDS to an estimated 1-2 U/mL. Generally, the maximum dilution per step did not exceed 1:100 and the initial sample size for the first dilution was not less than 20 µL. The minimum sample volumes needed to perform the assay were: In-process Samples, FPLC Fractions: 80 µL; tissue culture supernatants:1 mL; concentrated material:80 µL; purified or final step material:80 µL. The dilutions were made in triplicate in a Low Protein Binding 96-well plate, and 30 µL of each dilution was transferred to Optilux black/clear bottom plates (BD BioSciences).

Dilutions of known soluble rHuPH20 with a concentration of 2.5 U/mL were prepared in Enzyme Diluent Solution to generate a standard curve and added to the Optilux plate in triplicate. The dilutions included 0 U/mL, 0.25 U/mL, 0.5 U/mL, 1.0 U/mL, 1.5 U/mL, 2.0 U/mL, and 2.5 U/mL. "Reagent blank" wells that contained 60 µL of Enzyme Diluent Solution were included in the plate as a negative control. The plate was then covered and warmed on a heat block for 5 minutes at 37° C. The cover was removed and the plate was shaken for 10 seconds. After shaking, the plate was returned to the heat block and the MULTIDROP 384 Liquid Handling Device was primed with the warm 0.25 mg/mL sodium hyaluronate solution (prepared by dissolving 100 mg of sodium hyaluronate (LifeCore Biomedical) in 20.0 mL of SWFI. This was mixed by gently rotating and/or rocking at 2-8° C. for 2-4 hours, or until completely dissolved. The substrate solution was prepared by mixing 9 mL SWFI, 10 mL PIPES and 1 mL of 5 mg/mL hyaluronate). The reaction plate was transferred to the MULTIDROP 384 and the reaction was initiated by pressing the start key to dispense 30 µL sodium hyaluronate substrate solution into each well. The plate was then removed from the MULTIDROP 384 and shaken for 10 seconds before being transferred to a heat block with the plate cover replaced. The plate was incubated at 37° C. for 10 minutes.

The MULTIDROP 384 was prepared to stop the reaction by priming the machine with serum working solution (25 mL of serum stock solution [1 volume of horse serum (Sigma) was diluted with 9 volumes of 500 mM acetate buffer solution, pH 4.3, and the pH was adjusted to 3.1 with hydrochloric acid] in 75 mL of 500 mM acetate buffer solution, pH 4.3) and changing the volume setting to 240 µL. The plate was removed from the heat block and placed onto the MULTIDROP 384 and 240 µL of serum working solution was dispensed into the wells. The plate was removed and shaken on a plate reader for 10 seconds. After a further 15 minutes, the turbidity of the samples was measured at 640 nm and the hyaluronidase activity (in U/mL) of each sample was determined by fitting to the standard curve.

Specific activity (Units/mg) was calculated by dividing the hyaluronidase activity (U/mL) by the protein concentration (mg/mL).

Example 5

Effect of Sodium Chloride on the Stability of rHuPH20

The rHuPH20 was in a solution at pH 6.5 containing 10 mg/mL in histidine/HCl and 130 mM sodium chloride (NaCl). As shown in Table 24, a total of 6 different formulations containing the following components were prepared: 25 mM Tris, pH 7.3, 100 µg/mL rHuPH20, 0.01% Tween 80 and NaCl (0, 50, 100, 150, 200 or 250 mM). The solutions were aliquotted into 2 mL type I glass vials with rubber stoppers and sealed with aluminum caps. One set of vials was stored at 40° C. for four days, and the other set was kept in the refrigerator at 2 to 8° C.

TABLE 24

Formulation of rHuPH20 with NaCl

| Formulation # | NaCl |
|---|---|
| 1 | 0 mM |
| 2 | 50 mM |
| 3 | 100 mM |
| 4 | 150 mM |
| 5 | 200 mM |
| 6 | 250 mM |

After 4 days of storage, each of the formulations mentioned in Table 24 was tested for hyaluronidase enzymatic activity using the microturbidity assay described in Example 4. Size exclusion chromatography (SEC) was performed to evaluate the level of aggregates using the following conditions: 1×PBS, Toso BioScience G2000 SWXL column, flow rate=1 mL/min.

Table 25 shows the results of the study, including hyaluronidase activity (U/mL), % main peak area (percentage of the rHuPH20 that was contained in the main peak area) and % aggregate peak area (percentage of rHuPH20 that was contained in the peak area attributed to aggregates) for each formulation. The results indicate that the stability of rHuPH20, when incubated at 40° C., was dependent on NaCl concentration: an increase in NaCl concentration led to increased enzymatic activity of rHuPH20. The samples stored at 2 to 8° C. retained similar levels of rHuPH20 enzymatic activity throughout the course of the study, regardless of the formulation. In the absence of NaCl at elevated temperatures (40° C.), the entire enzymatic activity of rHuPH20 was lost.

The results in Table 25 also show the effect of NaCl concentration on the aggregate levels of rHuPH20. Aggregate levels increased with decreasing NaCl concentration in samples stored at 40° C. There was essentially no change in the samples stored at 2 to 8° C.

Thus, the results show that within the NaCl concentration range tested (0-250 nM), there was a direct relationship between NaCl concentration and increased rHuPH20 stability, suggesting that the NaCl concentration be maintained as high as possible within solubility and tonicity limits in order to increase the stability of rHuPH20 at elevated temperature.

TABLE 25

Enzymatic activities and SEC results of the samples stored 4 days at 40° C. and 28° C.

| Formulation | Enzymatic Activity | | % Main Peak | | % Aggregate Peak | |
|---|---|---|---|---|---|---|
| | 2-8° C. | 40° C. | 2-8° C. | 40° C. | 2-8° C. | 40° C. |
| 0 mM NaCl | 10430 | <LOD | 99.40 | 0.00 | 0.60 | 100.00 |
| 50 mM NaCl | 12370 | 3070 | 99.34 | 22.05 | 0.66 | 77.95 |
| 100 mM NaCl | 12580 | 9930 | 99.47 | 72.81 | 0.53 | 27.19 |
| 150 mM NaCl | 12750 | 11180 | 99.48 | 88.16 | 0.52 | 11.84 |
| 200 mM NaCl | 13660 | 13340 | 99.64 | 96.22 | 0.36 | 3.78 |
| 250 mM NaCl | 11370 | 11090 | 100.00 | 98.05 | 0.00 | 1.95 |

Example 6

Stability of Co-Formulated rHuPH20 and IG

A. Stability of Co-Formulated 10% IG or 20% IG with rHuPH20 rHuPH20 was formulated as follows: 1 mL contained 1048071 units of recombinant human hyaluronidase from lot HUB0702CA (generated using Gen2 production described in Example 3) in 10 mM histidine and 130 mM sodium chloride (NaCl) at pH 6.0. rHuPH20 was diluted to 100000 U/mL using 10 mM histidine+130 mM NaCl, pH 6.0, prior to mixing with immunoglobulin. For this purpose, 200 μL of rHuPH20 stock solution was diluted with 1896 μL of histidine/NaCl buffer, pH 6.0.

The pre-diluted rHuPH20 was added to different IG formulations formulated in 0.25 M glycine at pH 4.4 to 4.9 to give final concentrations of 100 U/mL or 300 U/mL in the solution. One of three different 10% IG lots from large scale manufacturing (LE12H020, LE12H062, and LE12H173) or one of three different pre-clinical 20% IG lots (SC00107NG, SC00207NG, and SC00307NG) was utilized according to Table 26. The solutions were filtered through a 0.2 μm filter and transferred in 1 mL portions into sterile 5 mL glass vials. The vials were stored at 2 to 8° C. or 28 to 32° C. Hence, the resulting co-formulations of rHuPH20 and IG were formulated in 0.25 M glycine at pH 4.4 to 4.9.

TABLE 26

Co-formulations of rHuPH20 and 10% IG or 20% IG

| Sample name | Amount of 10% IG or 20% IG | Amount of rHuPH20 diluted to 100000 U/mL |
|---|---|---|
| 10% IG | 50.00 mL | 0 |
| 10% IG + 100 U/mL rHuPH20 | 49.95 mL | 50 μL |
| 10% IG + 300 U/mL rHuPH20 | 49.85 mL | 150 μL |
| 20% IG | 50.00 mL | 0 |
| 20% IG + 100 U/mL rHuPH20 | 49.95 mL | 50 μL |
| 20% IG + 300 U/mL rHuPH20 | 49.85 mL | 150 μL |

After 0 (start), 1, 3, 6, 12, 24 and 36 weeks (2 to 8° C. only) of storage, one sample from each of the 6 formulations mentioned in Table 26 and from each of the storage chambers (2 to 8° C. and 28 to 32° C.) was withdrawn from the incubation and analyzed for hyaluronidase activity using the microturbidity assay described in Example 4. To assess effects on IG, molecular size distribution of the IG in formulations containing 20% IG was determined at 0 (start) and 6 months by high performance size exclusion chromatography (HP-SEC) using a TSK G 3000 SW 600×7.5 mm column (Tosoh Bioscience) and a DMSO-containing buffer system (Kolarich et al. (2006) *Transfusion*, 46:1959-1977).

Table 27 shows hyaluronidase activity (U/mL) at 7 time points (0, 1, 3, 6, 12, 24 and 36 weeks) for each co-formulation stored at 2 to 8° C. Table 28 shows hyaluronidase activity (U/mL) at 6 time points (0, 1, 3, 6, 12 and 2 weeks) for the co-formulations stored at 28 to 32° C. A significant, steady loss of hyaluronidase activity was observed in the presence of 10% and 20% IG co-formulations stored at 28 to 32° C. after 24 weeks, indicating rHuPH20 instability. The 10% IG co-formulations were stable after 9 months of storage at 2 to 8° C., while the rHuPH20 activity slightly decreased in the 20% IG co-formulations. The molecular size distribution of the IG in formulations containing 20% IG was unchanged at both temperatures after 6 months of storage (Tables 29 and 30).

TABLE 27

Hyaluronidase activity (U/mL) of co-formulations after storage at 2-8° C.

| | Weeks | | | | | | |
|---|---|---|---|---|---|---|---|
| Sample | 0 (start) | 1 | 3 | 6 | 12 | 24 | 36 |
| LE12H020 + 100 U/mL | 99.2 | 95.4 | 97.3 | 101 | 93 | 92 | 98 |
| LE12H020 + 300 U/mL | 298.5 | 321.7 | 285.9 | 299 | 283 | 271 | 291 |
| LE12H062 + 100 U/mL | 108.5 | 97.5 | 99.6 | 103 | 99 | 92 | 102 |

TABLE 27-continued

Hyaluronidase activity (U/mL) of co-formulations after storage at 2-8° C.

| Sample | 0 (start) | 1 | 3 | 6 | 12 | 24 | 36 |
|---|---|---|---|---|---|---|---|
| LE12H062 + 300 U/mL | 325 | 306.8 | 297.9 | 302 | 273 | 279 | 300 |
| LE12H173 + 100 U/mL | 103.1 | 95.9 | 97.3 | 107 | 98 | 99 | 106 |
| LE12H173 + 300 U/mL | 295.0 | 291.2 | 281.8 | 293 | 282 | 296 | 292 |
| SC00107NG + 100 U/mL | 94.0 | 97.8 | 81.4 | 85 | 87 | 78 | 66 |
| SC00107NG + 300 U/mL | 284.3 | 280.2 | 264.0 | 261 | 245 | 223 | 210 |
| SC00207NG + 100 U/mL | 99.7 | 93.1 | 91.0 | 86 | 83 | 84 | 69 |
| SC00207NG + 300 U/mL | 286 | 277 | 266.2 | 244 | 263 | 227 | 197 |
| SC00307NG + 100 U/mL | 92.8 | 95.0 | 82.7 | 87 | 83 | 82 | 68 |
| SC00307NG + 300 U/mL | 254.3 | 281.4 | 274.3 | 245 | 247 | 230 | 256 |

TABLE 28

Hyaluronidase activity (U/mL) of co-formulations after storage at 28-32° C.

| Sample | 0 (start) | 1 | 3 | 6 | 12 | 24 |
|---|---|---|---|---|---|---|
| LE12H020 + 100 U/mL | 99.2 | 84.9 | 59.6 | 36 | 22 | 5 |
| LE12H020 + 300 U/mL | 298.5 | 259.3 | 185.4 | 104 | 57 | 19 |
| LE12H062 + 100 U/mL | 108.5 | 88.2 | 60.1 | 43 | 29 | 10 |
| LE12H062 + 300 U/mL | 325 | 266.2 | 185.6 | 129 | 76 | 28 |
| LE12H173 + 100 U/mL | 103.1 | 70.5 | 39.6 | 24 | 13 | 1 |
| LE12H173 + 300 U/mL | 295.0 | 210.1 | 122.0 | 60 | 31 | 9 |
| SC00107NG + 100 U/mL | 94.0 | 83.1 | 57.4 | 43 | 49 | 32 |
| SC00107NG + 300 U/mL | 284.3 | 242.2 | 182.0 | 124 | 148 | 96 |
| SC00207NG + 100 U/mL | 99.7 | 84.5 | 61.1 | 46 | 51 | 35 |
| SC00207NG + 300 U/mL | 286 | 251 | 198.1 | 131 | 145 | 106 |
| SC00307NG + 100 U/mL | 92.8 | 82.7 | 67.9 | 48 | 52 | 34 |
| SC00307NG + 300 U/mL | 254.3 | 253.6 | 209.7 | 140 | 157 | 106 |

TABLE 29

Molecular size distribution of IG in 20% IG co-formulated with rHuPH20 after storage at 2-8° C.

| | 0 (start) | | | | 6 months | | | |
|---|---|---|---|---|---|---|---|---|
| Sample | >450 kDa | ~350 kDa | ~160 kDa | <60 kDa | >450 kDa | ~350 kDa | ~160 kDa | <60 kDa |
| SC00107NG | 0.67 | 12.56 | 86.50 | 0.27 | 0.70 | 13.50 | 85.50 | 0.30 |
| SC00107NG + 100 U/mL rHuPH20 | 0.62 | 12.39 | 86.75 | 0.24 | 0.70 | 13.59 | 85.43 | 0.28 |
| SC00107NG + 300 U/mL rHuPH20 | 0.65 | 12.38 | 86.70 | 0.26 | 0.69 | 13.80 | 85.19 | 0.32 |
| SC00207NG | 0.73 | 13.25 | 85.76 | 0.26 | 0.86 | 14.52 | 84.34 | 0.28 |
| SC00207NG + 100 U/mL rHuPH20 | 0.75 | 13.22 | 85.74 | 0.29 | 0.86 | 14.61 | 84.21 | 0.32 |
| SC00207NG + 300 U/mL rHuPH20 | 0.77 | 13.39 | 85.63 | 0.21 | 0.83 | 14.57 | 84.30 | 0.30 |
| SC00307NG | 0.93 | 11.76 | 87.06 | 0.25 | 1.01 | 12.78 | 85.96 | 0.25 |
| SC00307NG + 100 U/mL rHuPH20 | 0.96 | 11.91 | 86.94 | 0.20 | 1.03 | 13.04 | 85.62 | 0.31 |
| SC00307NG + 300 U/mL rHuPH20 | 0.91 | 12.00 | 86.86 | 0.23 | 0.99 | 12.88 | 85.85 | 0.27 |

TABLE 30

Molecular size distribution of IG in 20% IG co-formulated with rHuPH20 after storage at 28-32° C.

| | 0 (start) | | | | 6 months | | | |
|---|---|---|---|---|---|---|---|---|
| Sample | >450 kDa | ~350 kDa | ~160 kDa | <60 kDa | >450 kDa | ~350 kDa | ~160 kDa | <60 kDa |
| SC00107NG | 0.67 | 12.56 | 86.50 | 0.27 | 0.50 | 12.53 | 85.94 | 1.02 |
| SC00107NG + 100 U/mL rHuPH20 | 0.62 | 12.39 | 86.75 | 0.24 | 0.47 | 12.41 | 86.10 | 1.02 |
| SC00107NG + 300 U/mL rHuPH20 | 0.65 | 12.38 | 86.70 | 0.26 | 0.52 | 12.41 | 85.97 | 1.09 |
| SC00207NG | 0.73 | 13.25 | 85.76 | 0.26 | 0.44 | 13.21 | 85.42 | 0.94 |

TABLE 30-continued

Molecular size distribution of IG in 20% IG co-formulated with rHuPH20 after storage at 28-32° C.

| Sample | 0 (start) | | | | 6 months | | | |
|---|---|---|---|---|---|---|---|---|
| | >450 kDa | ~350 kDa | ~160 kDa | <60 kDa | >450 kDa | ~350 kDa | ~160 kDa | <60 kDa |
| SC00207NG + 100 U/mL rHuPH20 | 0.75 | 13.22 | 85.74 | 0.29 | 0.42 | 13.15 | 85.52 | 0.91 |
| SC00207NG + 300 U/mL rHuPH20 | 0.77 | 13.39 | 85.63 | 0.21 | 0.47 | 13.01 | 85.62 | 0.90 |
| SC00307NG | 0.93 | 11.76 | 87.06 | 0.25 | 0.47 | 11.91 | 86.78 | 0.84 |
| SC00307NG + 100 U/mL rHuPH20 | 0.96 | 11.91 | 86.94 | 0.20 | 0.50 | 11.85 | 86.78 | 0.87 |
| SC00307NG + 300 U/mL rHuPH20 | 0.91 | 12.00 | 86.86 | 0.23 | 0.40 | 11.50 | 87.21 | 0.89 |

B. Stability of Co-Formulated 10% IG with rHuPH20 and Sodium Chloride (0-150 mM)

To improve rHuPH20 stability in the co-formulations, the effect of sodium chloride (NaCl) addition was investigated. Co-formulations of 300 U/mL rHuPH20 (lot HUB0702CA; generated using Gen2 production described in Example 3) in 10% IG (lot LE12F047) were prepared as described in Example 7A above, with the addition of NaCl at 4 different concentrations (0, 50, 100 and 150 mM). The co-formulations were stored at 2 to 8° C. or 28 to 32° C. Thus, the resulting co-formulations of rHuPH20 and IG were formulated in 0.25 M glycine at pH 4.6 to 5.1 (as measured in the diluted solution) in the presence of varying amounts of NaCl.

After 0 (start), 1, 3, 6, 12, 18 and 24 weeks of storage, one sample from each of the co-formulations (with NaCl concentrations of 0, 50, 100, and 150 mM) and from each of the storage chambers (2 to 8° C. and 28 to 32° C.) was withdrawn from the incubation and analyzed for hyaluronidase activity using the microturbidity assay described in Example 4. Aggregation of IG was determined by molecular size distribution (MSD) by high performance size exclusion chromatography (HP-SEC) using a TSK G 3000 SW 600×7.5 mm column and a DMSO-containing buffer system (Kolarich et al. (2006) *Transfusion*, 46:1959-1977).

Tables 31 and 32 show hyaluronidase activity (U/mL) at 7 time points (0, 1, 3, 6, 12, 18 and 24 weeks) for each co-formulation. The results show that the stability of rHuPH20 co-formulated with 10% IG in the presence of 50, 100 or 150 mM NaCl remained unchanged for up to 24 weeks of storage at 2 to 8° C., while the rHuPH20 stability improved for those samples stored at 28 to 32° C. However, hyaluronidase activity rapidly decreased in the co-formulations having a NaCl concentration of 0 mM when stored at 28 to 32° C.

Tables 33 and 34 show that NaCl slightly enhanced IG dimerization (~350 kDa) at both storage temperatures and IG aggregation (>450 kDa) at 28 to 32° C., and all values remain within the MSD specification limits (≥90% monomer/dimers, ≤5% aggregates, ≤5% fragments) after 6 months.

Although the addition of NaCl negatively impacted (increased) the anticomplementary activity (ACA) titer of IG formulations stored at 28 to 32° C., ACA titer is a specification indicator for intravenous (IV) administration and is not relevant for subcutaneous administration of the co-formulations.

TABLE 31

Hyaluronidase activity (U/mL) of 10% IG/rHuPH20 co-formulations with NaCl after storage at 2-8° C.

| Salt Conc. | Weeks | | | | | | | |
|---|---|---|---|---|---|---|---|---|
| | 0 (start) | 1 | 2 | 3 | 6 | 12 | 18 | 24 |
| 0 mM NaCl | 276 | 288 | 269 | 289 | 317 | 264 | 276 | 274 |
| 50 mM | 292 | 286 | 296 | 306 | 320 | 287 | 276 | 295 |
| 100 mM | 285 | 295 | 273 | 315 | 319 | 287 | 281 | 288 |
| 150 mM | 294 | 280 | 301 | 305 | 327 | 294 | 277 | 298 |

TABLE 32

Hyaluronidase activity (U/mL) of 10% IG/rHuPH20 co-formulations with NaCl after storage at 28-32° C.

| Salt Conc. | Weeks | | | | | | | |
|---|---|---|---|---|---|---|---|---|
| | 0 (start) | 1 | 2 | 3 | 6 | 12 | 18 | 24 |
| 0 mM | 276 | 232 | 237 | 216 | 201 | 121 | 109 | 81 |
| 50 mM | 292 | 288 | 280 | 301 | 302 | 247 | 225 | 223 |
| 100 mM | 285 | 286 | 280 | 292 | 315 | 277 | 253 | 258 |
| 150 mM | 294 | 314 | 272 | 298 | 323 | 221 | 253 | 276 |

TABLE 33

Molecular size distribution of IG in 10% IG/rHuPH20 co-formulations with NaCl after storage at 2-8° C.

| Sample | 0 (start) | | | | 6 months | | | |
|---|---|---|---|---|---|---|---|---|
| | >450 kDa | ~350 kDa | ~160 kDa | <60 kDa | >450 kDa | ~350 kDa | ~160 kDa | <60 kDa |
| 0 mM NaCl | 0.16 | 8.21 | 91.01 | 0.61 | 0.16 | 11.29 | 87.98 | 0.58 |
| 50 mM NaCl | 0.17 | 8.99 | 90.24 | 0.60 | 0.22 | 12.54 | 86.62 | 0.62 |
| 100 mM NaCl | 0.19 | 9.03 | 90.13 | 0.64 | 0.23 | 12.97 | 86.17 | 0.63 |
| 150 mM NaCl | 0.19 | 9.08 | 90.13 | 0.61 | 0.24 | 12.93 | 86.30 | 0.53 |

TABLE 34

Molecular size distribution of IG in 10% IG/rHuPH20 co-formulations with NaCl after storage at 28-32° C.

| | 0 (start) | | | | 6 months | | | |
|---|---|---|---|---|---|---|---|---|
| Sample | >450 kDa | ~350 kDa | ~160 kDa | <60 kDa | >450 kDa | ~350 kDa | ~160 kDa | <60 kDa |
| 0 mM NaCl | 0.16 | 8.21 | 91.01 | 0.61 | 0.35 | 9.37 | 88.77 | 1.51 |
| 50 mM NaCl | 0.17 | 8.99 | 90.24 | 0.60 | 0.75 | 10.83 | 86.85 | 1.57 |
| 100 mM NaCl | 0.19 | 9.03 | 90.13 | 0.64 | 0.87 | 11.20 | 86.38 | 1.55 |
| 150 mM NaCl | 0.19 | 9.08 | 90.13 | 0.61 | 1.02 | 11.15 | 86.18 | 1.66 |

C. Stability of Co-Formulated 10% IG or 20% IG with rHuPH20 and Sodium Chloride (0-50 mM)

The effect of sodium chloride addition to co-formulations of 10% IG or 20% IG with rHuPH20 stored at 28 to 32° C. was investigated. Co-formulations of 300 U/mL rHuPH20 (lot HUB0702CA; generated using Gen2 production described in Example 1) in 10% IG (lot LE12F047) and 300 U/mL rHuPH20 (lot HUB0702CA; generated using Gen2 production described in Example 1) in 20% IG (lot SC00108NG) were prepared as described in Example 6B above, using NaCl concentrations of 0, 5, 10, 20, 30, 40 and 50 mM. Thus, the resulting co-formulations of rHuPH20 and IG were formulated in 0.25 M glycine at pH 4.6 to 5.1 (as measured in the diluted solution) in the presence of varying amounts of NaCl.

After 0 (start), 1, 3, 6, 12 and 24 weeks of storage one sample from each of the co-formulations (with NaCl concentrations of 0, 5, 10, 20, 30, 40 and 50 mM) was withdrawn from the incubation and analyzed for hyaluronidase activity using the microturbidity assay described in Example 4. IG aggregation was determined by molecular size distribution by high performance size exclusion chromatography (HP-SEC) using a TSK G 3000 SW 600×7.5 mm column and a DMSO containing buffer system.

Tables 35 and 36 show hyaluronidase activity (U/mL) at various time points (0, 1, 3, 6 and 12 and 24 weeks) for each co-formulation. The results show that the stability of rHuPH20 co-formulated with 10% IG in the presence of higher NaCl concentrations (20, 30, 40 and 50 mM) remained relatively unchanged through 24 weeks of storage at 28 to 32° C. Hyaluronidase activity rapidly decreased in the co-formulations having a NaCl concentration of less than 20 mM when stored at 28 to 32° C. The stability of rHuPH20 co-formulated with 20% IG remained relatively unchanged through 24 weeks of storage at 28 to 32° C. at all NaCl concentrations.

Sodium chloride slightly enhanced IG dimerization (~350 kDa) and aggregation in both 10% and 20% IG co-formulations at 28 to 32° C. The effect is less pronounced in 20% IG (i.e., higher IG concentration) on IG aggregation (Tables 37 and 38).

TABLE 35

Hyaluronidase activity (U/mL) of 10% IG/rHuPH20 co-formulations with NaCl after storage at 28-32° C.

| Salt Concentration | Weeks | | | | | |
|---|---|---|---|---|---|---|
| | 0 | 1 | 3 | 6 | 12 | 24 |
| 0 mM | 292 | 260 | 225 | 211 | 135 | <87 |
| 5 mM | 294 | 247 | 242 | 225 | 162 | <87 |
| 10 mM | 272 | 255 | 242 | 240 | 177 | 91 |
| 20 mM | 281 | 302 | 261 | 259 | 232 | 154 |
| 30 mM | 279 | 273 | 256 | 261 | 229 | 180 |
| 40 mM | 274 | 254 | 266 | 275 | 246 | 196 |
| 50 mM | 275 | 254 | 278 | 281 | 252 | 200 |

TABLE 36

Hyaluronidase activity (U/mL) of 20% IG/rHuPH20 co-formulations with NaCl after storage at 28-32° C.

| Salt Concentration | Weeks | | | | | |
|---|---|---|---|---|---|---|
| | 0 | 1 | 3 | 6 | 12 | 24 |
| 0 mM | 267 | 264 | 251 | 238 | 212 | 138 |
| 5 mM | 290 | 261 | 249 | 242 | 214 | 143 |
| 10 mM | 276 | 264 | 262 | 232 | 207 | 141 |
| 20 mM | 314 | 249 | 274 | 239 | 222 | 155 |
| 30 mM | 252 | 253 | 276 | 241 | 211 | 162 |
| 40 mM | 273 | 240 | 275 | 242 | 216 | 170 |
| 50 mM | 289 | 238 | 266 | 234 | 232 | 165 |

TABLE 37

Molecular size distribution of IG in 10% IG/rHuPH20 co-formulations with NaCl after storage at 28-32° C.

| | 0 (start) | | | | 6 months | | | |
|---|---|---|---|---|---|---|---|---|
| Sample | >450 kDa | ~350 kDa | ~160 kDa | <60 kDa | >450 kDa | ~350 kDa | ~160 kDa | <60 kDa |
| 0 mM NaCl | 0.16 | 9.35 | 90.01 | 0.48 | 0.19 | 7.08 | 91.69 | 1.04 |
| 5 mM NaCl | 0.16 | 9.53 | 89.71 | 0.60 | 0.21 | 7.66 | 91.11 | 1.02 |

TABLE 37-continued

Molecular size distribution of IG in 10% IG/rHuPH20 co-formulations with NaCl after storage at 28-32° C.

| Sample | 0 (start) | | | | 6 months | | | |
|---|---|---|---|---|---|---|---|---|
| | >450 kDa | ~350 kDa | ~160 kDa | <60 kDa | >450 kDa | ~350 kDa | ~160 kDa | <60 kDa |
| 10 mM NaCl | 0.16 | 9.77 | 89.52 | 0.56 | 0.22 | 8.20 | 90.52 | 1.05 |
| 20 mM NaCl | 0.17 | 9.96 | 89.27 | 0.60 | 0.26 | 8.42 | 90.27 | 1.05 |
| 30 mM NaCl | 0.17 | 10.25 | 89.06 | 0.53 | 0.30 | 9.07 | 89.59 | 1.04 |
| 40 mM NaCl | 0.17 | 10.48 | 88.82 | 0.53 | 0.34 | 9.06 | 89.56 | 1.05 |
| 50 mM NaCl | 0.18 | 10.55 | 88.72 | 0.54 | 0.39 | 9.22 | 89.33 | 1.07 |

TABLE 38

Molecular size distribution of IG in 20% IG/rHuPH20 co-formulations with NaCl after storage at 28-32° C.

| Sample | 0 (start) | | | | 6 months | | | |
|---|---|---|---|---|---|---|---|---|
| | >450 kDa | ~350 kDa | ~160 kDa | <60 kDa | >450 kDa | ~350 kDa | ~160 kDa | <60 kDa |
| 0 mM NaCl | 0.32 | 14.65 | 84.72 | 0.31 | 0.34 | 11.77 | 87.18 | 0.71 |
| 5 mM NaCl | 0.32 | 14.70 | 84.70 | 0.27 | 0.34 | 11.57 | 87.35 | 0.74 |
| 10 mM NaCl | 0.35 | 14.86 | 84.48 | 0.31 | 0.35 | 12.05 | 86.94 | 0.67 |
| 20 mM NaCl | 0.30 | 14.95 | 84.48 | 0.27 | 0.37 | 12.17 | 86.76 | 0.69 |
| 30 mM NaCl | 0.32 | 15.12 | 84.29 | 0.27 | 0.40 | 12.60 | 86.32 | 0.68 |
| 40 mM NaCl | 0.32 | 14.92 | 84.48 | 0.27 | 0.47 | 12.68 | 86.16 | 0.69 |
| 50 mM NaCl | 0.33 | 15.00 | 84.36 | 0.30 | 0.45 | 12.56 | 86.34 | 0.65 |

D. Stability of rHuPH20 in Co-Formulations with 10% IG or 20% IG in the Presence of Sodium Chloride (100-250 mM) or Amino Acids (500 mM)

The effect on rHuPH20 stability of co-formulations containing 10% IG or 20% IG with rHuPH20 and sodium chloride or amino acid stabilizers was studied. Co-formulations of 100 U/mL or 300 U/mL rHuPH20 (lot HUB0702CA; generated using Gen2 production described in Example 3) in 10% IG (with 0.25 M glycine at pH 4.4) (lot LE12F047) or 20% IG (lot SC00108NG) were prepared as described in Example 6A above. Samples contained either NaCl (concentrations of 100, 150 or 250 mM), glycine (500 mM) or proline (500 mM). The co-formulations were stored at 2 to 8° C. or 28 to 32° C. Thus, the resulting co-formulations of rHuPH20 and IG were formulated in 0.25 M glycine at pH 4.6 to 5.1 in the presence of varying amounts of NaCl, glycine or proline.

After 0 (start), 1, 2, 3, 6 and 12 (300 U/mL only) weeks of storage, one sample from each of the co-formulations (with either NaCl concentrations of 100, 150 or 250 mM, glycine concentration of 500 mM or proline concentration of 500 mM) was withdrawn from the incubation and analyzed for hyaluronidase activity using the microturbidity assay described in Example 4. Aggregation of IG was determined by molecular size distribution at 0 (start) and 12 weeks by high performance size exclusion chromatography (HP-SEC) using a TSK G 3000 SW 600×7.5 mm column and a DMSO-containing buffer system (Kolarich et al. (2006) *Transfusion*, 46:1959-1977).

Tables 39 and 41 show hyaluronidase activity (U/mL) at 5 time points (0, 1, 2, 3 and 6 weeks) for co-formulations containing 100 U/mL rHuPH20 and 10% or 20% IG, respectively. Tables 40 and 42 show hyaluronidase activity (U/mL) at 6 time points (0, 1, 2, 3, 6 and 12 weeks) for co-formulations containing 300 U/mL rHuPH20 and 10% or 20% IG, respectively. The results show that high amino acid concentrations (500 mM glycine or 500 mM proline) were less effective then NaCl in stabilizing rHuPH20 in 10% IG or 20% IG co-formulations with rHuPH20.

Sodium chloride, at all concentrations studied, enhanced IG aggregation (>450 kDa) after storage at 28 to 32° C. in all co-formulations. All co-formulations containing 500 mM proline have a reduced IG dimer content (~350 kDa) and an increased monomer content (~160 kDa) after 6 weeks of storage at 28 to 32° C. IG dimer content was also reduced in co-formulations with glycine, though not as pronounced as in the proline co-formulations (Tables 43 and 44). High concentrations of proline have proven to be effective at inhibiting protein aggregation during refolding by effectively blocking non-specific hydrophobic interactions between proteins (Kumar et al. (1998) *Biochem. Mol. Biol. Int.* 4:59-517).

TABLE 39

Hyaluronidase activity (U/mL) of 10% IG and 100 U/mL rHuPH20 co-formulations with stabilizers after storage at 28-32° C.

| Stabilizer Concentration | Weeks | | | | | |
|---|---|---|---|---|---|---|
| | 0 (start) | 1 | 2 | 3 | 6 | 12 |
| 100 mM NaCl | 97 | 97 | 88 | 99 | 85 | 84 |
| 150 mM NaCl | 99 | 91 | 102 | 93 | 94 | 85 |
| 250 mM NaCl | 89 | 105 | 93 | 88 | 91 | 89 |
| 500 mM glycine | 94 | 105 | 85 | 84 | 77 | 56 |
| 500 mM proline | 88 | 96 | 83 | 80 | 88 | 59 |

TABLE 40

Hyaluronidase activity (U/mL) of 10% IG and 300 U/mL rHuPH20 co-formulations with stabilizers after storage at 28-32° C.

| Stabilizer Concentration | Weeks | | | | | |
|---|---|---|---|---|---|---|
| | 0 (start) | 1 | 2 | 3 | 6 | 12 |
| 100 mM NaCl | 294 | 303 | 284 | 266 | 260 | 233 |
| 150 mM NaCl | 301 | 282 | 280 | 272 | 288 | 246 |
| 250 mM NaCl | 280 | 290 | 275 | 278 | 255 | 250 |
| 500 mM glycine | 254 | 296 | 246 | 256 | 229 | 194 |
| 500 mM proline | 242 | 304 | 266 | 244 | 226 | 204 |

TABLE 41

Hyaluronidase activity (U/mL) of 20% IG and 100 U/mL rHuPH20 co-formulations with stabilizers after storage at 28-32° C.

| Stabilizer Concentration | Weeks | | | | | |
|---|---|---|---|---|---|---|
| | 0 (start) | 1 | 2 | 3 | 6 | 12 |
| 100 mM NaCl | 268 | 313 | 262 | 256 | 223 | 214 |
| 150 mM NaCl | 252 | 292 | 249 | 260 | 232 | 202 |
| 250 mM NaCl | 262 | 302 | 270 | 254 | 236 | 213 |
| 500 mM glycine | 285 | 286 | 291 | 244 | 221 | 191 |
| 500 mM proline | 308 | 303 | 242 | 248 | 230 | 197 |

TABLE 42

Hyaluronidase activity (U/mL) of 20% IG and 300 U/mL rHuPH20 co-formulations with stabilizers after storage at 28-32° C.

| Stabilizer Concentration | Weeks | | | | | |
|---|---|---|---|---|---|---|
| | 0 (start) | 1 | 2 | 3 | 6 | 12 |
| 100 mM NaCl | 268 | 266 | 264 | 226 | 237 | 255 |
| 150 mM NaCl | 252 | 256 | 270 | 220 | 231 | 261 |
| 250 mM NaCl | 262 | 243 | 273 | 246 | 243 | 273 |
| 500 mM glycine | 285 | 257 | 289 | 211 | 230 | 267 |
| 500 mM proline | 308 | 257 | 268 | 231 | 229 | 259 |

TABLE 43

Molecular size distribution of IG in 10% IG/rHuPH20 co-formulations with NaCl, glycine or proline after storage at 28-32° C.

| Sample | 0 (start) | | | | 6 months | | | |
|---|---|---|---|---|---|---|---|---|
| | >450 kDa | ~350 kDa | ~160 kDa | <60 kDa | >450 kDa | ~350 kDa | ~160 kDa | <60 kDa |
| 10% IG + 100 U/mL rHuPH20 + 250 mM NaCl | 0.15 | 10.92 | 88.35 | 0.59 | 0.50 | 9.58 | 89.13 | 0.80 |
| 10% IG + 300 U/mL rHuPH20 + 250 mM NaCl | 0.14 | 11.05 | 88.27 | 0.54 | 0.46 | 9.59 | 89.11 | 0.84 |
| 10% IG + 100 U/mL rHuPH20 + 150 mM NaCl | 0.14 | 11.07 | 88.15 | 0.65 | 0.45 | 9.71 | 88.97 | 0.87 |
| 10% IG + 300 U/mL rHuPH20 + 150 mM NaCl | 0.14 | 11.42 | 87.82 | 0.62 | 0.45 | 9.76 | 89.09 | 0.70 |
| 10% IG + 100 U/mL rHuPH20 + 100 mM NaCl | 0.18 | 11.29 | 87.91 | 0.63 | 0.38 | 9.36 | 89.53 | 0.74 |
| 10% IG + 300 U/mL rHuPH20 + 100 mM NaCl | 0.13 | 11.43 | 87.89 | 0.55 | 0.38 | 9.32 | 89.52 | 0.78 |
| 10% IG + 100 U/mL rHuPH20 + 500 mM glycine | 0.16 | 10.67 | 88.55 | 0.62 | 0.12 | 8.12 | 90.92 | 0.84 |
| 10% IG + 300 U/mL rHuPH20 + 100 mM glycine | 0.16 | 10.80 | 88.43 | 0.61 | 0.16 | 8.17 | 90.95 | 0.73 |
| 10% IG + 100 U/mL rHuPH20 + 500 mM proline | 0.14 | 9.55 | 89.75 | 0.56 | 0.11 | 5.53 | 93.58 | 0.78 |
| 10% IG + 300 U/mL rHuPH20 + 100 mM proline | 0.14 | 9.43 | 89.86 | 0.57 | 0.12 | 5.65 | 93.52 | 0.71 |

TABLE 44

Molecular size distribution of IG in 20% IG/rHuPH20 co-formulations with NaCl, glycine or proline after storage at 28-32° C.

| | 0 (start) | | | | 6 months | | | |
|---|---|---|---|---|---|---|---|---|
| Sample | >450 kDa | ~350 kDa | ~160 kDa | <60 kDa | >450 kDa | ~350 kDa | ~160 kDa | <60 kDa |
| 20% IG + 100 U/mL rHuPH20 + 250 mM NaCl | 0.25 | 15.03 | 84.28 | 0.44 | 0.48 | 12.55 | 86.37 | 0.60 |
| 20% IG + 300 U/mL rHuPH20 + 250 mM NaCl | 0.26 | 15.12 | 84.16 | 0.46 | 0.51 | 12.53 | 86.36 | 0.59 |
| 20% IG + 100 U/mL rHuPH20 + 150 mM NaCl | 0.26 | 15.32 | 83.97 | 0.45 | 0.45 | 12.74 | 86.12 | 0.69 |
| 20% IG + 300 U/mL rHuPH20 + 150 mM NaCl | 0.25 | 15.21 | 84.08 | 0.46 | 0.47 | 12.78 | 86.13 | 0.61 |
| 20% IG + 100 U/mL rHuPH20 + 100 mM NaCl | 0.24 | 15.40 | 83.87 | 0.50 | 0.43 | 12.69 | 86.24 | 0.65 |
| 20% IG + 300 U/mL rHuPH20 + 100 mM NaCl | 0.25 | 15.53 | 83.81 | 0.42 | 0.48 | 12.72 | 86.17 | 0.63 |
| 20% IG + 100 U/mL rHuPH20 + 500 mM glycine | 0.21 | 14.40 | 84.99 | 0.39 | 0.22 | 12.31 | 86.90 | 0.56 |
| 20% IG + 300 U/mL rHuPH20 + 100 mM glycine | 0.21 | 14.38 | 85.00 | 0.41 | 0.22 | 12.47 | 86.73 | 0.58 |
| 20% IG + 100 U/mL rHuPH20 + 500 mM proline | 0.25 | 15.47 | 83.83 | 0.45 | 0.24 | 10.18 | 88.92 | 0.66 |
| 20% IG + 300 U/mL rHuPH20 + 100 mM proline | 0.25 | 15.72 | 83.54 | 0.49 | 0.24 | 10.35 | 88.81 | 0.61 |

Example 7

Effects of Co-Formulated rHuPH20 and 10% IG or 20% IG in Yucatan Mini Pigs

A. Experimental Design

The feasibility of dosing rHuPH20 co-formulated with 10% or 20% immune globulin (IG) solution (130 mM NaCl, 10 mM histidine, pH 6.6) subcutaneously in Yucatan Mini Pigs was determined and compared to Leading Edge dosing (successive dosing of rHuPH20 followed by IG solution). A dose response utilizing several concentrations of rHuPH20 was also evaluated for each IG solution.

Eighteen male Yucatan Mini Pigs weighing 18.4-23.2 kg (SNS Farms) were assigned to one or two of eleven treatment groups as shown in Table 45 so that each group utilized three pigs. All formulations were administered subcutaneously with 10-gauge 90 degree soft bend Huber needles on the backs of anesthetized male pigs. For Leading Edge dosing, rHuPH20 followed by IgG was injected consecutively using the same needle in the exact location, employing a simple syringe switch. No delay between dosing rHuPH20 and IgG was required or employed. Up to two different formulations, each from a different treatment group, were tested on each pig at a maximum volume of 110 mL per injection site. Infusions lasted approximately 20 minutes for co-formulations and 22-28 minutes for Leading Edge formulations.

TABLE 45

Summary of experimental design

| Group | Treatment | Dose Type | Total Dose Volume (mL) |
|---|---|---|---|
| 1 | 100 mL 10% IG | Co-formulation | 100 |
| 2 | 100 mL 10% IG/rHuPH20 (50 U/mL) | Co-formulation | 100 |
| 3 | 100 mL 10% IG/rHuPH20 (100 U/mL) | Co-formulation | 100 |
| 4 | 100 mL 10% IG/rHuPH20 (300 U/mL) | Co-formulation | 100 |
| 5 | 50 mL 20% IG | Co-formulation | 50 |
| 6 | 50 mL 20% IG/rHuPH20 (50 U/mL) | Co-formulation | 50 |
| 7 | 50 mL 20% IG/rHuPH20 (100 U/mL) | Co-formulation | 50 |
| 8 | 50 mL 20% IG/rHuPH20 (300 U/mL) | Co-formulation | 50 |
| 9 | 10 mL rHuPH20 (150 U/mL) + 100 mL 10% IG | Leading Edge | 110 |
| 10 | 20 mL rHuPH20 (150 U/mL) + 50 mL 20% IG | Leading Edge | 60 |
| 11 | 20 mL rHuPH20 (150 U/mL) + 50 mL 20% IG | Leading Edge | 70 |

Injection site observations were assessed following dosing. Transducers were utilized to measure the continuous pressure (mmHg) exerted to administer each formulation, and blood was collected for Complete Blood Count (CBC) and gamma immunoglobulin (IgG) analysis. At study termination, 3 days post-dosing, all animals were euthanized and two sample sections (A and B) were collected from each of Injection Site 1, Injection Site 2, and Control (collected from a site distant from the two injection sites) and preserved in 10% neutral buffered formalin, and evaluated by light microscopy (Nova Pathology, PC, San Diego, Calif.). Site A was a 2-3 mm thick section through the center of the injection site and Site B was a 2-3 mm thick section taken from the end of the harvested injection site.

B. Injection Site Observations

Within 5 minutes of dosing 10% IG alone (~25 mL into infusion; Group 1), a distinct 'bleb' was visible on all three pigs. Approximately 10 minutes into dosing 20% IG alone (~25 mL into infusion; Group 5), a distinct bleb was visible. Observed bleb formation area increased with all formulations containing rHuPH20 (including Leading Edge) compared to IG dosing alone, signifying greater dispersion of fluids when utilizing rHuPH20 (Table 46).

Co-formulations of rHuPH20 with 10% and 20% IG resulted in significantly reduced hardening of skin at all rHuPH20 concentrations (sites remained soft), and reduced pink/redness of the skin in all rHuPH20 concentrations. Leading Edge comparison dosing resulted in similar pink/redness observations as co-formulations. Occurrences of pink/redness at injection sites observed post-dosing showed full recovery within 24 hours for all groups (Table 46).

TABLE 46

Injection site appearance and analysis

| Group | Treatment | Mean Bleb Area (cm²) | Mean Bleb Observation |
|---|---|---|---|
| 1 | 100 mL 10% IG | 97.5 | Slightly pink; Hard |
| 2 | 100 mL 10% IG/rHuPH20 (50 U/mL) | 91.7 | Slightly pink Soft |
| 3 | 100 mL 10% IG/rHuPH20 (100 U/mL) | 180.3 | Slightly pink/pink; Soft |
| 4 | 100 mL 10% IG/rHuPH20 (300 U/mL) | 178.0 | Slightly pink/pink; Soft |
| 5 | 50 mL 20% IG | 95.2 | Pink/red; Hard |
| 6 | 50 mL 20% IG/rHuPH20 (50 U/mL) | 102.6 | Pink/red; Soft |
| 7 | 50 mL 20% IG/rHuPH20 (100 U/mL) | 111.9 | Slightly pink/pink; Soft |
| 8 | 50 mL 20% IG/rHuPH20 (300 U/mL) | 111.1 | Normal; Soft |
| 9 | 10 mL rHuPH20 (150 U/mL) + 100 mL 10% IG | 173.5 | Normal; Soft |
| 10 | 20 mL rHuPH20 (150 U/mL) + 50 mL 20% IG | 116.8 | Normal/Slightly Pink; Soft |
| 11 | 20 mL rHuPH20 (150 U/mL) + 50 mL 20% IG | 131.4 | Normal/Slightly Pink; Soft |

C. Pressure Measurement Observations

Table 47 summarizes the mean pressure measurements. At 2.5 minutes or sooner post-dosing 20% IG alone (Group 5), pressures were out of measurable range (>460 mmHg) for all three pigs. Two of three pigs were out of the measurable pressure range in Group 6, and one pig was out of range for each of Groups 7 and 8. Groups 1 and 2 each had one pig out of range. The results show that the pressure needed to accomplish the injections decreased with all co-formulations containing rHuPH20.

TABLE 47

Mean pressure measurement analysis

| Group | N | Mean Pressure (mmHg) | Rising Max Pressure (mmHg) | Pressure Max (mmHg) | Rising Max Time (min) | Time Max (min) |
|---|---|---|---|---|---|---|
| 1 | 2 | 242 | 266 | 281 | 2.7 | 5.1 |
| 2 | 2 | 209 | N/A* | 223 | N/A* | 4.0 |
| 3 | 3 | 164 | 0.3 | 223 | 0.3 | 4.1 |
| 4 | 3 | 289 | 0.5 | 255 | 0.5 | 2.3 |
| 5 | 0 | N/A | N/A | N/A | N/A | N/A |
| 6 | 1 | 164 | 250 | 250 | 1.6 | 1.6 |
| 7 | 2 | 179 | 215 | 215 | 0.7 | 0.7 |
| 8 | 2 | 194 | 188 | 203 | 1.6 | 4.6 |
| 9 | 3 | 117 | 119 | 125 | 1.9 | 4.9 |
| 10 | 3 | 241 | 232 | 261 | 3.8 | 12.9 |
| 11 | 3 | 241 | 281 | 264 | 4.7 | 15.2 |

N/A = Not Available, >460 mmHg
N/A* = Rising curve of pressure recording unclear to interpret D. Complete Blood Count and IgG Plasma Analysis Blood was collected into K₃EDTA tubes at pre-dose (~2.0 mL) and at 30 minutes post-dosing (~2.0 mL) for Complete Blood Count (CBC) analysis. Samples were stored at 4° C. until analysis (Bioquant, Inc., San Diego, Calif.). CBC results do not give any product related specific safety concerns. The majority of pigs remained within normal CBC levels (normal CBC range referenced from SNS farms). Five of eighteen pigs had non-visible clots in the samples and could not be evaluated.

Blood for gamma immunoglobulin (IgG) analysis was collected into Sodium Citrate tubes at pre-dose (~2.0 mL) and at study termination (~4.0 mL) to confirm systemic availability after subcutaneous administration of human IgG. Samples were centrifuged at 4° C. for 10 minutes at 3000 rpm, plasma was aliquotted, and samples were stored at −20° C. until analysis. A general increase in IgG was observed in all animals 3 days after administration, as shown in Table 48. IgG plasma levels for each pig reflect the mean of the two different treatments each pig was administered (with the exception of pigs 7-9 that received a single treatment only).

TABLE 48

IgG analysis

| Pig # | Treatment Group(s) | IgG (g/L) Predose | IgG (g/L) Termination |
|---|---|---|---|
| 1 | 1 and 2 | 3.46 | 8.53 |
| 2 | 1 and 2 | 2.97 | 9.27 |
| 3 | 1 and 2 | 4.35 | 9.03 |
| 4 | 3 and 4 | 6.67 | 10.51 |
| 5 | 3 and 4 | 3.81 | 10.15 |
| 6 | 3 and 4 | 4.79 | 9.83 |
| 7 | 5 | 4.96 | 6.06 |
| 8 | 5 | 3.50 | 5.94 |
| 9 | 5 | 3.73 | 6.86 |
| 10 | 6 and 7 | 2.83 | 8.19 |
| 11 | 6 and 7 | 3.47 | 10.08 |
| 12 | 6 and 7 | 4.08 | 11.12 |
| 13 | 8 and 9 | 5.07 | 9.62 |
| 14 | 8 and 9 | 4.02 | 8.82 |
| 15 | 8 and 9 | 3.94 | 8.63 |
| 16 | 10 and 11 | 3.97 | 9.25 |
| 17 | 10 and 11 | 4.60 | 9.68 |
| 18 | 10 and 11 | 4.76 | 9.51 |

E. Histopathology Results

Histologic findings were present in the epidermis, dermis and subcutaneous tissue, and contained a mixed leukocyte inflammation, edema and hemorrhage. Each histologic finding was assigned a severity grade based on the following scheme: Not Present: 0; Present, Not Graded: 0; Minimal: 1; Mild: 2; Moderate: 3; Marked: 4 Histologic findings are summarized by incidence and mean group severity score in Tables 49-51.

TABLE 49

Summary of histologic findings: 10% IG + rHuPH20

| Histologic Findings | Treatment Group 1 | 2 | 3 | 4 |
|---|---|---|---|---|
| Inflammation, Mixed Leukocyte, subcutaneous | 6/6* | 6/6 | 5/6 | 6/6 |
| Mean Group Severity Score** | 1.83 | 1.00 | 1.00 | 1.17 |
| Edema, subcutaneous | 6/6 | 5/6 | 6/6 | 5/6 |
| Mean Group Severity Score | 2.00 | 0.83 | 1.00 | 1.17 |
| Hemorrhage, subcutaneous | 3/6 | 3/6 | 2/6 | 1/6 |
| Mean Group Severity Score | 0.67 | 0.50 | 0.33 | 0.33 |
| Sum of Mean Group Severity Scores | 4.50 | 2.33 | 2.33 | 2.67 |

*Number of Sections Affected/Number of Sections Evaluated
**Sum of severity scores in the group divided by the number of sections evaluated in the group

TABLE 50

Summary of histologic findings: 20% IG + rHuPH20

| Histologic Findings | Treatment Group 5 | 6 | 7 | 8 |
|---|---|---|---|---|
| Inflammation, Mixed Leukocyte, subcutaneous | 6/6* | 6/6 | 5/6 | 6/6 |
| Mean Group Severity Score** | 1.00 | 1.17 | 1.00 | 2.17 |
| Edema, subcutaneous | 6/6 | 6/6 | 5/6 | 5/6 |
| Mean Group Severity Score | 1.17 | 1.17 | 1.17 | 2.00 |
| Hemorrhage, subcutaneous | 0/6 | 2/6 | 0/6 | 1/6 |
| Mean Group Severity Score | 0.00 | 0.33 | 0.00 | 0.17 |
| Sum of Mean Group Severity Scores | 2.17 | 2.67 | 2.17 | 4.34 |

*Number of Sections Affected/Number of Sections Evaluated
**Sum of severity scores in the group divided by the number of sections evaluated in the group

TABLE 51

Summary of histologic findings: Leading Edge dosing

| Histologic Findings | Treatment Group 9 | 10 | 11 |
|---|---|---|---|
| Inflammation, Mixed Leukocyte, subcutaneous | 6/6* | 6/6 | 6/6 |
| Mean Group Severity Score** | 1.17 | 1.17 | 1.17 |
| Edema, subcutaneous | 5/6 | 6/6 | 6/6 |
| Mean Group Severity Score | 1.50 | 1.67 | 1.83 |
| Hemorrhage, subcutaneous | 1/6 | 3/6 | 1/6 |
| Mean Group Severity Score | 0.17 | 0.67 | 0.17 |
| Sum of Mean Group Severity Scores | 2.84 | 3.51 | 3.17 |

*Number of Sections Affected/Number of Sections Evaluated
**Sum of severity scores in the group divided by the number of sections evaluated in the group The response to the administration of IG and rHuPH20 was qualitatively similar in each dose group in this study. These responses were characterized by mixed leukocyte inflammation, edema and hemorrhage in the subcutaneous tissue in the injection sites. Table 52 compares the mean group severity score in all of the dose groups.

TABLE 52

Summary of mean group severity scores

| Group | Treatment | Dose Type | Sum of Mean Group Severity Scores |
|---|---|---|---|
| 1 | 100 mL 10% IG | Co-formulation | 4.50 |
| 2 | 100 mL 10% IG/rHuPH20 (50 U/mL) | Co-formulation | 2.33 |
| 3 | 100 mL 10% IG/rHuPH20 (100 U/mL) | Co-formulation | 2.33 |
| 4 | 100 mL 10% IG/rHuPH20 (300 U/mL) | Co-formulation | 2.67 |
| 5 | 50 mL 20% IG | Co-formulation | 2.17 |
| 6 | 50 mL 20% IG/rHuPH20 (50 U/mL) | Co-formulation | 2.67 |
| 7 | 50 mL 20% IG/rHuPH20 (100 U/mL) | Co-formulation | 2.17 |
| 8 | 50 mL 20% IG/rHuPH20 (300 U/mL) | Co-formulation | 4.34 |

TABLE 52-continued

Summary of mean group severity scores

| Group | Treatment | Dose Type | Sum of Mean Group Severity Scores |
|---|---|---|---|
| 9 | 10 mL rHuPH20 (150 U/mL) + 100 mL 10% IG | Leading Edge | 2.84 |
| 10 | 20 mL rHuPH20 (150 U/mL) + 50 mL 20% IG | Leading Edge | 3.51 |
| 11 | 20 mL rHuPH20 (150 U/mL) + 50 mL 20% IG | Leading Edge | 3.17 |

Based on mean group severity scores, the most severe injection site responses were associated with administration of 100 mL of 10% IG alone (Group 1) and with administration of 50 mL of 20% IG co-formulated with 300 U/mL rHuPH20 (Group 8). The response to administration of 100 mL of 10% IG co-formulated with rHuPH20 at 50, 100 and 300 U/mL of 10% IG (Groups 2-4) was similar to the response to administration of 50 mL of 20% IG alone (Group 5), co-formulated with rHuPH20 at 50 and 100 U/mL of 20% IG (Groups 6 and 7), and Leading Edge dosing with 10 mL of rHuPH20 (150 U/mL) followed by 100 mL of 10% IG (Group 9). However, Leading Edge dosing with 10 or 20 mL of rHuPH20 (150 U/mL) followed by 50 mL of 20% IG (Groups 10 and 11) resulted in a more severe response than did similar co-formulations (Groups 6 and 7). Sections of control skin contained few histological findings, which can be attributed to diffusion of the injected formulations from the test article injection sites, and incidental findings unrelated to the formulations.

F. SUMMARY

The results confirmed the feasibility of dosing rHuPH20 co-formulated with 10% and 20% IG subcutaneously in Yucatan Mini Pigs. IG (10% or 20%) administered alone is feasible, although a moderate to severe degree of hardening and pink/redness of the skin resulted. Co-formulations with rHuPH20 resulted in a decrease in pressure needed to accomplish the injections, significantly reduced hardening of the skin, and reduced pink/redness of the skin. Observed bleb formation area was similar or increased with all formulations that contained rHuPH20 compared to IG dosing alone, confirming greater dispersion of fluids when rHuPH20 was utilized. Leading Edge dosing was feasible, and similar pressure, pink/redness and bleb areas are observed as with co-formulations. Histopathological findings present in the deep subcutaneous tissue attributed to dosing included mixed leukocyte inflammation, edema and hemorrhage, with the most severe responses associated with administration of 10% IG alone and 20% IG co-formulated with rHuPH20 (300 U/mL).

Since modifications will be apparent to those of skill in this art, it is intended that this invention be limited only by the scope of the appended claims.

The invention claimed is:

1. A stable composition formulated for subcutaneous administration, wherein:
   the stable composition contains hyaluronidase and immune globulin (IG);
   the stable composition is a liquid co-formulation;
   the composition has a pH of between 4 or about 4 to 5 or about 5, inclusive; and
   the composition comprises:
   (a) immune globulin (IG) at a concentration that is at least 10% w/v;
   a soluble hyaluronidase at a concentration that is at least 50 U/mL and is present in an amount sufficient to allow for the subcutaneous administration of the composition at a single injection site at an infusion rate equal to or greater than the intravenous infusion rate for intravenous immunoglobulin; and
   an alkali metal chloride salt at a concentration of 0.05 M to 0.25 M, whereby the co-formulated composition is stable at temperatures of 28° C. to 32° C. for at least 6 months; or
   (b) immune globulin (IG) at a concentration that is at least 10% w/v;
   a soluble hyaluronidase at a concentration that is at least 50 U/mL and is present at a ratio of at least 100 Units (U) of hyaluronidase per gram (g) of the IG; and
   an alkali metal chloride salt at a concentration of 0.05 M to 0.25 M, whereby the co-formulated composition is stable at temperatures of 28° C. to 32° C. for at least 6 months.

2. The stable composition of claim 1, further comprising an amino acid stabilizer at a concentration that is at least 0.1 M.

3. The stable composition of claim 2, wherein the amino acid stabilizer is selected from among alanine, histidine, arginine, lysine, ornithine, isoleucine, valine, methionine, glycine and proline.

4. The stable composition of claim 2, wherein the amino acid stabilizer is at a concentration that is 0.25 M or at least 0.25 M.

5. The stable composition of claim 1, wherein the concentration of IG is at least 20% w/v.

6. The stable composition of claim 1, wherein the concentration of IG is between at or about 10% w/v to at or about 20% w/v.

7. The stable composition of claim 1, wherein the IG is from human plasma.

8. The stable composition of claim 1, wherein the IG is purified from human plasma by a purification method comprising alcohol fractionation.

9. The stable composition of claim 8, wherein the IG is further purified by any one or more of a polyethylene glycol (PEG) precipitation, ion-exchange chromatography, enzymatic cleavage, diafiltration or ultrafiltration.

10. The stable composition of claim 1, wherein the IG contains greater than 95% IgG.

11. The stable composition of claim 1, wherein the alkali metal chloride salt is KCl or NaCl.

12. The stable composition of claim 1, wherein the concentration of NaCl is at least 0.15 M.

13. The stable composition of claim 1, wherein the soluble hyaluronidase is a PH20, or a truncated form thereof.

14. The stable composition of claim 13, wherein the PH20 is selected from an ovine, bovine or truncated human PH20.

15. The stable composition of claim 14, wherein PH20 is a truncated human PH20 and the truncated human PH20 is selected from among polypeptides having a sequence of amino acids set forth in any of SEQ ID NOS:4-9, or variants thereof having at least 91% sequence identity to any of SEQ ID NOS:4-9.

16. The stable composition of claim 1, wherein the soluble hyaluronidase is a composition designated rHuPH20.

17. The stable composition of claim 1, wherein the soluble hyaluronidase is at a concentration that is 50 U/mL to 500 U/mL.

18. The stable composition of claim 1, wherein the soluble hyaluronidase is at a ratio of 100 U of hyaluronidase per gram of the IG to 3000 U of hyaluronidase per gram of the IG.

19. The stable composition of claim 1 that in concentrated form has a pH of 4.4 to 4.9, inclusive.

20. The stable composition of claim 1, wherein the co-formulation is formulated for multiple dosage administration or for single dosage administration.

21. The stable composition of claim 1 that is formulated for single dosage administration in an amount sufficient to treat an IG-treatable disease or condition when administered daily, weekly, biweekly, every 2-3 weeks, every 3-4 weeks or monthly.

22. The stable composition of claim 1, wherein the amount of IG in the co-formulation is substantially the same as the amount in a single dosage administration when administered intravenously for treatment of an IG-treatable disease or condition.

23. The stable composition of claim 1, wherein the co-formulation is formulated for single dosage administration and the amount of IG is or is about at least 1 gram (g) to 200 g.

24. The stable composition of claim 1, wherein the co-formulation is formulated for single dosage administration and the amount of hyaluronidase in the composition is or is about at least 500 Units, 1000 Units, 2000 Units, 5000 Units, 10,000 Units, 30,000 Units, 40,000 Units, 50,000 Units, 60,000 Units, 70,000 Units, 80,000 Units, 90,000 Units, 100,000 Units or more.

25. A container, comprising a stable composition of claim 1.

26. A container of claim 25 that is a tube, bottle, vial or syringe and optionally includes a needle for injection.

27. A kit, comprising the container of claim 25, and a means for infusing the composition.

28. The stable composition of claim 1 that comprises:
immune globulin (IG) at a concentration that is at least 10% w/v;
a soluble hyaluronidase at a concentration that is 50 U/mL to 500 U/mL and is present at a ratio of at least 100 Units (U) of hyaluronidase per gram (g) of the IG; and
an alkali metal chloride salt at a concentration of 0.05 M to 0.25 M, whereby the co-formulated composition is stable at temperatures of 28° C. to 32° C. for at least 6 months.

29. The stable composition of claim 1 that comprises:
immune globulin (IG) at a concentration that is at least 10% w/v;
a soluble hyaluronidase at a concentration that is 50 U/mL to 500 U/mL and is present in an amount sufficient to allow for the subcutaneous administration of the composition at a single injection site at an infusion rate equal to or greater than the intravenous infusion rate for intravenous immunoglobulin; and
an alkali metal chloride salt at a concentration of 0.05 M to 0.25 M, whereby the co-formulated composition is stable at temperatures of 28° C. to 32° C. for at least 6 months.

* * * * *